US010364259B2

(12) United States Patent
Kim et al.

(10) Patent No.: US 10,364,259 B2
(45) Date of Patent: Jul. 30, 2019

(54) ZIRCONIUM, HAFNIUM, TITANIUM PRECURSORS AND DEPOSITION OF GROUP 4 CONTAINING FILMS USING THE SAME

(71) Applicant: L'Air Liquide, Societe Anonyme pour l'Etude et l'Exploitation des Procedes Georges Claude, Paris (FR)

(72) Inventors: Daehyeon Kim, Seoul (KR); Satoko Gatineau, Seoul (KR); Wontae Noh, Seoul (KR); Julien Gatineau, Seoul (KR); Jean-Marc Girard, Versailles (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/396,159

(22) Filed: Dec. 30, 2016

(65) Prior Publication Data

US 2017/0107623 A1 Apr. 20, 2017

(51) Int. Cl.
*C07F 7/00* (2006.01)
*C07F 17/00* (2006.01)
(Continued)

(52) U.S. Cl.
CPC ................ *C07F 7/00* (2013.01); *C07F 17/00* (2013.01); *C23C 16/18* (2013.01); *C23C 16/45525* (2013.01)

(58) Field of Classification Search
None
See application file for complete search history.

(56) References Cited

U.S. PATENT DOCUMENTS 5,621,127 A 4/1997 Langhauser et al.
5,665,818 A 9/1997 Tilston et al.
(Continued)

FOREIGN PATENT DOCUMENTS

EP 0 475 671 3/1992
KR 10 1263454 11/2013
(Continued)

OTHER PUBLICATIONS

Hughes, A.K. et al, Efficient new synthetic route to bidentate, monomeric cyclopentadienyl-amide complexes of group 4 transition metals: synthesis and characterization of the zirconium and hafnium complexes [$\eta^5$:$\sigma$-$C_5H_4(CH_2)_3NMe$}$MX_2$ ($NHMe_2$)] (X=Cl, I, M=Zr; X=I, M=Hf) and [{$\eta^5$:$\sigma$-$C_5H_4(CH_2)_3NMe$}$ZrX_2$] (X=$NMe_2$, $CH_2Ph$, $CH_2SiMe_3$, $BH_4$) and molecular structure of [{$\eta^5$:$\sigma$-$C_5H_4(CH_2)_3NMe$}ZrCl($CH_2Ph$)]$_2$], Organometallics 1993, 12, 1936-1945.
(Continued)

*Primary Examiner* — Clinton A Brooks
(74) *Attorney, Agent, or Firm* — Yan Jiang; Patricia E. McQueeney

(57) ABSTRACT

Group 4 transition metal-containing film forming compositions are disclosed. The Group 4 transition metal-containing film forming compositions comprise Group 4 transition metal precursors having the formula $L_2$-M-$C_5R_4$-[$(ER_2)_2$—NR]—, wherein M is Ti, Zr, or Hf bonded in an $\eta^5$ bonding mode to the Cp group; each E is independently C, Si, B or P; each R is independently a hydrogen or a $C_1$-$C_4$ hydrocarbon group; and each L is independently a −1 anionic ligand selected from the group consisting of NR'$_2$, OR', Cp, amidinate, β-diketonate, or keto-iminate, wherein R' is a H or a $C_1$-$C_4$ hydrocarbon group and adjacent R's may be joined to form a hydrocarbyl ring; provided that at least one R on the Cp is $C_1$ to $C_4$. Also disclosed are methods of
(Continued)

synthesizing and using the disclosed precursors to deposit Group 4 transition metal-containing films on one or more substrates via vapor deposition processes.

21 Claims, 3 Drawing Sheets

(51) Int. Cl.
*C23C 16/18* (2006.01)
*C23C 16/455* (2006.01)

(56) References Cited

U.S. PATENT DOCUMENTS

| | | | |
|---|---|---|---|
| 5,693,727 | A | 12/1997 | Goode et al. |
| 5,703,187 | A | 12/1997 | Timmers |
| 6,107,421 | A | 8/2000 | Timmers et al. |
| 8,946,096 | B2 | 2/2015 | Ahn et al. |
| 2012/0145953 | A1 | 6/2012 | Pallem et al. |
| 2012/0196449 | A1 | 8/2012 | Xu et al. |
| 2013/0337659 | A1 | 12/2013 | Ahn et al. |
| 2015/0255276 | A1 | 9/2015 | Cho et al. |
| 2016/0273103 | A1 | 9/2016 | Moon et al. |
| 2017/0107612 | A1 | 4/2017 | Noh et al. |
| 2017/0107617 | A1 | 4/2017 | Gatineau et al. |
| 2017/0107618 | A1 | 4/2017 | Gatineau et al. |

FOREIGN PATENT DOCUMENTS

| | | |
|---|---|---|
| KR | 2015 0105747 | 3/2014 |
| KR | 2014 0078534 | 6/2014 |
| KR | 10 1598485 | 2/2016 |
| KR | 10 1684660 | 12/2016 |
| WO | WO 88 10275 | 12/1988 |
| WO | WO 99 64476 | 12/1999 |
| WO | WO 2009 036046 | 3/2009 |

OTHER PUBLICATIONS

Jung, J.-S. et al., "Atomic layer deposition of $ZrO_2$ thin film on Si(100) using $\{\eta^5:\eta^1$—$Cp(CH_2)_3NMe\}Zr(NMe_2)_2/O_3$ as precursors," Thin Solid Films 589 (2015) 831-837.

Cano, J. et al., "How to synthesize a constrained geometry catalyst (CGC)—a survey," Journal of Organometallic Chemistry 692 (2007) 4411-4423.

Edelmann, F.T., "Lanthanide amidinates and guanidinates: from laboratory curiosities to efficient homogeneous catalysts and precursors for rare-earth oxide thin films," Chem. Soc. Rev., 2009 38, 2253-2268.

Herrmann, W.A. et al., "Doubly bridged rac-metallocenes of zirconium and hafnium," Angew. Chem. Int. Ed. Engl. 1994, 33, No. 19, 1946-1949.

Kang, C. et al., "Growth behavior and structural characteristics of $TiO_2$ thin films using $(CpN)Ti(NMe_2)_2$ and oxygen remote plasma," Phys. Status Solidi A 212, No. 3, 674-679.

Kim, T.H. et al., "$sp^3$-$C^1$-bridged 1,3-$Me_2Cp$/amido titanium and zirconium complexes and their reactivities towards ethylene polymerization," Eur. J. Inorg. Chem. 2004, 1522-1529.

Okuda, J., "Linked amido-cyclopentadienyl complexes of group 3 and 4 metals: the first "post-metallocenes," Metalorganic catalysts for synthesis and polymerization," Springer-Verlag Berlin Heidelerg 1999, ISBN-13: 978-3-642-64292-0, Walter Kaminsky, editor, 200-211.

Sinnema, P.-J., "Carbon-bridged cyclopentadienyl amido group 4 metal complexes: ligands tuning and olefin polymerization," Groningen: s.n. 1999, 215 pages.

Chirinos, J. et al., "Ethene homo- and ethane/propene copolymerization using a MOA activated cyclopentadienyl-amido half-sandwich complex," Macromol. Chem. Phys. 2000, 201, 2581-2585.

International Search Report and Written Opinion for corresponding PCT/IB2017/001739, dated May 29, 2018.

Mu, Y. et al., "Zirconium complexes of a cyclopentadienyl-amido ligand with a pendant amine donor via amine and alkane elimination," Can. J. Chem., vol. 74, 1996, 1696-1703.

Zia, M. et al., "Comparative thermal stability studies of some isomeric phenolic β-diketones and their phenolic pyrazoles by thermogravimetric analysis," Journal of Contemporary Research in Chemistry (2016) 1(1), 34-41.

International Search Report and Written Opinion for related PCT/IB2017/001654, dated May 31, 2018.

International Search Report and Written Opinion for related PCT/IB2017/001658, dated Nov. 19, 2018.

ZIRCONIUM, HAFNIUM, TITANIUM PRECURSORS AND DEPOSITION OF GROUP 4 CONTAINING FILMS USING THE SAME

TECHNICAL FIELD

Disclosed are Group 4 transition metal-containing film forming compositions comprising Group 4 transition metal precursors having the formula $L_2$-M-$C_5R_4$-[$(ER_2)_2$—NR]—, wherein M is Ti, Zr, or Hf bonded in an $\eta^5$ bonding mode to the Cp group; each E is independently C, Si, B or P; each R is independently an hydrogen or a $C_1$-$C_4$ hydrocarbon group; adjacent R's may be joined to a hydrocarbyl ring; and each L is independently a −1 anionic ligand selected from the group consisting of $NR'_2$, OR', Cp, amidinate, β-diketonate, or keto-iminate, wherein R' is a H or a $C_1$-$C_4$ hydrocarbon group and adjacent R's may be joined to form a hydrocarbyl ring; provided that at least one R on the Cp is $C_1$ to $C_4$. Also disclosed are methods of synthesizing and using the disclosed precursors to deposit Group 4 transition metal-containing films on one or more substrates via vapor deposition processes.

BACKGROUND

With the scaling down of semiconductor devices, new materials with high dielectric constant are required. Chemical Vapor Deposition (CVD) and Atomic Layer Deposition (ALD) have become the main deposition techniques for such thin films since CVD and ALD may provide different films (metal, oxide, nitride, etc.) having a finely defined thickness and high step coverage. In CVD and ALD, the precursor molecule plays a critical role to obtain high quality films with high conformality and low impurities.

Among high-k dielectrics, Group 4 based materials, such as $TiO_2$, $HfO_2$ or $ZrO_2$, are very promising, whether used as pure or mixed oxides or in laminates. In addition, Group 4 metal-containing films, such as TiN, may also be used for electrode and/or Cu diffusion barrier applications. The Group 4 oxides may also be used for their etch resistance properties in lithography applications, such as for hard masks or spacer-defined multiple patterning applications.

Cyclopentadienyl (Cp) bridged Group 4 metal compounds have been used as precursors for CVD and/or ALD of Group 4 metal-containing films. For example, U.S. Pat. No. 8,946,096 to Ahn et al. discloses group 4 metalorganic compounds utilized in CVD or ALD having the formula

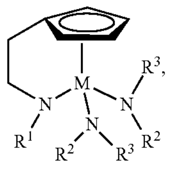

wherein M is Ti, Zr or Hf, $R^1$ is $C_1$ to $C_4$ alkyl, $R^2$ and $R^3$ are independently $C_1$ to $C_6$ alkyl.

US 2015/0255276 to Cho et al. discloses an organometallic precursor, used as a deposition source in CVD and ALD processes, represented by a chemical formula of $X_n(M)(R^1)_m(R^2)_k$, wherein M is Ti, Zr or Hf. X is a ligand of M and one of 6,6-dimethylfulvenyl, indenyl, cyclopentadienyl and cyclopentadienyl substituted with an amino group. $R^1$ and $R^2$ are ligands of M, and each independently an amino group or an ethylendiamino group. Each n, m and k is a positive integer, and n+m+k=3 or 4.

KR10-2014-0078534 to Castle et al. discloses metal precursors and metal-containing thin film prepared with the metal precursors including Group 4 complexes having the structure formula:

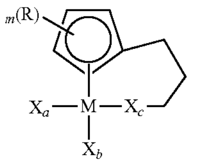

wherein M is selected from the group consisting of Zr, Hf and Ti, $X_a$ and $X_b$ are each independently $NR_aR_b$ or $OR_c$, $X_c$ is $(NR_d)$ or O, $R_a$ to $R_d$ are each independently a hydrogen atom or a $C_1$ to $C_5$ alkyl group, R are each independently a hydrogen atom or a $C_1$ to $C_5$ alkyl group, and m is an integer of 0 to 4.

Kang et al. disclose forming $TiO_2$ thin films using (CpN)$Ti(NMe_2)_2$ and oxygen remote plasma (Kang et al., "Growth behavior and structural characteristics of $TiO_2$ thin films using (CpN)$Ti(NMe_2)_2$ and oxygen remote Plasma", Phys. Status Solidi A, 2014, 212, No. 3, p 674-679).

Some Cp bridged Group 4 metal compounds are synthesized and used for catalysts or other purposes. For example, J Okuda discloses metalorganic catalysts having linked amido-cyclopentadienyl ligands such as Ti(R-Cp-$SiMe_2$-NR—)$(NR_2)_2$ (J Okuda, "Linked Amido-Cyclopentadienyl Complexes of Group 3 and 4 Metals: The First "Post-Metallocenes" Metalorganic Catalysts for Synthesis and Polymerization, pp 200-211, 1999). Herrmann et al. disclose Cp($CH_2CH_2$—O—) $Zr(NMe_2)_2$ prepared as potential catalysts (Herrmann et al., "Doubly Bridged vac-Metallocenes of Zirconium and Hafnium", Angewandte. Chem. Int. Ed. Eng, 1994, 33(19), p 1946-1949). Kim et al. disclose synthesis of ($Me_4Cp$-$CH_2$—NtBu)$Zr(NEt_2)_2$ and (1,3-$Me_2C_5H_2$—CHPh-NtB-κN)$Zr(NMe_2)_2$ (Kim et al., "$sp^3$-$C^1$-Bridged 1,3-$Me_2$Cp/Amido Titanium and Zirconium Complexes and Their Reactivities towards Ethylene Polymerization", Eur. J. Inorg. Chem. 2004, p 1522-1529). Jesus Cano and Klaus Kunz disclose syntheses of some P, C, Si contained Cp-amino bridged compounds (Jesus Cano, Klaus Kunz, "How to synthesize a constrained geometry catalyst (CGC)—A survey", Journal of Organometallic Chemistry 692, 2007, p 4411-4423). Syntheses of carbon-bridged cyclopentadienyl amido Group 4 metal complexes were reported in Piet-Jan Sinnema's PhD dissertation in 1999 (Piet-Jan Sinnema, "Carbon-Bridged Cyclopentadienyl Amido Group 4 Metal Complexes", University of Groningen, 1999).

Accordingly, those skilled in the art continue to seek thermally stable, Group 4 compounds suitable for vapor phase thin film deposition with controlled thickness and composition at high temperature.

SUMMARY

Group 4 transition metal-containing film forming compositions are disclosed. The Group 4 transition metal-containing film forming compositions comprise Group 4 transition metal precursors having the formula $L_2$-M-$C_5R_4$-[$(ER_2)_2$—NR]—, referring to the following structure formula:

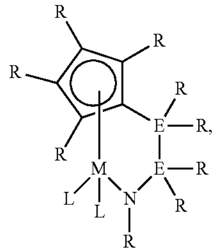

wherein M is Ti, Zr, or Hf bonded in an $\eta^5$ bonding mode to the Cp group; each E is independently C, Si, B or P; each R is independently an hydrogen or a $C_1$-$C_4$ hydrocarbon group; adjacent Rs may be joined to a hydrocarbyl ring; and each L is independently a −1 anionic ligand selected from the group consisting of $NR'_2$, OR', Cp, amidinate, β-diketonate, or keto-iminate, wherein R' is a H or a $C_1$-$C_4$ hydrocarbon group and adjacent R's may be joined to form a hydrocarbyl ring; provided that at least one R on the Cp is $C_1$ to $C_4$.

The disclosed Group 4 transition metal-containing film forming compositions may further include one or more of the following aspects:

- M being Ti;
- M being Zr;
- M being Hf;
- Each E independently being C, Si, B or P;
- E being C;
- E being Si;
- E being B;
- E being P;
- Each R independently being H, Me, Et, $^n$Pr, $^i$Pr, $^n$Bu, $^s$Bu, $^i$Bu, or $^t$Bu;
- R being H;
- R being Me;
- R being Et;
- R being $^n$Pr;
- R being $^i$Pr;
- R being $^n$Bu;
- R being $^i$Bu;
- R being $^s$Bu;
- R being $^t$Bu;
- L being $NH_2$;
- L being $NMe_2$;
- L being $NEt_2$
- L being N$^n$Pr$_2$;
- L being N$^i$Pr$_2$;
- L being N$^n$Bu$_2$;
- L being N$^i$Bu$_2$;
- L being N$^s$Bu$_2$;
- L being N$^t$Bu$_2$;
- L being NHMe;
- L being NHEt;
- L being NH$^n$Pr;
- L being NH$^i$Pr;
- L being NH$^n$Bu;
- L being NH$^i$Bu;
- L being NH$^s$Bu;
- L being NH$^t$Bu;
- L being NMeEt;
- L being NMe$^n$Pr;
- L being NMe$^i$Pr;
- L being NMe$^n$Bu;
- L being NMe$^i$Bu;
- L being NMe$^s$Bu;
- L being NMe$^t$Bu;
- L being NEt$^n$Pr;
- L being NEt$^i$Pr;
- L being NEt$^n$Bu;
- L being NEt$^i$Bu;
- L being NEt$^s$Bu;
- L being NEt$^t$Bu;
- L being N$^n$Pr$^i$Pr;
- L being N$^n$Pr$^n$Bu;
- L being N$^n$Pr$^i$Bu;
- L being N$^n$Pr$^s$Bu;
- L being N$^n$Pr$^t$Bu;
- L being N$^i$Pr$^n$Bu;
- L being N$^i$Pr$^i$Bu;
- L being N$^i$Pr$^s$Bu;
- L being N$^i$Pr$^t$Bu;
- L being N$^n$Bu$^i$Bu;
- L being N$^n$Bu$^s$Bu;
- L being N$^n$Bu$^t$Bu;
- L being N$^i$Bu$^s$Bu;
- L being N$^i$Bu$^t$Bu;
- L being N$^s$Bu$^t$Bu;
- L being OH;
- L being OMe;
- L being OEt;
- L being O$^n$Pr;
- L being O$^i$Pr;
- L being O$^n$u;
- L being O$^i$Bu;
- L being O$^s$Bu;
- L being O$^t$Bu;
- L being Cp;
- L being amidinate;
- L being β-diketonate;
- L being keto-iminate;
- the Cp group being a methyl substituted the Cp group;
- the Cp group being an ethyl substituted the Cp group;
- the Cp group being an isopropyl substituted the Cp group;
- the Group 4 transition metal precursor being $(Me_2N)_2$—Zr—$C_5H_3$-1-Me-3-($CH_2$—$CH_2$—NMe)-;
- the Group 4 transition metal precursor being $(Me_2N)_2$—Zr—$C_5H_3$-1-Et-3-($CH_2$—$CH_2$—NMe)-;
- the Group 4 transition metal precursor being $(Me_2N)_2$—Zr—$C_5H_3$-1-$^i$Pr-3-($CH_2$—$CH_2$—NMe)-;
- the Group 4 transition metal precursor being $(Me_2N)_2$—Hf—$C_5H_3$-1-Me-3-($CH_2$—$CH_2$—NMe)-;
- the Group 4 transition metal precursor being $(Me_2N)_2$—Hf—$C_5H_3$-1-Et-3-($CH_2$—$CH_2$—NMe)-;
- the Group 4 transition metal precursor being $(Me_2N)_2$—Hf—$C_5H_3$-1-$^i$Pr-3-($CH_2$—$CH_2$—NMe)-.
- the Group 4 transition metal precursor being $(Me_2N)$(Cp)-Zr—$C_5H_3$-1-Me-3-($CH_2$—$CH_2$—NMe)-;
- the Group 4 transition metal precursor being $(Me_2N)$(Cp)-Zr—$C_5H_3$-1-Et-3-($CH_2$—$CH_2$—NMe)-;
- the Group 4 transition metal precursor being $(Me_2N)$(Cp)-Zr—$C_5H_3$-1-$^i$Pr-3-($CH_2$—$CH_2$—NMe)-;
- the Group 4 transition metal precursor being $(Me_2N)$(Cp)-Hf—$C_5H_3$-1-Me-3-($CH_2$—$CH_2$—NMe)-;
- the Group 4 transition metal precursor being $(Me_2N)$(Cp)-Hf—$C_5H_3$-1-Et-3-($CH_2$—$CH_2$—NMe)-;
- the Group 4 transition metal precursor being $(Me_2N)$(Cp)-Hf—$C_5H_3$-1-$^i$Pr-3-($CH_2$—$CH_2$—NMe)-;
- the Group 4 transition metal precursor being $(Me_2N)_2$—Zr—$C_5Me_4$-$CH_2$—$CH_2$—NMe)-;
- the Group 4 transition metal precursor being $(Me_2N)_2$—Zr—$C_5Me_3$-1-Et-3-($CH_2$—$CH_2$—NMe)-;
- the Group 4 transition metal precursor being $(Me_2N)_2$—Zr—$C_5Me_3$-1-$^i$Pr-3-($CH_2$—$CH_2$—NMe)-;

the Group 4 transition metal precursor being $(Me_2N)_2$—Hf—$C_5Me_4$-($CH_2$—$CH_2$—NMe)-;

the Group 4 transition metal precursor being $(Me_2N)_2$—Hf—$C_5Me_3$-1-Et-3-($CH_2$—$CH_2$—NMe)-; or the Group 4 transition metal precursor being $(Me_2N)_2$—Hf—$C_5Me_3$-1-$^i$Pr-3-($CH_2$—$CH_2$—NMe)-;

the Group 4 transition metal precursor being $(Me_2N)$(Cp)-Zr—$C_5Me_4$-($CH_2$—$CH_2$—NMe)-;

the Group 4 transition metal precursor being $(Me_2N)$(Cp)-Zr—$C_5Me_3$-1-Et-3-($CH_2$—$CH_2$—NMe)-;

the Group 4 transition metal precursor being $(Me_2N)$(Cp)-Zr—$C_5Me_3$-1-$^i$Pr-3-($CH_2$—$CH_2$—NMe)-;

the Group 4 transition metal precursor being $(Me_2N)$(Cp)-Hf—$C_5Me_4$-($CH_2$—$CH_2$—NMe)-;

the Group 4 transition metal precursor being $(Me_2N)$(Cp)-Hf—$C_5Me_3$-1-Et-3-($CH_2$—$CH_2$—NMe)-;

the Group 4 transition metal precursor being $(Me_2N)$(Cp)-Hf—$C_5Me_3$-1-$^i$Pr-3-($CH_2$—$CH_2$—NMe)-;

the Group 4 transition metal-containing film forming composition comprising between approximately 0.1 molar % and approximately 50 molar % of the Group 4 transition metal precursor;

the Group 4 transition metal-containing film forming composition having a viscosity between approximately 1 and approximately 20 cps, preferably between approximately 1 and approximately 5 cps, preferably around 3 cps;

the Group 4 transition metal-containing film forming composition comprising between approximately 95% w/w to approximately 100% w/w of the Group 4 transition metal precursors;

the Group 4 transition metal-containing film forming composition comprising between approximately 99% w/w to approximately 100% w/w of the Group 4 transition metal precursor;

the Group 4 transition metal-containing film forming composition further comprising a solvent;

the Group 4 transition metal-containing film forming composition comprising between approximately 0% w/w and 5% w/w of a hydrocarbon solvent;

the solvent being selected from the group consisting of $C_1$-$C_{16}$ hydrocarbons, whether saturated or unsaturated, ketones, ethers, glymes, esters, tetrahydrofuran (THF), dimethyl oxalate (DMO), and combinations thereof;

the solvent being a $C_1$-$C_{16}$ hydrocarbon;

the solvent being tetrahydrofuran (THF);

the solvent being DMO;

the solvent being an ether;

the solvent being a glyme; or the difference between the boiling point of the Group 4 transition metal precursor and the solvent being less than 100° C.

Also disclosed are Group 4 transition metal-containing film forming composition delivery devices comprising a canister having an inlet conduit and an outlet conduit and containing any of the Group 4 transition metal-containing film forming compositions disclosed above. The disclosed delivery devices may include one or more of the following aspects:

the Group 4 transition metal-containing film forming composition having a total concentration of non Group 4 metal contaminants of less than 10 ppmw;

an end of the inlet conduit located above a surface of the Group 4 transition metal-containing film forming composition and an end of the outlet conduit located above the surface of the Group 4 transition metal-containing film forming composition;

an end of the inlet conduit end located above a surface of the Group 4 transition metal-containing film forming composition and an end of the outlet conduit located below the surface of the Group 4 transition metal-containing film forming composition; or an end of the inlet conduit end located below a surface of the Group 4 transition metal-containing film forming composition and an end of the outlet conduit located above the surface of the Group 4 transition metal-containing film forming composition.

Also disclosed are processes for the deposition of Group 4 transition metal-containing films on one or more substrates. At least one Group 4 transition metal-containing film forming compositions disclosed above is introduced into a reactor having at least one substrate disposed therein. At least part of the Group 4 transition metal precursor is deposited onto the substrate(s) to form the Group 4 transition metal-containing film. The disclosed processes may further include one or more of the following aspects:

introducing at least one reactant into the reactor;

the reactant being plasma-treated;

the reactant being remote plasma-treated;

the reactant not being plasma-treated;

the reactant being selected from the group consisting of $H_2$, $NH_3$, hydrazines (such as $N_2H_4$, $MeHNNH_2$, MeHNNHMe), organic amines (such as $NMeH_2$, $NEtH_2$, $NMe_2H$, $NEt_2H$, $NMe_3$, $NEt_3$, cyclic amines like pyrrolidine or pyrimidine), diamines (such as ethylene diamine, dimethylethylene diamine, tetramethylethylene diamine), aminoalcohols (such as ethanolamine [HO—$CH_2$—$CH_2$—$NH_2$], bis ethanolamine [HN($C_2H_5OH)_2$] or tris ethanolamine[N($C_2H_5OH)_3$]), pyrazoline, and pyridine;

the reactant being selected from the group consisting of $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkylsilanes (such as $Me_2SiH_2$, $Et_2SiH_2$, $MeSiH_3$, $EtSiH_3$), and aminosilanes (such as tris-dimethylaminosilane, bis-diethylaminosilane, di-isopropylaminosilane and other mono, dis or tris aminosilanes);

the reactant being selected from the group consisting of $NH_3$, $N(SiH_3)_3$, aminosilanes, and mixtures thereof;

the reactant being selected from trialkylaluminum, dialkylaluminum halide, alkylamino and alkoxy derivatives of aluminum, and mixtures thereof;

the reactant being $NH_3$;

the reactant being selected from the group consisting of: $O_2$, $O_3$, $H_2O$, $H_2O_2$, NO, $N_2O$, $NO_2$, an alcohol, a diol (such as ethylene glycol), oxygen radicals thereof, and mixtures thereof;

the reactant being $H_2O$;

the reactant being $O_2$;

the reactant being plasma treated $O_2$;

the reactant being $O_3$;

the Group 4 transition metal-containing film forming composition and the reactant being introduced into the reactor simultaneously;

the reactor being configured for chemical vapor deposition;

the reactor being configured for plasma enhanced chemical vapor deposition;

the Group 4 transition metal-containing film forming composition and the reactant being introduced into the chamber sequentially;

the reactor being configured for atomic layer deposition;

- the reactor being configured for plasma enhanced atomic layer deposition;
- the reactor being configured for spatial atomic layer deposition;
- the Group 4 transition metal-containing film being a Group 4 transition metal oxide ($M_nO_m$, wherein M is the Group 4 transition metal and each of n and m is an integer which inclusively range from 1 to 6);
- the Group 4 transition metal-containing film being $TiO_2$, $ZrO_2$ or $HfO_2$;
- the Group 4 transition metal-containing film being $MM'_iO_x$, wherein i ranges from 0 to 1; x ranges from 1 to 6; and M' is selected from a Group 3 element, a different Group 4 element (i.e., M≠M'), a Group 5 element, a lanthanide, Si, Al, B, P or Ge; or
- the Group 4 transition metal-containing film being $MM'_iN_yO_x$, wherein i ranges from 0 to 1; x and y range from 1 to 6; and M' is selected from a Group 3 element, a different Group 4 element (i.e., M≠M), a Group 5 element, a lanthanide, Si, Al, B, P or Ge.

NOTATION AND NOMENCLATURE

Certain abbreviations, symbols, and terms are used throughout the following description and claims, and include:

As used in the disclosed embodiments, the indefinite article "a" or "an" means one or more.

As used in the disclosed embodiments, "about" or "around" or "approximately" in the text or in a claim means±10% of the value stated.

As used in the disclosed embodiments, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used in the disclosed embodiments, the term "hydrocarbyl group" refers to a functional group containing carbon and hydrogen; the term "alkyl group" refers to saturated functional groups containing exclusively carbon and hydrogen atoms. The hydrocarbyl group may be saturated or unsaturated. Either term refers to linear, branched, or cyclic groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used in the disclosed embodiments, the abbreviation "Me" refers to a methyl group; the abbreviation "Et" refers to an ethyl group; the abbreviation "Pr" refers to a propyl group; the abbreviation "$^n$Pr" refers to a "normal" or linear propyl group; the abbreviation "$^i$Pr" refers to an isopropyl group; the abbreviation "Bu" refers to a butyl group; the abbreviation "$^n$Bu" refers to a "normal" or linear butyl group; the abbreviation "$^t$Bu" refers to a tert-butyl group, also known as 1,1-dimethylethyl; the abbreviation "$^s$Bu" refers to a sec-butyl group, also known as 1-methylpropyl; the abbreviation "$^i$Bu" refers to an iso-butyl group, also known as 2-methylpropyl; the abbreviation "Cp" refers to cyclopentadienyl; and the abbreviation "Cp*" refers to pentamethylcyclopentadienyl.

As used in the disclosed embodiments, the chemical formula $L_2$-M-$C_5R_4$-[$(ER_2)_2$—NR]— refers to the compounds having the following structure formula:

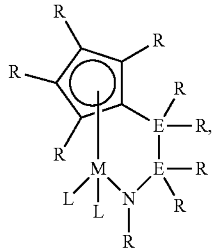

wherein M is Ti, Zr, or Hf bonded in an $\eta^5$ bonding mode to the Cp group; each E is independently C, Si, B or P; each R is independently a hydrogen or a hydrocarbyl group having up to 4 carbon atoms; adjacent Rs may be jointed to form a hydrocarbyl ring; and each L is independently a −1 anionic ligand selected from the group consisting of $NR'_2$, OR', Cp, Amidinate, β-diketonate, and keto-iminate, wherein R' is a H or a $C_1$-$C_4$ hydrocarbon group and adjacent R's may be jointed to form a hydrocarbyl ring; provided that at least one R on the Cp is $C_1$ to $C_4$. Herein $\eta^5$ is a notation for a hapticity of 5 which represents bonding between the π-electrons of the aromatic Cp ring group and the M atom.

As used in the disclosed embodiments, the chemical formula $(Me_2N)_2$-M-$C_5H_3$-1-Me-3-($CH_2$—$CH_2$—NMe)-, $(Me_2N)_2$-M-$C_5H_3$-1-Et-3-($CH_2$—$CH_2$—NMe)- and $(Me_2N)_2$-M-$C_5H_3$-1-$^i$Pr-3-($CH_2$—$CH_2$—NMe)- refer to the compounds having the following structure formula, respectively:

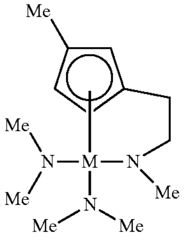
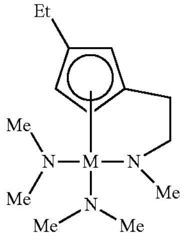
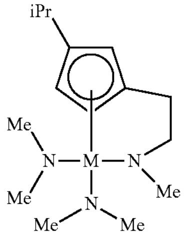

wherein M is Ti, Zr, or Hf bonded in an $\eta^5$ bonding mode to the Cp group; Cs bonded to the Cp group may be replaced with Si, B or P; and one of $NMe_2$ groups may be replaced with a Cp group.

The standard abbreviations of the elements from the periodic table of elements are used in the disclosed embodiments. It should be understood that elements may be referred to by these abbreviations (e.g., Mn refers to manganese, Si refers to silicon, C refers to carbon, etc.). Additionally, Group 3 refers to Group 3 of the Periodic Table (i.e., Sc, Y, La, or Ac). Similarly, Group 4 refers to Group 4 of the Periodic Table (i.e., Ti, Zr, or Hf) and Group 5 refers to Group 5 of the Periodic Table (i.e., V, Nb, or Ta).

Any and all ranges recited in the disclosed embodiments are inclusive of their endpoints (i.e., x=1 to 4 or x ranges from 1 to 4 includes x=1, x=4, and x=any number in between), irrespective of whether the term "inclusively" is used.

Please note that the films or layers deposited, such as silicon oxide or silicon nitride, may be listed throughout the specification and claims without reference to their proper stoichiometry (i.e., $SiO_2$, $SiO_3$, $Si_3N_4$). The layers may include pure (Si) layers, carbide ($Si_oC_p$) layers, nitride ($Si_kN_l$) layers, oxide ($Si_nO_m$) layers, or mixtures thereof, wherein k, l, m, n, o, and p inclusively range from 1 to 6. For instance, silicon oxide is $Si_nO_m$, wherein n ranges from 0.5 to 1.5 and m ranges from 1.5 to 3.5. More preferably, the silicon oxide layer is $SiO_2$ or $SiO_3$. These films may also contain Hydrogen, typically from 0 at % to 15 at %. However, since not routinely measured, any film compositions given ignore their H content, unless explicitly stated otherwise.

BRIEF DESCRIPTION OF THE FIGURES

For a further understanding of the nature and objects of the present invention, reference should be made to the following detailed description, taken in conjunction with the accompanying figures wherein.

DESCRIPTION OF PREFERRED EMBODIMENTS

Figure 1:
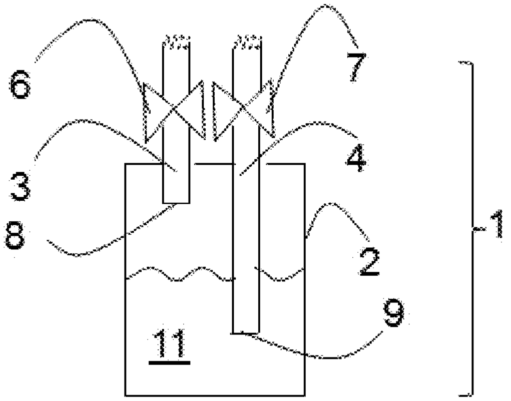
FIG. 1 is a side view of one embodiment of a liquid Group 4 transition metal-containing film forming composition delivery device 1.

Group 4 transition metal-containing film forming compositions are disclosed. The Group 4 transition metal-containing film forming compositions comprise Group 4 transition metal precursors having the following chemical formula $L_2$-M-$C_5R_4$-[$(ER_2)_2$—NR]— referring to the following structure formula:

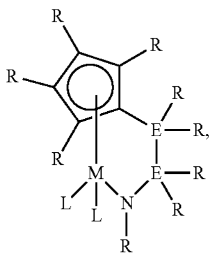

wherein M is Ti, Zr, or Hf bonded in an $\eta^5$ bonding mode to the Cp group; each E is independently C, Si, B or P; each R is independently a hydrogen or a hydrocarbyl group having up to 4 carbon atoms; adjacent Rs may be jointed to form a hydrocarbyl ring; and each L is independently a −1 anionic ligand selected from the group consisting of $NR'_2$, OR', Cp, Amidinate, β-diketonate, and keto-iminate, wherein R' is a H or a $C_1$-$C_4$ hydrocarbon group and adjacent R's may be jointed to form a hydrocarbyl ring; provided that at least one R on the Cp is $C_1$ to $C_4$.

Exemplary Group 4 transition metal precursors wherein each E is C include but are not limited to $L_2$-M-$C_5R_4$—[$(CR_2)_2$—NR]—, wherein M is Ti, Zr, or Hf bonded in an $\eta^5$ bonding mode to the Cp group; each R is independently a hydrogen or a hydrocarbyl group having up to 4 carbon atoms and adjacent Rs may be jointed to form a hydrocarbyl ring; and each L is independently a −1 anionic ligand selected from the group consisting of $NR'_2$, OR', Cp, Amidinate, β-diketonate, and keto-iminate, wherein R' is a H or a $C_1$-$C_4$ hydrocarbon group and adjacent R's may be jointed to form a hydrocarbyl ring; provided that at least one R on the Cp is $C_1$ to $C_4$. Specific examples include but are not limited to $(NH_2)_2$-M-$C_5H_3$-1-Me-2-[$(CH_2)_2$—NH]—, $(NMe_2)_2$-M-$C_5H_3$-1-Me-2-[$(CH_2)_2$—NH]—, $(NEt_2)_2$-M-$C_5H_3$-1-Me-2-[$(CH_2)_2$—NH]—, $(N^nPr_2)_2$-M-$C_5H_3$-1-Me-2-[$(CH_2)_2$—NH]—, $(N^iPr_2)_2$-M-$C_5H_3$-1-Me-2-[$(CH_2)_2$—NH]—, $(N^nBu_2)_2$-M-$C_5H_3$-1-Me-2-[$(CH_2)_2$—NH]—, $(N^iBu_2)_2$-M-$C_5H_3$-1-Me-2-[$(CH_2)_2$—NH]—, $(N^sBu_2)_2$-M-$C_5H_3$-1-Me-2-[$(CH_2)_2$—NH]—, $(N^tBu_2)_2$-M-$C_5H_3$-1-Me-2-[$(CH_2)_2$—NH]—, $(NH_2)$(Cp)-M-$C_5H_3$-1-Me-2-[$(CH_2)_2$—NH]—, $(NMe_2)$(Cp)-M-$C_5H_3$-1-Me-2-[$(CH_2)_2$—NH]—, $(NEt_2)$(Cp)-M-$C_5H_3$-1-Me-2-[$(CH_2)_2$—NH]—, $(N^nPr_2)$(Cp)-M-$C_5H_3$-1-Me-2-[$(CH_2)_2$—NH]—, $(N^iPr_2)$(Cp)-M-$C_5H_3$-1-Me-2-[$(CH_2)_2$—NH]—, $(N^nBu_2)$(Cp)-M-$C_5H_3$-1-Me-2-[$(CH_2)_2$—NH]—, $(N^iBu_2)$(Cp)-M-$C_5H_3$-1-Me-2-[$(CH_2)_2$—NH]—, $(N^sBu_2)$(Cp)-M-$C_5H_3$-1-Me-2-[$(CH_2)_2$—NH]—, $(N^tBu_2)$(Cp)-M-$C_5H_3$-1-Me-2-[$(CH_2)_2$—NH]—, $(OH)_2$-M-$C_5H_3$-1-Me-2-[$(CH_2)_2$—NH]—, $(OMe)_2$-M-$C_5H_3$-1-Me-2-[$(CH_2)_2$—NH]—, $(OEt)_2$-M-$C_5H_3$-1-Me-2-[$(CH_2)_2$—NH]—, $(O^nPr)_2$-M-$C_5H_3$-1-Me-2-[$(CH_2)_2$—NH]—, $(O^iPr)_2$-M-$C_5H_3$-1-Me-2-[$(CH_2)_2$—NH]—, $(O^nBu)_2$-M-$C_5H_3$-1-Me-2-[$(CH_2)_2$—NH]—, $(O^iBu_2$-M-$C_5H_3$-1-Me-2-[$(CH_2)_2$—NH]—, $(O^tSu)_2$-M-$C_5H_3$-1-Me-2-[$(CH_2)_2$—NH]—, $(O^sBu)_2$-M-$C_5H_3$-1-Me-2-[$(CH_2)_2$—NH]—, $(NH_2)_2$-M-$C_5H_3$-1-Me-3-[$(CH_2)_2$—NH]—, $(NMe_2)_2$-M-$C_5H_3$-1-Me-3-[$(CH_2)_2$—NH]—, $(NEt_2)_2$-M-$C_5H_3$-1-Me-3-[$(CH_2)_2$—NH]—, $(N^nPr_2)_2$-M-$C_5H_3$-1-Me-3-[$(CH_2)_2$—NH]—, $(N^iPr_2)_2$-M-$C_5H_3$-1-Me-3-[$(CH_2)_2$—NH]—, $(N^nBu_2)_2$-M-$C_5H_3$-1-Me-3-[$(CH_2)_2$—NH]—, $(N^iBu_2)_2$-M-$C_5H_3$-1-Me-3-[$(CH_2)_2$—NH]—, $(N^sBu_2)_2$-M-$C_5H_3$-1-Me-3-[$(CH_2)_2$—NH]—, $(N^tBu_2)_2$-M-$C_5H_3$-1-Me-3-[$(CH_2)_2$—NH]—, $(NH_2)$(Cp)-M-$C_5H_3$-1-Me-3-[$(CH_2)_2$—NH]—, $(NMe_2)$(Cp)-M-$C_5H_3$-1-Me-3-[$(CH_2)_2$—NH]—, $(NEt_2)$(Cp)-M-$C_5H_3$-1-Me-3-[$(CH_2)_2$—NH]—, $(N^nPr_2)$(Cp)-M-$C_5H_3$-1-Me-3-[$(CH_2)_2$—NH]—, $(N^iPr_2)$(Cp)-M-$C_5H_3$-1-Me-3-[$(CH_2)_2$—NH]—, $(N^nBu_2)$(Cp)-M-$C_5H_3$-1-Me-3-[$(CH_2)_2$—NH]—, $(N^iBu_2)$(Cp)-M-$C_5H_3$-1-Me-3-[$(CH_2)_2$—NH]—, $(N^sBu_2)$(Cp)-M-$C_5H_3$-1-Me-3-[$(CH_2)_2$—NH]—, $(N^tBu_2)$(Cp)-M-$C_5H_3$-1-Me-3-[$(CH_2)_2$—NH]—, $(OH)_2$-M-$C_5H_3$-1-Me-3-[$(CH_2)_2$—NH]—, $(OMe)_2$-M-$C_5H_3$-1-Me-3-[$(CH_2)_2$—NH]—, $(OEt)_2$-M-$C_5H_3$-1-Me-3-[$(CH_2)_2$—NH]—, $(O^nPr)_2$-M-$C_5H_3$-1-Me-3-[$(CH_2)_2$—NH]—, $(O^iPr)_2$-M-$C_5H_3$-1-Me-3-[$(CH_2)_2$—NH]—, $(O^nBu)_2$-M-$C_5H_3$-1-Me-3-[$(CH_2)_2$—NH]—, $(O^iBu_2$-M-$C_5H_3$-1-Me-3-[$(CH_2)_2$—NH]—, $(O^tBu)_2$-M-$C_5H_3$-1-Me-3-[$(CH_2)_2$—NH]—, $(O^sBu)_2$-M-$C_5H_3$-1-Me-3-[$(CH_2)_2$—NH]—, $(NH_2)_2$-M-$C_5H_3$-1-Et-2-[$(CH_2)_2$—NH]—, $(NMe_2)_2$-M-$C_5H_3$-1-Et-2-[$(CH_2)_2$—NH]—, $(NEt_2)_2$-M-$C_5H_3$-1-Et-2-

$[(CH_2)_2$—NH]—, $(N^nPr_2)_2$-M-$C_5H_3$-1-Et-2-$[(CH_2)_2$—NH]—, $(N^nPr_2)_2$-M-$C_5H_3$-1-Et-2-$[(CH_2)_2$—NH]—, $(N^nBu_2)_2$-M-$C_5H_3$-1-Et-2-$[(CH_2)_2$—NH]—, $(N^iBu_2)_2$-M-$C_5H_3$-1-Et-2-$[(CH_2)_2$—NH]—, $(N^sBu_2)_2$-M-$C_5H_3$-1-Et-2-$[(CH_2)_2$—NH]—, $(N^tBu_2)_2$-M-$C_5H_3$-1-Et-2-$[(CH_2)_2$—NH]—, $(NH_2)(Cp)$-M-$C_5H_3$-1-Et-2-$[(CH_2)_2$—NH]—, $(NMe_2)(Cp)$-M-$C_5H_3$-1-Et-2-$[(CH_2)_2$—NH]—, $(NEt_2)(Cp)$-M-$C_5H_3$-1-Et-2-$[(CH_2)_2$—NH]—, $(N^nPr_2)(Cp)$-M-$C_5H_3$-1-Et-2-$[(CH_2)_2$—NH]—, $(N^iPr_2)(Cp)$-M-$C_5H_3$-1-Et-2-$[(CH_2)_2$—NH]—, $(N^nBu_2)(Cp)$-M-$C_5H_3$-1-Et-2-$[(CH_2)_2$—NH]—, $(N^iBu_2)(Cp)$-M-$C_5H_3$-1-Et-2-$[(CH_2)_2$—NH]—, $(N^sBu_2)(Cp)$-M-$C_5H_3$-1-Et-2-$[(CH_2)_2$—NH]—, $(N^tBu_2)(Cp)$-M-$C_5H_3$-1-Et-2-$[(CH_2)_2$—NH]—, $(OH)_2$-M-$C_5H_3$-1-Et-2-$[(CH_2)_2$—NH]—, $(OMe)_2$-M-$C_5H_3$-1-Et-2-$[(CH_2)_2$—NH]—, $(OEt)_2$-M-$C_5H_3$-1-Et-2-$[(CH_2)_2$—NH]—, $(O^nPr)_2$-M-$C_5H_3$-1-Et-2-$[(CH_2)_2$—NH]—, $(O^iPr)_2$-M-$C_5H_3$-1-Et-2-$[(CH_2)_2$—NH]—, $(O^nBu)_2$-M-$C_5H_3$-1-Et-2-$[(CH_2)_2$—NH]—, $(O^iBu_2$-M-$C_5H_3$-1-Et-2-$[(CH_2)_2$—NH]—, $(O^tBu)_2$-M-$C_5H_3$-1-Et-2-$[(CH_2)_2$—NH]—, $(O^sBu)_2$-M-$C_5H_3$-1-Et-2-$[(CH_2)_2$—NH]—, $(NH_2)_2$-M-$C_5H_3$-1-Et-3-$[(CH_2)_2$—NH]—, $(NMe_2)_2$-M-$C_5H_3$-1-Et-3-$[(CH_2)_2$—NH]—, $(NEt_2)_2$-M-$C_5H_3$-1-Et-3-$[(CH_2)_2$—NH]—, $(N^nPr_2)_2$-M-$C_5H_3$-1-Et-3-$[(CH_2)_2$—NH]—, $(N^iPr_2)_2$-M-$C_5H_3$-1-Et-3-$[(CH_2)_2$—NH]—, $(N^nBu_2)_2$-M-$C_5H_3$-1-Et-3-$[(CH_2)_2$—NH]—, $(N^iBu_2)_2$-M-$C_5H_3$-1-Et-3-$[(CH_2)_2$—NH]—, $(N^sBu_2)_2$-M-$C_5H_3$-1-Et-3-$[(CH_2)_2$—NH]—, $(N^tBu_2)_2$-M-$C_5H_3$-1-Et-3-$[(CH_2)_2$—NH]—, $(NH_2)(Cp)$-M-$C_5H_3$-1-Et-3-$[(CH_2)_2$—NH]—, $(NMe_2)(Cp)$-M-$C_5H_3$-1-Et-3-$[(CH_2)_2$—NH]—, $(NEt_2)(Cp)$-M-$C_5H_3$-1-Et-3-$[(CH_2)_2$—NH]—, $(N^nPr_2)(Cp)$-M-$C_5H_3$-1-Et-3-$[(CH_2)_2$—NH]—, $(N^iPr_2)(Cp)$-M-$C_5H_3$-1-Et-3-$[(CH_2)_2$—NH]—, $(N^nBu_2)(Cp)$-M-$C_5H_3$-1-Et-3-$[(CH_2)_2$—NH]—, $(N^iBu_2)(Cp)$-M-$C_5H_3$-1-Et-3-$[(CH_2)_2$—NH]—, $(N^sBu_2)(Cp)$-M-$C_5H_3$-1-Et-3-$[(CH_2)_2$—NH]—, $(N^tBu_2)(Cp)$-M-$C_5H_3$-1-Et-3-$[(CH_2)_2$—NH]—, $(OH)_2$-M-$C_5H_3$-1-Et-3-$[(CH_2)_2$—NH]—, $(OMe)_2$-M-$C_5H_3$-1-Et-3-$[(CH_2)_2$—NH]—, $(OEt)_2$-M-$C_5H_3$-1-Et-3-$[(CH_2)_2$—NH]—, $(O^nPr)_2$-M-$C_5H_3$-1-Et-3-$[(CH_2)_2$—NH]—, $(O^iPr)_2$-M-$C_5H_3$-1-Et-3-$[(CH_2)_2$—NH]—, $(O^nBu)_2$-M-$C_5H_3$-1-Et-3-$[(CH_2)_2$—NH]—, $(O^iBu_2$-M-$C_5H_3$-1-Et-3-$[(CH_2)_2$—NH]—, $(O^tBu)_2$-M-$C_5H_3$-1-Et-3-$[(CH_2)_2$—NH]—, $(O^sBu)_2$-M-$C_5H_3$-1-Et-3-$[(CH_2)_2$—NH]—, $(NH_2)_2$-M-$C_5H_3$-1-$^i$Pr-2-$[(CH_2)_2$—NH]—, $(NMe_2)_2$-M-$C_5H_3$-1-$^i$Pr-2-$[(CH_2)_2$—NH]—, $(NEt_2)_2$-M-$C_5H_3$-1-$^i$Pr-2-$[(CH_2)_2$—NH]—, $(N^nPr_2)_2$-M-$C_5H_3$-1-$^i$Pr-2-$[(CH_2)_2$—NH]—, $(N^iPr_2)_2$-M-$C_5H_3$-1-$^i$Pr-2-$[(CH_2)_2$—NH]—, $(N^nBu_2)_2$-M-$C_5H_3$-1-$^i$Pr-2-$[(CH_2)_2$—NH]—, $(N^iBu_2)_2$-M-$C_5H_3$-1-$^i$Pr-2-$[(CH_2)_2$—NH]—, $(N^sBu_2)_2$-M-$C_5H_3$-1-$^i$Pr-2-$[(CH_2)_2$—NH]—, $(N^tBu_2)_2$-M-$C_5H_3$-1-$^i$Pr-2-$[(CH_2)_2$—NH]—, $(NH_2)(Cp)$-M-$C_5H_3$-1-$^i$Pr-2-$[(CH_2)_2$—NH]—, $(NMe_2)(Cp)$-M-$C_5H_3$-1-$^i$Pr-2-$[(CH_2)_2$—NH]—, $(NEt_2)(Cp)$-M-$C_5H_3$-1-$^i$Pr-2-$[(CH_2)_2$—NH]—, $(N^nPr_2)(Cp)$-M-$C_5H_3$-1-$^i$Pr-2-$[(CH_2)_2$—NH]—, $(N^iPr_2)(Cp)$-M-$C_5H_3$-1-$^i$Pr-2-$[(CH_2)_2$—NH]—, $(N^nBu_2)(Cp)$-M-$C_5H_3$-1-$^i$Pr-2-$[(CH_2)_2$—NH]—, $(N^iBu_2)(Cp)$-M-$C_5H_3$-1-$^i$Pr-2-$[(CH_2)_2$—NH]—, $(N^sBu_2)(Cp)$-M-$C_5H_3$-1-$^i$Pr-2-$[(CH_2)_2$—NH]—, $(N^tBu_2)(Cp)$-M-$C_5H_3$-1-$^i$Pr-2-$[(CH_2)_2$—NH]—, $(OH)_2$-M-$C_5H_3$-1-$^i$Pr-2-$[(CH_2)_2$—NH]—, $(OMe)_2$-M-$C_5H_3$-1-$^i$Pr-2-$[(CH_2)_2$—NH]—, $(OEt)_2$-M-$C_5H_3$-1-$^i$Pr-2-$[(CH_2)_2$—NH]—, $(O^nPr)_2$-M-$C_5H_3$-1-$^i$Pr-2-$[(CH_2)_2$—NH]—, $(O^iPr)_2$-M-$C_5H_3$-1-$^i$Pr-2-$[(CH_2)_2$—NH]—, $(O^nBu)_2$-M-$C_5H_3$-1-$^i$Pr-2-$[(CH_2)_2$—NH]—, $(O^iBu_2$-M-$C_5H_3$-1-$^i$Pr-2-$[(CH_2)_2$—NH]—, $(O^tBu)_2$-M-$C_5H_3$-1-$^i$Pr-2-$[(CH_2)_2$—NH]—, $(O^sBu)_2$-M-$C_5H_3$-1-$^i$Pr-2-$[(CH_2)_2$—NH]—, $(NH_2)_2$-M-$C_5H_3$-1-$^i$Pr-3-$[(CH_2)_2$—NH]—, $(NMe_2)_2$-M-$C_5H_3$-1-$^i$Pr-3-$[(CH_2)_2$—NH]—, $(NEt_2)_2$-M-$C_5H_3$-1-$^i$Pr-3-$[(CH_2)_2$—NH]—, $(N^nPr_2)_2$-M-$C_5H_3$-1-$^i$Pr-3-$[(CH_2)_2$—NH]—, $(N^iPr_2)_2$-M-$C_5H_3$-1-$^i$Pr-3-$[(CH_2)_2$—NH]—, $(N^nBu_2)_2$-M-$C_5H_3$-1-$^i$Pr-3-$[(CH_2)_2$—NH]—, $(N^iBu_2)_2$-M-$C_5H_3$-1-$^i$Pr-3-$[(CH_2)_2$—NH]—, $(N^sBu_2)_2$-M-$C_5H_3$-1-$^i$Pr-3-$[(CH_2)_2$—NH]—, $(N^tBu_2)_2$-M-$C_5H_3$-1-$^i$Pr-3-$[(CH_2)_2$—NH]—, $(NH_2)(Cp)$-M-$C_5H_3$-1-$^i$Pr-3-$[(CH_2)_2$—NH]—, $(NMe_2)(Cp)$-M-$C_5H_3$-1-$^i$Pr-3-$[(CH_2)_2$—NH]—, $(NEt_2)(Cp)$-M-$C_5H_3$-1-$^i$Pr-3-$[(CH_2)_2$—NH]—, $(N^nPr_2)(Cp)$-M-$C_5H_3$-1-$^i$Pr-3-$[(CH_2)_2$—NH]—, $(N^iPr_2)(Cp)$-M-$C_5H_3$-1-$^i$Pr-3-$[(CH_2)_2$—NH]—, $(N^nBu_2)(Cp)$-M-$C_5H_3$-1-$^i$Pr-3-$[(CH_2)_2$—NH]—, $(N^iBu_2)(Cp)$-M-$C_5H_3$-1-$^i$Pr-3-$[(CH_2)_2$—NH]—, $(N^sBu_2)(Cp)$-M-$C_5H_3$-1-$^i$Pr-3-$[(CH_2)_2$—NH]—, $(N^tBu_2)(Cp)$-M-$C_5H_3$-1-$^i$Pr-3-$[(CH_2)_2$—NH]—, $(OH)_2$-M-$C_5H_3$-1-$^i$Pr-3-$[(CH_2)_2$—NH]—, $(OMe)_2$-M-$C_5H_3$-1-$^i$Pr-3-$[(CH_2)_2$—NH]—, $(OEt)_2$-M-$C_5H_3$-1-$^i$Pr-3-$[(CH_2)_2$—NH]—, $(O^nPr)_2$-M-$C_5H_3$-1-$^i$Pr-3-$[(CH_2)_2$—NH]—, $(O^iPr)_2$-M-$C_5H_3$-1-$^i$Pr-3-$[(CH_2)_2$—NH]—, $(O^nBu)_2$-M-$C_5H_3$-1-$^i$Pr-3-$[(CH_2)_2$—NH]—, $(O^iBu_2$-M-$C_5H_3$-1-$^i$Pr-3-$[(CH_2)_2$—NH]—, $(O^tBu)_2$-M-$C_5H_3$-1-$^i$Pr-3-$[(CH_2)_2$—NH]—, $(O^sBu)_2$-M-$C_5H_3$-1-$^i$Pr-3-$[(CH_2)_2$—NH]—, $(NH_2)_2$-M-$C_5H_3$-1-$^t$Bu-2-$[(CH_2)_2$—NH]—, $(NMe_2)_2$-M-$C_5H_3$-1-$^t$Bu-2-$[(CH_2)_2$—NH]—, $(NEt_2)_2$-M-$C_5H_3$-1-$^t$Bu-2-$[(CH_2)_2$—NH]—, $(N^nPr_2)_2$-M-$C_5H_3$-1-$^t$Bu-2-$[(CH_2)_2$—NH]—, $(N^iPr_2)_2$-M-$C_5H_3$-1-$^t$Bu-2-$[(CH_2)_2$—NH]—, $(N^nBu_2)_2$-M-$C_5H_3$-1-$^t$Bu-2-$[(CH_2)_2$—NH]—, $(N^iBu_2)_2$-M-$C_5H_3$-1-$^t$Bu-2-$[(CH_2)_2$—NH]—, $(N^sBu_2)_2$-M-$C_5H_3$-1-$^t$Bu-2-$[(CH_2)_2$—NH]—, $(N^tBu_2)_2$-M-$C_5H_3$-1-$^t$Bu-2-$[(CH_2)_2$—NH]—, $(NH_2)(Cp)$-M-$C_5H_3$-1-$^t$Bu-2-$[(CH_2)_2$—NH]—, $(NMe_2)(Cp)$-M-$C_5H_3$-1-$^t$Bu-2-$[(CH_2)_2$—NH]—, $(NEt_2)(Cp)$-M-$C_5H_3$-1-$^t$Bu-2-$[(CH_2)_2$—NH]—, $(N^nPr_2)(Cp)$-M-$C_5H_3$-1-$^t$Bu-2-$[(CH_2)_2$—NH]—, $(N^iPr_2)(Cp)$-M-$C_5H_3$-1-$^t$Bu-2-$[(CH_2)_2$—NH]—, $(N^nBu_2)(Cp)$-M-$C_5H_3$-1-$^t$Bu-2-$[(CH_2)_2$—NH]—, $(N^iBu_2)(Cp)$-M-$C_5H_3$-1-$^t$Bu-2-$[(CH_2)_2$—NH]—, $(N^sBu_2)(Cp)$-M-$C_5H_3$-1-$^t$Bu-2-$[(CH_2)_2$—NH]—, $(N^tBu_2)(Cp)$-M-$C_5H_3$-1-$^t$Bu-2-$[(CH_2)_2$—NH]—, $(OH)_2$-M-$C_5H_3$-1-$^t$Bu-2-$[(CH_2)_2$—NH]—, $(OMe)_2$-M-$C_5H_3$-1-$^t$Bu-2-$[(CH_2)_2$—NH]—, $(OEt)_2$-M-$C_5H_3$-1-$^t$Bu-2-$[(CH_2)_2$—NH]—, $(O^nPr)_2$-M-$C_5H_3$-1-$^t$Bu-2-$[(CH_2)_2$—NH]—, $(O^iPr)_2$-M-$C_5H_3$-1-$^t$Bu-2-$[(CH_2)_2$—NH]—, $(O^nBu)_2$-M-$C_5H_3$-1-$^t$Bu-2-$[(CH_2)_2$—NH]—, $(O^iBu_2$-M-$C_5H_3$-1-$^t$Bu-2-$[(CH_2)_2$—NH]—, $(O^tBu)_2$-M-$C_5H_3$-1-$^t$Bu-2-$[(CH_2)_2$—NH]—, $(O^sBu)_2$-M-$C_5H_3$-1-$^t$Bu-2-$[(CH_2)_2$—NH]—, $(NH_2)_2$-M-$C_5H_3$-1-$^t$Bu-3-$[(CH_2)_2$—NH]—, $(NMe_2)_2$-M-$C_5H_3$-1-$^t$Bu-3-$[(CH_2)_2$—NH]—, $(NEt_2)_2$-M-$C_5H_3$-1-$^t$Bu-3-$[(CH_2)_2$—NH]—, $(N^nPr_2)_2$-M-$C_5H_3$-1-$^t$Bu-3-$[(CH_2)_2$—NH]—, $(N^iPr_2)_2$-M-$C_5H_3$-1-$^t$Bu-3-$[(CH_2)_2$—NH]—, $(N^nBu_2)_2$-M-$C_5H_3$-1-$^t$Bu-3-$[(CH_2)_2$—NH]—, $(N^iBu_2)_2$-M-$C_5H_3$-1-$^t$Bu-3-$[(CH_2)_2$—NH]—, $(N^sBu_2)_2$-M-$C_5H_3$-1-$^t$Bu-3-$[(CH_2)_2$—NH]—, $(N^tBu_2)_2$-M-$C_5H_3$-1-$^t$Bu-3-$[(CH_2)_2$—NH]—, $(NH_2)(Cp)$-M-$C_5H_3$-1-$^t$Bu-3-$[(CH_2)_2$—NH]—, $(NMe_2)(Cp)$-M-$C_5H_3$-1-$^t$Bu-3-$[(CH_2)_2$—NH]—, $(NEt_2)(Cp)$-M-$C_5H_3$-1-$^t$Bu-3-$[(CH_2)_2$—NH]—, $(N^nPr_2)(Cp)$-M-$C_5H_3$-1-$^t$Bu-3-$[(CH_2)_2$—NH]—, $(N^iPr_2)(Cp)$-M-$C_5H_3$-1-$^t$Bu-3-$[(CH_2)_2$—NH]—, $(N^nBu_2)(Cp)$-M-$C_5H_3$-1-$^t$Bu-3-$[(CH_2)_2$—NH]—, $(N^iBu_2)(Cp)$-M-$C_5H_3$-1-$^t$Bu-3-$[(CH_2)_2$—NH]—, $(N^sBu_2)(Cp)$-M-$C_5H_3$-1-$^t$Bu-3-$[(CH_2)_2$—NH]—, $(N^tBu_2)(Cp)$-M-$C_5H_3$-1-$^t$Bu-3-$[(CH_2)_2$—NH]—, $(OH)_2$-M-$C_5H_3$-1-$^t$Bu-3-$[(CH_2)_2$—NH]—, $(OMe)_2$-M-$C_5H_3$-1-$^t$Bu-3-$[(CH_2)_2$—NH]—, $(OEt)_2$-M-$C_5H_3$-1-$^t$Bu-3-$[(CH_2)_2$—NH]—, $(O^nPr)_2$-M-$C_5H_3$-1-$^t$Bu-3-$[(CH_2)_2$—NH]—, $(O^iPr)_2$-M-$C_5H_3$-1-$^t$Bu-3-$[(CH_2)_2$—NH]—, $(O^nBu)_2$-M-$C_5H_3$-1-$^t$Bu-3-$[(CH_2)_2$—NH]—, $(O^iBu_2$-M-$C_5H_3$-1-$^t$Bu-3-$[(CH_2)_2$—NH]—, $(O^tBu)_2$-M-$C_5H_3$-1-$^t$Bu-3-$[(CH_2)_2$—NH]—, $(O^sBu)_2$-M-$C_5H_3$-1-$^t$Bu-3-$[(CH_2)_2$—NH]—, $(NH_2)_2$-M-$C_5H_3$-1-Me-2-$[(CH_2)_2$—NMe]-, $(NMe_2)_2$-M-$C_5H_3$-1-Me-2-$[(CH_2)_2$—NMe]-, $(NEt_2)_2$-M-$C_5H_3$-1-Me-2-$[(CH_2)_2$—NMe]-, $(N^nPr_2)_2$-M-$C_5H_3$-1-Me-2-$[(CH_2)_2$—NMe]-, $(N^iPr_2)_2$-M-$C_5H_3$-1-Me-2-$[(CH_2)_2$—NMe]-, $(N^nBu_2)_2$-M-$C_5H_3$-1-Me-2-$[(CH_2)_2$—NMe]-, $(N^iBu_2)_2$-M-$C_5H_3$-1-Me-2-$[(CH_2)_2$—NMe]-, $(N^sBu_2)_2$-M-$C_5H_3$-1-Me-2-$[(CH_2)_2$—

NMe]-, (N$^t$Bu$_2$)$_2$-M-C$_5$H$_3$-1-Me-2-[(CH$_2$)$_2$—NMe]-, (NH$_2$)(Cp)-M-C$_5$H$_3$-1-Me-2-[(CH$_2$)$_2$—NMe]-, (NMe$_2$)(Cp)-M-C$_5$H$_3$-1-Me-2-[(CH$_2$)$_2$—NMe]-, (NEt$_2$)(Cp)-M-C$_5$H$_3$-1-Me-2-[(CH$_2$)$_2$—NMe]-, (N$^n$Pr$_2$)(Cp)-M-C$_5$H$_3$-1-Me-2-[(CH$_2$)$_2$—NMe]-, (N$^i$Pr$_2$)(Cp)-M-C$_5$H$_3$-1-Me-2-[(CH$_2$)$_2$—NMe]-, (N$^n$Bu$_2$)(Cp)-M-C$_5$H$_3$-1-Me-2-[(CH$_2$)$_2$—NMe]-, (N$^i$Bu$_2$)(Cp)-M-C$_5$H$_3$-1-Me-2-[(CH$_2$)$_2$—NMe]-, (N$^s$Bu$_2$)(Cp)-M-C$_5$H$_3$-1-Me-2-[(CH$_2$)$_2$—NMe]-, (N$^t$Bu$_2$)(Cp)-M-C$_5$H$_3$-1-Me-2-[(CH$_2$)$_2$—NMe]-, (OH)$_2$-M-C$_5$H$_3$-1-Me-2-[(CH$_2$)$_2$—NMe]-, (OMe)$_2$-M-C$_5$H$_3$-1-Me-2-[(CH$_2$)$_2$—NMe]-, (OEt)$_2$-M-C$_5$H$_3$-1-Me-2-[(CH$_2$)$_2$—NMe]-, (O$^n$Pr)$_2$-M-C$_5$H$_3$-1-Me-2-[(CH$_2$)$_2$—NMe]-, (O$^i$Pr)$_2$-M-C$_5$H$_3$-1-Me-2-[(CH$_2$)$_2$—NMe]-, (O$^n$Bu)$_2$-M-C$_5$H$_3$-1-Me-2-[(CH$_2$)$_2$—NMe]-, (O$^i$Bu$_2$-M-C$_5$H$_3$-1-Me-2-[(CH$_2$)$_2$—NMe]-, (O$^t$Bu)$_2$-M-C$_5$H$_3$-1-Me-2-[(CH$_2$)$_2$—NMe]-, (O$^s$Bu)$_2$-M-C$_5$H$_3$-1-Me-2-[(CH$_2$)$_2$—NMe]-, (NH$_2$)$_2$-M-C$_5$H$_3$-1-Me-3-[(CH$_2$)$_2$—NMe]-, (NMe$_2$)$_2$-M-C$_5$H$_3$-1-Me-3-[(CH$_2$)$_2$—NMe]-, (NEt$_2$)$_2$-M-C$_5$H$_3$-1-Me-3-[(CH$_2$)$_2$—NMe]-, (N$^n$Pr$_2$)$_2$-M-C$_5$H$_3$-1-Me-3-[(CH$_2$)$_2$—NMe]-, (N$^i$Pr$_2$)$_2$-M-C$_5$H$_3$-1-Me-3-[(CH$_2$)$_2$—NMe]-, (N$^n$Bu$_2$)$_2$-M-C$_5$H$_3$-1-Me-3-[(CH$_2$)$_2$—NMe]-, (N$^i$Bu$_2$)$_2$-M-C$_5$H$_3$-1-Me-3-[(CH$_2$)$_2$—NMe]-, (N$^s$Bu$_2$)$_2$-M-C$_5$H$_3$-1-Me-3-[(CH$_2$)$_2$—NMe]-, (N$^t$Bu$_2$)$_2$-M-C$_5$H$_3$-1-Me-3-[(CH$_2$)$_2$—NMe]-, (NH$_2$)(Cp)-M-C$_5$H$_3$-1-Me-3-[(CH$_2$)$_2$—NMe]-, (NMe$_2$)(Cp)-M-C$_5$H$_3$-1-Me-3-[(CH$_2$)$_2$—NMe]-, (NEt$_2$)(Cp)-M-C$_5$H$_3$-1-Me-3-[(CH$_2$)$_2$—NMe]-, (N$^n$Pr$_2$)(Cp)-M-C$_5$H$_3$-1-Me-3-[(CH$_2$)$_2$—NMe]-, (N$^i$Pr$_2$)(Cp)-M-C$_5$H$_3$-1-Me-3-[(CH$_2$)$_2$—NMe]-, (N$^n$Bu$_2$)(Cp)-M-C$_5$H$_3$-1-Me-3-[(CH$_2$)$_2$—NMe]-, (N$^i$Bu$_2$)(Cp)-M-C$_5$H$_3$-1-Me-3-[(CH$_2$)$_2$—NMe]-, (N$^s$Bu$_2$)(Cp)-M-C$_5$H$_3$-1-Me-3-[(CH$_2$)$_2$—NMe]-, (N$^t$Bu$_2$)(Cp)-M-C$_5$H$_3$-1-Me-3-[(CH$_2$)$_2$—NMe]-, (OH)$_2$-M-C$_5$H$_3$-1-Me-3-[(CH$_2$)$_2$—NMe]-, (OMe)$_2$-M-C$_5$H$_3$-1-Me-3-[(CH$_2$)$_2$—NMe]-, (OEt)$_2$-M-C$_5$H$_3$-1-Me-3-[(CH$_2$)$_2$—NMe]-, (O$^n$Pr)$_2$-M-C$_5$H$_3$-1-Me-3-[(CH$_2$)$_2$—NMe]-, (O$^i$Pr)$_2$-M-C$_5$H$_3$-1-Me-3-[(CH$_2$)$_2$—NMe]-, (O$^n$Bu)$_2$-M-C$_5$H$_3$-1-Me-3-[(CH$_2$)$_2$—NMe]-, (O$^i$Bu$_2$-M-C$_5$H$_3$-1-Me-3-[(CH$_2$)$_2$—NMe]-, (O$^t$Bu)$_2$-M-C$_5$H$_3$-1-Me-3-[(CH$_2$)$_2$—NMe]-, (O$^s$Bu)$_2$-M-C$_5$H$_3$-1-Me-3-[(CH$_2$)$_2$—NMe]-, (NH$_2$)$_2$-M-C$_5$H$_3$-1-Et-2-[(CH$_2$)$_2$—NMe]-, (NMe$_2$)$_2$-M-C$_5$H$_3$-1-Et-2-[(CH$_2$)$_2$—NMe]-, (NEt$_2$)$_2$-M-C$_5$H$_3$-1-Et-2-[(CH$_2$)$_2$—NMe]-, (N$^n$Pr$_2$)$_2$-M-C$_5$H$_3$-1-Et-2-[(CH$_2$)$_2$—NMe]-, (N$^i$Pr$_2$)$_2$-M-C$_5$H$_3$-1-Et-2-[(CH$_2$)$_2$—NMe]-, (N$^n$Bu$_2$)$_2$-M-C$_5$H$_3$-1-Et-2-[(CH$_2$)$_2$—NMe]-, (N$^i$Bu$_2$)$_2$-M-C$_5$H$_3$-1-Et-2-[(CH$_2$)$_2$—NMe]-, (N$^s$Bu$_2$)$_2$-M-C$_5$H$_3$-1-Et-2-[(CH$_2$)$_2$—NMe]-, (N$^t$Bu$_2$)$_2$-M-C$_5$H$_3$-1-Et-2-[(CH$_2$)$_2$—NMe]-, (NH$_2$)(Cp)-M-C$_5$H$_3$-1-Et-2-[(CH$_2$)$_2$—NMe]-, (NMe$_2$)(Cp)-M-C$_5$H$_3$-1-Et-2-[(CH$_2$)$_2$—NMe]-, (NEt$_2$)(Cp)-M-C$_5$H$_3$-1-Et-2-[(CH$_2$)$_2$—NMe]-, (N$^n$Pr$_2$)(Cp)-M-C$_5$H$_3$-1-Et-2-[(CH$_2$)$_2$—NMe]-, (N$^i$Pr$_2$)(Cp)-M-C$_5$H$_3$-1-Et-2-[(CH$_2$)$_2$—NMe]-, (N$^n$Bu$_2$)(Cp)-M-C$_5$H$_3$-1-Et-2-[(CH$_2$)$_2$—NMe]-, (N$^i$Bu$_2$)(Cp)-M-C$_5$H$_3$-1-Et-2-[(CH$_2$)$_2$—NMe]-, (N$^s$Bu$_2$)(Cp)-M-C$_5$H$_3$-1-Et-2-[(CH$_2$)$_2$—NMe]-, (N$^t$Bu$_2$)(Cp)-M-C$_5$H$_3$-1-Et-2-[(CH$_2$)$_2$—NMe]-, (OH)$_2$-M-C$_5$H$_3$-1-Et-2-[(CH$_2$)$_2$—NMe]-, (OMe)$_2$-M-C$_5$H$_3$-1-Et-2-[(CH$_2$)$_2$—NMe]-, (OEt)$_2$-M-C$_5$H$_3$-1-Et-2-[(CH$_2$)$_2$—NMe]-, (O$^n$Pr)$_2$-M-C$_5$H$_3$-1-Et-2-[(CH$_2$)$_2$—NMe]-, (O$^i$Pr)$_2$-M-C$_5$H$_3$-1-Et-2-[(CH$_2$)$_2$—NMe]-, (O$^n$Bu)$_2$-M-C$_5$H$_3$-1-Et-2-[(CH$_2$)$_2$—NMe]-, (O$^i$Bu$_2$-M-C$_5$H$_3$-1-Et-2-[(CH$_2$)$_2$—NMe]-, (O$^t$Bu)$_2$-M-C$_5$H$_3$-1-Et-2-[(CH$_2$)$_2$—NMe]-, (O$^s$Bu)$_2$-M-C$_5$H$_3$-1-Et-2-[(CH$_2$)$_2$—NMe]-, (NH$_2$)$_2$-M-C$_5$H$_3$-1-Et-3-[(CH$_2$)$_2$—NMe]-, (NMe$_2$)$_2$-M-C$_5$H$_3$-1-Et-3-[(CH$_2$)$_2$—NMe]-, (NEt$_2$)$_2$-M-C$_5$H$_3$-1-Et-3-[(CH$_2$)$_2$—NMe]-, (N$^n$Pr$_2$)$_2$-M-C$_5$H$_3$-1-Et-3-[(CH$_2$)$_2$—NMe]-, (N$^i$Pr$_2$)$_2$-M-C$_5$H$_3$-1-Et-3-[(CH$_2$)$_2$—NMe]-, (N$^n$Bu$_2$)$_2$-M-C$_5$H$_3$-1-Et-3-[(CH$_2$)$_2$—NMe]-, (N$^i$Bu$_2$)$_2$-M-C$_5$H$_3$-1-Et-3-[(CH$_2$)$_2$—NMe]-, (N$^s$Bu$_2$)$_2$-M-C$_5$H$_3$-1-Et-3-[(CH$_2$)$_2$—NMe]-, (N$^t$Bu$_2$)$_2$-M-C$_5$H$_3$-1-Et-3-[(CH$_2$)$_2$—NMe]-, (NH$_2$)(Cp)-M-C$_5$H$_3$-1-Et-3-[(CH$_2$)$_2$—NMe]-, (NMe$_2$)(Cp)-M-C$_5$H$_3$-1-Et-3-[(CH$_2$)$_2$—NMe]-, (NEt$_2$)(Cp)-M-C$_5$H$_3$-1-Et-3-[(CH$_2$)$_2$—NMe]-, (N$^n$Pr$_2$)(Cp)-M-C$_5$H$_3$-1-Et-3-[(CH$_2$)$_2$—NMe]-, (N$^i$Pr$_2$)(Cp)-M-C$_5$H$_3$-1-Et-3-[(CH$_2$)$_2$—NMe]-, (N$^n$Bu$_2$)(Cp)-M-C$_5$H$_3$-1-Et-3-[(CH$_2$)$_2$—NMe]-, (N$^i$Bu$_2$)(Cp)-M-C$_5$H$_3$-1-Et-3-[(CH$_2$)$_2$—NMe]-, (N$^s$Bu$_2$)(Cp)-M-C$_5$H$_3$-1-Et-3-[(CH$_2$)$_2$—NMe]-, (N$^t$Bu$_2$)(Cp)-M-C$_5$H$_3$-1-Et-3-[(CH$_2$)$_2$—NMe]-, (OH)$_2$-M-C$_5$H$_3$-1-Et-3-[(CH$_2$)$_2$—NMe]-, (OMe)$_2$-M-C$_5$H$_3$-1-Et-3-[(CH$_2$)$_2$—NMe]-, (OEt)$_2$-M-C$_5$H$_3$-1-Et-3-[(CH$_2$)$_2$—NMe]-, (O$^n$Pr)$_2$-M-C$_5$H$_3$-1-Et-3-[(CH$_2$)$_2$—NMe]-, (O$^i$Pr)$_2$-M-C$_5$H$_3$-1-Et-3-[(CH$_2$)$_2$—NMe]-, (O$^n$Bu)$_2$-M-C$_5$H$_3$-1-Et-3-[(CH$_2$)$_2$—NMe]-, (O$^i$Bu$_2$-M-C$_5$H$_3$-1-Et-3-[(CH$_2$)$_2$—NMe]-, (O$^t$Bu)$_2$-M-C$_5$H$_3$-1-Et-3-[(CH$_2$)$_2$—NMe]-, (O$^s$Bu)$_2$-M-C$_5$H$_3$-1-Et-3-[(CH$_2$)$_2$—NMe]-, (NH$_2$)$_2$-M-C$_5$H$_3$-1-$^i$Pr-2-[(CH$_2$)$_2$—NMe]-, (NMe$_2$)$_2$-M-C$_5$H$_3$-1-$^i$Pr-2-[(CH$_2$)$_2$—NMe]-, (NEt$_2$)$_2$-M-C$_5$H$_3$-1-$^i$Pr-2-[(CH$_2$)$_2$—NMe]-, (N$^n$Pr$_2$)$_2$-M-C$_5$H$_3$-1-$^i$Pr-2-[(CH$_2$)$_2$—NMe]-, (N$^i$Pr$_2$)$_2$-M-C$_5$H$_3$-1-$^i$Pr-2-[(CH$_2$)$_2$—NMe]-, (N$^n$Bu$_2$)$_2$-M-C$_5$H$_3$-1-$^i$Pr-2-[(CH$_2$)$_2$—NMe]-, (N$^i$Bu$_2$)$_2$-M-C$_5$H$_3$-1-$^i$Pr-2-[(CH$_2$)$_2$—NMe]-, (N$^s$Bu$_2$)$_2$-M-C$_5$H$_3$-1-$^i$Pr-2-[(CH$_2$)$_2$—NMe]-, (N$^t$Bu$_2$)$_2$-M-C$_5$H$_3$-1-$^i$Pr-2-[(CH$_2$)$_2$—NMe]-, (NH$_2$)(Cp)-M-C$_5$H$_3$-1-$^i$Pr-2-[(CH$_2$)$_2$—NMe]-, (NMe$_2$)(Cp)-M-C$_5$H$_3$-1-$^i$Pr-2-[(CH$_2$)$_2$—NMe]-, (NEt$_2$)(Cp)-M-C$_5$H$_3$-1-$^i$Pr-2-[(CH$_2$)$_2$—NMe]-, (N$^n$Pr$_2$)(Cp)-M-C$_5$H$_3$-1-$^i$Pr-2-[(CH$_2$)$_2$—NMe]-, (N$^i$Pr$_2$)(Cp)-M-C$_5$H$_3$-1-$^i$Pr-2-[(CH$_2$)$_2$—NMe]-, (N$^n$Bu$_2$)(Cp)-M-C$_5$H$_3$-1-$^i$Pr-2-[(CH$_2$)$_2$—NMe]-, (N$^i$Bu$_2$)(Cp)-M-C$_5$H$_3$-1-$^i$Pr-2-[(CH$_2$)$_2$—NMe]-, (N$^s$Bu$_2$)(Cp)-M-C$_5$H$_3$-1-$^i$Pr-2-[(CH$_2$)$_2$—NMe]-, (N$^t$Bu$_2$)(Cp)-M-C$_5$H$_3$-1-$^i$Pr-2-[(CH$_2$)$_2$—NMe]-, (OH)$_2$-M-C$_5$H$_3$-1-$^i$Pr-2-[(CH$_2$)$_2$—NMe]-, (OMe)$_2$-M-C$_5$H$_3$-1-$^i$Pr-2-[(CH$_2$)$_2$—NMe]-, (OEt)$_2$-M-C$_5$H$_3$-1-$^i$Pr-2-[(CH$_2$)$_2$—NMe]-, (O$^n$Pr)$_2$-M-C$_5$H$_3$-1-$^i$Pr-2-[(CH$_2$)$_2$—NMe]-, (O$^i$Pr)$_2$-M-C$_5$H$_3$-1-$^i$Pr-2-[(CH$_2$)$_2$—NMe]-, (O$^n$Bu)$_2$-M-C$_5$H$_3$-1-$^i$Pr-2-[(CH$_2$)$_2$—NMe]-, (O$^i$Bu$_2$-M-C$_5$H$_3$-1-$^i$Pr-2-[(CH$_2$)$_2$—NMe]-, (O$^t$Bu)$_2$-M-C$_5$H$_3$-1-$^i$Pr-2-[(CH$_2$)$_2$—NMe]-, (O$^s$Bu)$_2$-M-C$_5$H$_3$-1-$^i$Pr-2-[(CH$_2$)$_2$—NMe]-, (NH$_2$)$_2$-M-C$_5$H$_3$-1-$^i$Pr-3-[(CH$_2$)$_2$—NMe]-, (NMe$_2$)$_2$-M-C$_5$H$_3$-1-$^i$Pr-3-[(CH$_2$)$_2$—NMe]-, (NEt$_2$)$_2$-M-C$_5$H$_3$-1-$^i$Pr-3-[(CH$_2$)$_2$—NMe]-, (N$^n$Pr$_2$)$_2$-M-C$_5$H$_3$-1-$^i$Pr-3-[(CH$_2$)$_2$—NMe]-, (N$^i$Pr$_2$)$_2$-M-C$_5$H$_3$-1-$^i$Pr-3-[(CH$_2$)$_2$—NMe]-, (N$^n$Bu$_2$)$_2$-M-C$_5$H$_3$-1-$^i$Pr-3-[(CH$_2$)$_2$—NMe]-, (N$^i$Bu$_2$)$_2$-M-C$_5$H$_3$-1-$^i$Pr-3-[(CH$_2$)$_2$—NMe]-, (N$^s$Bu$_2$)$_2$-M-C$_5$H$_3$-1-$^i$Pr-3-[(CH$_2$)$_2$—NMe]-, (N$^t$Bu$_2$)$_2$-M-C$_5$H$_3$-1-$^i$Pr-3-[(CH$_2$)$_2$—NMe]-, (NH$_2$)(Cp)-M-C$_5$H$_3$-1-$^i$Pr-3-[(CH$_2$)$_2$—NMe]-, (NMe$_2$)(Cp)-M-C$_5$H$_3$-1-$^i$Pr-3-[(CH$_2$)$_2$—NMe]-, (NEt$_2$)(Cp)-M-C$_5$H$_3$-1-$^i$Pr-3-[(CH$_2$)$_2$—NMe]-, (N$^n$Pr$_2$)(Cp)-M-C$_5$H$_3$-1-$^i$Pr-3-[(CH$_2$)$_2$—NMe]-, (N$^i$Pr$_2$)(Cp)-M-C$_5$H$_3$-1-$^i$Pr-3-[(CH$_2$)$_2$—NMe]-, (N$^n$Bu$_2$)(Cp)-M-C$_5$H$_3$-1-$^i$Pr-3-[(CH$_2$)$_2$—NMe]-, (N$^i$Bu$_2$)(Cp)-M-C$_5$H$_3$-1-$^i$Pr-3-[(CH$_2$)$_2$—NMe]-, (N$^s$Bu$_2$)(Cp)-M-C$_5$H$_3$-1-$^i$Pr-3-[(CH$_2$)$_2$—NMe]-, (N$^t$Bu$_2$)(Cp)-M-C$_5$H$_3$-1-$^i$Pr-3-[(CH$_2$)$_2$—NMe]-, (OH)$_2$-M-C$_5$H$_3$-1-$^i$Pr-3-[(CH$_2$)$_2$—NMe]-, (OMe)$_2$-M-C$_5$H$_3$-1-$^i$Pr-3-[(CH$_2$)$_2$—NMe]-, (OEt)$_2$-M-C$_5$H$_3$-1-$^i$Pr-3-[(CH$_2$)$_2$—NMe]-, (O$^n$Pr)$_2$-M-C$_5$H$_3$-1-$^i$Pr-3-[(CH$_2$)$_2$—NMe]-, (O$^i$Pr)$_2$-M-C$_5$H$_3$-1-$^i$Pr-3-[(CH$_2$)$_2$—NMe]-, (O$^n$Bu)$_2$-M-C$_5$H$_3$-1-$^i$Pr-3-[(CH$_2$)$_2$—NMe]-, (O$^i$Bu$_2$-M-C$_5$H$_3$-1-$^i$Pr-3-[(CH$_2$)$_2$—NMe]-, (O$^t$Bu)$_2$-M-C$_5$H$_3$-1-$^i$Pr-3-[(CH$_2$)$_2$—NMe]-, (O$^s$Bu)$_2$-M-C$_5$H$_3$-1-$^i$Pr-3-[(CH$_2$)$_2$—NMe]-, (NH$_2$)$_2$-M-C$_5$H$_3$-1-$^t$Bu-2-[(CH$_2$)$_2$—NMe]-, (NMe$_2$)$_2$-M-C$_5$H$_3$-1-$^t$Bu-2-[(CH$_2$)$_2$—NMe]-, (NEt$_2$)$_2$-M-C$_5$H$_3$-1-$^t$Bu-2-[(CH$_2$)$_2$—NMe]-, (N$^n$Pr$_2$)$_2$-M-C$_5$H$_3$-1-$^t$Bu-2-[(CH$_2$)$_2$—NMe]-, (N$^i$Pr$_2$)$_2$-M-C$_5$H$_3$-1-$^t$Bu-2-[(CH$_2$)$_2$—NMe]-, (N$^n$Bu$_2$)$_2$-M-C$_5$H$_3$-1-$^t$Bu-2-[(CH$_2$)$_2$—NMe]-, (N$^i$Bu$_2$)$_2$-M-C$_5$H$_3$-1-$^t$Bu-2-[(CH$_2$)$_2$—NMe]-, (N$^s$Bu$_2$)$_2$-M-C$_5$H$_3$-1-$^t$Bu-2-[(CH$_2$)$_2$—NMe]-, (N$^t$Bu$_2$)$_2$-M-C$_5$H$_3$-1-$^t$Bu-2-[(CH$_2$)$_2$—NMe]-, (NH$_2$)(Cp)-M-C$_5$H$_3$-1-$^t$Bu-2-[(CH$_2$)$_2$—NMe]-, (NMe$_2$)(Cp)-M-C$_5$H$_3$-1-$^t$Bu-2-[(CH$_2$)$_2$—NMe]-, (NEt$_2$)(Cp)-M-C$_5$H$_3$-1-$^t$Bu-2-[(CH$_2$)$_2$—NMe]-, (N$^n$Pr$_2$)(Cp)-M-C$_5$H$_3$-1-$^t$Bu-2-[(CH$_2$)$_2$—NMe]-, (N$^i$Pr$_2$)(Cp)-M-C$_5$H$_3$-1-$^t$Bu-2-[(CH$_2$)$_2$—NMe]-, (N$^n$Bu$_2$)

(Cp)-M-C$_5$H$_3$-1-$^t$Bu-2-[(CH$_2$)$_2$—NMe]-, (N$^i$Bu$_2$)(Cp)-M-C$_5$H$_3$-1-$^t$Bu-2-[(CH$_2$)$_2$—NMe]-, (N$^s$Bu$_2$)(Cp)-M-C$_5$H$_3$-1-$^t$Bu-2-[(CH$_2$)$_2$—NMe]-, (N$^t$Bu$_2$)(Cp)-M-C$_5$H$_3$-1-$^t$Bu-2-[(CH$_2$)$_2$—NMe]-, (OH)$_2$-M-C$_5$H$_3$-1-$^t$Bu-2-[(CH$_2$)$_2$—NMe]-, (OMe)$_2$-M-C$_5$H$_3$-1-$^t$Bu-2-[(CH$_2$)$_2$—NMe]-, (OEt)$_2$-M-C$_5$H$_3$-1-$^t$Bu-2-[(CH$_2$)$_2$—NMe]-, (O$^n$Pr)$_2$-M-C$_5$H$_3$-1-$^t$Bu-2-[(CH$_2$)$_2$—NMe]-, (O$^i$Pr)$_2$-M-C$_5$H$_3$-1-$^t$Bu-2-[(CH$_2$)$_2$—NMe]-, (O$^n$Bu)$_2$-M-C$_5$H$_3$-1-$^t$Bu-2-[(CH$_2$)$_2$—NMe]-, (O$^i$Bu$_2$-M-C$_5$H$_3$-1-$^t$Bu-2-[(CH$_2$)$_2$—NMe]-, (O$^t$Bu)$_2$-M-C$_5$H$_3$-1-$^t$Bu-2-[(CH$_2$)$_2$—NMe]-, (O$^s$Bu)$_2$-M-C$_5$H$_3$-1-$^t$Bu-2-[(CH$_2$)$_2$—NMe]-, (NH$_2$)$_2$-M-C$_5$H$_3$-1-$^t$Bu-3-[(CH$_2$)$_2$—NMe]-, (NMe$_2$)$_2$-M-C$_5$H$_3$-1-$^t$Bu-3-[(CH$_2$)$_2$—NMe]-, (NEt$_2$)$_2$-M-C$_5$H$_3$-1-$^t$Bu-3-[(CH$_2$)$_2$—NMe]-, (N$^n$Pr$_2$)$_2$-M-C$_5$H$_3$-1-$^t$Bu-3-[(CH$_2$)$_2$—NMe]-, (N$^i$Pr$_2$)$_2$-M-C$_5$H$_3$-1-$^t$Bu-3-[(CH$_2$)$_2$—NMe]-, (N$^n$Bu$_2$)$_2$-M-C$_5$H$_3$-1-$^t$Bu-3-[(CH$_2$)$_2$—NMe]-, (N$^i$Bu$_2$)$_2$-M-C$_5$H$_3$-1-$^t$Bu-3-[(CH$_2$)$_2$—NMe]-, (N$^s$Bu$_2$)$_2$-M-C$_5$H$_3$-1-$^t$Bu-3-[(CH$_2$)$_2$—NMe]-, (N$^t$Bu$_2$)$_2$-M-C$_5$H$_3$-1-$^t$Bu-3-[(CH$_2$)$_2$—NMe]-, (NH$_2$)(Cp)-M-C$_5$H$_3$-1-$^t$Bu-3-[(CH$_2$)$_2$—NMe]-, (NMe$_2$)(Cp)-M-C$_5$H$_3$-1-$^t$Bu-3-[(CH$_2$)$_2$—NMe]-, (NEt$_2$)(Cp)-M-C$_5$H$_3$-1-$^t$Bu-3-[(CH$_2$)$_2$—NMe]-, (N$^n$Pr$_2$)(Cp)-M-C$_5$H$_3$-1-$^t$Bu-3-[(CH$_2$)$_2$—NMe]-, (N$^i$Pr$_2$)(Cp)-M-C$_5$H$_3$-1-$^t$Bu-3-[(CH$_2$)$_2$—NMe]-, (N$^n$Bu$_2$)(Cp)-M-C$_5$H$_3$-1-$^t$Bu-3-[(CH$_2$)$_2$—NMe]-, (N$^i$Bu$_2$)(Cp)-M-C$_5$H$_3$-1-$^t$Bu-3-[(CH$_2$)$_2$—NMe]-, (N$^s$Bu$_2$)(Cp)-M-C$_5$H$_3$-1-$^t$Bu-3-[(CH$_2$)$_2$—NMe]-, (N$^t$Bu$_2$)(Cp)-M-C$_5$H$_3$-1-$^t$Bu-3-[(CH$_2$)$_2$—NMe]-, (OH)$_2$-M-C$_5$H$_3$-1-$^t$Bu-3-[(CH$_2$)$_2$—NMe]-, (OMe)$_2$-M-C$_5$H$_3$-1-$^t$Bu-3-[(CH$_2$)$_2$—NMe]-, (OEt)$_2$-M-C$_5$H$_3$-1-$^t$Bu-3-[(CH$_2$)$_2$—NMe]-, (O$^n$Pr)$_2$-M-C$_5$H$_3$-1-$^t$Bu-3-[(CH$_2$)$_2$—NMe]-, (O$^i$Pr)$_2$-M-C$_5$H$_3$-1-$^t$Bu-3-[(CH$_2$)$_2$—NMe]-, (O$^n$Bu)$_2$-M-C$_5$H$_3$-1-$^t$Bu-3-[(CH$_2$)$_2$—NMe]-, (O$^i$Bu$_2$-M-C$_5$H$_3$-1-$^t$Bu-3-[(CH$_2$)$_2$—NMe]-, (O$^t$Bu)$_2$-M-C$_5$H$_3$-1-$^t$Bu-3-[(CH$_2$)$_2$—NMe]-, (O$^s$Bu)$_2$-M-C$_5$H$_3$-1-$^t$Bu-3-[(CH$_2$)$_2$—NMe]-, (NH$_2$)$_2$-M-C$_5$H$_3$-1-Me-2-[(CH$_2$)$_2$—NEt]-, (NMe$_2$)$_2$-M-C$_5$H$_3$-1-Me-2-[(CH$_2$)$_2$—NEt]-, (NEt$_2$)$_2$-M-C$_5$H$_3$-1-Me-2-[(CH$_2$)$_2$—NEt]-, (N$^n$Pr$_2$)$_2$-M-C$_5$H$_3$-1-Me-2-[(CH$_2$)$_2$—NEt]-, (N$^i$Pr$_2$)$_2$-M-C$_5$H$_3$-1-Me-2-[(CH$_2$)$_2$—NEt]-, (N$^n$Bu$_2$)$_2$-M-C$_5$H$_3$-1-Me-2-[(CH$_2$)$_2$—NEt]-, (N$^i$Bu$_2$)$_2$-M-C$_5$H$_3$-1-Me-2-[(CH$_2$)$_2$—NEt]-, (N$^s$Bu$_2$)$_2$-M-C$_5$H$_3$-1-Me-2-[(CH$_2$)$_2$—NEt]-, (N$^t$Bu$_2$)$_2$-M-C$_5$H$_3$-1-Me-2-[(CH$_2$)$_2$—NEt]-, (NH$_2$)(Cp)-M-C$_5$H$_3$-1-Me-2-[(CH$_2$)$_2$—NEt]-, (NMe$_2$)(Cp)-M-C$_5$H$_3$-1-Me-2-[(CH$_2$)$_2$—NEt]-, (NEt$_2$)(Cp)-M-C$_5$H$_3$-1-Me-2-[(CH$_2$)$_2$—NEt]-, (N$^n$Pr$_2$)(Cp)-M-C$_5$H$_3$-1-Me-2-[(CH$_2$)$_2$—NEt]-, (N$^i$Pr$_2$)(Cp)-M-C$_5$H$_3$-1-Me-2-[(CH$_2$)$_2$—NEt]-, (N$^n$Bu$_2$)(Cp)-M-C$_5$H$_3$-1-Me-2-[(CH$_2$)$_2$—NEt]-, (N$^i$Bu$_2$)(Cp)-M-C$_5$H$_3$-1-Me-2-[(CH$_2$)$_2$—NEt]-, (N$^s$Bu$_2$)(Cp)-M-C$_5$H$_3$-1-Me-2-[(CH$_2$)$_2$—NEt]-, (N$^t$Bu$_2$)(Cp)-M-C$_5$H$_3$-1-Me-2-[(CH$_2$)$_2$—NEt]-, (OH)$_2$-M-C$_5$H$_3$-1-Me-2-[(CH$_2$)$_2$—NEt]-, (OMe)$_2$-M-C$_5$H$_3$-1-Me-2-[(CH$_2$)$_2$—NEt]-, (OEt)$_2$-M-C$_5$H$_3$-1-Me-2-[(CH$_2$)$_2$—NEt]-, (O$^n$Pr)$_2$-M-C$_5$H$_3$-1-Me-2-[(CH$_2$)$_2$—NEt]-, (O$^i$Pr)$_2$-M-C$_5$H$_3$-1-Me-2-[(CH$_2$)$_2$—NEt]-, (O$^n$Bu)$_2$-M-C$_5$H$_3$-1-Me-2-[(CH$_2$)$_2$—NEt]-, (O$^i$Bu$_2$-M-C$_5$H$_3$-1-Me-2-[(CH$_2$)$_2$—NEt]-, (O$^t$Bu)$_2$-M-C$_5$H$_3$-1-Me-2-[(CH$_2$)$_2$—NEt]-, (O$^s$Bu)$_2$-M-C$_5$H$_3$-1-Me-2-[(CH$_2$)$_2$—NEt]-, (NH$_2$)$_2$-M-C$_5$H$_3$-1-Me-3-[(CH$_2$)$_2$—NEt]-, (NMe$_2$)$_2$-M-C$_5$H$_3$-1-Me-3-[(CH$_2$)$_2$—NEt]-, (NEt$_2$)$_2$-M-C$_5$H$_3$-1-Me-3-[(CH$_2$)$_2$—NEt]-, (N$^n$Pr$_2$)$_2$-M-C$_5$H$_3$-1-Me-3-[(CH$_2$)$_2$—NEt]-, (N$^i$Pr$_2$)$_2$-M-C$_5$H$_3$-1-Me-3-[(CH$_2$)$_2$—NEt]-, (N$^n$Bu$_2$)$_2$-M-C$_5$H$_3$-1-Me-3-[(CH$_2$)$_2$—NEt]-, (N$^i$Bu$_2$)$_2$-M-C$_5$H$_3$-1-Me-3-[(CH$_2$)$_2$—NEt]-, (N$^s$Bu$_2$)$_2$-M-C$_5$H$_3$-1-Me-3-[(CH$_2$)$_2$—NEt]-, (N$^t$Bu$_2$)$_2$-M-C$_5$H$_3$-1-Me-3-[(CH$_2$)$_2$—NEt]-, (NH$_2$)(Cp)-M-C$_5$H$_3$-1-Me-3-[(CH$_2$)$_2$—NEt]-, (NMe$_2$)(Cp)-M-C$_5$H$_3$-1-Me-3-[(CH$_2$)$_2$—NEt]-, (NEt$_2$)(Cp)-M-C$_5$H$_3$-1-Me-3-[(CH$_2$)$_2$—NEt]-, (N$^n$Pr$_2$)(Cp)-M-C$_5$H$_3$-1-Me-3-[(CH$_2$)$_2$—NEt]-, (N$^i$Pr$_2$)(Cp)-M-C$_5$H$_3$-1-Me-3-[(CH$_2$)$_2$—NEt]-, (N$^n$Bu$_2$)(Cp)-M-C$_5$H$_3$-1-Me-3-[(CH$_2$)$_2$—NEt]-, (N$^i$Bu$_2$)(Cp)-M-C$_5$H$_3$-1-Me-3-[(CH$_2$)$_2$—NEt]-, (N$^s$Bu$_2$)(Cp)-M-C$_5$H$_3$-1-Me-3-[(CH$_2$)$_2$—NEt]-, (N$^t$Bu$_2$)(Cp)-M-C$_5$H$_3$-1-Me-3-[(CH$_2$)$_2$—NEt]-, (OH)$_2$-M-C$_5$H$_3$-1-Me-3-[(CH$_2$)$_2$—NEt]-, (OMe)$_2$-M-C$_5$H$_3$-1-Me-3-[(CH$_2$)$_2$—NEt]-, (OEt)$_2$-M-C$_5$H$_3$-1-Me-3-[(CH$_2$)$_2$—NEt]-, (O$^n$Pr)$_2$-M-C$_5$H$_3$-1-Me-3-[(CH$_2$)$_2$—NEt]-, (O$^i$Pr)$_2$-M-C$_5$H$_3$-1-Me-3-[(CH$_2$)$_2$—NEt]-, (O$^n$Bu)$_2$-M-C$_5$H$_3$-1-Me-3-[(CH$_2$)$_2$—NEt]-, (O$^i$Bu$_2$-M-C$_5$H$_3$-1-Me-3-[(CH$_2$)$_2$—NEt]-, (O$^t$Bu)$_2$-M-C$_5$H$_3$-1-Me-3-[(CH$_2$)$_2$—NEt]-, (O$^s$Bu)$_2$-M-C$_5$H$_3$-1-Me-3-[(CH$_2$)$_2$—NEt]-, (NH$_2$)$_2$-M-C$_5$H$_3$-1-Et-2-[(CH$_2$)$_2$—NEt]-, (NMe$_2$)$_2$-M-C$_5$H$_3$-1-Et-2-[(CH$_2$)$_2$—NEt]-, (NEt$_2$)$_2$-M-C$_5$H$_3$-1-Et-2-[(CH$_2$)$_2$—NEt]-, (N$^n$Pr$_2$)$_2$-M-C$_5$H$_3$-1-Et-2-[(CH$_2$)$_2$—NEt]-, (N$^i$Pr$_2$)$_2$-M-C$_5$H$_3$-1-Et-2-[(CH$_2$)$_2$—NEt]-, (N$^n$Bu$_2$)$_2$-M-C$_5$H$_3$-1-Et-2-[(CH$_2$)$_2$—NEt]-, (N$^i$Bu$_2$)$_2$-M-C$_5$H$_3$-1-Et-2-[(CH$_2$)$_2$—NEt]-, (N$^s$Bu$_2$)$_2$-M-C$_5$H$_3$-1-Et-2-[(CH$_2$)$_2$—NEt]-, (N$^t$Bu$_2$)$_2$-M-C$_5$H$_3$-1-Et-2-[(CH$_2$)$_2$—NEt]-, (NH$_2$)(Cp)-M-C$_5$H$_3$-1-Et-2-[(CH$_2$)$_2$—NEt]-, (NMe$_2$)(Cp)-M-C$_5$H$_3$-1-Et-2-[(CH$_2$)$_2$—NEt]-, (NEt$_2$)(Cp)-M-C$_5$H$_3$-1-Et-2-[(CH$_2$)$_2$—NEt]-, (N$^n$Pr$_2$)(Cp)-M-C$_5$H$_3$-1-Et-2-[(CH$_2$)$_2$—NEt]-, (N$^i$Pr$_2$)(Cp)-M-C$_5$H$_3$-1-Et-2-[(CH$_2$)$_2$—NEt]-, (N$^n$Bu$_2$)(Cp)-M-C$_5$H$_3$-1-Et-2-[(CH$_2$)$_2$—NEt]-, (N$^i$Bu$_2$)(Cp)-M-C$_5$H$_3$-1-Et-2-[(CH$_2$)$_2$—NEt]-, (N$^s$Bu$_2$)(Cp)-M-C$_5$H$_3$-1-Et-2-[(CH$_2$)$_2$—NEt]-, (N$^t$Bu$_2$)(Cp)-M-C$_5$H$_3$-1-Et-2-[(CH$_2$)$_2$—NEt]-, (OH)$_2$-M-C$_5$H$_3$-1-Et-2-[(CH$_2$)$_2$—NEt]-, (OMe)$_2$-M-C$_5$H$_3$-1-Et-2-[(CH$_2$)$_2$—NEt]-, (OEt)$_2$-M-C$_5$H$_3$-1-Et-2-[(CH$_2$)$_2$—NEt]-, (O$^n$Pr)$_2$-M-C$_5$H$_3$-1-Et-2-[(CH$_2$)$_2$—NEt]-, (O$^i$Pr)$_2$-M-C$_5$H$_3$-1-Et-2-[(CH$_2$)$_2$—NEt]-, (O$^n$Bu)$_2$-M-C$_5$H$_3$-1-Et-2-[(CH$_2$)$_2$—NEt]-, (O$^i$Bu$_2$-M-C$_5$H$_3$-1-Et-2-[(CH$_2$)$_2$—NEt]-, (O$^t$Bu)$_2$-M-C$_5$H$_3$-1-Et-2-[(CH$_2$)$_2$—NEt]-, (O$^s$Bu)$_2$-M-C$_5$H$_3$-1-Et-2-[(CH$_2$)$_2$—NEt]-, (NH$_2$)$_2$-M-C$_5$H$_3$-1-Et-3-[(CH$_2$)$_2$—NEt]-, (NMe$_2$)$_2$-M-C$_5$H$_3$-1-Et-3-[(CH$_2$)$_2$—NEt]-, (NEt$_2$)$_2$-M-C$_5$H$_3$-1-Et-3-[(CH$_2$)$_2$—NEt]-, (N$^n$Pr$_2$)$_2$-M-C$_5$H$_3$-1-Et-3-[(CH$_2$)$_2$—NEt]-, (N$^i$Pr$_2$)$_2$-M-C$_5$H$_3$-1-Et-3-[(CH$_2$)$_2$—NEt]-, (N$^n$Bu$_2$)$_2$-M-C$_5$H$_3$-1-Et-3-[(CH$_2$)$_2$—NEt]-, (N$^i$Bu$_2$)$_2$-M-C$_5$H$_3$-1-Et-3-[(CH$_2$)$_2$—NEt]-, (N$^s$Bu$_2$)$_2$-M-C$_5$H$_3$-1-Et-3-[(CH$_2$)$_2$—NEt]-, (N$^t$Bu$_2$)$_2$-M-C$_5$H$_3$-1-Et-3-[(CH$_2$)$_2$—NEt]-, (NH$_2$)(Cp)-M-C$_5$H$_3$-1-Et-3-[(CH$_2$)$_2$—NEt]-, (NMe$_2$)(Cp)-M-C$_5$H$_3$-1-Et-3-[(CH$_2$)$_2$—NEt]-, (NEt$_2$)(Cp)-M-C$_5$H$_3$-1-Et-3-[(CH$_2$)$_2$—NEt]-, (N$^n$Pr$_2$)(Cp)-M-C$_5$H$_3$-1-Et-3-[(CH$_2$)$_2$—NEt]-, (N$^i$Pr$_2$)(Cp)-M-C$_5$H$_3$-1-Et-3-[(CH$_2$)$_2$—NEt]-, (N$^n$Bu$_2$)(Cp)-M-C$_5$H$_3$-1-Et-3-[(CH$_2$)$_2$—NEt]-, (N$^i$Bu$_2$)(Cp)-M-C$_5$H$_3$-1-Et-3-[(CH$_2$)$_2$—NEt]-, (N$^s$Bu$_2$)(Cp)-M-C$_5$H$_3$-1-Et-3-[(CH$_2$)$_2$—NEt]-, (N$^t$Bu$_2$)(Cp)-M-C$_5$H$_3$-1-Et-3-[(CH$_2$)$_2$—NEt]-, (OH)$_2$-M-C$_5$H$_3$-1-Et-3-[(CH$_2$)$_2$—NEt]-, (OMe)$_2$-M-C$_5$H$_3$-1-Et-3-[(CH$_2$)$_2$—NEt]-, (OEt)$_2$-M-C$_5$H$_3$-1-Et-3-[(CH$_2$)$_2$—NEt]-, (O$^n$Pr)$_2$-M-C$_5$H$_3$-1-Et-3-[(CH$_2$)$_2$—NEt]-, (O$^i$Pr)$_2$-M-C$_5$H$_3$-1-Et-3-[(CH$_2$)$_2$—NEt]-, (O$^n$Bu)$_2$-M-C$_5$H$_3$-1-Et-3-[(CH$_2$)$_2$—NEt]-, (O$^i$Bu$_2$-M-C$_5$H$_3$-1-Et-3-[(CH$_2$)$_2$—NEt]-, (O$^t$Bu)$_2$-M-C$_5$H$_3$-1-Et-3-[(CH$_2$)$_2$—NEt]-, (O$^s$Bu)$_2$-M-C$_5$H$_3$-1-Et-3-[(CH$_2$)$_2$—NEt]-, (NH$_2$)$_2$-M-C$_5$H$_3$-1-$^i$Pr-2-[(CH$_2$)$_2$—NEt]-, (NMe$_2$)$_2$-M-C$_5$H$_3$-1-$^i$Pr-2-[(CH$_2$)$_2$—NEt]-, (NEt$_2$)$_2$-M-C$_5$H$_3$-1-$^i$Pr-2-[(CH$_2$)$_2$—NEt]-, (N$^n$Pr$_2$)$_2$-M-C$_5$H$_3$-1-$^i$Pr-2-[(CH$_2$)$_2$—NEt]-, (N$^i$Pr$_2$)$_2$-M-C$_5$H$_3$-1-$^i$Pr-2-[(CH$_2$)$_2$—NEt]-, (N$^n$Bu$_2$)$_2$-M-C$_5$H$_3$-1-$^i$Pr-2-[(CH$_2$)$_2$—NEt]-, (N$^i$Bu$_2$)$_2$-M-C$_5$H$_3$-1-$^i$Pr-2-[(CH$_2$)$_2$—NEt]-, (N$^s$Bu$_2$)$_2$-M-C$_5$H$_3$-1-$^i$Pr-2-[(CH$_2$)$_2$—NEt]-, (N$^t$Bu$_2$)$_2$-M-C$_5$H$_3$-1-$^i$Pr-2-[(CH$_2$)$_2$—NEt]-, (NH$_2$)(Cp)-M-C$_5$H$_3$-1-$^i$Pr-2-[(CH$_2$)$_2$—NEt]-, (NMe$_2$)(Cp)-M-C$_5$H$_3$-1-$^i$Pr-2-[(CH$_2$)$_2$—NEt]-, (NEt$_2$)(Cp)-M-C$_5$H$_3$-1-$^i$Pr-2-[(CH$_2$)$_2$—NEt]-, (N$^n$Pr$_2$)(Cp)-M-C$_5$H$_3$-1-$^i$Pr-2-[(CH$_2$)$_2$—NEt]-, (N$^i$Pr$_2$)(Cp)-M-C$_5$H$_3$-1-$^i$Pr-2-[(CH$_2$)$_2$—NEt]-, (N$^n$Bu$_2$)(Cp)-M-C$_5$H$_3$-1-$^i$Pr-2-[(CH$_2$)$_2$—NEt]-, (N$^i$Bu$_2$)(Cp)-M-C$_5$H$_3$-1-$^i$Pr-2-[(CH$_2$)$_2$—NEt]-, (N$^s$Bu$_2$)(Cp)-M-C$_5$H$_3$-1-$^i$Pr-2-[(CH$_2$)$_2$—NEt]-, (N$^t$Bu$_2$)(Cp)-M-C$_5$H$_3$-1-$^i$Pr-2-[(CH$_2$)$_2$—NEt]-, (OH)$_2$-M-C$_5$H$_3$-1-$^i$Pr-2-[(CH$_2$)$_2$—NEt]-, (OMe)$_2$-M-C$_5$H$_3$-1-$^i$Pr-2-[(CH$_2$)$_2$—NEt]-, (OEt)$_2$-M-C$_5$H$_3$-1-$^i$Pr-2-[(CH$_2$)$_2$—NEt]-, (O$^n$Pr)$_2$-M-C$_5$H$_3$-1-$^i$Pr-2-[(CH$_2$)$_2$—NEt]-, (O$^i$Pr)$_2$-M-C$_5$H$_3$-1-$^i$Pr-2-[(CH$_2$)$_2$—NEt]-, (O$^n$Bu)$_2$-M-C$_5$H$_3$-1-$^i$Pr-

2-[(CH$_2$)$_2$—NEt]-, (O$^i$Bu$_2$-M-C$_5$H$_3$-1-$^i$Pr-2-[(CH$_2$)$_2$—NEt]-, (O$^t$Bu)$_2$-M-C$_5$H$_3$-1-$^i$Pr-2-[(CH$_2$)$_2$—NEt]-, (O$^s$Bu)$_2$-M-C$_5$H$_3$-1-$^i$Pr-2-[(CH$_2$)$_2$—NEt]-, (NH$_2$)$_2$-M-C$_5$H$_3$-1-$^i$Pr-3-[(CH$_2$)$_2$—NEt]-, (NMe$_2$)$_2$-M-C$_5$H$_3$-1-$^i$Pr-3-[(CH$_2$)$_2$—NEt]-, (NEt$_2$)$_2$-M-C$_5$H$_3$-1-$^i$Pr-3-[(CH$_2$)$_2$—NEt]-, (N$^n$Pr$_2$)$_2$-M-C$_5$H$_3$-1-$^i$Pr-3-[(CH$_2$)$_2$—NEt]-, (N$^i$Pr$_2$)$_2$-M-C$_5$H$_3$-1-$^i$Pr-3-[(CH$_2$)$_2$—NEt]-, (N$^n$Bu$_2$)$_2$-M-C$_5$H$_3$-1-$^i$Pr-3-[(CH$_2$)$_2$—NEt]-, (N$^i$Bu$_2$)$_2$-M-C$_5$H$_3$-1-$^i$Pr-3-[(CH$_2$)$_2$—NEt]-, (N$^s$Bu$_2$)$_2$-M-C$_5$H$_3$-1-$^i$Pr-3-[(CH$_2$)$_2$—NEt]-, (N$^t$Bu$_2$)$_2$-M-C$_5$H$_3$-1-$^i$Pr-3-[(CH$_2$)$_2$—NEt]-, (NH$_2$)(Cp)-M-C$_5$H$_3$-1-$^i$Pr-3-[(CH$_2$)$_2$—NEt]-, (NMe$_2$)(Cp)-M-C$_5$H$_3$-1-$^i$Pr-3-[(CH$_2$)$_2$—NEt]-, (NEt$_2$)(Cp)-M-C$_5$H$_3$-1-$^i$Pr-3-[(CH$_2$)$_2$—NEt]-, (N$^n$Pr$_2$)(Cp)-M-C$_5$H$_3$-1-$^i$Pr-3-[(CH$_2$)$_2$—NEt]-, (N$^i$Pr$_2$)(Cp)-M-C$_5$H$_3$-1-$^i$Pr-3-[(CH$_2$)$_2$—NEt]-, (N$^n$Bu$_2$)(Cp)-M-C$_5$H$_3$-1-$^i$Pr-3-[(CH$_2$)$_2$—NEt]-, (N$^i$Bu$_2$)(Cp)-M-C$_5$H$_3$-1-$^i$Pr-3-[(CH$_2$)$_2$—NEt]-, (N$^s$Bu$_2$)(Cp)-M-C$_5$H$_3$-1-$^i$Pr-3-[(CH$_2$)$_2$—NEt]-, (N$^t$Bu$_2$)(Cp)-M-C$_5$H$_3$-1-$^i$Pr-3-[(CH$_2$)$_2$—NEt]-, (OH)$_2$-M-C$_5$H$_3$-1-$^i$Pr-3-[(CH$_2$)$_2$—NEt]-, (OMe)$_2$-M-C$_5$H$_3$-1-$^i$Pr-3-[(CH$_2$)$_2$—NEt]-, (OEt)$_2$-M-C$_5$H$_3$-1-$^i$Pr-3-[(CH$_2$)$_2$—NEt]-, (O$^n$Pr)$_2$-M-C$_5$H$_3$-1-$^i$Pr-3-[(CH$_2$)$_2$—NEt]-, (O$^i$Pr)$_2$-M-C$_5$H$_3$-1-$^i$Pr-3-[(CH$_2$)$_2$—NEt]-, (O$^n$Bu)$_2$-M-C$_5$H$_3$-1-$^i$Pr-3-[(CH$_2$)$_2$—NEt]-, (O$^i$Bu$_2$-M-C$_5$H$_3$-1-$^i$Pr-3-[(CH$_2$)$_2$—NEt]-, (O$^t$Bu)$_2$-M-C$_5$H$_3$-1-$^i$Pr-3-[(CH$_2$)$_2$—NEt]-, (O$^s$Bu)$_2$-M-C$_5$H$_3$-1-$^i$Pr-3-[(CH$_2$)$_2$—NEt]-, (NH$_2$)$_2$-M-C$_5$H$_3$-1-$^t$Bu-2-[(CH$_2$)$_2$—NEt]-, (NMe$_2$)$_2$-M-C$_5$H$_3$-1-$^t$Bu-2-[(CH$_2$)$_2$—NEt]-, (NEt$_2$)$_2$-M-C$_5$H$_3$-1-$^t$Bu-2-[(CH$_2$)$_2$—NEt]-, (N$^n$Pr$_2$)$_2$-M-C$_5$H$_3$-1-$^t$Bu-2-[(CH$_2$)$_2$—NEt]-, (N$^i$Pr$_2$)$_2$-M-C$_5$H$_3$-1-$^t$Bu-2-[(CH$_2$)$_2$—NEt]-, (N$^n$Bu$_2$)$_2$-M-C$_5$H$_3$-1-$^t$Bu-2-[(CH$_2$)$_2$—NEt]-, (N$^i$Bu$_2$)$_2$-M-C$_5$H$_3$-1-$^t$Bu-2-[(CH$_2$)$_2$—NEt]-, (N$^s$Bu$_2$)$_2$-M-C$_5$H$_3$-1-$^t$Bu-2-[(CH$_2$)$_2$—NEt]-, (N$^t$Bu$_2$)$_2$-M-C$_5$H$_3$-1-$^t$Bu-2-[(CH$_2$)$_2$—NEt]-, (NH$_2$)(Cp)-M-C$_5$H$_3$-1-$^t$Bu-2-[(CH$_2$)$_2$—NEt]-, (NMe$_2$)(Cp)-M-C$_5$H$_3$-1-$^t$Bu-2-[(CH$_2$)$_2$—NEt]-, (NEt$_2$)(Cp)-M-C$_5$H$_3$-1-$^t$Bu-2-[(CH$_2$)$_2$—NEt]-, (N$^n$Pr$_2$)(Cp)-M-C$_5$H$_3$-1-$^t$Bu-2-[(CH$_2$)$_2$—NEt]-, (N$^i$Pr$_2$)(Cp)-M-C$_5$H$_3$-1-$^t$Bu-2-[(CH$_2$)$_2$—NEt]-, (N$^n$Bu$_2$)(Cp)-M-C$_5$H$_3$-1-$^t$Bu-2-[(CH$_2$)$_2$—NEt]-, (N$^i$Bu$_2$)(Cp)-M-C$_5$H$_3$-1-$^t$Bu-2-[(CH$_2$)$_2$—NEt]-, (N$^s$Bu$_2$)(Cp)-M-C$_5$H$_3$-1-$^t$Bu-2-[(CH$_2$)$_2$—NEt]-, (N$^t$Bu$_2$)(Cp)-M-C$_5$H$_3$-1-$^t$Bu-2-[(CH$_2$)$_2$—NEt]-, (OH)$_2$-M-C$_5$H$_3$-1-$^t$Bu-2-[(CH$_2$)$_2$—NEt]-, (OMe)$_2$-M-C$_5$H$_3$-1-$^t$Bu-2-[(CH$_2$)$_2$—NEt]-, (OEt)$_2$-M-C$_5$H$_3$-1-$^t$Bu-2-[(CH$_2$)$_2$—NEt]-, (O$^n$Pr)$_2$-M-C$_5$H$_3$-1-$^t$Bu-2-[(CH$_2$)$_2$—NEt]-, (O$^i$Pr)$_2$-M-C$_5$H$_3$-1-$^t$Bu-2-[(CH$_2$)$_2$—NEt]-, (O$^n$Bu)$_2$-M-C$_5$H$_3$-1-$^t$Bu-2-[(CH$_2$)$_2$—NEt]-, (O$^i$Bu$_2$-M-C$_5$H$_3$-1-$^t$Bu-2-[(CH$_2$)$_2$—NEt]-, (O$^t$Bu)$_2$-M-C$_5$H$_3$-1-$^t$Bu-2-[(CH$_2$)$_2$—NEt]-, (O$^s$Bu)$_2$-M-C$_5$H$_3$-1-$^t$Bu-2-[(CH$_2$)$_2$—NEt]-, (NH$_2$)$_2$-M-C$_5$H$_3$-1-$^t$Bu-3-[(CH$_2$)$_2$—NEt]-, (NMe$_2$)$_2$-M-C$_5$H$_3$-1-$^t$Bu-3-[(CH$_2$)$_2$—NEt]-, (NEt$_2$)$_2$-M-C$_5$H$_3$-1-$^t$Bu-3-[(CH$_2$)$_2$—NEt]-, (N$^n$Pr$_2$)$_2$-M-C$_5$H$_3$-1-$^t$Bu-3-[(CH$_2$)$_2$—NEt]-, (N$^i$Pr$_2$)$_2$-M-C$_5$H$_3$-1-$^t$Bu-3-[(CH$_2$)$_2$—NEt]-, (N$^n$Bu$_2$)$_2$-M-C$_5$H$_3$-1-$^t$Bu-3-[(CH$_2$)$_2$—NEt]-, (N$^i$Bu$_2$)$_2$-M-C$_5$H$_3$-1-$^t$Bu-3-[(CH$_2$)$_2$—NEt]-, (N$^s$Bu$_2$)$_2$-M-C$_5$H$_3$-1-$^t$Bu-3-[(CH$_2$)$_2$—NEt]-, (N$^t$Bu$_2$)$_2$-M-C$_5$H$_3$-1-$^t$Bu-3-[(CH$_2$)$_2$—NEt]-, (NH$_2$)(Cp)-M-C$_5$H$_3$-1-$^t$Bu-3-[(CH$_2$)$_2$—NEt]-, (NMe$_2$)(Cp)-M-C$_5$H$_3$-1-$^t$Bu-3-[(CH$_2$)$_2$—NEt]-, (NEt$_2$)(Cp)-M-C$_5$H$_3$-1-$^t$Bu-3-[(CH$_2$)$_2$—NEt]-, (N$^n$Pr$_2$)(Cp)-M-C$_5$H$_3$-1-$^t$Bu-3-[(CH$_2$)$_2$—NEt]-, (N$^i$Pr$_2$)(Cp)-M-C$_5$H$_3$-1-$^t$Bu-3-[(CH$_2$)$_2$—NEt]-, (N$^n$Bu$_2$)(Cp)-M-C$_5$H$_3$-1-$^t$Bu-3-[(CH$_2$)$_2$—NEt]-, (N$^i$Bu$_2$)(Cp)-M-C$_5$H$_3$-1-$^t$Bu-3-[(CH$_2$)$_2$—NEt]-, (N$^s$Bu$_2$)(Cp)-M-C$_5$H$_3$-1-$^t$Bu-3-[(CH$_2$)$_2$—NEt]-, (N$^t$Bu$_2$)(Cp)-M-C$_5$H$_3$-1-$^t$Bu-3-[(CH$_2$)$_2$—NEt]-, (OH)$_2$-M-C$_5$H$_3$-1-$^t$Bu-3-[(CH$_2$)$_2$—NEt]-, (OMe)$_2$-M-C$_5$H$_3$-1-$^t$Bu-3-[(CH$_2$)$_2$—NEt]-, (OEt)$_2$-M-C$_5$H$_3$-1-$^t$Bu-3-[(CH$_2$)$_2$—NEt]-, (O$^n$Pr)$_2$-M-C$_5$H$_3$-1-$^t$Bu-3-[(CH$_2$)$_2$—NEt]-, (O$^i$Pr)$_2$-M-C$_5$H$_3$-1-$^t$Bu-3-[(CH$_2$)$_2$—NEt]-, (O$^n$Bu)$_2$-M-C$_5$H$_3$-1-$^t$Bu-3-[(CH$_2$)$_2$—NEt]-, (O$^i$Bu$_2$-M-C$_5$H$_3$-1-$^t$Bu-3-[(CH$_2$)$_2$—NEt]-, (O$^t$Bu)$_2$-M-C$_5$H$_3$-1-$^t$Bu-3-[(CH$_2$)$_2$—NEt]-, (O$^s$Bu)$_2$-M-C$_5$H$_3$-1-$^t$Bu-3-[(CH$_2$)$_2$—NEt]-, (NH$_2$)$_2$-M-C$_5$H$_3$-1-Me-2-[(CH$_2$)$_2$—N$^i$Pr]—, (NMe$_2$)$_2$-M-C$_5$H$_3$-1-Me-2-[(CH$_2$)$_2$—N$^i$Pr]—, (NEt$_2$)$_2$-M-C$_5$H$_3$-1-Me-2-[(CH$_2$)$_2$—N$^i$Pr]—, (N$^n$Pr$_2$)$_2$-M-C$_5$H$_3$-1-Me-2-[(CH$_2$)$_2$—N$^i$Pr]—, (N$^i$Pr$_2$)$_2$-M-C$_5$H$_3$-1-Me-2-[(CH$_2$)$_2$—N$^i$Pr]—, (N$^n$Bu$_2$)$_2$-M-C$_5$H$_3$-1-Me-2-[(CH$_2$)$_2$—N$^i$Pr]—, (N$^i$Bu$_2$)$_2$-M-C$_5$H$_3$-1-Me-2-[(CH$_2$)$_2$—N$^i$Pr]—, (N$^s$Bu$_2$)$_2$-M-C$_5$H$_3$-1-Me-2-[(CH$_2$)$_2$—N$^i$Pr]—, (N$^t$Bu$_2$)$_2$-M-C$_5$H$_3$-1-Me-2-[(CH$_2$)$_2$—N$^i$Pr]—, (NH$_2$)(Cp)-M-C$_5$H$_3$-1-Me-2-[(CH$_2$)$_2$—N$^i$Pr]—, (NMe$_2$)(Cp)-M-C$_5$H$_3$-1-Me-2-[(CH$_2$)$_2$—N$^i$Pr]—, (NEt$_2$)(Cp)-M-C$_5$H$_3$-1-Me-2-[(CH$_2$)$_2$—N$^i$Pr]—, (N$^n$Pr$_2$)(Cp)-M-C$_5$H$_3$-1-Me-2-[(CH$_2$)$_2$—N$^i$Pr]—, (N$^i$Pr$_2$)(Cp)-M-C$_5$H$_3$-1-Me-2-[(CH$_2$)$_2$—N$^i$Pr]—, (N$^n$Bu$_2$)(Cp)-M-C$_5$H$_3$-1-Me-2-[(CH$_2$)$_2$—N$^i$Pr]—, (N$^i$Bu$_2$)(Cp)-M-C$_5$H$_3$-1-Me-2-[(CH$_2$)$_2$—N$^i$Pr]—, (N$^s$Bu$_2$)(Cp)-M-C$_5$H$_3$-1-Me-2-[(CH$_2$)$_2$—N$^i$Pr]—, (N$^t$Bu$_2$)(Cp)-M-C$_5$H$_3$-1-Me-2-[(CH$_2$)$_2$—N$^i$Pr]—, (OH)$_2$-M-C$_5$H$_3$-1-Me-2-[(CH$_2$)$_2$—N$^i$Pr]—, (OMe)$_2$-M-C$_5$H$_3$-1-Me-2-[(CH$_2$)$_2$—N$^i$Pr]—, (OEt)$_2$-M-C$_5$H$_3$-1-Me-2-[(CH$_2$)$_2$—N$^i$Pr]—, (O$^n$Pr)$_2$-M-C$_5$H$_3$-1-Me-2-[(CH$_2$)$_2$—N$^i$Pr]—, (O$^i$Pr)$_2$-M-C$_5$H$_3$-1-Me-2-[(CH$_2$)$_2$—N$^i$Pr]—, (O$^n$Bu)$_2$-M-C$_5$H$_3$-1-Me-2-[(CH$_2$)$_2$—N$^i$Pr]—, (O$^i$Bu$_2$-M-C$_5$H$_3$-1-Me-2-[(CH$_2$)$_2$—N$^i$Pr]—, (O$^t$Bu)$_2$-M-C$_5$H$_3$-1-Me-2-[(CH$_2$)$_2$—N$^i$Pr]—, (O$^s$Bu)$_2$-M-C$_5$H$_3$-1-Me-2-[(CH$_2$)$_2$—N$^i$Pr]—, (NH$_2$)$_2$-M-C$_5$H$_3$-1-Me-3-[(CH$_2$)$_2$—N$^i$Pr]—, (NMe$_2$)$_2$-M-C$_5$H$_3$-1-Me-3-[(CH$_2$)$_2$—N$^i$Pr]—, (NEt$_2$)$_2$-M-C$_5$H$_3$-1-Me-3-[(CH$_2$)$_2$—N$^i$Pr]—, (N$^n$Pr$_2$)$_2$-M-C$_5$H$_3$-1-Me-3-[(CH$_2$)$_2$—N$^i$Pr]—, (N$^i$Pr$_2$)$_2$-M-C$_5$H$_3$-1-Me-3-[(CH$_2$)$_2$—N$^i$Pr]—, (N$^n$Bu$_2$)$_2$-M-C$_5$H$_3$-1-Me-3-[(CH$_2$)$_2$—N$^i$Pr]—, (N$^i$Bu$_2$)$_2$-M-C$_5$H$_3$-1-Me-3-[(CH$_2$)$_2$—N$^i$Pr]—, (N$^s$Bu$_2$)$_2$-M-C$_5$H$_3$-1-Me-3-[(CH$_2$)$_2$—N$^i$Pr]—, (N$^t$Bu$_2$)$_2$-M-C$_5$H$_3$-1-Me-3-[(CH$_2$)$_2$—N$^i$Pr]—, (NH$_2$)(Cp)-M-C$_5$H$_3$-1-Me-3-[(CH$_2$)$_2$—N$^i$Pr]—, (NMe$_2$)(Cp)-M-C$_5$H$_3$-1-Me-3-[(CH$_2$)$_2$—N$^i$Pr]—, (NEt$_2$)(Cp)-M-C$_5$H$_3$-1-Me-3-[(CH$_2$)$_2$—N$^i$Pr]—, (N$^n$Pr$_2$)(Cp)-M-C$_5$H$_3$-1-Me-3-[(CH$_2$)$_2$—N$^i$Pr]—, (N$^i$Pr$_2$)(Cp)-M-C$_5$H$_3$-1-Me-3-[(CH$_2$)$_2$—N$^i$Pr]—, (N$^n$Bu$_2$)(Cp)-M-C$_5$H$_3$-1-Me-3-[(CH$_2$)$_2$—N$^i$Pr]—, (N$^i$Bu$_2$)(Cp)-M-C$_5$H$_3$-1-Me-3-[(CH$_2$)$_2$—N$^i$Pr]—, (N$^s$Bu$_2$)(Cp)-M-C$_5$H$_3$-1-Me-3-[(CH$_2$)$_2$—N$^i$Pr]—, (N$^t$Bu$_2$)(Cp)-M-C$_5$H$_3$-1-Me-3-[(CH$_2$)$_2$—N$^i$Pr]—, (OH)$_2$-M-C$_5$H$_3$-1-Me-3-[(CH$_2$)$_2$—N$^i$Pr]—, (OMe)$_2$-M-C$_5$H$_3$-1-Me-3-[(CH$_2$)$_2$—N$^i$Pr]—, (OEt)$_2$-M-C$_5$H$_3$-1-Me-3-[(CH$_2$)$_2$—N$^i$Pr]—, (O$^n$Pr)$_2$-M-C$_5$H$_3$-1-Me-3-[(CH$_2$)$_2$—N$^i$Pr]—, (O$^i$Pr)$_2$-M-C$_5$H$_3$-1-Me-3-[(CH$_2$)$_2$—N$^i$Pr]—, (O$^n$Bu)$_2$-M-C$_5$H$_3$-1-Me-3-[(CH$_2$)$_2$—N$^i$Pr]—, (O$^i$Bu$_2$-M-C$_5$H$_3$-1-Me-3-[(CH$_2$)$_2$—N$^i$Pr]—, (O$^t$Bu)$_2$-M-C$_5$H$_3$-1-Me-3-[(CH$_2$)$_2$—N$^i$Pr]—, (O$^s$Bu)$_2$-M-C$_5$H$_3$-1-Me-3-[(CH$_2$)$_2$—N$^i$Pr]—, (NH$_2$)$_2$-M-C$_5$H$_3$-1-Et-2-[(CH$_2$)$_2$—N$^i$Pr]—, (NMe$_2$)$_2$-M-C$_5$H$_3$-1-Et-2-[(CH$_2$)$_2$—N$^i$Pr]—, (NEt$_2$)$_2$-M-C$_5$H$_3$-1-Et-2-[(CH$_2$)$_2$—N$^i$Pr]—, (N$^n$Pr$_2$)$_2$-M-C$_5$H$_3$-1-Et-2-[(CH$_2$)$_2$—N$^i$Pr]—, (N$^i$Pr$_2$)$_2$-M-C$_5$H$_3$-1-Et-2-[(CH$_2$)$_2$—N$^i$Pr]—, (N$^n$Bu$_2$)$_2$-M-C$_5$H$_3$-1-Et-2-[(CH$_2$)$_2$—N$^i$Pr]—, (N$^i$Bu$_2$)$_2$-M-C$_5$H$_3$-1-Et-2-[(CH$_2$)$_2$—N$^i$Pr]—, (N$^s$Bu$_2$)$_2$-M-C$_5$H$_3$-1-Et-2-[(CH$_2$)$_2$—N$^i$Pr]—, (N$^t$Bu$_2$)$_2$-M-C$_5$H$_3$-1-Et-2-[(CH$_2$)$_2$—N$^i$Pr]—, (NH$_2$)(Cp)-M-C$_5$H$_3$-1-Et-2-[(CH$_2$)$_2$—N$^i$Pr]—, (NMe$_2$)(Cp)-M-C$_5$H$_3$-1-Et-2-[(CH$_2$)$_2$—N$^i$Pr]—, (NEt$_2$)(Cp)-M-C$_5$H$_3$-1-Et-2-[(CH$_2$)$_2$—N$^i$Pr]—, (N$^n$Pr$_2$)(Cp)-M-C$_5$H$_3$-1-Et-2-[(CH$_2$)$_2$—N$^i$Pr]—, (N$^i$Pr$_2$)(Cp)-M-C$_5$H$_3$-1-Et-2-[(CH$_2$)$_2$—N$^i$Pr]—, (N$^n$Bu$_2$)(Cp)-M-C$_5$H$_3$-1-Et-2-[(CH$_2$)$_2$—N$^i$Pr]—, (N$^i$Bu$_2$)(Cp)-M-C$_5$H$_3$-1-Et-2-[(CH$_2$)$_2$—N$^i$Pr]—, (N$^s$Bu$_2$)(Cp)-M-C$_5$H$_3$-1-Et-2-[(CH$_2$)$_2$—N$^i$Pr]—, (N$^t$Bu$_2$)(Cp)-M-C$_5$H$_3$-1-Et-2-[(CH$_2$)$_2$—N$^i$Pr]—, (OH)$_2$-M-C$_5$H$_3$-1-Et-2-[(CH$_2$)$_2$—N$^i$Pr]—, (OMe)$_2$-M-C$_5$H$_3$-1-Et-2-[(CH$_2$)$_2$—N$^i$Pr]—, (OEt)$_2$-M-C$_5$H$_3$-1-Et-2-[(CH$_2$)$_2$—N$^i$Pr]—, (O$^n$Pr)$_2$-M-C$_5$H$_3$-1-Et-2-[(CH$_2$)$_2$—N$^i$Pr]—, (O$^i$Pr)$_2$-M-C$_5$H$_3$-1-Et-2-[(CH$_2$)$_2$—N$^i$Pr]—, (O$^n$Bu)$_2$-M-C$_5$H$_3$-1-Et-2-[(CH$_2$)$_2$—N$^i$Pr]—, (O$^i$Bu$_2$-M-C$_5$H$_3$-1-Et-2-[(CH$_2$)$_2$—N$^i$Pr]—, (O$^t$Bu)$_2$-M-C$_5$H$_3$-1-Et-2-[(CH$_2$)$_2$—N$^i$Pr]—, (O$^s$Bu)$_2$-M-

$C_5H_3$-1-Et-2-[$(CH_2)_2$—N$^i$Pr]—, $(NH_2)_2$-M-$C_5H_3$-1-Et-3-[$(CH_2)_2$—N$^i$Pr]—, $(NMe_2)_2$-M-$C_5H_3$-1-Et-3-[$(CH_2)_2$—N$^i$Pr]—, $(NEt_2)_2$-M-$C_5H_3$-1-Et-3-[$(CH_2)_2$—N$^i$Pr]—, $(N^nPr_2)_2$-M-$C_5H_3$-1-Et-3-[$(CH_2)_2$—N$^i$Pr]—, $(N^iPr_2)_2$-M-$C_5H_3$-1-Et-3-[$(CH_2)_2$—N$^i$Pr]—, $(N^nBu_2)_2$-M-$C_5H_3$-1-Et-3-[$(CH_2)_2$—N$^i$Pr]—, $(N^iBu_2)_2$-M-$C_5H_3$-1-Et-3-[$(CH_2)_2$—N$^i$Pr]—, $(N^sBu_2)_2$-M-$C_5H_3$-1-Et-3-[$(CH_2)_2$—N$^i$Pr]—, $(N^tBu_2)_2$-M-$C_5H_3$-1-Et-3-[$(CH_2)_2$—N$^i$Pr]—, $(NH_2)(Cp)$-M-$C_5H_3$-1-Et-3-[$(CH_2)_2$—N$^i$Pr]—, $(NMe_2)(Cp)$-M-$C_5H_3$-1-Et-3-[$(CH_2)_2$—N$^i$Pr]—, $(NEt_2)(Cp)$-M-$C_5H_3$-1-Et-3-[$(CH_2)_2$—N$^i$Pr]—, $(N^nPr_2)(Cp)$-M-$C_5H_3$-1-Et-3-[$(CH_2)_2$—N$^i$Pr]—, $(N^iPr_2)(Cp)$-M-$C_5H_3$-1-Et-3-[$(CH_2)_2$—N$^i$Pr]—, $(N^nBu_2)(Cp)$-M-$C_5H_3$-1-Et-3-[$(CH_2)_2$—N$^i$Pr]—, $(N^iBu_2)(Cp)$-M-$C_5H_3$-1-Et-3-[$(CH_2)_2$—N$^i$Pr]—, $(N^sBu_2)(Cp)$-M-$C_5H_3$-1-Et-3-[$(CH_2)_2$—N$^i$Pr]—, $(N^tBu_2)(Cp)$-M-$C_5H_3$-1-Et-3-[$(CH_2)_2$—N$^i$Pr]—, $(OH)_2$-M-$C_5H_3$-1-Et-3-[$(CH_2)_2$—N$^i$Pr]—, $(OMe)_2$-M-$C_5H_3$-1-Et-3-[$(CH_2)_2$—N$^i$Pr]—, $(OEt)_2$-M-$C_5H_3$-1-Et-3-[$(CH_2)_2$—N$^i$Pr]—, $(O^nPr)_2$-M-$C_5H_3$-1-Et-3-[$(CH_2)_2$—N$^i$Pr]—, $(O^iPr)_2$-M-$C_5H_3$-1-Et-3-[$(CH_2)_2$—N$^i$Pr]—, $(O^nBu)_2$-M-$C_5H_3$-1-Et-3-[$(CH_2)_2$—N$^i$Pr]—, $(O^iBu_2$-M-$C_5H_3$-1-Et-3-[$(CH_2)_2$—N$^i$Pr]—, $(O^tBu)_2$-M-$C_5H_3$-1-Et-3-[$(CH_2)_2$—N$^i$Pr]—, $(O^sBu)_2$-M-$C_5H_3$-1-Et-3-[$(CH_2)_2$—N$^i$Pr]—, $(NH_2)_2$-M-$C_5H_3$-1-$^i$Pr-2-[$(CH_2)_2$—N$^i$Pr]—, $(NMe_2)_2$-M-$C_5H_3$-1-$^i$Pr-2-[$(CH_2)_2$—N$^i$Pr]—, $(NEt_2)_2$-M-$C_5H_3$-1-$^i$Pr-2-[$(CH_2)_2$—N$^i$Pr]—, $(N^nPr_2)_2$-M-$C_5H_3$-1-$^i$Pr-2-[$(CH_2)_2$—N$^i$Pr]—, $(N^iPr_2)_2$-M-$C_5H_3$-1-$^i$Pr-2-[$(CH_2)_2$—N$^i$Pr]—, $(N^nBu_2)_2$-M-$C_5H_3$-1-$^i$Pr-2-[$(CH_2)_2$—N$^i$Pr]—, $(N^iBu_2)_2$-M-$C_5H_3$-1-$^i$Pr-2-[$(CH_2)_2$—N$^i$Pr]—, $(N^sBu_2)_2$-M-$C_5H_3$-1-$^i$Pr-2-[$(CH_2)_2$—N$^i$Pr]—, $(N^tBu_2)_2$-M-$C_5H_3$-1-$^i$Pr-2-[$(CH_2)_2$—N$^i$Pr]—, $(NH_2)(Cp)$-M-$C_5H_3$-1-$^i$Pr-2-[$(CH_2)_2$—N$^i$Pr]—, $(NMe_2)(Cp)$-M-$C_5H_3$-1-$^i$Pr-2-[$(CH_2)_2$—N$^i$Pr]—, $(NEt_2)(Cp)$-M-$C_5H_3$-1-$^i$Pr-2-[$(CH_2)_2$—N$^i$Pr]—, $(N^nPr_2)(Cp)$-M-$C_5H_3$-1-$^i$Pr-2-[$(CH_2)_2$—N$^i$Pr]—, $(N^iPr_2)(Cp)$-M-$C_5H_3$-1-$^i$Pr-2-[$(CH_2)_2$—N$^i$Pr]—, $(N^nBu_2)(Cp)$-M-$C_5H_3$-1-$^i$Pr-2-[$(CH_2)_2$—N$^i$Pr]—, $(N^iBu_2)(Cp)$-M-$C_5H_3$-1-$^i$Pr-2-[$(CH_2)_2$—N$^i$Pr]—, $(N^sBu_2)(Cp)$-M-$C_5H_3$-1-$^i$Pr-2-[$(CH_2)_2$—N$^i$Pr]—, $(N^tBu_2)(Cp)$-M-$C_5H_3$-1-$^i$Pr-2-[$(CH_2)_2$—N$^i$Pr]—, $(OH)_2$-M-$C_5H_3$-1-$^i$Pr-2-[$(CH_2)_2$—N$^i$Pr]—, $(OMe)_2$-M-$C_5H_3$-1-$^i$Pr-2-[$(CH_2)_2$—N$^i$Pr]—, $(OEt)_2$-M-$C_5H_3$-1-$^i$Pr-2-[$(CH_2)_2$—N$^i$Pr]—, $(O^nPr)_2$-M-$C_5H_3$-1-$^i$Pr-2-[$(CH_2)_2$—N$^i$Pr]—, $(O^iPr)_2$-M-$C_5H_3$-1-$^i$Pr-2-[$(CH_2)_2$—N$^i$Pr]—, $(O^nBu)_2$-M-$C_5H_3$-1-$^i$Pr-2-[$(CH_2)_2$—N$^i$Pr]—, $(O^iBu_2$-M-$C_5H_3$-1-$^i$Pr-2-[$(CH_2)_2$—N$^i$Pr]—, $(O^tBu)_2$-M-$C_5H_3$-1-$^i$Pr-2-[$(CH_2)_2$—N$^i$Pr]—, $(O^sBu)_2$-M-$C_5H_3$-1-$^i$Pr-2-[$(CH_2)_2$—N$^i$Pr]—, $(NH_2)_2$-M-$C_5H_3$-1-$^i$Pr-3-[$(CH_2)_2$—N$^i$Pr]—, $(NMe_2)_2$-M-$C_5H_3$-1-$^i$Pr-3-[$(CH_2)_2$—N$^i$Pr]—, $(NEt_2)_2$-M-$C_5H_3$-1-$^i$Pr-3-[$(CH_2)_2$—N$^i$Pr]—, $(N^nPr_2)_2$-M-$C_5H_3$-1-$^i$Pr-3-[$(CH_2)_2$—N$^i$Pr]—, $(N^iPr_2)_2$-M-$C_5H_3$-1-$^i$Pr-3-[$(CH_2)_2$—N$^i$Pr]—, $(N^nBu_2)_2$-M-$C_5H_3$-1-$^i$Pr-3-[$(CH_2)_2$—N$^i$Pr]—, $(N^iBu_2)_2$-M-$C_5H_3$-1-$^i$Pr-3-[$(CH_2)_2$—N$^i$Pr]—, $(N^sBu_2)_2$-M-$C_5H_3$-1-$^i$Pr-3-[$(CH_2)_2$—N$^i$Pr]—, $(N^tBu_2)_2$-M-$C_5H_3$-1-$^i$Pr-3-[$(CH_2)_2$—N$^i$Pr]—, $(NH_2)(Cp)$-M-$C_5H_3$-1-$^i$Pr-3-[$(CH_2)_2$—N$^i$Pr]—, $(NMe_2)(Cp)$-M-$C_5H_3$-1-$^i$Pr-3-[$(CH_2)_2$—N$^i$Pr]—, $(NEt_2)(Cp)$-M-$C_5H_3$-1-$^i$Pr-3-[$(CH_2)_2$—N$^i$Pr]—, $(N^nPr_2)(Cp)$-M-$C_5H_3$-1-$^i$Pr-3-[$(CH_2)_2$—N$^i$Pr]—, $(N^iPr_2)(Cp)$-M-$C_5H_3$-1-$^i$Pr-3-[$(CH_2)_2$—N$^i$Pr]—, $(N^nBu_2)(Cp)$-M-$C_5H_3$-1-$^i$Pr-3-[$(CH_2)_2$—N$^i$Pr]—, $(N^iBu_2)(Cp)$-M-$C_5H_3$-1-$^i$Pr-3-[$(CH_2)_2$—N$^i$Pr]—, $(N^sBu_2)(Cp)$-M-$C_5H_3$-1-$^i$Pr-3-[$(CH_2)_2$—N$^i$Pr]—, $(N^tBu_2)(Cp)$-M-$C_5H_3$-1-$^i$Pr-3-[$(CH_2)_2$—N$^i$Pr]—, $(OH)_2$-M-$C_5H_3$-1-$^i$Pr-3-[$(CH_2)_2$—N$^i$Pr]—, $(OMe)_2$-M-$C_5H_3$-1-$^i$Pr-3-[$(CH_2)_2$—N$^i$Pr]—, $(OEt)_2$-M-$C_5H_3$-1-$^i$Pr-3-[$(CH_2)_2$—N$^i$Pr]—, $(O^nPr)_2$-M-$C_5H_3$-1-$^i$Pr-3-[$(CH_2)_2$—N$^i$Pr]—, $(O^iPr)_2$-M-$C_5H_3$-1-$^i$Pr-3-[$(CH_2)_2$—N$^i$Pr]—, $(O^nBu)_2$-M-$C_5H_3$-1-$^i$Pr-3-[$(CH_2)_2$—N$^i$Pr]—, $(O^iBu_2$-M-$C_5H_3$-1-$^i$Pr-3-[$(CH_2)_2$—N$^i$Pr]—, $(O^tBu)_2$-M-$C_5H_3$-1-$^i$Pr-3-[$(CH_2)_2$—N$^i$Pr]—, $(O^sBu)_2$-M-$C_5H_3$-1-$^i$Pr-3-[$(CH_2)_2$—N$^i$Pr]—, $(NH_2)_2$-M-$C_5H_3$-1-$^t$Bu-2-[$(CH_2)_2$—N$^i$Pr]—, $(NMe_2)_2$-M-$C_5H_3$-1-$^t$Bu-2-[$(CH_2)_2$—N$^i$Pr]—, $(NEt_2)_2$-M-$C_5H_3$-1-$^t$Bu-2-[$(CH_2)_2$—N$^i$Pr]—, $(N^nPr_2)_2$-M-$C_5H_3$-1-$^t$Bu-2-[$(CH_2)_2$—N$^i$Pr]—, $(N^iPr_2)_2$-M-$C_5H_3$-1-$^t$Bu-2-[$(CH_2)_2$—N$^i$Pr]—, $(N^nBu_2)_2$-M-$C_5H_3$-1-$^t$Bu-2-[$(CH_2)_2$—N$^i$Pr]—, $(N^iBu_2)_2$-M-$C_5H_3$-1-$^t$Bu-2-[$(CH_2)_2$—N$^i$Pr]—, $(N^sBu_2)_2$-M-$C_5H_3$-1-$^t$Bu-2-[$(CH_2)_2$—N$^i$Pr]—, $(N^tBu_2)_2$-M-$C_5H_3$-1-$^t$Bu-2-[$(CH_2)_2$—N$^i$Pr]—, $(NH_2)(Cp)$-M-$C_5H_3$-1-$^t$Bu-2-[$(CH_2)_2$—N$^i$Pr]—, $(NMe_2)(Cp)$-M-$C_5H_3$-1-$^t$Bu-2-[$(CH_2)_2$—N$^i$Pr]—, $(NEt_2)(Cp)$-M-$C_5H_3$-1-$^t$Bu-2-[$(CH_2)_2$—N$^i$Pr]—, $(N^nPr_2)(Cp)$-M-$C_5H_3$-1-$^t$Bu-2-[$(CH_2)_2$—N$^i$Pr]—, $(N^iPr_2)(Cp)$-M-$C_5H_3$-1-$^t$Bu-2-[$(CH_2)_2$—N$^i$Pr]—, $(N^nBu_2)(Cp)$-M-$C_5H_3$-1-$^t$Bu-2-[$(CH_2)_2$—N$^i$Pr]—, $(N^iBu_2)(Cp)$-M-$C_5H_3$-1-$^t$Bu-2-[$(CH_2)_2$—N$^i$Pr]—, $(N^sBu_2)(Cp)$-M-$C_5H_3$-1-$^t$Bu-2-[$(CH_2)_2$—N$^i$Pr]—, $(N^tBu_2)(Cp)$-M-$C_5H_3$-1-$^t$Bu-2-[$(CH_2)_2$—N$^i$Pr]—, $(OH)_2$-M-$C_5H_3$-1-$^t$Bu-2-[$(CH_2)_2$—N$^i$Pr]—, $(OMe)_2$-M-$C_5H_3$-1-$^t$Bu-2-[$(CH_2)_2$—N$^i$Pr]—, $(OEt)_2$-M-$C_5H_3$-1-$^t$Bu-2-[$(CH_2)_2$—N$^i$Pr]—, $(O^nPr)_2$-M-$C_5H_3$-1-$^t$Bu-2-[$(CH_2)_2$—N$^i$Pr]—, $(O^iPr)_2$-M-$C_5H_3$-1-$^t$Bu-2-[$(CH_2)_2$—N$^i$Pr]—, $(O^nBu)_2$-M-$C_5H_3$-1-$^t$Bu-2-[$(CH_2)_2$—N$^i$Pr]—, $(O^iBu_2$-M-$C_5H_3$-1-$^t$Bu-2-[$(CH_2)_2$—N$^i$Pr]—, $(O^tBu)_2$-M-$C_5H_3$-1-$^t$Bu-2-[$(CH_2)_2$—N$^i$Pr]—, $(O^sBu)_2$-M-$C_5H_3$-1-$^t$Bu-2-[$(CH_2)_2$—N$^i$Pr]—, $(NH_2)_2$-M-$C_5H_3$-1-$^t$Bu-3-[$(CH_2)_2$—N$^i$Pr]—, $(NMe_2)_2$-M-$C_5H_3$-1-$^t$Bu-3-[$(CH_2)_2$—N$^i$Pr]—, $(NEt_2)_2$-M-$C_5H_3$-1-$^t$Bu-3-[$(CH_2)_2$—N$^i$Pr]—, $(N^nPr_2)_2$-M-$C_5H_3$-1-$^t$Bu-3-[$(CH_2)_2$—N$^i$Pr]—, $(N^iPr_2)_2$-M-$C_5H_3$-1-$^t$Bu-3-[$(CH_2)_2$—N$^i$Pr]—, $(N^nBu_2)_2$-M-$C_5H_3$-1-$^t$Bu-3-[$(CH_2)_2$—N$^i$Pr]—, $(N^iBu_2)_2$-M-$C_5H_3$-1-$^t$Bu-3-[$(CH_2)_2$—N$^i$Pr]—, $(N^sBu_2)_2$-M-$C_5H_3$-1-$^t$Bu-3-[$(CH_2)_2$—N$^i$Pr]—, $(N^tBu_2)_2$-M-$C_5H_3$-1-$^t$Bu-3-[$(CH_2)_2$—N$^i$Pr]—, $(NH_2)(Cp)$-M-$C_5H_3$-1-$^t$Bu-3-[$(CH_2)_2$—N$^i$Pr]—, $(NMe_2)(Cp)$-M-$C_5H_3$-1-$^t$Bu-3-[$(CH_2)_2$—N$^i$Pr]—, $(NEt_2)(Cp)$-M-$C_5H_3$-1-$^t$Bu-3-[$(CH_2)_2$—N$^i$Pr]—, $(N^nPr_2)(Cp)$-M-$C_5H_3$-1-$^t$Bu-3-[$(CH_2)_2$—N$^i$Pr]—, $(N^iPr_2)(Cp)$-M-$C_5H_3$-1-$^t$Bu-3-[$(CH_2)_2$—N$^i$Pr]—, $(N^nBu_2)(Cp)$-M-$C_5H_3$-1-$^t$Bu-3-[$(CH_2)_2$—N$^i$Pr]—, $(N^iBu_2)(Cp)$-M-$C_5H_3$-1-$^t$Bu-3-[$(CH_2)_2$—N$^i$Pr]—, $(N^sBu_2)(Cp)$-M-$C_5H_3$-1-$^t$Bu-3-[$(CH_2)_2$—N$^i$Pr]—, $(N^tBu_2)(Cp)$-M-$C_5H_3$-1-$^t$Bu-3-[$(CH_2)_2$—N$^i$Pr]—, $(OH)_2$-M-$C_5H_3$-1-$^t$Bu-3-[$(CH_2)_2$—N$^i$Pr]—, $(OMe)_2$-M-$C_5H_3$-1-$^t$Bu-3-[$(CH_2)_2$—N$^i$Pr]—, $(OEt)_2$-M-$C_5H_3$-1-$^t$Bu-3-[$(CH_2)_2$—N$^i$Pr]—, $(O^nPr)_2$-M-$C_5H_3$-1-$^t$Bu-3-[$(CH_2)_2$—N$^i$Pr]—, $(O^iPr)_2$-M-$C_5H_3$-1-$^t$Bu-3-[$(CH_2)_2$—N$^i$Pr]—, $(O^nBu)_2$-M-$C_5H_3$-1-$^t$Bu-3-[$(CH_2)_2$—N$^i$Pr]—, $(O^iBu_2$-M-$C_5H_3$-1-$^t$Bu-3-[$(CH_2)_2$—N$^i$Pr]—, $(O^tBu)_2$-M-$C_5H_3$-1-$^t$Bu-3-[$(CH_2)_2$—N$^i$Pr]—, $(O^sBu)_2$-M-$C_5H_3$-1-$^t$Bu-3-[$(CH_2)_2$—N$^i$Pr]—, $(NH_2)_2$-M-$C_5H_3$-1-Me-2-[$(CH_2)_2$—N$^n$Pr]—, $(NMe_2)_2$-M-$C_5H_3$-1-Me-2-[$(CH_2)_2$—N$^n$Pr]—, $(NEt_2)_2$-M-$C_5H_3$-1-Me-2-[$(CH_2)_2$—N$^n$Pr]—, $(N^nPr_2)_2$-M-$C_5H_3$-1-Me-2-[$(CH_2)_2$—N$^n$Pr]—, $(N^iPr_2)_2$-M-$C_5H_3$-1-Me-2-[$(CH_2)_2$—N$^n$Pr]—, $(N^nBu_2)_2$-M-$C_5H_3$-1-Me-2-[$(CH_2)_2$—N$^n$Pr]—, $(N^iBu_2)_2$-M-$C_5H_3$-1-Me-2-[$(CH_2)_2$—N$^n$Pr]—, $(N^sBu_2)_2$-M-$C_5H_3$-1-Me-2-[$(CH_2)_2$—N$^n$Pr]—, $(N^tBu_2)_2$-M-$C_5H_3$-1-Me-2-[$(CH_2)_2$—N$^n$Pr]—, $(NH_2)(Cp)$-M-$C_5H_3$-1-Me-2-[$(CH_2)_2$—N$^n$Pr]—, $(NMe_2)(Cp)$-M-$C_5H_3$-1-Me-2-[$(CH_2)_2$—N$^n$Pr]—, $(NEt_2)(Cp)$-M-$C_5H_3$-1-Me-2-[$(CH_2)_2$—N$^n$Pr]—, $(N^nPr_2)(Cp)$-M-$C_5H_3$-1-Me-2-[$(CH_2)_2$—N$^n$Pr]—, $(N^iPr_2)(Cp)$-M-$C_5H_3$-1-Me-2-[$(CH_2)_2$—N$^n$Pr]—, $(N^nBu_2)(Cp)$-M-$C_5H_3$-1-Me-2-[$(CH_2)_2$—N$^n$Pr]—, $(N^iBu_2)(Cp)$-M-$C_5H_3$-1-Me-2-[$(CH_2)_2$—N$^n$Pr]—, $(N^sBu_2)(Cp)$-M-$C_5H_3$-1-Me-2-[$(CH_2)_2$—N$^n$Pr]—, $(N^tBu_2)(Cp)$-M-$C_5H_3$-1-Me-2-[$(CH_2)_2$—N$^n$Pr]—, $(OH)_2$-M-$C_5H_3$-1-Me-2-[$(CH_2)_2$—N$^n$Pr]—, $(OMe)_2$-M-$C_5H_3$-1-Me-2-[$(CH_2)_2$—N$^n$Pr]—, $(OEt)_2$-M-$C_5H_3$-1-Me-2-[$(CH_2)_2$—N$^n$Pr]—, $(O^nPr)_2$-M-$C_5H_3$-1-Me-2-[$(CH_2)_2$—N$^n$Pr]—, $(O^iPr)_2$-M-$C_5H_3$-1-Me-2-[$(CH_2)_2$—N$^n$Pr]—, $(O^nBu)_2$-M-$C_5H_3$-1-Me-2-[$(CH_2)_2$—

$N^nPr]$—, $(O^iBu_2$-M-$C_5H_3$-1-Me-2-$[(CH_2)_2$—$N^nPr]$—, $(O^tBu)_2$-M-$C_5H_3$-1-Me-2-$[(CH_2)_2$—$N^nPr]$—, $(O^sBu)_2$-M-$C_5H_3$-1-Me-2-$[(CH_2)_2$—$N^nPr]$—, $(NH_2)_2$-M-$C_5H_3$-1-Me-3-$[(CH_2)_2$—$N^nPr]$—, $(NMe_2)_2$-M-$C_5H_3$-1-Me-3-$[(CH_2)_2$—$N^nPr]$—, $(NEt_2)_2$-M-$C_5H_3$-1-Me-3-$[(CH_2)_2$—$N^nPr]$—, $(N^nPr_2)_2$-M-$C_5H_3$-1-Me-3-$[(CH_2)_2$—$N^nPr]$—, $(N^iPr_2)_2$-M-$C_5H_3$-1-Me-3-$[(CH_2)_2$—$N^nPr]$—, $(N^nBu_2)_2$-M-$C_5H_3$-1-Me-3-$[(CH_2)_2$—$N^nPr]$—, $(N^iBu_2)_2$-M-$C_5H_3$-1-Me-3-$[(CH_2)_2$—$N^nPr]$—, $(N^sBu_2)_2$-M-$C_5H_3$-1-Me-3-$[(CH_2)_2$—$N^nPr]$—, $(N^tBu_2)_2$-M-$C_5H_3$-1-Me-3-$[(CH_2)_2$—$N^nPr]$—, $(NH_2)(Cp)$-M-$C_5H_3$-1-Me-3-$[(CH_2)_2$—$N^nPr]$—, $(NMe_2)(Cp)$-M-$C_5H_3$-1-Me-3-$[(CH_2)_2$—$N^nPr]$—, $(NEt_2)(Cp)$-M-$C_5H_3$-1-Me-3-$[(CH_2)_2$—$N^nPr]$—, $(N^nPr_2)(Cp)$-M-$C_5H_3$-1-Me-3-$[(CH_2)_2$—$N^nPr]$—, $(N^iPr_2)(Cp)$-M-$C_5H_3$-1-Me-3-$[(CH_2)_2$—$N^nPr]$—, $(N^nBu_2)(Cp)$-M-$C_5H_3$-1-Me-3-$[(CH_2)_2$—$N^nPr]$—, $(N^iBu_2)(Cp)$-M-$C_5H_3$-1-Me-3-$[(CH_2)_2$—$N^nPr]$—, $(N^sBu_2)(Cp)$-M-$C_5H_3$-1-Me-3-$[(CH_2)_2$—$N^nPr]$—, $(N^tBu_2)(Cp)$-M-$C_5H_3$-1-Me-3-$[(CH_2)_2$—$N^nPr]$—, $(OH)_2$-M-$C_5H_3$-1-Me-3-$[(CH_2)_2$—$N^nPr]$—, $(OMe)_2$-M-$C_5H_3$-1-Me-3-$[(CH_2)_2$—$N^nPr]$—, $(OEt)_2$-M-$C_5H_3$-1-Me-3-$[(CH_2)_2$—$N^nPr]$—, $(O^nPr)_2$-M-$C_5H_3$-1-Me-3-$[(CH_2)_2$—$N^nPr]$—, $(O^iPr)_2$-M-$C_5H_3$-1-Me-3-$[(CH_2)_2$—$N^nPr]$—, $(O^nBu)_2$-M-$C_5H_3$-1-Me-3-$[(CH_2)_2$—$N^nPr]$—, $(O^iBu_2$-M-$C_5H_3$-1-Me-3-$[(CH_2)_2$—$N^nPr]$—, $(O^tBu)_2$-M-$C_5H_3$-1-Me-3-$[(CH_2)_2$—$N^nPr]$—, $(O^sBu)_2$-M-$C_5H_3$-1-Me-3-$[(CH_2)_2$—$N^nPr]$—, $(NH_2)_2$-M-$C_5H_3$-1-Et-2-$[(CH_2)_2$—$N^nPr]$—, $(NMe_2)_2$-M-$C_5H_3$-1-Et-2-$[(CH_2)_2$—$N^nPr]$—, $(NEt_2)_2$-M-$C_5H_3$-1-Et-2-$[(CH_2)_2$—$N^nPr]$—, $(N^nPr_2)_2$-M-$C_5H_3$-1-Et-2-$[(CH_2)_2$—$N^nPr]$—, $(N^iPr_2)_2$-M-$C_5H_3$-1-Et-2-$[(CH_2)_2$—$N^nPr]$—, $(N^nBu_2)_2$-M-$C_5H_3$-1-Et-2-$[(CH_2)_2$—$N^nPr]$—, $(N^iBu_2)_2$-M-$C_5H_3$-1-Et-2-$[(CH_2)_2$—$N^nPr]$—, $(N^sBu_2)_2$-M-$C_5H_3$-1-Et-2-$[(CH_2)_2$—$N^nPr]$—, $(N^tBu_2)_2$-M-$C_5H_3$-1-Et-2-$[(CH_2)_2$—$N^nPr]$—, $(NH_2)(Cp)$-M-$C_5H_3$-1-Et-2-$[(CH_2)_2$—$N^nPr]$—, $(NMe_2)(Cp)$-M-$C_5H_3$-1-Et-2-$[(CH_2)_2$—$N^nPr]$—, $(NEt_2)(Cp)$-M-$C_5H_3$-1-Et-2-$[(CH_2)_2$—$N^nPr]$—, $(N^nPr_2)(Cp)$-M-$C_5H_3$-1-Et-2-$[(CH_2)_2$—$N^nPr]$—, $(N^iPr_2)(Cp)$-M-$C_5H_3$-1-Et-2-$[(CH_2)_2$—$N^nPr]$—, $(N^nBu_2)(Cp)$-M-$C_5H_3$-1-Et-2-$[(CH_2)_2$—$N^nPr]$—, $(N^iBu_2)(Cp)$-M-$C_5H_3$-1-Et-2-$[(CH_2)_2$—$N^nPr]$—, $(N^sBu_2)(Cp)$-M-$C_5H_3$-1-Et-2-$[(CH_2)_2$—$N^nPr]$—, $(N^tBu_2)(Cp)$-M-$C_5H_3$-1-Et-2-$[(CH_2)_2$—$N^nPr]$—, $(OH)_2$-M-$C_5H_3$-1-Et-2-$[(CH_2)_2$—$N^nPr]$—, $(OMe)_2$-M-$C_5H_3$-1-Et-2-$[(CH_2)_2$—$N^nPr]$—, $(OEt)_2$-M-$C_5H_3$-1-Et-2-$[(CH_2)_2$—$N^nPr]$—, $(O^nPr)_2$-M-$C_5H_3$-1-Et-2-$[(CH_2)_2$—$N^nPr]$—, $(O^iPr)_2$-M-$C_5H_3$-1-Et-2-$[(CH_2)_2$—$N^nPr]$—, $(O^nBu)_2$-M-$C_5H_3$-1-Et-2-$[(CH_2)_2$—$N^nPr]$—, $(O^iBu_2$-M-$C_5H_3$-1-Et-2-$[(CH_2)_2$—$N^nPr]$—, $(O^tBu)_2$-M-$C_5H_3$-1-Et-2-$[(CH_2)_2$—$N^nPr]$—, $(O^sBu)_2$-M-$C_5H_3$-1-Et-2-$[(CH_2)_2$—$N^nPr]$—, $(NH_2)_2$-M-$C_5H_3$-1-Et-3-$[(CH_2)_2$—$N^nPr]$—, $(NMe_2)_2$-M-$C_5H_3$-1-Et-3-$[(CH_2)_2$—$N^nPr]$—, $(NEt_2)_2$-M-$C_5H_3$-1-Et-3-$[(CH_2)_2$—$N^nPr]$—, $(N^nPr_2)_2$-M-$C_5H_3$-1-Et-3-$[(CH_2)_2$—$N^nPr]$—, $(N^iPr_2)_2$-M-$C_5H_3$-1-Et-3-$[(CH_2)_2$—$N^nPr]$—, $(N^nBu_2)_2$-M-$C_5H_3$-1-Et-3-$[(CH_2)_2$—$N^nPr]$—, $(N^iBu_2)_2$-M-$C_5H_3$-1-Et-3-$[(CH_2)_2$—$N^nPr]$—, $(N^sBu_2)_2$-M-$C_5H_3$-1-Et-3-$[(CH_2)_2$—$N^nPr]$—, $(N^tBu_2)_2$-M-$C_5H_3$-1-Et-3-$[(CH_2)_2$—$N^nPr]$—, $(NH_2)(Cp)$-M-$C_5H_3$-1-Et-3-$[(CH_2)_2$—$N^nPr]$—, $(NMe_2)(Cp)$-M-$C_5H_3$-1-Et-3-$[(CH_2)_2$—$N^nPr]$—, $(NEt_2)(Cp)$-M-$C_5H_3$-1-Et-3-$[(CH_2)_2$—$N^nPr]$—, $(N^nPr_2)(Cp)$-M-$C_5H_3$-1-Et-3-$[(CH_2)_2$—$N^nPr]$—, $(N^iPr_2)(Cp)$-M-$C_5H_3$-1-Et-3-$[(CH_2)_2$—$N^nPr]$—, $(N^nBu_2)(Cp)$-M-$C_5H_3$-1-Et-3-$[(CH_2)_2$—$N^nPr]$—, $(N^iBu_2)(Cp)$-M-$C_5H_3$-1-Et-3-$[(CH_2)_2$—$N^nPr]$—, $(N^sBu_2)(Cp)$-M-$C_5H_3$-1-Et-3-$[(CH_2)_2$—$N^nPr]$—, $(N^tBu_2)(Cp)$-M-$C_5H_3$-1-Et-3-$[(CH_2)_2$—$N^nPr]$—, $(OH)_2$-M-$C_5H_3$-1-Et-3-$[(CH_2)_2$—$N^nPr]$—, $(OMe)_2$-M-$C_5H_3$-1-Et-3-$[(CH_2)_2$—$N^nPr]$—, $(OEt)_2$-M-$C_5H_3$-1-Et-3-$[(CH_2)_2$—$N^nPr]$—, $(O^nPr)_2$-M-$C_5H_3$-1-Et-3-$[(CH_2)_2$—$N^nPr]$—, $(O^iPr)_2$-M-$C_5H_3$-1-Et-3-$[(CH_2)_2$—$N^nPr]$—, $(O^nBu)_2$-M-$C_5H_3$-1-Et-3-$[(CH_2)_2$—$N^nPr]$—, $(O^iBu_2$-M-$C_5H_3$-1-Et-3-$[(CH_2)_2$—$N^nPr]$—, $(O^tBu)_2$-M-$C_5H_3$-1-Et-3-$[(CH_2)_2$—$N^nPr]$—, $(O^sBu)_2$-M-$C_5H_3$-1-Et-3-$[(CH_2)_2$—$N^nPr]$—, $(NH_2)_2$-M-$C_5H_3$-1-$^i$Pr-2-$[(CH_2)_2$—$N^nPr]$—, $(NMe_2)_2$-M-$C_5H_3$-1-$^i$Pr-2-$[(CH_2)_2$—$N^nPr]$—, $(NEt_2)_2$-M-$C_5H_3$-1-$^i$Pr-2-$[(CH_2)_2$—$N^nPr]$—, $(N^nPr_2)_2$-M-$C_5H_3$-1-$^i$Pr-2-$[(CH_2)_2$—$N^nPr]$—, $(N^iPr_2)_2$-M-$C_5H_3$-1-$^i$Pr-2-$[(CH_2)_2$—$N^nPr]$—, $(N^nBu_2)_2$-M-$C_5H_3$-1-$^i$Pr-2-$[(CH_2)_2$—$N^nPr]$—, $(N^iBu_2)_2$-M-$C_5H_3$-1-$^i$Pr-2-$[(CH_2)_2$—$N^nPr]$—, $(N^sBu_2)_2$-M-$C_5H_3$-1-$^i$Pr-2-$[(CH_2)_2$—$N^nPr]$—, $(N^tBu_2)_2$-M-$C_5H_3$-1-$^i$Pr-2-$[(CH_2)_2$—$N^nPr]$—, $(NH_2)(Cp)$-M-$C_5H_3$-1-$^i$Pr-2-$[(CH_2)_2$—$N^nPr]$—, $(NMe_2)(Cp)$-M-$C_5H_3$-1-$^i$Pr-2-$[(CH_2)_2$—$N^nPr]$—, $(NEt_2)(Cp)$-M-$C_5H_3$-1-$^i$Pr-2-$[(CH_2)_2$—$N^nPr]$—, $(N^nPr_2)(Cp)$-M-$C_5H_3$-1-$^i$Pr-2-$[(CH_2)_2$—$N^nPr]$—, $(N^iPr_2)(Cp)$-M-$C_5H_3$-1-$^i$Pr-2-$[(CH_2)_2$—$N^nPr]$—, $(N^nBu_2)(Cp)$-M-$C_5H_3$-1-$^i$Pr-2-$[(CH_2)_2$—$N^nPr]$—, $(N^iBu_2)(Cp)$-M-$C_5H_3$-1-$^i$Pr-2-$[(CH_2)_2$—$N^nPr]$—, $(N^sBu_2)(Cp)$-M-$C_5H_3$-1-$^i$Pr-2-$[(CH_2)_2$—$N^nPr]$—, $(N^tBu_2)(Cp)$-M-$C_5H_3$-1-$^i$Pr-2-$[(CH_2)_2$—$N^nPr]$—, $(OH)_2$-M-$C_5H_3$-1-$^i$Pr-2-$[(CH_2)_2$—$N^nPr]$—, $(OMe)_2$-M-$C_5H_3$-1-$^i$Pr-2-$[(CH_2)_2$—$N^nPr]$—, $(OEt)_2$-M-$C_5H_3$-1-$^i$Pr-2-$[(CH_2)_2$—$N^nPr]$—, $(O^nPr)_2$-M-$C_5H_3$-1-$^i$Pr-2-$[(CH_2)_2$—$N^nPr]$—, $(O^iPr)_2$-M-$C_5H_3$-1-$^i$Pr-2-$[(CH_2)_2$—$N^nPr]$—, $(O^nBu)_2$-M-$C_5H_3$-1-$^i$Pr-2-$[(CH_2)_2$—$N^nPr]$—, $(O^iBu_2$-M-$C_5H_3$-1-$^i$Pr-2-$[(CH_2)_2$—$N^nPr]$—, $(O^tBu)_2$-M-$C_5H_3$-1-$^i$Pr-2-$[(CH_2)_2$—$N^nPr]$—, $(O^sBu)_2$-M-$C_5H_3$-1-$^i$Pr-2-$[(CH_2)_2$—$N^nPr]$—, $(NH_2)_2$-M-$C_5H_3$-1-$^i$Pr-3-$[(CH_2)_2$—$N^nPr]$—, $(NMe_2)_2$-M-$C_5H_3$-1-$^i$Pr-3-$[(CH_2)_2$—$N^nPr]$—, $(NEt_2)_2$-M-$C_5H_3$-1-$^i$Pr-3-$[(CH_2)_2$—$N^nPr]$—, $(N^nPr_2)_2$-M-$C_5H_3$-1-$^i$Pr-3-$[(CH_2)_2$—$N^nPr]$—, $(N^iPr_2)_2$-M-$C_5H_3$-1-$^i$Pr-3-$[(CH_2)_2$—$N^nPr]$—, $(N^nBu_2)_2$-M-$C_5H_3$-1-$^i$Pr-3-$[(CH_2)_2$—$N^nPr]$—, $(N^iBu_2)_2$-M-$C_5H_3$-1-$^i$Pr-3-$[(CH_2)_2$—$N^nPr]$—, $(N^sBu_2)_2$-M-$C_5H_3$-1-$^i$Pr-3-$[(CH_2)_2$—$N^nPr]$—, $(N^tBu_2)_2$-M-$C_5H_3$-1-$^i$Pr-3-$[(CH_2)_2$—$N^nPr]$—, $(NH_2)(Cp)$-M-$C_5H_3$-1-$^i$Pr-3-$[(CH_2)_2$—$N^nPr]$—, $(NMe_2)(Cp)$-M-$C_5H_3$-1-$^i$Pr-3-$[(CH_2)_2$—$N^nPr]$—, $(NEt_2)(Cp)$-M-$C_5H_3$-1-$^i$Pr-3-$[(CH_2)_2$—$N^nPr]$—, $(N^nPr_2)(Cp)$-M-$C_5H_3$-1-$^i$Pr-3-$[(CH_2)_2$—$N^nPr]$—, $(N^iPr_2)(Cp)$-M-$C_5H_3$-1-$^i$Pr-3-$[(CH_2)_2$—$N^nPr]$—, $(N^nBu_2)(Cp)$-M-$C_5H_3$-1-$^i$Pr-3-$[(CH_2)_2$—$N^nPr]$—, $(N^iBu_2)(Cp)$-M-$C_5H_3$-1-$^i$Pr-3-$[(CH_2)_2$—$N^nPr]$—, $(N^sBu_2)(Cp)$-M-$C_5H_3$-1-$^i$Pr-3-$[(CH_2)_2$—$N^nPr]$—, $(N^tBu_2)(Cp)$-M-$C_5H_3$-1-$^i$Pr-3-$[(CH_2)_2$—$N^nPr]$—, $(OH)_2$-M-$C_5H_3$-1-$^i$Pr-3-$[(CH_2)_2$—$N^nPr]$—, $(OMe)_2$-M-$C_5H_3$-1-$^i$Pr-3-$[(CH_2)_2$—$N^nPr]$—, $(OEt)_2$-M-$C_5H_3$-1-$^i$Pr-3-$[(CH_2)_2$—$N^nPr]$—, $(O^nPr)_2$-M-$C_5H_3$-1-$^i$Pr-3-$[(CH_2)_2$—$N^nPr]$—, $(O^iPr)_2$-M-$C_5H_3$-1-$^i$Pr-3-$[(CH_2)_2$—$N^nPr]$—, $(O^nBu)_2$-M-$C_5H_3$-1-$^i$Pr-3-$[(CH_2)_2$—$N^nPr]$—, $(O^iBu_2$-M-$C_5H_3$-1-$^i$Pr-3-$[(CH_2)_2$—$N^nPr]$—, $(O^tBu)_2$-M-$C_5H_3$-1-$^i$Pr-3-$[(CH_2)_2$—$N^nPr]$—, $(O^sBu)_2$-M-$C_5H_3$-1-$^i$Pr-3-$[(CH_2)_2$—$N^nPr]$—, $(NH_2)_2$-M-$C_5H_3$-1-$^t$Bu-2-$[(CH_2)_2$—$N^nPr]$—, $(NMe_2)_2$-M-$C_5H_3$-1-$^t$Bu-2-$[(CH_2)_2$—$N^nPr]$—, $(NEt_2)_2$-M-$C_5H_3$-1-$^t$Bu-2-$[(CH_2)_2$—$N^nPr]$—, $(N^nPr_2)_2$-M-$C_5H_3$-1-$^t$Bu-2-$[(CH_2)_2$—$N^nPr]$—, $(N^iPr_2)_2$-M-$C_5H_3$-1-$^t$Bu-2-$[(CH_2)_2$—$N^nPr]$—, $(N^nBu_2)_2$-M-$C_5H_3$-1-$^t$Bu-2-$[(CH_2)_2$—$N^nPr]$—, $(N^iBu_2)_2$-M-$C_5H_3$-1-$^t$Bu-2-$[(CH_2)_2$—$N^nPr]$—, $(N^sBu_2)_2$-M-$C_5H_3$-1-$^t$Bu-2-$[(CH_2)_2$—$N^nPr]$—, $(N^tBu_2)_2$-M-$C_5H_3$-1-$^t$Bu-2-$[(CH_2)_2$—$N^nPr]$—, $(NH_2)(Cp)$-M-$C_5H_3$-1-$^t$Bu-2-$[(CH_2)_2$—$N^nPr]$—, $(NMe_2)(Cp)$-M-$C_5H_3$-1-$^t$Bu-2-$[(CH_2)_2$—$N^nPr]$—, $(NEt_2)(Cp)$-M-$C_5H_3$-1-$^t$Bu-2-$[(CH_2)_2$—$N^nPr]$—, $(N^nPr_2)(Cp)$-M-$C_5H_3$-1-$^t$Bu-2-$[(CH_2)_2$—$N^nPr]$—, $(N^iPr_2)(Cp)$-M-$C_5H_3$-1-$^t$Bu-2-$[(CH_2)_2$—$N^nPr]$—, $(N^nBu_2)(Cp)$-M-$C_5H_3$-1-$^t$Bu-2-$[(CH_2)_2$—$N^nPr]$—, $(N^iBu_2)(Cp)$-M-$C_5H_3$-1-$^t$Bu-2-$[(CH_2)_2$—$N^nPr]$—, $(N^sBu_2)(Cp)$-M-$C_5H_3$-1-$^t$Bu-2-$[(CH_2)_2$—$N^nPr]$—, $(N^tBu_2)(Cp)$-M-$C_5H_3$-1-$^t$Bu-2-$[(CH_2)_2$—$N^nPr]$—, $(OH)_2$-M-$C_5H_3$-1-$^t$Bu-2-$[(CH_2)_2$—$N^nPr]$—, $(OMe)_2$-M-$C_5H_3$-1-$^t$Bu-2-$[(CH_2)_2$—$N^nPr]$—, $(OEt)_2$-M-$C_5H_3$-1-$^t$Bu-2-$[(CH_2)_2$—$N^nPr]$—, $(O^nPr)_2$-M-$C_5H_3$-1-$^t$Bu-2-$[(CH_2)_2$—$N^nPr]$—, $(O^iPr)_2$-M-$C_5H_3$-1-$^t$Bu-

2-[(CH$_2$)$_2$—N$^n$Pr]—, (O$^n$Bu)$_2$-M-C$_5$H$_3$-1-$^t$Bu-2-[(CH$_2$)$_2$—N$^n$Pr]—, (O$^i$Bu$_2$-M-C$_5$H$_3$-1-$^t$Bu-2-[(CH$_2$)$_2$—N$^n$Pr]—, (O$^t$Bu)$_2$-M-C$_5$H$_3$-1-$^t$Bu-2-[(CH$_2$)$_2$—N$^n$Pr]—, (O$^s$Bu)$_2$-M-C$_5$H$_3$-1-$^t$Bu-2-[(CH$_2$)$_2$—N$^n$Pr]—, (NH$_2$)$_2$-M-C$_5$H$_3$-1-$^t$Bu-3-[(CH$_2$)$_2$—N$^n$Pr]—, (NMe$_2$)$_2$-M-C$_5$H$_3$-1-$^t$Bu-3-[(CH$_2$)$_2$—N$^n$Pr]—, (NEt$_2$)$_2$-M-C$_5$H$_3$-1-$^t$Bu-3-[(CH$_2$)$_2$—N$^n$Pr]—, (N$^n$Pr$_2$)$_2$-M-C$_5$H$_3$-1-$^t$Bu-3-[(CH$_2$)$_2$—N$^n$Pr]—, (N$^i$Pr$_2$)$_2$-M-C$_5$H$_3$-1-$^t$Bu-3-[(CH$_2$)$_2$—N$^n$Pr]—, (N$^n$Bu$_2$)$_2$-M-C$_5$H$_3$-1-$^t$Bu-3-[(CH$_2$)$_2$—N$^n$Pr]—, (N$^i$Bu$_2$)$_2$-M-C$_5$H$_3$-1-$^t$Bu-3-[(CH$_2$)$_2$—N$^n$Pr]—, (N$^s$Bu$_2$)$_2$-M-C$_5$H$_3$-1-$^t$Bu-3-[(CH$_2$)$_2$—N$^n$Pr]—, (N$^t$Bu$_2$)$_2$-M-C$_5$H$_3$-1-$^t$Bu-3-[(CH$_2$)$_2$—N$^n$Pr]—, (NH$_2$)(Cp)-M-C$_5$H$_3$-1-$^t$Bu-3-[(CH$_2$)$_2$—N$^n$Pr]—, (NMe$_2$)(Cp)-M-C$_5$H$_3$-1-$^t$Bu-3-[(CH$_2$)$_2$—N$^n$Pr]—, (NEt$_2$)(Cp)-M-C$_5$H$_3$-1-$^t$Bu-3-[(CH$_2$)$_2$—N$^n$Pr]—, (N$^n$Pr$_2$)(Cp)-M-C$_5$H$_3$-1-$^t$Bu-3-[(CH$_2$)$_2$—N$^n$Pr]—, (N$^i$Pr$_2$)(Cp)-M-C$_5$H$_3$-1-$^t$Bu-3-[(CH$_2$)$_2$—N$^n$Pr]—, (N$^n$Bu$_2$)(Cp)-M-C$_5$H$_3$-1-$^t$Bu-3-[(CH$_2$)$_2$—N$^n$Pr]—, (N$^i$Bu$_2$)(Cp)-M-C$_5$H$_3$-1-$^t$Bu-3-[(CH$_2$)$_2$—N$^n$Pr]—, (N$^s$Bu$_2$)(Cp)-M-C$_5$H$_3$-1-$^t$Bu-3-[(CH$_2$)$_2$—N$^n$Pr]—, (N$^t$Bu$_2$)(Cp)-M-C$_5$H$_3$-1-$^t$Bu-3-[(CH$_2$)$_2$—N$^n$Pr]—, (OH)$_2$-M-C$_5$H$_3$-1-$^t$Bu-3-[(CH$_2$)$_2$—N$^n$Pr]—, (OMe)$_2$-M-C$_5$H$_3$-1-$^t$Bu-3-[(CH$_2$)$_2$—N$^n$Pr]—, (OEt)$_2$-M-C$_5$H$_3$-1-$^t$Bu-3-[(CH$_2$)$_2$—N$^n$Pr]—, (O$^n$Pr)$_2$-M-C$_5$H$_3$-1-$^t$Bu-3-[(CH$_2$)$_2$—N$^n$Pr]—, (O$^i$Pr)$_2$-M-C$_5$H$_3$-1-$^t$Bu-3-[(CH$_2$)$_2$—N$^n$Pr]—, (O$^n$Bu)$_2$-M-C$_5$H$_3$-1-$^t$Bu-3-[(CH$_2$)$_2$—N$^n$Pr]—, (O$^i$Bu$_2$-M-C$_5$H$_3$-1-$^t$Bu-3-[(CH$_2$)$_2$—N$^n$Pr]—, (O$^t$Bu)$_2$-M-C$_5$H$_3$-1-$^t$Bu-3-[(CH$_2$)$_2$—N$^n$Pr]—, (O$^s$Bu)$_2$-M-C$_5$H$_3$-1-$^t$Bu-3-[(CH$_2$)$_2$—N$^n$Pr]—, (NH$_2$)$_2$-M-C$_5$H$_3$-1-Me-2-[(CH$_2$)$_2$—N$^n$Bu]-, (NMe$_2$)$_2$-M-C$_5$H$_3$-1-Me-2-[(CH$_2$)$_2$—N$^n$Bu]-, (NEt$_2$)$_2$-M-C$_5$H$_3$-1-Me-2-[(CH$_2$)$_2$—N$^n$Bu]-, (N$^n$Pr$_2$)$_2$-M-C$_5$H$_3$-1-Me-2-[(CH$_2$)$_2$—N$^n$Bu]-, (N$^i$Pr$_2$)$_2$-M-C$_5$H$_3$-1-Me-2-[(CH$_2$)$_2$—N$^n$Bu]-, (N$^n$Bu$_2$)$_2$-M-C$_5$H$_3$-1-Me-2-[(CH$_2$)$_2$—N$^n$Bu]-, (N$^i$Bu$_2$)$_2$-M-C$_5$H$_3$-1-Me-2-[(CH$_2$)$_2$—N$^n$Bu]-, (N$^s$Bu$_2$)$_2$-M-C$_5$H$_3$-1-Me-2-[(CH$_2$)$_2$—N$^n$Bu]-, (N$^t$Bu$_2$)$_2$-M-C$_5$H$_3$-1-Me-2-[(CH$_2$)$_2$—N$^n$Bu]-, (NH$_2$)(Cp)-M-C$_5$H$_3$-1-Me-2-[(CH$_2$)$_2$—N$^n$Bu]-, (NMe$_2$)(Cp)-M-C$_5$H$_3$-1-Me-2-[(CH$_2$)$_2$—N$^n$Bu]-, (NEt$_2$)(Cp)-M-C$_5$H$_3$-1-Me-2-[(CH$_2$)$_2$—N$^n$Bu]-, (N$^n$Pr$_2$)(Cp)-M-C$_5$H$_3$-1-Me-2-[(CH$_2$)$_2$—N$^n$Bu]-, (N$^i$Pr$_2$)(Cp)-M-C$_5$H$_3$-1-Me-2-[(CH$_2$)$_2$—N$^n$Bu]-, (N$^n$Bu$_2$)(Cp)-M-C$_5$H$_3$-1-Me-2-[(CH$_2$)$_2$—N$^n$Bu]-, (N$^i$Bu$_2$)(Cp)-M-C$_5$H$_3$-1-Me-2-[(CH$_2$)$_2$—N$^n$Bu]-, (N$^s$Bu$_2$)(Cp)-M-C$_5$H$_3$-1-Me-2-[(CH$_2$)$_2$—N$^n$Bu]-, (N$^t$Bu$_2$)(Cp)-M-C$_5$H$_3$-1-Me-2-[(CH$_2$)$_2$—N$^n$Bu]-, (OH)$_2$-M-C$_5$H$_3$-1-Me-2-[(CH$_2$)$_2$—N$^n$Bu]-, (OMe)$_2$-M-C$_5$H$_3$-1-Me-2-[(CH$_2$)$_2$—N$^n$Bu]-, (OEt)$_2$-M-C$_5$H$_3$-1-Me-2-[(CH$_2$)$_2$—N$^n$Bu]-, (O$^n$Pr)$_2$-M-C$_5$H$_3$-1-Me-2-[(CH$_2$)$_2$—N$^n$Bu]-, (O$^i$Pr)$_2$-M-C$_5$H$_3$-1-Me-2-[(CH$_2$)$_2$—N$^n$Bu]-, (O$^n$Bu)$_2$-M-C$_5$H$_3$-1-Me-2-[(CH$_2$)$_2$—N$^n$Bu]-, (O$^i$Bu$_2$-M-C$_5$H$_3$-1-Me-2-[(CH$_2$)$_2$—N$^n$Bu]-, (O$^t$Bu)$_2$-M-C$_5$H$_3$-1-Me-2-[(CH$_2$)$_2$—N$^n$Bu]-, (O$^s$Bu)$_2$-M-C$_5$H$_3$-1-Me-2-[(CH$_2$)$_2$—N$^n$Bu]-, (NH$_2$)$_2$-M-C$_5$H$_3$-1-Me-3-[(CH$_2$)$_2$—N$^n$Bu]-, (NMe$_2$)$_2$-M-C$_5$H$_3$-1-Me-3-[(CH$_2$)$_2$—N$^n$Bu]-, (NEt$_2$)$_2$-M-C$_5$H$_3$-1-Me-3-[(CH$_2$)$_2$—N$^n$Bu]-, (N$^n$Pr$_2$)$_2$-M-C$_5$H$_3$-1-Me-3-[(CH$_2$)$_2$—N$^n$Bu]-, (N$^i$Pr$_2$)$_2$-M-C$_5$H$_3$-1-Me-3-[(CH$_2$)$_2$—N$^n$Bu]-, (N$^n$Bu$_2$)$_2$-M-C$_5$H$_3$-1-Me-3-[(CH$_2$)$_2$—N$^n$Bu]-, (N$^i$Bu$_2$)$_2$-M-C$_5$H$_3$-1-Me-3-[(CH$_2$)$_2$—N$^n$Bu]-, (N$^s$Bu$_2$)$_2$-M-C$_5$H$_3$-1-Me-3-[(CH$_2$)$_2$—N$^n$Bu]-, (N$^t$Bu$_2$)$_2$-M-C$_5$H$_3$-1-Me-3-[(CH$_2$)$_2$—N$^n$Bu]-, (NH$_2$)(Cp)-M-C$_5$H$_3$-1-Me-3-[(CH$_2$)$_2$—N$^n$Bu]-, (NMe$_2$)(Cp)-M-C$_5$H$_3$-1-Me-3-[(CH$_2$)$_2$—N$^n$Bu]-, (NEt$_2$)(Cp)-M-C$_5$H$_3$-1-Me-3-[(CH$_2$)$_2$—N$^n$Bu]-, (N$^n$Pr$_2$)(Cp)-M-C$_5$H$_3$-1-Me-3-[(CH$_2$)$_2$—N$^n$Bu]-, (N$^i$Pr$_2$)(Cp)-M-C$_5$H$_3$-1-Me-3-[(CH$_2$)$_2$—N$^n$Bu]-, (N$^n$Bu$_2$)(Cp)-M-C$_5$H$_3$-1-Me-3-[(CH$_2$)$_2$—N$^n$Bu]-, (N$^i$Bu$_2$)(Cp)-M-C$_5$H$_3$-1-Me-3-[(CH$_2$)$_2$—N$^n$Bu]-, (N$^s$Bu$_2$)(Cp)-M-C$_5$H$_3$-1-Me-3-[(CH$_2$)$_2$—N$^n$Bu]-, (N$^t$Bu$_2$)(Cp)-M-C$_5$H$_3$-1-Me-3-[(CH$_2$)$_2$—N$^n$Bu]-, (OH)$_2$-M-C$_5$H$_3$-1-Me-3-[(CH$_2$)$_2$—N$^n$Bu]-, (OMe)$_2$-M-C$_5$H$_3$-1-Me-3-[(CH$_2$)$_2$—N$^n$Bu]-, (OEt)$_2$-M-C$_5$H$_3$-1-Me-3-[(CH$_2$)$_2$—N$^n$Bu]-, (O$^n$Pr)$_2$-M-C$_5$H$_3$-1-Me-3-[(CH$_2$)$_2$—N$^n$Bu]-, (O$^i$Pr)$_2$-M-C$_5$H$_3$-1-Me-3-[(CH$_2$)$_2$—N$^n$Bu]-, (O$^n$Bu)$_2$-M-C$_5$H$_3$-1-Me-3-[(CH$_2$)$_2$—N$^n$Bu]-, (O$^i$Bu$_2$-M-C$_5$H$_3$-1-Me-3-[(CH$_2$)$_2$—N$^n$Bu]-, (O$^t$Bu)$_2$-M-C$_5$H$_3$-1-Me-3-[(CH$_2$)$_2$—N$^n$Bu]-, (O$^s$Bu)$_2$-M-C$_5$H$_3$-1-Me-3-[(CH$_2$)$_2$—N$^n$Bu]-, (NH$_2$)$_2$-M-C$_5$H$_3$-1-Et-2-[(CH$_2$)$_2$—N$^n$Bu]-, (NMe$_2$)$_2$-M-C$_5$H$_3$-1-Et-2-[(CH$_2$)$_2$—N$^n$Bu]-, (NEt$_2$)$_2$-M-C$_5$H$_3$-1-Et-2-[(CH$_2$)$_2$—N$^n$Bu]-, (N$^n$Pr$_2$)$_2$-M-C$_5$H$_3$-1-Et-2-[(CH$_2$)$_2$—N$^n$Bu]-, (N$^i$Pr$_2$)$_2$-M-C$_5$H$_3$-1-Et-2-[(CH$_2$)$_2$—N$^n$Bu]-, (N$^n$Bu$_2$)$_2$-M-C$_5$H$_3$-1-Et-2-[(CH$_2$)$_2$—N$^n$Bu]-, (N$^i$Bu$_2$)$_2$-M-C$_5$H$_3$-1-Et-2-[(CH$_2$)$_2$—N$^n$Bu]-, (N$^s$Bu$_2$)$_2$-M-C$_5$H$_3$-1-Et-2-[(CH$_2$)$_2$—N$^n$Bu]-, (N$^t$Bu$_2$)$_2$-M-C$_5$H$_3$-1-Et-2-[(CH$_2$)$_2$—N$^n$Bu]-, (NH$_2$)(Cp)-M-C$_5$H$_3$-1-Et-2-[(CH$_2$)$_2$—N$^n$Bu]-, (NMe$_2$)(Cp)-M-C$_5$H$_3$-1-Et-2-[(CH$_2$)$_2$—N$^n$Bu]-, (NEt$_2$)(Cp)-M-C$_5$H$_3$-1-Et-2-[(CH$_2$)$_2$—N$^n$Bu]-, (N$^n$Pr$_2$)(Cp)-M-C$_5$H$_3$-1-Et-2-[(CH$_2$)$_2$—N$^n$Bu]-, (N$^i$Pr$_2$)(Cp)-M-C$_5$H$_3$-1-Et-2-[(CH$_2$)$_2$—N$^n$Bu]-, (N$^n$Bu$_2$)(Cp)-M-C$_5$H$_3$-1-Et-2-[(CH$_2$)$_2$—N$^n$Bu]-, (N$^i$Bu$_2$)(Cp)-M-C$_5$H$_3$-1-Et-2-[(CH$_2$)$_2$—N$^n$Bu]-, (N$^s$Bu$_2$)(Cp)-M-C$_5$H$_3$-1-Et-2-[(CH$_2$)$_2$—N$^n$Bu]-, (N$^t$Bu$_2$)(Cp)-M-C$_5$H$_3$-1-Et-2-[(CH$_2$)$_2$—N$^n$Bu]-, (OH)$_2$-M-C$_5$H$_3$-1-Et-2-[(CH$_2$)$_2$—N$^n$Bu]-, (OMe)$_2$-M-C$_5$H$_3$-1-Et-2-[(CH$_2$)$_2$—N$^n$Bu]-, (OEt)$_2$-M-C$_5$H$_3$-1-Et-2-[(CH$_2$)$_2$—N$^n$Bu]-, (O$^n$Pr)$_2$-M-C$_5$H$_3$-1-Et-2-[(CH$_2$)$_2$—N$^n$Bu]-, (O$^i$Pr)$_2$-M-C$_5$H$_3$-1-Et-2-[(CH$_2$)$_2$—N$^n$Bu]-, (O$^n$Bu)$_2$-M-C$_5$H$_3$-1-Et-2-[(CH$_2$)$_2$—N$^n$Bu]-, (O$^i$Bu$_2$-M-C$_5$H$_3$-1-Et-2-[(CH$_2$)$_2$—N$^n$Bu]-, (O$^t$Bu)$_2$-M-C$_5$H$_3$-1-Et-2-[(CH$_2$)$_2$—N$^n$Bu]-, (O$^s$Bu)$_2$-M-C$_5$H$_3$-1-Et-2-[(CH$_2$)$_2$—N$^n$Bu]-, (NH$_2$)$_2$-M-C$_5$H$_3$-1-Et-3-[(CH$_2$)$_2$—N$^n$Bu]-, (NMe$_2$)$_2$-M-C$_5$H$_3$-1-Et-3-[(CH$_2$)$_2$—N$^n$Bu]-, (NEt$_2$)$_2$-M-C$_5$H$_3$-1-Et-3-[(CH$_2$)$_2$—N$^n$Bu]-, (N$^n$Pr$_2$)$_2$-M-C$_5$H$_3$-1-Et-3-[(CH$_2$)$_2$—N$^n$Bu]-, (N$^i$Pr$_2$)$_2$-M-C$_5$H$_3$-1-Et-3-[(CH$_2$)$_2$—N$^n$Bu]-, (N$^n$Bu$_2$)$_2$-M-C$_5$H$_3$-1-Et-3-[(CH$_2$)$_2$—N$^n$Bu]-, (N$^i$Bu$_2$)$_2$-M-C$_5$H$_3$-1-Et-3-[(CH$_2$)$_2$—N$^n$Bu]-, (N$^s$Bu$_2$)$_2$-M-C$_5$H$_3$-1-Et-3-[(CH$_2$)$_2$—N$^n$Bu]-, (N$^t$Bu$_2$)$_2$-M-C$_5$H$_3$-1-Et-3-[(CH$_2$)$_2$—N$^n$Bu]-, (NH$_2$)(Cp)-M-C$_5$H$_3$-1-Et-3-[(CH$_2$)$_2$—N$^n$Bu]-, (NMe$_2$)(Cp)-M-C$_5$H$_3$-1-Et-3-[(CH$_2$)$_2$—N$^n$Bu]-, (NEt$_2$)(Cp)-M-C$_5$H$_3$-1-Et-3-[(CH$_2$)$_2$—N$^n$Bu]-, (N$^n$Pr$_2$)(Cp)-M-C$_5$H$_3$-1-Et-3-[(CH$_2$)$_2$—N$^n$Bu]-, (N$^i$Pr$_2$)(Cp)-M-C$_5$H$_3$-1-Et-3-[(CH$_2$)$_2$—N$^n$Bu]-, (N$^n$Bu$_2$)(Cp)-M-C$_5$H$_3$-1-Et-3-[(CH$_2$)$_2$—N$^n$Bu]-, (N$^i$Bu$_2$)(Cp)-M-C$_5$H$_3$-1-Et-3-[(CH$_2$)$_2$—N$^n$Bu]-, (N$^s$Bu$_2$)(Cp)-M-C$_5$H$_3$-1-Et-3-[(CH$_2$)$_2$—N$^n$Bu]-, (N$^t$Bu$_2$)(Cp)-M-C$_5$H$_3$-1-Et-3-[(CH$_2$)$_2$—N$^n$Bu]-, (OH)$_2$-M-C$_5$H$_3$-1-Et-3-[(CH$_2$)$_2$—N$^n$Bu]-, (OMe)$_2$-M-C$_5$H$_3$-1-Et-3-[(CH$_2$)$_2$—N$^n$Bu]-, (OEt)$_2$-M-C$_5$H$_3$-1-Et-3-[(CH$_2$)$_2$—N$^n$Bu]-, (O$^n$Pr)$_2$-M-C$_5$H$_3$-1-Et-3-[(CH$_2$)$_2$—N$^n$Bu]-, (O$^i$Pr)$_2$-M-C$_5$H$_3$-1-Et-3-[(CH$_2$)$_2$—N$^n$Bu]-, (O$^n$Bu)$_2$-M-C$_5$H$_3$-1-Et-3-[(CH$_2$)$_2$—N$^n$Bu]-, (O$^i$Bu$_2$-M-C$_5$H$_3$-1-Et-3-[(CH$_2$)$_2$—N$^n$Bu]-, (O$^t$Bu)$_2$-M-C$_5$H$_3$-1-Et-3-[(CH$_2$)$_2$—N$^n$Bu]-, (O$^s$Bu)$_2$-M-C$_5$H$_3$-1-Et-3-[(CH$_2$)$_2$—N$^n$Bu]-, (NH$_2$)$_2$-M-C$_5$H$_3$-1-$^i$Pr-2-[(CH$_2$)$_2$—N$^n$Bu]-, (NMe$_2$)$_2$-M-C$_5$H$_3$-1-$^i$Pr-2-[(CH$_2$)$_2$—N$^n$Bu]-, (NEt$_2$)$_2$-M-C$_5$H$_3$-1-$^i$Pr-2-[(CH$_2$)$_2$—N$^n$Bu]-, (N$^n$Pr$_2$)$_2$-M-C$_5$H$_3$-1-$^i$Pr-2-[(CH$_2$)$_2$—N$^n$Bu]-, (N$^i$Pr$_2$)$_2$-M-C$_5$H$_3$-1-$^i$Pr-2-[(CH$_2$)$_2$—N$^n$Bu]-, (N$^n$Bu$_2$)$_2$-M-C$_5$H$_3$-1-$^i$Pr-2-[(CH$_2$)$_2$—N$^n$Bu]-, (N$^i$Bu$_2$)$_2$-M-C$_5$H$_3$-1-$^i$Pr-2-[(CH$_2$)$_2$—N$^n$Bu]-, (N$^s$Bu$_2$)$_2$-M-C$_5$H$_3$-1-$^i$Pr-2-[(CH$_2$)$_2$—N$^n$Bu]-, (N$^t$Bu$_2$)$_2$-M-C$_5$H$_3$-1-$^i$Pr-2-[(CH$_2$)$_2$—N$^n$Bu]-, (NH$_2$)(Cp)-M-C$_5$H$_3$-1-$^i$Pr-2-[(CH$_2$)$_2$—N$^n$Bu]-, (NMe$_2$)(Cp)-M-C$_5$H$_3$-1-$^i$Pr-2-[(CH$_2$)$_2$—N$^n$Bu]-, (NEt$_2$)(Cp)-M-C$_5$H$_3$-1-$^i$Pr-2-[(CH$_2$)$_2$—N$^n$Bu]-, (N$^n$Pr$_2$)(Cp)-M-C$_5$H$_3$-1-$^i$Pr-2-[(CH$_2$)$_2$—N$^n$Bu]-, (N$^i$Pr$_2$)(Cp)-M-C$_5$H$_3$-1-$^i$Pr-2-[(CH$_2$)$_2$—N$^n$Bu]-, (N$^n$Bu$_2$)(Cp)-M-C$_5$H$_3$-1-$^i$Pr-2-[(CH$_2$)$_2$—N$^n$Bu]-, (N$^i$Bu$_2$)(Cp)-M-C$_5$H$_3$-1-$^i$Pr-2-[(CH$_2$)$_2$—N$^n$Bu]-, (N$^s$Bu$_2$)(Cp)-M-C$_5$H$_3$-1-$^i$Pr-2-[(CH$_2$)$_2$—N$^n$Bu]-, (N$^t$Bu$_2$)(Cp)-M-C$_5$H$_3$-1-$^i$Pr-2-[(CH$_2$)$_2$—N$^n$Bu]-, (OH)$_2$-M-C$_5$H$_3$-1-$^i$Pr-2-[(CH$_2$)$_2$—N$^n$Bu]-, (OMe)$_2$-M-C$_5$H$_3$-1-$^i$Pr-2-[(CH$_2$)$_2$—N$^n$Bu]-, (OEt)$_2$-M-C$_5$H$_3$-1-$^i$Pr-2-[(CH$_2$)$_2$—N$^n$Bu]-, (O$^n$Pr)$_2$-M-C$_5$H$_3$-1-$^i$Pr-2-[(CH$_2$)$_2$—N$^n$Bu]-, (O$^i$Pr)$_2$-M-C$_5$H$_3$-1-$^i$Pr-2-

[(CH$_2$)$_2$—N$^n$Bu]-, (O$^n$Bu)$_2$-M-C$_5$H$_3$-1-$^i$Pr-2-[(CH$_2$)$_2$—N$^n$Bu]-, (O$^i$Bu$_2$-M-C$_5$H$_3$-1-$^i$Pr-2-[(CH$_2$)$_2$—N$^n$Bu]-, (O$^t$Bu)$_2$-M-C$_5$H$_3$-1-$^i$Pr-2-[(CH$_2$)$_2$—N$^n$Bu]-, (O$^s$Bu)$_2$-M-C$_5$H$_3$-1-$^i$Pr-2-[(CH$_2$)$_2$—N$^n$Bu]-, (NH$_2$)$_2$-M-C$_5$H$_3$-1-$^i$Pr-3-[(CH$_2$)$_2$—N$^n$Bu]-, (NMe$_2$)$_2$-M-C$_5$H$_3$-1-$^i$Pr-3-[(CH$_2$)$_2$—N$^n$Bu]-, (NEt$_2$)$_2$-M-C$_5$H$_3$-1-$^i$Pr-3-[(CH$_2$)$_2$—N$^n$Bu]-, (N$^n$Pr$_2$)$_2$-M-C$_5$H$_3$-1-$^i$Pr-3-[(CH$_2$)$_2$—N$^n$Bu]-, (N$^i$Pr$_2$)$_2$-M-C$_5$H$_3$-1-$^i$Pr-3-[(CH$_2$)$_2$—N$^n$Bu]-, (N$^n$Bu$_2$)$_2$-M-C$_5$H$_3$-1-$^i$Pr-3-[(CH$_2$)$_2$—N$^n$Bu]-, (N$^i$Bu$_2$)$_2$-M-C$_5$H$_3$-1-$^i$Pr-3-[(CH$_2$)$_2$—N$^n$Bu]-, (N$^s$Bu$_2$)$_2$-M-C$_5$H$_3$-1-$^i$Pr-3-[(CH$_2$)$_2$—N$^n$Bu]-, (N$^t$Bu$_2$)$_2$-M-C$_5$H$_3$-1-$^i$Pr-3-[(CH$_2$)$_2$—N$^n$Bu]-, (NH$_2$)(Cp)-M-C$_5$H$_3$-1-$^i$Pr-3-[(CH$_2$)$_2$—N$^n$Bu]-, (NMe$_2$)(Cp)-M-C$_5$H$_3$-1-$^i$Pr-3-[(CH$_2$)$_2$—N$^n$Bu]-, (NEt$_2$)(Cp)-M-C$_5$H$_3$-1-$^i$Pr-3-[(CH$_2$)$_2$—N$^n$Bu]-, (N$^n$Pr$_2$)(Cp)-M-C$_5$H$_3$-1-$^i$Pr-3-[(CH$_2$)$_2$—N$^n$Bu]-, (N$^i$Pr$_2$)(Cp)-M-C$_5$H$_3$-1-$^i$Pr-3-[(CH$_2$)$_2$—N$^n$Bu]-, (N$^n$Bu$_2$)(Cp)-M-C$_5$H$_3$-1-$^i$Pr-3-[(CH$_2$)$_2$—N$^n$Bu]-, (N$^i$Bu$_2$)(Cp)-M-C$_5$H$_3$-1-$^i$Pr-3-[(CH$_2$)$_2$—N$^n$Bu]-, (N$^s$Bu$_2$)(Cp)-M-C$_5$H$_3$-1-$^i$Pr-3-[(CH$_2$)$_2$—N$^n$Bu]-, (N$^t$Bu$_2$)(Cp)-M-C$_5$H$_3$-1-$^i$Pr-3-[(CH$_2$)$_2$—N$^n$Bu]-, (OH)$_2$-M-C$_5$H$_3$-1-$^i$Pr-3-[(CH$_2$)$_2$—N$^n$Bu]-, (OMe)$_2$-M-C$_5$H$_3$-1-$^i$Pr-3-[(CH$_2$)$_2$—N$^n$Bu]-, (OEt)$_2$-M-C$_5$H$_3$-1-$^i$Pr-3-[(CH$_2$)$_2$—N$^n$Bu]-, (O$^n$Pr)$_2$-M-C$_5$H$_3$-1-$^i$Pr-3-[(CH$_2$)$_2$—N$^n$Bu]-, (O$^i$Pr)$_2$-M-C$_5$H$_3$-1-$^i$Pr-3-[(CH$_2$)$_2$—N$^n$Bu]-, (O$^n$Bu)$_2$-M-C$_5$H$_3$-1-$^i$Pr-3-[(CH$_2$)$_2$—N$^n$Bu]-, (O$^i$Bu$_2$-M-C$_5$H$_3$-1-$^i$Pr-3-[(CH$_2$)$_2$—N$^n$Bu]-, (O$^t$Bu)$_2$-M-C$_5$H$_3$-1-$^i$Pr-3-[(CH$_2$)$_2$—N$^n$Bu]-, (O$^s$Bu)$_2$-M-C$_5$H$_3$-1-$^i$Pr-3-[(CH$_2$)$_2$—N$^n$Bu]-, (NH$_2$)$_2$-M-C$_5$H$_3$-1-$^t$Bu-2-[(CH$_2$)$_2$—N$^n$Bu]-, (NMe$_2$)$_2$-M-C$_5$H$_3$-1-$^t$Bu-2-[(CH$_2$)$_2$—N$^n$Bu]-, (NEt$_2$)$_2$-M-C$_5$H$_3$-1-$^t$Bu-2-[(CH$_2$)$_2$—N$^n$Bu]-, (N$^n$Pr$_2$)$_2$-M-C$_5$H$_3$-1-$^t$Bu-2-[(CH$_2$)$_2$—N$^n$Bu]-, (N$^i$Pr$_2$)$_2$-M-C$_5$H$_3$-1-$^t$Bu-2-[(CH$_2$)$_2$—N$^n$Bu]-, (N$^n$Bu$_2$)$_2$-M-C$_5$H$_3$-1-$^t$Bu-2-[(CH$_2$)$_2$—N$^n$Bu]-, (N$^i$Bu$_2$)$_2$-M-C$_5$H$_3$-1-$^t$Bu-2-[(CH$_2$)$_2$—N$^n$Bu]-, (N$^s$al$_2$)$_2$-M-C$_5$H$_3$-1-$^t$Bu-2-[(CH$_2$)$_2$—N$^n$Bu]-, (N$^t$Bu$_2$)$_2$-M-C$_5$H$_3$-1-$^t$Bu-2-[(CH$_2$)$_2$—N$^n$Bu]-, (NH$_2$)(Cp)-M-C$_5$H$_3$-1-$^t$Bu-2-[(CH$_2$)$_2$—N$^n$Bu]-, (NMe$_2$)(Cp)-M-C$_5$H$_3$-1-$^t$Bu-2-[(CH$_2$)$_2$—N$^n$Bu]-, (NEt$_2$)(Cp)-M-C$_5$H$_3$-1-$^t$Bu-2-[(CH$_2$)$_2$—N$^n$Bu]-, (N$^n$Pr$_2$)(Cp)-M-C$_5$H$_3$-1-$^t$Bu-2-[(CH$_2$)$_2$—N$^n$Bu]-, (N$^i$Pr$_2$)(Cp)-M-C$_5$H$_3$-1-$^t$Bu-2-[(CH$_2$)$_2$—N$^n$Bu]-, (N$^n$Bu$_2$)(Cp)-M-C$_5$H$_3$-1-$^t$Bu-2-[(CH$_2$)$_2$—N$^n$Bu]-, (N$^i$Bu$_2$)(Cp)-M-C$_5$H$_3$-1-$^t$Bu-2-[(CH$_2$)$_2$—N$^n$Bu]-, (N$^s$Bu$_2$)(Cp)-M-C$_5$H$_3$-1-$^t$Bu-2-[(CH$_2$)$_2$—N$^n$Bu]-, (N$^t$Bu$_2$)(Cp)-M-C$_5$H$_3$-1-$^t$Bu-2-[(CH$_2$)$_2$—N$^n$Bu]-, (OH)$_2$-M-C$_5$H$_3$-1-$^t$Bu-2-[(CH$_2$)$_2$—N$^n$Bu]-, (OMe)$_2$-M-C$_5$H$_3$-1-$^t$Bu-2-[(CH$_2$)$_2$—N$^n$Bu]-, (OEt)$_2$-M-C$_5$H$_3$-1-$^t$Bu-2-[(CH$_2$)$_2$—N$^n$Bu]-, (O$^n$Pr)$_2$-M-C$_5$H$_3$-1-$^t$Bu-2-[(CH$_2$)$_2$—N$^n$Bu]-, (O$^i$Pr)$_2$-M-C$_5$H$_3$-1-$^t$Bu-2-[(CH$_2$)$_2$—N$^n$Bu]-, (O$^n$Bu)$_2$-M-C$_5$H$_3$-1-$^t$Bu-2-[(CH$_2$)$_2$—N$^n$Bu]-, (O$^i$Bu$_2$-M-C$_5$H$_3$-1-$^t$Bu-2-[(CH$_2$)$_2$—N$^n$Bu]-, (O$^t$Bu)$_2$-M-C$_5$H$_3$-1-$^t$Bu-2-[(CH$_2$)$_2$—N$^n$Bu]-, (O$^s$Bu)$_2$-M-C$_5$H$_3$-1-$^t$Bu-2-[(CH$_2$)$_2$—N$^n$Bu]-, (NH$_2$)$_2$-M-C$_5$H$_3$-1-$^t$Bu-3-[(CH$_2$)$_2$—N$^n$Bu]-, (NMe$_2$)$_2$-M-C$_5$H$_3$-1-$^t$Bu-3-[(CH$_2$)$_2$—N$^n$Bu]-, (NEt$_2$)$_2$-M-C$_5$H$_3$-1-$^t$Bu-3-[(CH$_2$)$_2$—N$^n$Bu]-, (N$^n$Pr$_2$)$_2$-M-C$_5$H$_3$-1-$^t$Bu-3-[(CH$_2$)$_2$—N$^n$Bu]-, (N$^i$Pr$_2$)$_2$-M-C$_5$H$_3$-1-$^t$Bu-3-[(CH$_2$)$_2$—N$^n$Bu]-, (N$^n$Bu$_2$)$_2$-M-C$_5$H$_3$-1-$^t$Bu-3-[(CH$_2$)$_2$—N$^n$Bu]-, (N$^i$Bu$_2$)$_2$-M-C$_5$H$_3$-1-$^t$Bu-3-[(CH$_2$)$_2$—N$^n$Bu]-, (N$^s$Bu$_2$)$_2$-M-C$_5$H$_3$-1-$^t$Bu-3-[(CH$_2$)$_2$—N$^n$Bu]-, (N$^t$Bu$_2$)$_2$-M-C$_5$H$_3$-1-$^t$Bu-3-[(CH$_2$)$_2$—N$^n$Bu]-, (NH$_2$)(Cp)-M-C$_5$H$_3$-1-$^t$Bu-3-[(CH$_2$)$_2$—N$^n$Bu]-, (NMe$_2$)(Cp)-M-C$_5$H$_3$-1-$^t$Bu-3-[(CH$_2$)$_2$—N$^n$Bu]-, (NEt$_2$)(Cp)-M-C$_5$H$_3$-1-$^t$Bu-3-[(CH$_2$)$_2$—N$^n$Bu]-, (N$^n$Pr$_2$)(Cp)-M-C$_5$H$_3$-1-$^t$Bu-3-[(CH$_2$)$_2$—N$^n$Bu]-, (N$^i$Pr$_2$)(Cp)-M-C$_5$H$_3$-1-$^t$Bu-3-[(CH$_2$)$_2$—N$^n$Bu]-, (N$^n$Bu$_2$)(Cp)-M-C$_5$H$_3$-1-$^t$Bu-3-[(CH$_2$)$_2$—N$^n$Bu]-, (N$^i$Bu$_2$)(Cp)-M-C$_5$H$_3$-1-$^t$Bu-3-[(CH$_2$)$_2$—N$^n$Bu]-, (N$^s$Bu$_2$)(Cp)-M-C$_5$H$_3$-1-$^t$Bu-3-[(CH$_2$)$_2$—N$^n$Bu]-, (N$^t$Bu$_2$)(Cp)-M-C$_5$H$_3$-1-$^t$Bu-3-[(CH$_2$)$_2$—N$^n$Bu]-, (OH)$_2$-M-C$_5$H$_3$-1-$^t$Bu-3-[(CH$_2$)$_2$—N$^n$Bu]-, (OMe)$_2$-M-C$_5$H$_3$-1-$^t$Bu-3-[(CH$_2$)$_2$—N$^n$Bu]-, (OEt)$_2$-M-C$_5$H$_3$-1-$^t$Bu-3-[(CH$_2$)$_2$—N$^n$Bu]-, (O$^n$Pr)$_2$-M-C$_5$H$_3$-1-$^t$Bu-3-[(CH$_2$)$_2$—N$^n$Bu]-, (O$^i$Pr)$_2$-M-C$_5$H$_3$-1-$^t$Bu-3-[(CH$_2$)$_2$—N$^n$Bu]-, (O$^n$Bu)$_2$-M-C$_5$H$_3$-1-$^t$Bu-3-[(CH$_2$)$_2$—N$^n$Bu]-, (O$^i$Bu$_2$-M-C$_5$H$_3$-1-$^t$Bu-3-[(CH$_2$)$_2$—N$^n$Bu]-, (O$^t$Bu)$_2$-M-C$_5$H$_3$-1-$^t$Bu-3-[(CH$_2$)$_2$—N$^n$Bu]-, (O$^s$Bu)$_2$-M-C$_5$H$_3$-1-$^t$Bu-3-[(CH$_2$)$_2$—N$^n$Bu]-, (NH$_2$)$_2$-M-C$_5$H$_3$-1-Me-2-[(CH$_2$)$_2$—N$^i$Bu]-, (NMe$_2$)$_2$-M-C$_5$H$_3$-1-Me-2-[(CH$_2$)$_2$—N$^i$Bu]-, (NEt$_2$)$_2$-M-C$_5$H$_3$-1-Me-2-[(CH$_2$)$_2$—N$^i$Bu]-, (N$^n$Pr$_2$)$_2$-M-C$_5$H$_3$-1-Me-2-[(CH$_2$)$_2$—N$^i$Bu]-, (N$^i$Pr$_2$)$_2$-M-C$_5$H$_3$-1-Me-2-[(CH$_2$)$_2$—N$^i$Bu]-, (N$^n$Bu$_2$)$_2$-M-C$_5$H$_3$-1-Me-2-[(CH$_2$)$_2$—N$^i$Bu]-, (N$^i$Bu$_2$)$_2$-M-C$_5$H$_3$-1-Me-2-[(CH$_2$)$_2$—N$^i$Bu]-, (N$^s$Bu$_2$)$_2$-M-C$_5$H$_3$-1-Me-2-[(CH$_2$)$_2$—N$^i$Bu]-, (N$^t$Bu$_2$)$_2$-M-C$_5$H$_3$-1-Me-2-[(CH$_2$)$_2$—N$^i$Bu]-, (NH$_2$)(Cp)-M-C$_5$H$_3$-1-Me-2-[(CH$_2$)$_2$—N$^i$Bu]-, (NMe$_2$)(Cp)-M-C$_5$H$_3$-1-Me-2-[(CH$_2$)$_2$—N$^i$Bu]-, (NEt$_2$)(Cp)-M-C$_5$H$_3$-1-Me-2-[(CH$_2$)$_2$—N$^i$Bu]-, (N$^n$Pr$_2$)(Cp)-M-C$_5$H$_3$-1-Me-2-[(CH$_2$)$_2$—N$^i$Bu]-, (N$^i$Pr$_2$)(Cp)-M-C$_5$H$_3$-1-Me-2-[(CH$_2$)$_2$—N$^i$Bu]-, (N$^n$Bu$_2$)(Cp)-M-C$_5$H$_3$-1-Me-2-[(CH$_2$)$_2$—N$^i$Bu]-, (N$^i$Bu$_2$)(Cp)-M-C$_5$H$_3$-1-Me-2-[(CH$_2$)$_2$—N$^i$Bu]-, (N$^s$Bu$_2$)(Cp)-M-C$_5$H$_3$-1-Me-2-[(CH$_2$)$_2$—N$^i$Bu]-, (N$^t$Bu$_2$)(Cp)-M-C$_5$H$_3$-1-Me-2-[(CH$_2$)$_2$—N$^i$Bu]-, (OH)$_2$-M-C$_5$H$_3$-1-Me-2-[(CH$_2$)$_2$—N$^i$Bu]-, (OMe)$_2$-M-C$_5$H$_3$-1-Me-2-[(CH$_2$)$_2$—N$^i$Bu]-, (OEt)$_2$-M-C$_5$H$_3$-1-Me-2-[(CH$_2$)$_2$—N$^i$Bu]-, (O$^n$Pr)$_2$-M-C$_5$H$_3$-1-Me-2-[(CH$_2$)$_2$—N$^i$Bu]-, (O$^i$Pr)$_2$-M-C$_5$H$_3$-1-Me-2-[(CH$_2$)$_2$—N$^i$Bu]-, (O$^n$Bu)$_2$-M-C$_5$H$_3$-1-Me-2-[(CH$_2$)$_2$—N$^i$Bu]-, (O$^i$Bu$_2$-M-C$_5$H$_3$-1-Me-2-[(CH$_2$)$_2$—N$^i$Bu]-, (O$^t$Bu)$_2$-M-C$_5$H$_3$-1-Me-2-[(CH$_2$)$_2$—N$^i$Bu]-, (O$^s$Bu)$_2$-M-C$_5$H$_3$-1-Me-2-[(CH$_2$)$_2$—N$^i$Bu]-, (NH$_2$)$_2$-M-C$_5$H$_3$-1-Me-3-[(CH$_2$)$_2$—N$^i$Bu]-, (NMe$_2$)$_2$-M-C$_5$H$_3$-1-Me-3-[(CH$_2$)$_2$—N$^i$Bu]-, (NEt$_2$)$_2$-M-C$_5$H$_3$-1-Me-3-[(CH$_2$)$_2$—N$^i$Bu]-, (N$^n$Pr$_2$)$_2$-M-C$_5$H$_3$-1-Me-3-[(CH$_2$)$_2$—N$^i$Bu]-, (N$^i$Pr$_2$)$_2$-M-C$_5$H$_3$-1-Me-3-[(CH$_2$)$_2$—N$^i$Bu]-, (N$^n$Bu$_2$)$_2$-M-C$_5$H$_3$-1-Me-3-[(CH$_2$)$_2$—N$^i$Bu]-, (N$^i$Bu$_2$)$_2$-M-C$_5$H$_3$-1-Me-3-[(CH$_2$)$_2$—N$^i$Bu]-, (N$^s$Bu$_2$)$_2$-M-C$_5$H$_3$-1-Me-3-[(CH$_2$)$_2$—N$^i$Bu]-, (N$^t$Bu$_2$)$_2$-M-C$_5$H$_3$-1-Me-3-[(CH$_2$)$_2$—N$^i$Bu]-, (NH$_2$)(Cp)-M-C$_5$H$_3$-1-Me-3-[(CH$_2$)$_2$—N$^i$Bu]-, (NMe$_2$)(Cp)-M-C$_5$H$_3$-1-Me-3-[(CH$_2$)$_2$—N$^i$Bu]-, (NEt$_2$)(Cp)-M-C$_5$H$_3$-1-Me-3-[(CH$_2$)$_2$—N$^i$Bu]-, (N$^n$Pr$_2$)(Cp)-M-C$_5$H$_3$-1-Me-3-[(CH$_2$)$_2$—N$^i$Bu]-, (N$^i$Pr$_2$)(Cp)-M-C$_5$H$_3$-1-Me-3-[(CH$_2$)$_2$—N$^i$Bu]-, (N$^n$Bu$_2$)(Cp)-M-C$_5$H$_3$-1-Me-3-[(CH$_2$)$_2$—N$^i$Bu]-, (N$^i$Bu$_2$)(Cp)-M-C$_5$H$_3$-1-Me-3-[(CH$_2$)$_2$—N$^i$Bu]-, (N$^s$Bu$_2$)(Cp)-M-C$_5$H$_3$-1-Me-3-[(CH$_2$)$_2$—N$^i$Bu]-, (N$^t$Bu$_2$)(Cp)-M-C$_5$H$_3$-1-Me-3-[(CH$_2$)$_2$—N$^i$Bu]-, (OH)$_2$-M-C$_5$H$_3$-1-Me-3-[(CH$_2$)$_2$—N$^i$Bu]-, (OMe)$_2$-M-C$_5$H$_3$-1-Me-3-[(CH$_2$)$_2$—N$^i$Bu]-, (OEt)$_2$-M-C$_5$H$_3$-1-Me-3-[(CH$_2$)$_2$—N$^i$Bu]-, (O$^n$Pr)$_2$-M-C$_5$H$_3$-1-Me-3-[(CH$_2$)$_2$—N$^i$Bu]-, (O$^i$Pr)$_2$-M-C$_5$H$_3$-1-Me-3-[(CH$_2$)$_2$—N$^i$Bu]-, (O$^n$Bu)$_2$-M-C$_5$H$_3$-1-Me-3-[(CH$_2$)$_2$—N$^i$Bu]-, (O$^i$Bu$_2$-M-C$_5$H$_3$-1-Me-3-[(CH$_2$)$_2$—N$^i$Bu]-, (O$^t$Bu)$_2$-M-C$_5$H$_3$-1-Me-3-[(CH$_2$)$_2$—N$^i$Bu]-, (O$^s$Bu)$_2$-M-C$_5$H$_3$-1-Me-3-[(CH$_2$)$_2$—N$^i$Bu]-, (NH$_2$)$_2$-M-C$_5$H$_3$-1-Et-2-[(CH$_2$)$_2$—N$^i$Bu]-, (NMe$_2$)$_2$-M-C$_5$H$_3$-1-Et-2-[(CH$_2$)$_2$—N$^i$Bu]-, (NEt$_2$)$_2$-M-C$_5$H$_3$-1-Et-2-[(CH$_2$)$_2$—N$^i$Bu]-, (N$^n$Pr$_2$)$_2$-M-C$_5$H$_3$-1-Et-2-[(CH$_2$)$_2$—N$^i$Bu]-, (N$^i$Pr$_2$)$_2$-M-C$_5$H$_3$-1-Et-2-[(CH$_2$)$_2$—N$^i$Bu]-, (N$^n$Bu$_2$)$_2$-M-C$_5$H$_3$-1-Et-2-[(CH$_2$)$_2$—N$^i$Bu]-, (N$^i$Bu$_2$)$_2$-M-C$_5$H$_3$-1-Et-2-[(CH$_2$)$_2$—N$^i$Bu]-, (N$^s$Bu$_2$)$_2$-M-C$_5$H$_3$-1-Et-2-[(CH$_2$)$_2$—N$^i$Bu]-, (N$^t$Bu$_2$)$_2$-M-C$_5$H$_3$-1-Et-2-[(CH$_2$)$_2$—N$^i$Bu]-, (NH$_2$)(Cp)-M-C$_5$H$_3$-1-Et-2-[(CH$_2$)$_2$—N$^i$Bu]-, (NMe$_2$)(Cp)-M-C$_5$H$_3$-1-Et-2-[(CH$_2$)$_2$—N$^i$Bu]-, (NEt$_2$)(Cp)-M-C$_5$H$_3$-1-Et-2-[(CH$_2$)$_2$—N$^i$Bu]-, (N$^n$Pr$_2$)(Cp)-M-C$_5$H$_3$-1-Et-2-[(CH$_2$)$_2$—N$^i$Bu]-, (N$^i$Pr$_2$)(Cp)-M-C$_5$H$_3$-1-Et-2-[(CH$_2$)$_2$—N$^i$Bu]-, (N$^n$Bu$_2$)(Cp)-M-C$_5$H$_3$-1-Et-2-[(CH$_2$)$_2$—N$^i$Bu]-, (N$^i$Bu$_2$)(Cp)-M-C$_5$H$_3$-1-Et-2-[(CH$_2$)$_2$—N$^i$Bu]-, (N$^s$Bu$_2$)(Cp)-M-C$_5$H$_3$-1-Et-2-[(CH$_2$)$_2$—N$^i$Bu]-, (N$^t$Bu$_2$)(Cp)-M-C$_5$H$_3$-1-Et-2-[(CH$_2$)$_2$—N$^i$Bu]-, (OH)$_2$-M-C$_5$H$_3$-1-Et-2-[(CH$_2$)$_2$—N$^i$Bu]-, (OMe)$_2$-M-C$_5$H$_3$-1-Et-2-[(CH$_2$)$_2$—N$^i$Bu]-, (OEt)$_2$-M-C$_5$H$_3$-1-Et-2-[(CH$_2$)$_2$—N$^i$Bu]-, (O$^n$Pr)$_2$-M-C$_5$H$_3$-1-Et-2-[(CH$_2$)$_2$—N$^i$Bu]-, (O$^i$Pr)$_2$-M-C$_5$H$_3$-1-Et-2-[(CH$_2$)$_2$—N$^i$Bu]-, (O$^n$Bu)$_2$-M-C$_5$H$_3$-1-Et-

2-[(CH$_2$)$_2$—N$^i$Bu]-, (O$^i$Bu$_2$-M-C$_5$H$_3$-1-Et-2-[(CH$_2$)$_2$—N$^i$Bu]-, (O$^i$Bu)$_2$-M-C$_5$H$_3$-1-Et-2-[(CH$_2$)$_2$—N$^i$Bu]-, (O$^s$Bu)$_2$-M-C$_5$H$_3$-1-Et-2-[(CH$_2$)$_2$—N$^i$Bu]-, (NH$_2$)$_2$-M-C$_5$H$_3$-1-Et-3-[(CH$_2$)$_2$—N$^i$Bu]-, (NMe$_2$)$_2$-M-C$_5$H$_3$-1-Et-3-[(CH$_2$)$_2$—N$^i$Bu]-, (NEt$_2$)$_2$-M-C$_5$H$_3$-1-Et-3-[(CH$_2$)$_2$—N$^i$Bu]-, (N$^n$Pr$_2$)$_2$-M-C$_5$H$_3$-1-Et-3-[(CH$_2$)$_2$—N$^i$Bu]-, (N$^i$Pr$_2$)$_2$-M-C$_5$H$_3$-1-Et-3-[(CH$_2$)$_2$—N$^i$Bu]-, (N$^n$Bu$_2$)$_2$-M-C$_5$H$_3$-1-Et-3-[(CH$_2$)$_2$—N$^i$Bu]-, (N$^i$Bu$_2$)$_2$-M-C$_5$H$_3$-1-Et-3-[(CH$_2$)$_2$—N$^i$Bu]-, (N$^s$Bu$_2$)$_2$-M-C$_5$H$_3$-1-Et-3-[(CH$_2$)$_2$—N$^i$Bu]-, (N$^t$Bu$_2$)$_2$-M-C$_5$H$_3$-1-Et-3-[(CH$_2$)$_2$—N$^i$Bu]-, (NH$_2$)(Cp)-M-C$_5$H$_3$-1-Et-3-[(CH$_2$)$_2$—N$^i$Bu]-, (NMe$_2$)(Cp)-M-C$_5$H$_3$-1-Et-3-[(CH$_2$)$_2$—N$^i$Bu]-, (NEt$_2$)(Cp)-M-C$_5$H$_3$-1-Et-3-[(CH$_2$)$_2$—N$^i$Bu]-, (N$^n$Pr$_2$)(Cp)-M-C$_5$H$_3$-1-Et-3-[(CH$_2$)$_2$—N$^i$Bu]-, (N$^i$Pr$_2$)(Cp)-M-C$_5$H$_3$-1-Et-3-[(CH$_2$)$_2$—N$^i$Bu]-, (N$^n$Bu$_2$)(Cp)-M-C$_5$H$_3$-1-Et-3-[(CH$_2$)$_2$—N$^i$Bu]-, (N$^i$Bu$_2$)(Cp)-M-C$_5$H$_3$-1-Et-3-[(CH$_2$)$_2$—N$^i$Bu]-, (N$^s$Bu$_2$)(Cp)-M-C$_5$H$_3$-1-Et-3-[(CH$_2$)$_2$—N$^i$Bu]-, (N$^t$Bu$_2$)(Cp)-M-C$_5$H$_3$-1-Et-3-[(CH$_2$)$_2$—N$^i$Bu]-, (OH)$_2$-M-C$_5$H$_3$-1-Et-3-[(CH$_2$)$_2$—N$^i$Bu]-, (OMe)$_2$-M-C$_5$H$_3$-1-Et-3-[(CH$_2$)$_2$—N$^i$Bu]-, (OEt)$_2$-M-C$_5$H$_3$-1-Et-3-[(CH$_2$)$_2$—N$^i$Bu]-, (O$^n$Pr)$_2$-M-C$_5$H$_3$-1-Et-3-[(CH$_2$)$_2$—N$^i$Bu]-, (O$^i$Pr)$_2$-M-C$_5$H$_3$-1-Et-3-[(CH$_2$)$_2$—N$^i$Bu]-, (O$^n$Bu)$_2$-M-C$_5$H$_3$-1-Et-3-[(CH$_2$)$_2$—N$^i$Bu]-, (O$^i$Bu)$_2$-M-C$_5$H$_3$-1-Et-3-[(CH$_2$)$_2$—N$^i$Bu]-, (O$^i$Bu)$_2$-M-C$_5$H$_3$-1-Et-3-[(CH$_2$)$_2$—N$^i$Bu]-, (O$^s$Bu)$_2$-M-C$_5$H$_3$-1-Et-3-[(CH$_2$)$_2$—N$^i$Bu]-, (NH$_2$)$_2$-M-C$_5$H$_3$-1-$^i$Pr-2-[(CH$_2$)$_2$—N$^i$Bu]-, (NMe$_2$)$_2$-M-C$_5$H$_3$-1-$^i$Pr-2-[(CH$_2$)$_2$—N$^i$Bu]-, (NEt$_2$)$_2$-M-C$_5$H$_3$-1-$^i$Pr-2-[(CH$_2$)$_2$—N$^i$Bu]-, (N$^n$Pr$_2$)$_2$-M-C$_5$H$_3$-1-$^i$Pr-2-[(CH$_2$)$_2$—N$^i$Bu]-, (N$^i$Pr$_2$)$_2$-M-C$_5$H$_3$-1-$^i$Pr-2-[(CH$_2$)$_2$—N$^i$Bu]-, (N$^n$Bu$_2$)$_2$-M-C$_5$H$_3$-1-$^i$Pr-2-[(CH$_2$)$_2$—N$^i$Bu]-, (N$^i$Bu$_2$)$_2$-M-C$_5$H$_3$-1-$^i$Pr-2-[(CH$_2$)$_2$—N$^i$Bu]-, (N$^s$Bu$_2$)$_2$-M-C$_5$H$_3$-1-$^i$Pr-2-[(CH$_2$)$_2$—N$^i$Bu]-, (N$^t$Bu$_2$)$_2$-M-C$_5$H$_3$-1-$^i$Pr-2-[(CH$_2$)$_2$—N$^i$Bu]-, (NH$_2$)(Cp)-M-C$_5$H$_3$-1-$^i$Pr-2-[(CH$_2$)$_2$—N$^i$Bu]-, (NMe$_2$)(Cp)-M-C$_5$H$_3$-1-$^i$Pr-2-[(CH$_2$)$_2$—N$^i$Bu]-, (NEt$_2$)(Cp)-M-C$_5$H$_3$-1-$^i$Pr-2-[(CH$_2$)$_2$—N$^i$Bu]-, (N$^n$Pr$_2$)(Cp)-M-C$_5$H$_3$-1-$^i$Pr-2-[(CH$_2$)$_2$—N$^i$Bu]-, (N$^i$Pr$_2$)(Cp)-M-C$_5$H$_3$-1-$^i$Pr-2-[(CH$_2$)$_2$—N$^i$Bu]-, (N$^n$Bu$_2$)(Cp)-M-C$_5$H$_3$-1-$^i$Pr-2-[(CH$_2$)$_2$—N$^i$Bu]-, (N$^i$Bu$_2$)(Cp)-M-C$_5$H$_3$-1-$^i$Pr-2-[(CH$_2$)$_2$—N$^i$Bu]-, (N$^s$Bu$_2$)(Cp)-M-C$_5$H$_3$-1-$^i$Pr-2-[(CH$_2$)$_2$—N$^i$Bu]-, (N$^t$Bu$_2$)(Cp)-M-C$_5$H$_3$-1-$^i$Pr-2-[(CH$_2$)$_2$—N$^i$Bu]-, (OH)$_2$-M-C$_5$H$_3$-1-$^i$Pr-2-[(CH$_2$)$_2$—N$^i$Bu]-, (OMe)$_2$-M-C$_5$H$_3$-1-$^i$Pr-2-[(CH$_2$)$_2$—N$^i$Bu]-, (OEt)$_2$-M-C$_5$H$_3$-1-$^i$Pr-2-[(CH$_2$)$_2$—N$^i$Bu]-, (O$^n$Pr)$_2$-M-C$_5$H$_3$-1-$^i$Pr-2-[(CH$_2$)$_2$—N$^i$Bu]-, (O$^i$Pr)$_2$-M-C$_5$H$_3$-1-$^i$Pr-2-[(CH$_2$)$_2$—N$^i$Bu]-, (O$^n$Bu)$_2$-M-C$_5$H$_3$-1-$^i$Pr-2-[(CH$_2$)$_2$—N$^i$Bu]-, (O$^i$Bu)$_2$-M-C$_5$H$_3$-1-$^i$Pr-2-[(CH$_2$)$_2$—N$^i$Bu]-, (O$^i$Bu)$_2$-M-C$_5$H$_3$-1-$^i$Pr-2-[(CH$_2$)$_2$—N$^i$Bu]-, (O$^s$Bu)$_2$-M-C$_5$H$_3$-1-$^i$Pr-2-[(CH$_2$)$_2$—N$^i$Bu]-, (NH$_2$)$_2$-M-C$_5$H$_3$-1-$^i$Pr-3-[(CH$_2$)$_2$—N$^i$Bu]-, (NMe$_2$)$_2$-M-C$_5$H$_3$-1-$^i$Pr-3-[(CH$_2$)$_2$—N$^i$Bu]-, (NEt$_2$)$_2$-M-C$_5$H$_3$-1-$^i$Pr-3-[(CH$_2$)$_2$—N$^i$Bu]-, (N$^n$Pr$_2$)$_2$-M-C$_5$H$_3$-1-$^i$Pr-3-[(CH$_2$)$_2$—N$^i$Bu]-, (N$^i$Pr$_2$)$_2$-M-C$_5$H$_3$-1-$^i$Pr-3-[(CH$_2$)$_2$—N$^i$Bu]-, (N$^n$Bu$_2$)$_2$-M-C$_5$H$_3$-1-$^i$Pr-3-[(CH$_2$)$_2$—N$^i$Bu]-, (N$^i$Bu$_2$)$_2$-M-C$_5$H$_3$-1-$^i$Pr-3-[(CH$_2$)$_2$—N$^i$Bu]-, (N$^s$Bu$_2$)$_2$-M-C$_5$H$_3$-1-$^i$Pr-3-[(CH$_2$)$_2$—N$^i$Bu]-, (N$^t$Bu$_2$)$_2$-M-C$_5$H$_3$-1-$^i$Pr-3-[(CH$_2$)$_2$—N$^i$Bu]-, (NH$_2$)(Cp)-M-C$_5$H$_3$-1-$^i$Pr-3-[(CH$_2$)$_2$—N$^i$Bu]-, (NMe$_2$)(Cp)-M-C$_5$H$_3$-1-$^i$Pr-3-[(CH$_2$)$_2$—N$^i$Bu]-, (NEt$_2$)(Cp)-M-C$_5$H$_3$-1-$^i$Pr-3-[(CH$_2$)$_2$—N$^i$Bu]-, (N$^n$Pr$_2$)(Cp)-M-C$_5$H$_3$-1-$^i$Pr-3-[(CH$_2$)$_2$—N$^i$Bu]-, (N$^i$Pr$_2$)(Cp)-M-C$_5$H$_3$-1-$^i$Pr-3-[(CH$_2$)$_2$—N$^i$Bu]-, (N$^n$Bu$_2$)(Cp)-M-C$_5$H$_3$-1-$^i$Pr-3-[(CH$_2$)$_2$—N$^i$Bu]-, (N$^i$Bu$_2$)(Cp)-M-C$_5$H$_3$-1-$^i$Pr-3-[(CH$_2$)$_2$—N$^i$Bu]-, (N$^s$Bu$_2$)(Cp)-M-C$_5$H$_3$-1-$^i$Pr-3-[(CH$_2$)$_2$—N$^i$Bu]-, (N$^t$Bu$_2$)(Cp)-M-C$_5$H$_3$-1-$^i$Pr-3-[(CH$_2$)$_2$—N$^i$Bu]-, (OH)$_2$-M-C$_5$H$_3$-1-$^i$Pr-3-[(CH$_2$)$_2$—N$^i$Bu]-, (OMe)$_2$-M-C$_5$H$_3$-1-$^i$Pr-3-[(CH$_2$)$_2$—N$^i$Bu]-, (OEt)$_2$-M-C$_5$H$_3$-1-$^i$Pr-3-[(CH$_2$)$_2$—N$^i$Bu]-, (O$^n$Pr)$_2$-M-C$_5$H$_3$-1-$^i$Pr-3-[(CH$_2$)$_2$—N$^i$Bu]-, (O$^i$Pr)$_2$-M-C$_5$H$_3$-1-$^i$Pr-3-[(CH$_2$)$_2$—N$^i$Bu]-, (O$^n$Bu)$_2$-M-C$_5$H$_3$-1-$^i$Pr-3-[(CH$_2$)$_2$—N$^i$Bu]-, (O$^i$Bu$_2$-M-C$_5$H$_3$-1-$^i$Pr-3-[(CH$_2$)$_2$—N$^i$Bu]-, (O$^i$Bu)$_2$-M-C$_5$H$_3$-1-$^i$Pr-3-[(CH$_2$)$_2$—N$^i$Bu]-, (O$^s$Bu)$_2$-M-C$_5$H$_3$-1-$^i$Pr-3-[(CH$_2$)$_2$—N$^i$Bu]-, (NH$_2$)$_2$-M-C$_5$H$_3$-1-$^t$Bu-2-[(CH$_2$)$_2$—N$^i$Bu]-, (NMe$_2$)$_2$-M-C$_5$H$_3$-1-$^t$Bu-2-[(CH$_2$)$_2$—N$^i$Bu]-, (NEt$_2$)$_2$-M-C$_5$H$_3$-1-$^t$Bu-2-[(CH$_2$)$_2$—N$^i$Bu]-, (N$^n$Pr$_2$)$_2$-M-C$_5$H$_3$-1-$^t$Bu-2-[(CH$_2$)$_2$—N$^i$Bu]-, (N$^i$Pr$_2$)$_2$-M-C$_5$H$_3$-1-$^t$Bu-2-[(CH$_2$)$_2$—N$^i$Bu]-, (N$^n$Bu$_2$)$_2$-M-C$_5$H$_3$-1-$^t$Bu-2-[(CH$_2$)$_2$—N$^i$Bu]-, (N$^i$Bu$_2$)$_2$-M-C$_5$H$_3$-1-$^t$Bu-2-[(CH$_2$)$_2$—N$^i$Bu]-, (N$^s$Bu$_2$)$_2$-M-C$_5$H$_3$-1-$^t$Bu-2-[(CH$_2$)$_2$—N$^i$Bu]-, (N$^t$Bu$_2$)$_2$-M-C$_5$H$_3$-1-$^t$Bu-2-[(CH$_2$)$_2$—N$^i$Bu]-, (NH$_2$)(Cp)-M-C$_5$H$_3$-1-$^t$Bu-2-[(CH$_2$)$_2$—N$^i$Bu]-, (NMe$_2$)(Cp)-M-C$_5$H$_3$-1-$^t$Bu-2-[(CH$_2$)$_2$—N$^i$Bu]-, (NEt$_2$)(Cp)-M-C$_5$H$_3$-1-$^t$Bu-2-[(CH$_2$)$_2$—N$^i$Bu]-, (N$^n$Pr$_2$)(Cp)-M-C$_5$H$_3$-1-$^t$Bu-2-[(CH$_2$)$_2$—N$^i$Bu]-, (N$^i$Pr$_2$)(Cp)-M-C$_5$H$_3$-1-$^t$Bu-2-[(CH$_2$)$_2$—N$^i$Bu]-, (N$^n$Bu$_2$)(Cp)-M-C$_5$H$_3$-1-$^t$Bu-2-[(CH$_2$)$_2$—N$^i$Bu]-, (N$^i$Bu$_2$)(Cp)-M-C$_5$H$_3$-1-$^t$Bu-2-[(CH$_2$)$_2$—N$^i$Bu]-, (N$^s$Bu$_2$)(Cp)-M-C$_5$H$_3$-1-$^t$Bu-2-[(CH$_2$)$_2$—N$^i$Bu]-, (N$^t$Bu$_2$)(Cp)-M-C$_5$H$_3$-1-$^t$Bu-2-[(CH$_2$)$_2$—N$^i$Bu]-, (OH)$_2$-M-C$_5$H$_3$-1-$^t$Bu-2-[(CH$_2$)$_2$—N$^i$Bu]-, (OMe)$_2$-M-C$_5$H$_3$-1-$^t$Bu-2-[(CH$_2$)$_2$—N$^i$Bu]-, (OEt)$_2$-M-C$_5$H$_3$-1-$^t$Bu-2-[(CH$_2$)$_2$—N$^i$Bu]-, (O$^n$Pr)$_2$-M-C$_5$H$_3$-1-$^t$Bu-2-[(CH$_2$)$_2$—N$^i$Bu]-, (O$^i$Pr)$_2$-M-C$_5$H$_3$-1-$^t$Bu-2-[(CH$_2$)$_2$—N$^i$Bu]-, (O$^n$Bu)$_2$-M-C$_5$H$_3$-1-$^t$Bu-2-[(CH$_2$)$_2$—N$^i$Bu]-, (O$^i$Bu)$_2$-M-C$_5$H$_3$-1-$^t$Bu-2-[(CH$_2$)$_2$—N$^i$Bu]-, (O$^i$Bu)$_2$-M-C$_5$H$_3$-1-$^t$Bu-2-[(CH$_2$)$_2$—N$^i$Bu]-, (O$^s$Bu)$_2$-M-C$_5$H$_3$-1-$^t$Bu-2-[(CH$_2$)$_2$—N$^i$Bu]-, (NH$_2$)$_2$-M-C$_5$H$_3$-1-$^t$Bu-3-[(CH$_2$)$_2$—N$^i$Bu]-, (NMe$_2$)$_2$-M-C$_5$H$_3$-1-$^t$Bu-3-[(CH$_2$)$_2$—N$^i$Bu]-, (NEt$_2$)$_2$-M-C$_5$H$_3$-1-$^t$Bu-3-[(CH$_2$)$_2$—N$^i$Bu]-, (N$^n$Pr$_2$)$_2$-M-C$_5$H$_3$-1-$^t$Bu-3-[(CH$_2$)$_2$—N$^i$Bu]-, (N$^i$Pr$_2$)$_2$-M-C$_5$H$_3$-1-$^t$Bu-3-[(CH$_2$)$_2$—N$^i$Bu]-, (N$^n$Bu$_2$)$_2$-M-C$_5$H$_3$-1-$^t$Bu-3-[(CH$_2$)$_2$—N$^i$Bu]-, (N$^i$Bu$_2$)$_2$-M-C$_5$H$_3$-1-$^t$Bu-3-[(CH$_2$)$_2$—N$^i$Bu]-, (N$^s$Bu$_2$)$_2$-M-C$_5$H$_3$-1-$^t$Bu-3-[(CH$_2$)$_2$—N$^i$Bu]-, (N$^t$Bu$_2$)$_2$-M-C$_5$H$_3$-1-$^t$Bu-3-[(CH$_2$)$_2$—N$^i$Bu]-, (NH$_2$)(Cp)-M-C$_5$H$_3$-1-$^t$Bu-3-[(CH$_2$)$_2$—N$^i$Bu]-, (NMe$_2$)(Cp)-M-C$_5$H$_3$-1-$^t$Bu-3-[(CH$_2$)$_2$—N$^i$Bu]-, (NEt$_2$)(Cp)-M-C$_5$H$_3$-1-$^t$Bu-3-[(CH$_2$)$_2$—N$^i$Bu]-, (N$^n$Pr$_2$)(Cp)-M-C$_5$H$_3$-1-$^t$Bu-3-[(CH$_2$)$_2$—N$^i$Bu]-, (N$^i$Pr$_2$)(Cp)-M-C$_5$H$_3$-1-$^t$Bu-3-[(CH$_2$)$_2$—N$^i$Bu]-, (N$^n$Bu$_2$)(Cp)-M-C$_5$H$_3$-1-$^t$Bu-3-[(CH$_2$)$_2$—N$^i$Bu]-, (N$^i$Bu$_2$)(Cp)-M-C$_5$H$_3$-1-$^t$Bu-3-[(CH$_2$)$_2$—N$^i$Bu]-, (N$^s$Bu$_2$)(Cp)-M-C$_5$H$_3$-1-$^t$Bu-3-[(CH$_2$)$_2$—N$^i$Bu]-, (N$^t$Bu$_2$)(Cp)-M-C$_5$H$_3$-1-$^t$Bu-3-[(CH$_2$)$_2$—N$^i$Bu]-, (OH)$_2$-M-C$_5$H$_3$-1-$^t$Bu-3-[(CH$_2$)$_2$—N$^i$Bu]-, (OMe)$_2$-M-C$_5$H$_3$-1-$^t$Bu-3-[(CH$_2$)$_2$—N$^i$Bu]-, (OEt)$_2$-M-C$_5$H$_3$-1-$^t$Bu-3-[(CH$_2$)$_2$—N$^i$Bu]-, (O$^n$Pr)$_2$-M-C$_5$H$_3$-1-$^t$Bu-3-[(CH$_2$)$_2$—N$^i$Bu]-, (O$^i$Pr)$_2$-M-C$_5$H$_3$-1-$^t$Bu-3-[(CH$_2$)$_2$—N$^i$Bu]-, (O$^n$Bu)$_2$-M-C$_5$H$_3$-1-$^t$Bu-3-[(CH$_2$)$_2$—N$^i$Bu]-, (O$^i$Bu)$_2$-M-C$_5$H$_3$-1-$^t$Bu-3-[(CH$_2$)$_2$—N$^i$Bu]-, (O$^i$Bu)$_2$-M-C$_5$H$_3$-1-$^t$Bu-3-[(CH$_2$)$_2$—N$^i$Bu]-, (O$^s$Bu)$_2$-M-C$_5$H$_3$-1-$^t$Bu-3-[(CH$_2$)$_2$—N$^i$Bu]-, (NH$_2$)$_2$-M-C$_5$H$_3$-1-Me-2-[(CH$_2$)$_2$—N$^s$Bu]-, (NMe$_2$)$_2$-M-C$_5$H$_3$-1-Me-2-[(CH$_2$)$_2$—N$^s$Bu]-, (NEt$_2$)$_2$-M-C$_5$H$_3$-1-Me-2-[(CH$_2$)$_2$—N$^s$Bu]-, (N$^n$Pr$_2$)$_2$-M-C$_5$H$_3$-1-Me-2-[(CH$_2$)$_2$—N$^s$Bu]-, (N$^i$Pr$_2$)$_2$-M-C$_5$H$_3$-1-Me-2-[(CH$_2$)$_2$—N$^s$Bu]-, (N$^n$Bu$_2$)$_2$-M-C$_5$H$_3$-1-Me-2-[(CH$_2$)$_2$—N$^s$Bu]-, (N$^i$Bu$_2$)$_2$-M-C$_5$H$_3$-1-Me-2-[(CH$_2$)$_2$—N$^s$Bu]-, (N$^s$Bu$_2$)$_2$-M-C$_5$H$_3$-1-Me-2-[(CH$_2$)$_2$—N$^s$Bu]-, (N$^t$Bu$_2$)$_2$-M-C$_5$H$_3$-1-Me-2-[(CH$_2$)$_2$—N$^s$Bu]-, (NH$_2$)(Cp)-M-C$_5$H$_3$-1-Me-2-[(CH$_2$)$_2$—N$^s$Bu]-, (NMe$_2$)(Cp)-M-C$_5$H$_3$-1-Me-2-[(CH$_2$)$_2$—N$^s$Bu]-, (NEt$_2$)(Cp)-M-C$_5$H$_3$-1-Me-2-[(CH$_2$)$_2$—N$^s$Bu]-, (N$^n$Pr$_2$)(Cp)-M-C$_5$H$_3$-1-Me-2-[(CH$_2$)$_2$—N$^s$Bu]-, (N$^i$Pr$_2$)(Cp)-M-C$_5$H$_3$-1-Me-2-[(CH$_2$)$_2$—N$^s$Bu]-, (N$^n$Bu$_2$)(Cp)-M-C$_5$H$_3$-1-Me-2-[(CH$_2$)$_2$—N$^s$Bu]-, (N$^i$Bu$_2$)(Cp)-M-C$_5$H$_3$-1-Me-2-[(CH$_2$)$_2$—N$^s$Bu]-, (N$^s$Bu$_2$)(Cp)-M-C$_5$H$_3$-1-Me-2-[(CH$_2$)$_2$—N$^s$Bu]-, (N$^t$Bu$_2$)(Cp)-M-C$_5$H$_3$-1-Me-2-[(CH$_2$)$_2$—N$^s$Bu]-, (OH)$_2$-M-C$_5$H$_3$-1-Me-2-[(CH$_2$)$_2$—N$^s$Bu]-, (OMe)$_2$-M-C$_5$H$_3$-1-Me-2-[(CH$_2$)$_2$—N$^s$Bu]-, (OEt)$_2$-M-C$_5$H$_3$-1-Me-2-[(CH$_2$)$_2$—N$^s$Bu]-, (O$^n$Pr)$_2$-M-C$_5$H$_3$-1-Me-2-[(CH$_2$)$_2$—N$^s$Bu]-, (O$^i$Pr)$_2$-M-C$_5$H$_3$-1-Me-2-[(CH$_2$)$_2$—N$^s$Bu]-, (O$^n$Bu)$_2$-M-C$_5$H$_3$-1-Me-2-[(CH$_2$)$_2$—

$N^sBu$]-, $(O^iBu_2$-M-$C_5H_3$-1-Me-2-[$(CH_2)_2$—$N^sBu$]-, $(O^tBu)_2$-M-$C_5H_3$-1-Me-2-[$(CH_2)_2$—$N^sBu$]-, $(O^sBu)_2$-M-$C_5H_3$-1-Me-2-[$(CH_2)_2$—$N^sBu$]-, $(NH_2)_2$-M-$C_5H_3$-1-Me-3-[$(CH_2)_2$—$N^sBu$]-, $(NMe_2)_2$-M-$C_5H_3$-1-Me-3-[$(CH_2)_2$—$N^sBu$]-, $(NEt_2)_2$-M-$C_5H_3$-1-Me-3-[$(CH_2)_2$—$N^sBu$]-, $(N^nPr_2)_2$-M-$C_5H_3$-1-Me-3-[$(CH_2)_2$—$N^sBu$]-, $(N^iPr_2)_2$-M-$C_5H_3$-1-Me-3-[$(CH_2)_2$—$N^sBu$]-, $(N^nBu_2)_2$-M-$C_5H_3$-1-Me-3-[$(CH_2)_2$—$N^sBu$]-, $(N^iBu_2)_2$-M-$C_5H_3$-1-Me-3-[$(CH_2)_2$—$N^sBu$]-, $(N^sBu_2)_2$-M-$C_5H_3$-1-Me-3-[$(CH_2)_2$—$N^sBu$]-, $(N^tBu_2)_2$-M-$C_5H_3$-1-Me-3-[$(CH_2)_2$—$N^sBu$]-, $(NH_2)(Cp)$-M-$C_5H_3$-1-Me-3-[$(CH_2)_2$—$N^sBu$]-, $(NMe_2)(Cp)$-M-$C_5H_3$-1-Me-3-[$(CH_2)_2$—$N^sBu$]-, $(NEt_2)(Cp)$-M-$C_5H_3$-1-Me-3-[$(CH_2)_2$—$N^sBu$]-, $(N^nPr_2)(Cp)$-M-$C_5H_3$-1-Me-3-[$(CH_2)_2$—$N^sBu$]-, $(N^iPr_2)(Cp)$-M-$C_5H_3$-1-Me-3-[$(CH_2)_2$—$N^sBu$]-, $(N^nBu_2)(Cp)$-M-$C_5H_3$-1-Me-3-[$(CH_2)_2$—$N^sBu$]-, $(N^iBu_2)(Cp)$-M-$C_5H_3$-1-Me-3-[$(CH_2)_2$—$N^sBu$]-, $(N^sBu_2)(Cp)$-M-$C_5H_3$-1-Me-3-[$(CH_2)_2$—$N^sBu$]-, $(N^tBu_2)(Cp)$-M-$C_5H_3$-1-Me-3-[$(CH_2)_2$—$N^sBu$]-, $(OH)_2$-M-$C_5H_3$-1-Me-3-[$(CH_2)_2$—$N^sBu$]-, $(OMe)_2$-M-$C_5H_3$-1-Me-3-[$(CH_2)_2$—$N^sBu$]-, $(OEt)_2$-M-$C_5H_3$-1-Me-3-[$(CH_2)_2$—$N^sBu$]-, $(O^nPr)_2$-M-$C_5H_3$-1-Me-3-[$(CH_2)_2$—$N^sBu$]-, $(O^iPr)_2$-M-$C_5H_3$-1-Me-3-[$(CH_2)_2$—$N^sBu$]-, $(O^nBu)_2$-M-$C_5H_3$-1-Me-3-[$(CH_2)_2$—$N^sBu$]-, $(O^iBu_2$-M-$C_5H_3$-1-Me-3-[$(CH_2)_2$—$N^sBu$]-, $(O^tBu)_2$-M-$C_5H_3$-1-Me-3-[$(CH_2)_2$—$N^sBu$]-, $(O^sBu)_2$-M-$C_5H_3$-1-Me-3-[$(CH_2)_2$—$N^sBu$]-, $(NH_2)_2$-M-$C_5H_3$-1-Et-2-[$(CH_2)_2$—$N^sBu$]-, $(NMe_2)_2$-M-$C_5H_3$-1-Et-2-[$(CH_2)_2$—$N^sBu$]-, $(NEt_2)_2$-M-$C_5H_3$-1-Et-2-[$(CH_2)_2$—$N^sBu$]-, $(N^nPr_2)_2$-M-$C_5H_3$-1-Et-2-[$(CH_2)_2$—$N^sBu$]-, $(N^iPr_2)_2$-M-$C_5H_3$-1-Et-2-[$(CH_2)_2$—$N^sBu$]-, $(N^nBu_2)_2$-M-$C_5H_3$-1-Et-2-[$(CH_2)_2$—$N^sBu$]-, $(N^iBu_2)_2$-M-$C_5H_3$-1-Et-2-[$(CH_2)_2$—$N^sBu$]-, $(N^sBu_2)_2$-M-$C_5H_3$-1-Et-2-[$(CH_2)_2$—$N^sBu$]-, $(N^tBu_2)_2$-M-$C_5H_3$-1-Et-2-[$(CH_2)_2$—$N^sBu$]-, $(NH_2)(Cp)$-M-$C_5H_3$-1-Et-2-[$(CH_2)_2$—$N^sBu$]-, $(NMe_2)(Cp)$-M-$C_5H_3$-1-Et-2-[$(CH_2)_2$—$N^sBu$]-, $(NEt_2)(Cp)$-M-$C_5H_3$-1-Et-2-[$(CH_2)_2$—$N^sBu$]-, $(N^nPr_2)(Cp)$-M-$C_5H_3$-1-Et-2-[$(CH_2)_2$—$N^sBu$]-, $(N^iPr_2)(Cp)$-M-$C_5H_3$-1-Et-2-[$(CH_2)_2$—$N^sBu$]-, $(N^nBu_2)(Cp)$-M-$C_5H_3$-1-Et-2-[$(CH_2)_2$—$N^sBu$]-, $(N^iBu_2)(Cp)$-M-$C_5H_3$-1-Et-2-[$(CH_2)_2$—$N^sBu$]-, $(N^sBu_2)(Cp)$-M-$C_5H_3$-1-Et-2-[$(CH_2)_2$—$N^sBu$]-, $(N^tBu_2)(Cp)$-M-$C_5H_3$-1-Et-2-[$(CH_2)_2$—$N^sBu$]-, $(OH)_2$-M-$C_5H_3$-1-Et-2-[$(CH_2)_2$—$N^sBu$]-, $(OMe)_2$-M-$C_5H_3$-1-Et-2-[$(CH_2)_2$—$N^sBu$]-, $(OEt)_2$-M-$C_5H_3$-1-Et-2-[$(CH_2)_2$—$N^sBu$]-, $(O^nPr)_2$-M-$C_5H_3$-1-Et-2-[$(CH_2)_2$—$N^sBu$]-, $(O^iPr)_2$-M-$C_5H_3$-1-Et-2-[$(CH_2)_2$—$N^sBu$]-, $(O^nBu)_2$-M-$C_5H_3$-1-Et-2-[$(CH_2)_2$—$N^sBu$]-, $(O^iBu_2$-M-$C_5H_3$-1-Et-2-[$(CH_2)_2$—$N^sBu$]-, $(O^tBu)_2$-M-$C_5H_3$-1-Et-2-[$(CH_2)_2$—$N^sBu$]-, $(O^sBu)_2$-M-$C_5H_3$-1-Et-2-[$(CH_2)_2$—$N^sBu$]-, $(NH_2)_2$-M-$C_5H_3$-1-Et-3-[$(CH_2)_2$—$N^sBu$]-, $(NMe_2)_2$-M-$C_5H_3$-1-Et-3-[$(CH_2)_2$—$N^sBu$]-, $(NEt_2)_2$-M-$C_5H_3$-1-Et-3-[$(CH_2)_2$—$N^sBu$]-, $(N^nPr_2)_2$-M-$C_5H_3$-1-Et-3-[$(CH_2)_2$—$N^sBu$]-, $(N^iPr_2)_2$-M-$C_5H_3$-1-Et-3-[$(CH_2)_2$—$N^sBu$]-, $(N^nBu_2)_2$-M-$C_5H_3$-1-Et-3-[$(CH_2)_2$—$N^sBu$]-, $(N^iBu_2)_2$-M-$C_5H_3$-1-Et-3-[$(CH_2)_2$—$N^sBu$]-, $(N^sBu_2)_2$-M-$C_5H_3$-1-Et-3-[$(CH_2)_2$—$N^sBu$]-, $(N^tBu_2)_2$-M-$C_5H_3$-1-Et-3-[$(CH_2)_2$—$N^sBu$]-, $(NH_2)(Cp)$-M-$C_5H_3$-1-Et-3-[$(CH_2)_2$—$N^sBu$]-, $(NMe_2)(Cp)$-M-$C_5H_3$-1-Et-3-[$(CH_2)_2$—$N^sBu$]-, $(NEt_2)(Cp)$-M-$C_5H_3$-1-Et-3-[$(CH_2)_2$—$N^sBu$]-, $(N^nPr_2)(Cp)$-M-$C_5H_3$-1-Et-3-[$(CH_2)_2$—$N^sBu$]-, $(N^iPr_2)(Cp)$-M-$C_5H_3$-1-Et-3-[$(CH_2)_2$—$N^sBu$]-, $(N^nBu_2)(Cp)$-M-$C_5H_3$-1-Et-3-[$(CH_2)_2$—$N^sBu$]-, $(N^iBu_2)(Cp)$-M-$C_5H_3$-1-Et-3-[$(CH_2)_2$—$N^sBu$]-, $(N^sBu_2)(Cp)$-M-$C_5H_3$-1-Et-3-[$(CH_2)_2$—$N^sBu$]-, $(N^tBu_2)(Cp)$-M-$C_5H_3$-1-Et-3-[$(CH_2)_2$—$N^sBu$]-, $(OH)_2$-M-$C_5H_3$-1-Et-3-[$(CH_2)_2$—$N^sBu$]-, $(OMe)_2$-M-$C_5H_3$-1-Et-3-[$(CH_2)_2$—$N^sBu$]-, $(OEt)_2$-M-$C_5H_3$-1-Et-3-[$(CH_2)_2$—$N^sBu$]-, $(O^nPr)_2$-M-$C_5H_3$-1-Et-3-[$(CH_2)_2$—$N^sBu$]-, $(O^iPr)_2$-M-$C_5H_3$-1-Et-3-[$(CH_2)_2$—$N^sBu$]-, $(O^nBu)_2$-M-$C_5H_3$-1-Et-3-[$(CH_2)_2$—$N^sBu$]-, $(O^iBu_2$-M-$C_5H_3$-1-Et-3-[$(CH_2)_2$—$N^sBu$]-, $(O^tBu)_2$-M-$C_5H_3$-1-Et-3-[$(CH_2)_2$—$N^sBu$]-, $(O^sBu)_2$-M-$C_5H_3$-1-Et-3-[$(CH_2)_2$—$N^sBu$]-, $(NH_2)_2$-M-$C_5H_3$-1-$^i$Pr-2-[$(CH_2)_2$—$N^sBu$]-, $(NMe_2)_2$-M-$C_5H_3$-1-$^i$Pr-2-[$(CH_2)_2$—$N^sBu$]-, $(NEt_2)_2$-M-$C_5H_3$-1-$^i$Pr-2-[$(CH_2)_2$—$N^sBu$]-, $(N^nPr_2)_2$-M-$C_5H_3$-1-$^i$Pr-2-[$(CH_2)_2$—$N^sBu$]-, $(N^iPr_2)_2$-M-$C_5H_3$-1-$^i$Pr-2-[$(CH_2)_2$—$N^sBu$]-, $(N^nBu_2)_2$-M-$C_5H_3$-1-$^i$Pr-2-[$(CH_2)_2$—$N^sBu$]-, $(N^iBu_2)_2$-M-$C_5H_3$-1-$^i$Pr-2-[$(CH_2)_2$—$N^sBu$]-, $(N^sBu_2)_2$-M-$C_5H_3$-1-$^i$Pr-2-[$(CH_2)_2$—$N^sBu$]-, $(N^tBu_2)_2$-M-$C_5H_3$-1-$^i$Pr-2-[$(CH_2)_2$—$N^sBu$]-, $(NH_2)(Cp)$-M-$C_5H_3$-1-$^i$Pr-2-[$(CH_2)_2$—$N^sBu$]-, $(NMe_2)(Cp)$-M-$C_5H_3$-1-$^i$Pr-2-[$(CH_2)_2$—$N^sBu$]-, $(NEt_2)(Cp)$-M-$C_5H_3$-1-$^i$Pr-2-[$(CH_2)_2$—$N^sBu$]-, $(N^nPr_2)(Cp)$-M-$C_5H_3$-1-$^i$Pr-2-[$(CH_2)_2$—$N^sBu$]-, $(N^iPr_2)(Cp)$-M-$C_5H_3$-1-$^i$Pr-2-[$(CH_2)_2$—$N^sBu$]-, $(N^nBu_2)(Cp)$-M-$C_5H_3$-1-$^i$Pr-2-[$(CH_2)_2$—$N^sBu$]-, $(N^iBu_2)(Cp)$-M-$C_5H_3$-1-$^i$Pr-2-[$(CH_2)_2$—$N^sBu$]-, $(N^sBu_2)(Cp)$-M-$C_5H_3$-1-$^i$Pr-2-[$(CH_2)_2$—$N^sBu$]-, $(N^tBu_2)(Cp)$-M-$C_5H_3$-1-$^i$Pr-2-[$(CH_2)_2$—$N^sBu$]-, $(OH)_2$-M-$C_5H_3$-1-$^i$Pr-2-[$(CH_2)_2$—$N^sBu$]-, $(OMe)_2$-M-$C_5H_3$-1-$^i$Pr-2-[$(CH_2)_2$—$N^sBu$]-, $(OEt)_2$-M-$C_5H_3$-1-$^i$Pr-2-[$(CH_2)_2$—$N^sBu$]-, $(O^nPr)_2$-M-$C_5H_3$-1-$^i$Pr-2-[$(CH_2)_2$—$N^sBu$]-, $(O^iPr)_2$-M-$C_5H_3$-1-$^i$Pr-2-[$(CH_2)_2$—$N^sBu$]-, $(O^nBu)_2$-M-$C_5H_3$-1-$^i$Pr-2-[$(CH_2)_2$—$N^sBu$]-, $(O^iBu_2$-M-$C_5H_3$-1-$^i$Pr-2-[$(CH_2)_2$—$N^sBu$]-, $(O^tBu)_2$-M-$C_5H_3$-1-$^i$Pr-2-[$(CH_2)_2$—$N^sBu$]-, $(O^sBu)_2$-M-$C_5H_3$-1-$^i$Pr-2-[$(CH_2)_2$—$N^sBu$]-, $(NH_2)_2$-M-$C_5H_3$-1-$^i$Pr-3-[$(CH_2)_2$—$N^sBu$]-, $(NMe_2)_2$-M-$C_5H_3$-1-$^i$Pr-3-[$(CH_2)_2$—$N^sBu$]-, $(NEt_2)_2$-M-$C_5H_3$-1-$^i$Pr-3-[$(CH_2)_2$—$N^sBu$]-, $(N^nPr_2)_2$-M-$C_5H_3$-1-$^i$Pr-3-[$(CH_2)_2$—$N^sBu$]-, $(N^iPr_2)_2$-M-$C_5H_3$-1-$^i$Pr-3-[$(CH_2)_2$—$N^sBu$]-, $(N^nBu_2)_2$-M-$C_5H_3$-1-$^i$Pr-3-[$(CH_2)_2$—$N^sBu$]-, $(N^iBu_2)_2$-M-$C_5H_3$-1-$^i$Pr-3-[$(CH_2)_2$—$N^sBu$]-, $(N^sBu_2)_2$-M-$C_5H_3$-1-$^i$Pr-3-[$(CH_2)_2$—$N^sBu$]-, $(N^tBu_2)_2$-M-$C_5H_3$-1-$^i$Pr-3-[$(CH_2)_2$—$N^sBu$]-, $(NH_2)(Cp)$-M-$C_5H_3$-1-$^i$Pr-3-[$(CH_2)_2$—$N^sBu$]-, $(NMe_2)(Cp)$-M-$C_5H_3$-1-$^i$Pr-3-[$(CH_2)_2$—$N^sBu$]-, $(NEt_2)(Cp)$-M-$C_5H_3$-1-$^i$Pr-3-[$(CH_2)_2$—$N^sBu$]-, $(N^nPr_2)(Cp)$-M-$C_5H_3$-1-$^i$Pr-3-[$(CH_2)_2$—$N^sBu$]-, $(N^iPr_2)(Cp)$-M-$C_5H_3$-1-$^i$Pr-3-[$(CH_2)_2$—$N^sBu$]-, $(N^nBu_2)(Cp)$-M-$C_5H_3$-1-$^i$Pr-3-[$(CH_2)_2$—$N^sBu$]-, $(N^iBu_2)(Cp)$-M-$C_5H_3$-1-$^i$Pr-3-[$(CH_2)_2$—$N^sBu$]-, $(N^sBu_2)(Cp)$-M-$C_5H_3$-1-$^i$Pr-3-[$(CH_2)_2$—$N^sBu$]-, $(N^tBu_2)(Cp)$-M-$C_5H_3$-1-$^i$Pr-3-[$(CH_2)_2$—$N^sBu$]-, $(OH)_2$-M-$C_5H_3$-1-$^i$Pr-3-[$(CH_2)_2$—$N^sBu$]-, $(OMe)_2$-M-$C_5H_3$-1-$^i$Pr-3-[$(CH_2)_2$—$N^sBu$]-, $(OEt)_2$-M-$C_5H_3$-1-$^i$Pr-3-[$(CH_2)_2$—$N^sBu$]-, $(O^nPr)_2$-M-$C_5H_3$-1-$^i$Pr-3-[$(CH_2)_2$—$N^sBu$]-, $(O^iPr)_2$-M-$C_5H_3$-1-$^i$Pr-3-[$(CH_2)_2$—$N^sBu$]-, $(O^nBu)_2$-M-$C_5H_3$-1-$^i$Pr-3-[$(CH_2)_2$—$N^sBu$]-, $(O^iBu_2$-M-$C_5H_3$-1-$^i$Pr-3-[$(CH_2)_2$—$N^sBu$]-, $(O^tBu)_2$-M-$C_5H_3$-1-$^i$Pr-3-[$(CH_2)_2$—$N^sBu$]-, $(O^sBu)_2$-M-$C_5H_3$-1-$^i$Pr-3-[$(CH_2)_2$—$N^sBu$]-, $(NH_2)_2$-M-$C_5H_3$-1-$^t$Bu-2-[$(CH_2)_2$—$N^sBu$]-, $(NMe_2)_2$-M-$C_5H_3$-1-$^t$Bu-2-[$(CH_2)_2$—$N^sBu$]-, $(NEt_2)_2$-M-$C_5H_3$-1-$^t$Bu-2-[$(CH_2)_2$—$N^sBu$]-, $(N^nPr_2)_2$-M-$C_5H_3$-1-$^t$Bu-2-[$(CH_2)_2$—$N^sBu$]-, $(N^iPr_2)_2$-M-$C_5H_3$-1-$^t$Bu-2-[$(CH_2)_2$—$N^sBu$]-, $(N^nBu_2)_2$-M-$C_5H_3$-1-$^t$Bu-2-[$(CH_2)_2$—$N^sBu$]-, $(N^iBu_2)_2$-M-$C_5H_3$-1-$^t$Bu-2-[$(CH_2)_2$—$N^sBu$]-, $(N^sBu_2)_2$-M-$C_5H_3$-1-$^t$Bu-2-[$(CH_2)_2$—$N^sBu$]-, $(N^tBu_2)_2$-M-$C_5H_3$-1-$^t$Bu-2-[$(CH_2)_2$—$N^sBu$]-, $(NH_2)(Cp)$-M-$C_5H_3$-1-$^t$Bu-2-[$(CH_2)_2$—$N^sBu$]-, $(NMe_2)(Cp)$-M-$C_5H_3$-1-$^t$Bu-2-[$(CH_2)_2$—$N^sBu$]-, $(NEt_2)(Cp)$-M-$C_5H_3$-1-$^t$Bu-2-[$(CH_2)_2$—$N^sBu$]-, $(N^nPr_2)(Cp)$-M-$C_5H_3$-1-$^t$Bu-2-[$(CH_2)_2$—$N^sBu$]-, $(N^iPr_2)(Cp)$-M-$C_5H_3$-1-$^t$Bu-2-[$(CH_2)_2$—$N^sBu$]-, $(N^nBu_2)(Cp)$-M-$C_5H_3$-1-$^t$Bu-2-[$(CH_2)_2$—$N^sBu$]-, $(N^iBu_2)(Cp)$-M-$C_5H_3$-1-$^t$Bu-2-[$(CH_2)_2$—$N^sBu$]-, $(N^sBu_2)(Cp)$-M-$C_5H_3$-1-$^t$Bu-2-[$(CH_2)_2$—$N^sBu$]-, $(N^tBu_2)(Cp)$-M-$C_5H_3$-1-$^t$Bu-2-[$(CH_2)_2$—$N^sBu$]-, $(OH)_2$-M-$C_5H_3$-1-$^t$Bu-2-[$(CH_2)_2$—$N^sBu$]-, $(OMe)_2$-M-$C_5H_3$-1-$^t$Bu-2-[$(CH_2)_2$—$N^sBu$]-, $(OEt)_2$-M-$C_5H_3$-1-$^t$Bu-2-[$(CH_2)_2$—$N^sBu$]-, $(O^nPr)_2$-M-$C_5H_3$-1-$^t$Bu-2-[$(CH_2)_2$—$N^sBu$]-, $(O^iPr)_2$-M-$C_5H_3$-1-$^t$Bu-2-[$(CH_2)_2$—$N^sBu$]-, $(O^nBu)_2$-M-$C_5H_3$-1-$^t$Bu-2-[$(CH_2)_2$—$N^sBu$]-, $(O^iBu_2$-M-$C_5H_3$-1-$^t$Bu-2-[$(CH_2)_2$—$N^sBu$]-, $(O^tBu)_2$-M-$C_5H_3$-1-$^t$Bu-2-[$(CH_2)_2$—$N^sBu$]-, (O$^s$Bu)$_2$-M-C$_5$H$_3$-1-$^t$Bu-2-[(CH$_2$)$_2$—N$^s$Bu]-, (NH$_2$)$_2$-M-C$_5$H$_3$-1-$^t$Bu-3-[(CH$_2$)$_2$—N$^s$Bu]-, (NMe$_2$)$_2$-M-C$_5$H$_3$-1-$^t$Bu-3-[(CH$_2$)$_2$—N$^s$Bu]-, (NEt$_2$)$_2$-M-C$_5$H$_3$-1-$^t$Bu-3-[(CH$_2$)$_2$—N$^s$Bu]-, (N$^n$Pr$_2$)$_2$-M-C$_5$H$_3$-1-$^t$Bu-3-[(CH$_2$)$_2$—N$^s$Bu]-, (N$^i$Pr$_2$)$_2$-M-C$_5$H$_3$-1-$^t$Bu-3-[(CH$_2$)$_2$—N$^s$Bu]-, (N$^n$Bu$_2$)$_2$-M-C$_5$H$_3$-1-$^t$Bu-3-[(CH$_2$)$_2$—N$^s$Bu]-, (N$^i$Bu$_2$)$_2$-M-C$_5$H$_3$-1-$^t$Bu-3-[(CH$_2$)$_2$—N$^s$Bu]-, (N$^s$Bu$_2$)$_2$-M-C$_5$H$_3$-1-$^t$Bu-3-[(CH$_2$)$_2$—N$^s$Bu]-, (N$^t$Bu$_2$)$_2$-M-C$_5$H$_3$-1-$^t$Bu-3-[(CH$_2$)$_2$—N$^s$Bu]-, (NH$_2$)(Cp)-M-C$_5$H$_3$-1-$^t$Bu-3-[(CH$_2$)$_2$—N$^s$Bu]-, (NMe$_2$)(Cp)-M-C$_5$H$_3$-1-$^t$Bu-3-[(CH$_2$)$_2$—N$^s$Bu]-, (NEt$_2$)(Cp)-M-C$_5$H$_3$-1-$^t$Bu-3-[(CH$_2$)$_2$—N$^s$Bu]-, (N$^n$Pr$_2$)(Cp)-M-C$_5$H$_3$-1-$^t$Bu-3-[(CH$_2$)$_2$—N$^s$Bu]-, (N$^i$Pr$_2$)(Cp)-M-C$_5$H$_3$-1-$^t$Bu-3-[(CH$_2$)$_2$—N$^s$Bu]-, (N$^n$Bu$_2$)(Cp)-M-C$_5$H$_3$-1-$^t$Bu-3-[(CH$_2$)$_2$—N$^s$Bu]-, (N$^i$Bu$_2$)(Cp)-M-C$_5$H$_3$-1-$^t$Bu-3-[(CH$_2$)$_2$—N$^s$Bu]-, (N$^s$Bu$_2$)(Cp)-M-C$_5$H$_3$-1-$^t$Bu-3-[(CH$_2$)$_2$—N$^s$Bu]-, (N$^t$al$_2$)(Cp)-M-C$_5$H$_3$-1-$^t$Bu-3-[(CH$_2$)$_2$—N$^s$Bu]-, (OH)$_2$-M-C$_5$H$_3$-1-$^t$Bu-3-[(CH$_2$)$_2$—N$^s$Bu]-, (OMe)$_2$-M-C$_5$H$_3$-1-$^t$Bu-3-[(CH$_2$)$_2$—N$^s$Bu]-, (OEt)$_2$-M-C$_5$H$_3$-1-$^t$Bu-3-[(CH$_2$)$_2$—N$^s$Bu]-, (O$^n$Pr)$_2$-M-C$_5$H$_3$-1-$^t$Bu-3-[(CH$_2$)$_2$—N$^s$Bu]-, (O$^i$Pr)$_2$-M-C$_5$H$_3$-1$^t$Bu-3-[(CH$_2$)$_2$—N$^s$Bu]-, (O$^n$Bu)$_2$-M-C$_5$H$_3$-1-$^t$Bu-3-[(CH$_2$)$_2$—N$^s$Bu]-, (O$^i$Bu$_2$-M-C$_5$H$_3$-1-$^t$Bu-3-[(CH$_2$)$_2$—N$^s$Bu]-, (O$^t$Bu)$_2$-M-C$_5$H$_3$-1-$^t$Bu-3-[(CH$_2$)$_2$—N$^s$Bu]-, (O$^s$Bu)$_2$-M-C$_5$H$_3$-1-$^t$Bu-3-[(CH$_2$)$_2$—N$^s$Bu]-, (NH$_2$)$_2$-M-C$_5$H$_3$-1-Me-2-[(CH$_2$)$_2$—N$^t$Bu]-, (NMe$_2$)$_2$-M-C$_5$H$_3$-1-Me-2-[(CH$_2$)$_2$—N$^t$Bu]-, (NEt$_2$)$_2$-M-C$_5$H$_3$-1-Me-2-[(CH$_2$)$_2$—N$^t$Bu]-, (N$^n$Pr$_2$)$_2$-M-C$_5$H$_3$-1-Me-2-[(CH$_2$)$_2$—N$^t$Bu]-, (N$^i$Pr$_2$)$_2$-M-C$_5$H$_3$-1-Me-2-[(CH$_2$)$_2$—N$^t$Bu]-, (N$^n$Bu$_2$)$_2$-M-C$_5$H$_3$-1-Me-2-[(CH$_2$)$_2$—N$^t$Bu]-, (N$^i$Bu$_2$)$_2$-M-C$_5$H$_3$-1-Me-2-[(CH$_2$)$_2$—N$^t$Bu]-, (N$^s$Bu$_2$)$_2$-M-C$_5$H$_3$-1-Me-2-[(CH$_2$)$_2$—N$^t$Bu]-, (N$^t$Bu$_2$)$_2$-M-C$_5$H$_3$-1-Me-2-[(CH$_2$)$_2$—N$^t$Bu]-, (NH$_2$)(Cp)-M-C$_5$H$_3$-1-Me-2-[(CH$_2$)$_2$—N$^t$Bu]-, (NMe$_2$)(Cp)-M-C$_5$H$_3$-1-Me-2-[(CH$_2$)$_2$—N$^t$Bu]-, (NEt$_2$)(Cp)-M-C$_5$H$_3$-1-Me-2-[(CH$_2$)$_2$—N$^t$Bu]-, (N$^n$Pr$_2$)(Cp)-M-C$_5$H$_3$-1-Me-2-[(CH$_2$)$_2$—N$^t$Bu]-, (N$^i$Pr$_2$)(Cp)-M-C$_5$H$_3$-1-Me-2-[(CH$_2$)$_2$—N$^t$Bu]-, (N$^n$Bu$_2$)(Cp)-M-C$_5$H$_3$-1-Me-2-[(CH$_2$)$_2$—N$^t$Bu]-, (N$^i$Bu$_2$)(Cp)-M-C$_5$H$_3$-1-Me-2-[(CH$_2$)$_2$—N$^t$Bu]-, (N$^s$Bu$_2$)(Cp)-M-C$_5$H$_3$-1-Me-2-[(CH$_2$)$_2$—N$^t$Bu]-, (N$^t$Bu$_2$)(Cp)-M-C$_5$H$_3$-1-Me-2-[(CH$_2$)$_2$—N$^t$Bu]-, (OH)$_2$-M-C$_5$H$_3$-1-Me-2-[(CH$_2$)$_2$—N$^t$Bu]-, (OMe)$_2$-M-C$_5$H$_3$-1-Me-2-[(CH$_2$)$_2$—N$^t$Bu]-, (OEt)$_2$-M-C$_5$H$_3$-1-Me-2-[(CH$_2$)$_2$—N$^t$Bu]-, (O$^n$Pr)$_2$-M-C$_5$H$_3$-1-Me-2-[(CH$_2$)$_2$—N$^t$Bu]-, (O$^i$Pr)$_2$-M-C$_5$H$_3$-1-Me-2-[(CH$_2$)$_2$—N$^t$Bu]-, (O$^n$Bu)$_2$-M-C$_5$H$_3$-1-Me-2-[(CH$_2$)$_2$—N$^t$Bu]-, (O$^i$Bu$_2$-M-C$_5$H$_3$-1-Me-2-[(CH$_2$)$_2$—N$^t$Bu]-, (O$^t$Bu)$_2$-M-C$_5$H$_3$-1-Me-2-[(CH$_2$)$_2$—N$^t$Bu]-, (O$^s$Bu)$_2$-M-C$_5$H$_3$-1-Me-2-[(CH$_2$)$_2$—N$^t$Bu]-, (NH$_2$)$_2$-M-C$_5$H$_3$-1-Me-3-[(CH$_2$)$_2$—N$^t$Bu]-, (NMe$_2$)$_2$-M-C$_5$H$_3$-1-Me-3-[(CH$_2$)$_2$—N$^t$Bu]-, (NEt$_2$)$_2$-M-C$_5$H$_3$-1-Me-3-[(CH$_2$)$_2$—N$^t$Bu]-, (N$^n$Pr$_2$)$_2$-M-C$_5$H$_3$-1-Me-3-[(CH$_2$)$_2$—N$^t$Bu]-, (N$^i$Pr$_2$)$_2$-M-C$_5$H$_3$-1-Me-3-[(CH$_2$)$_2$—N$^t$Bu]-, (N$^n$Bu$_2$)$_2$-M-C$_5$H$_3$-1-Me-3-[(CH$_2$)$_2$—N$^t$Bu]-, (N$^i$Bu$_2$)$_2$-M-C$_5$H$_3$-1-Me-3-[(CH$_2$)$_2$—N$^t$Bu]-, (N$^s$Bu$_2$)$_2$-M-C$_5$H$_3$-1-Me-3-[(CH$_2$)$_2$—N$^t$Bu]-, (N$^t$Bu$_2$)$_2$-M-C$_5$H$_3$-1-Me-3-[(CH$_2$)$_2$—N$^t$Bu]-, (NH$_2$)(Cp)-M-C$_5$H$_3$-1-Me-3-[(CH$_2$)$_2$—N$^t$Bu]-, (NMe$_2$)(Cp)-M-C$_5$H$_3$-1-Me-3-[(CH$_2$)$_2$—N$^t$Bu]-, (NEt$_2$)(Cp)-M-C$_5$H$_3$-1-Me-3-[(CH$_2$)$_2$—N$^t$Bu]-, (N$^n$Pr$_2$)(Cp)-M-C$_5$H$_3$-1-Me-3-[(CH$_2$)$_2$—N$^t$Bu]-, (N$^i$Pr$_2$)(Cp)-M-C$_5$H$_3$-1-Me-3-[(CH$_2$)$_2$—N$^t$Bu]-, (N$^n$Bu$_2$)(Cp)-M-C$_5$H$_3$-1-Me-3-[(CH$_2$)$_2$—N$^t$Bu]-, (N$^i$Bu$_2$)(Cp)-M-C$_5$H$_3$-1-Me-3-[(CH$_2$)$_2$—N$^t$Bu]-, (N$^s$Bu$_2$)(Cp)-M-C$_5$H$_3$-1-Me-3-[(CH$_2$)$_2$—N$^t$Bu]-, (N$^t$Bu$_2$)(Cp)-M-C$_5$H$_3$-1-Me-3-[(CH$_2$)$_2$—N$^t$Bu]-, (OH)$_2$-M-C$_5$H$_3$-1-Me-3-[(CH$_2$)$_2$—N$^t$Bu]-, (OMe)$_2$-M-C$_5$H$_3$-1-Me-3-[(CH$_2$)$_2$—N$^t$Bu]-, (OEt)$_2$-M-C$_5$H$_3$-1-Me-3-[(CH$_2$)$_2$—N$^t$Bu]-, (O$^n$Pr)$_2$-M-C$_5$H$_3$-1-Me-3-[(CH$_2$)$_2$—N$^t$Bu]-, (O$^i$Pr)$_2$-M-C$_5$H$_3$-1-Me-3-[(CH$_2$)$_2$—N$^t$Bu]-, (O$^n$Bu)$_2$-M-C$_5$H$_3$-1-Me-3-[(CH$_2$)$_2$—N$^t$Bu]-, (O$^i$Bu$_2$-M-C$_5$H$_3$-1-Me-3-[(CH$_2$)$_2$—N$^t$Bu]-, (O$^t$Bu)$_2$-M-C$_5$H$_3$-1-Me-3-[(CH$_2$)$_2$—N$^t$Bu]-, (O$^s$Bu)$_2$-M-C$_5$H$_3$-1-Me-3-[(CH$_2$)$_2$—N$^t$Bu]-, (NH$_2$)$_2$-M-C$_5$H$_3$-1-Et-2-[(CH$_2$)$_2$—N$^t$Bu]-, (NMe$_2$)$_2$-M-C$_5$H$_3$-1-Et-2-[(CH$_2$)$_2$—N$^t$Bu]-, (NEt$_2$)$_2$-M-C$_5$H$_3$-1-Et-2-[(CH$_2$)$_2$—N$^t$Bu]-, (N$^n$Pr$_2$)$_2$-M-C$_5$H$_3$-1-Et-2-[(CH$_2$)$_2$—N$^t$Bu]-, (N$^i$Pr$_2$)$_2$-M-C$_5$H$_3$-1-Et-2-[(CH$_2$)$_2$—N$^t$Bu]-, (N$^n$Bu$_2$)$_2$-M-C$_5$H$_3$-1-Et-2-[(CH$_2$)$_2$—N$^t$Bu]-, (N$^i$Bu$_2$)$_2$-M-C$_5$H$_3$-1-Et-2-[(CH$_2$)$_2$—N$^t$Bu]-, (N$^s$Bu$_2$)$_2$-M-C$_5$H$_3$-1-Et-2-[(CH$_2$)$_2$—N$^t$Bu]-, (N$^t$Bu$_2$)$_2$-M-C$_5$H$_3$-1-Et-2-[(CH$_2$)$_2$—N$^t$Bu]-, (NH$_2$)(Cp)-M-C$_5$H$_3$-1-Et-2-[(CH$_2$)$_2$—N$^t$Bu]-, (NMe$_2$)(Cp)-M-C$_5$H$_3$-1-Et-2-[(CH$_2$)$_2$—N$^t$Bu]-, (NEt$_2$)(Cp)-M-C$_5$H$_3$-1-Et-2-[(CH$_2$)$_2$—N$^t$Bu]-, (N$^n$Pr$_2$)(Cp)-M-C$_5$H$_3$-1-Et-2-[(CH$_2$)$_2$—N$^t$Bu]-, (N$^i$Pr$_2$)(Cp)-M-C$_5$H$_3$-1-Et-2-[(CH$_2$)$_2$—N$^t$Bu]-, (N$^n$Bu$_2$)(Cp)-M-C$_5$H$_3$-1-Et-2-[(CH$_2$)$_2$—N$^t$Bu]-, (N$^i$Bu$_2$)(Cp)-M-C$_5$H$_3$-1-Et-2-[(CH$_2$)$_2$—N$^t$Bu]-, (N$^s$Bu$_2$)(Cp)-M-C$_5$H$_3$-1-Et-2-[(CH$_2$)$_2$—N$^t$Bu]-, (N$^t$Bu$_2$)(Cp)-M-C$_5$H$_3$-1-Et-2-[(CH$_2$)$_2$—N$^t$Bu]-, (OH)$_2$-M-C$_5$H$_3$-1-Et-2-[(CH$_2$)$_2$—N$^t$Bu]-, (OMe)$_2$-M-C$_5$H$_3$-1-Et-2-[(CH$_2$)$_2$—N$^t$Bu]-, (OEt)$_2$-M-C$_5$H$_3$-1-Et-2-[(CH$_2$)$_2$—N$^t$Bu]-, (O$^n$Pr)$_2$-M-C$_5$H$_3$-1-Et-2-[(CH$_2$)$_2$—N$^t$Bu]-, (O$^i$Pr)$_2$-M-C$_5$H$_3$-1-Et-2-[(CH$_2$)$_2$—N$^t$Bu]-, (O$^n$Bu)$_2$-M-C$_5$H$_3$-1-Et-2-[(CH$_2$)$_2$—N$^t$Bu]-, (O$^i$Bu$_2$-M-C$_5$H$_3$-1-Et-2-[(CH$_2$)$_2$—N$^t$Bu]-, (O$^t$Bu)$_2$-M-C$_5$H$_3$-1-Et-2-[(CH$_2$)$_2$—N$^t$Bu]-, (O$^s$Bu)$_2$-M-C$_5$H$_3$-1-Et-2-[(CH$_2$)$_2$—N$^t$Bu]-, (NH$_2$)$_2$-M-C$_5$H$_3$-1-Et-3-[(CH$_2$)$_2$—N$^t$Bu]-, (NMe$_2$)$_2$-M-C$_5$H$_3$-1-Et-3-[(CH$_2$)$_2$—N$^t$Bu]-, (NEt$_2$)$_2$-M-C$_5$H$_3$-1-Et-3-[(CH$_2$)$_2$—N$^t$Bu]-, (N$^n$Pr$_2$)$_2$-M-C$_5$H$_3$-1-Et-3-[(CH$_2$)$_2$—N$^t$Bu]-, (N$^i$Pr$_2$)$_2$-M-C$_5$H$_3$-1-Et-3-[(CH$_2$)$_2$—N$^t$Bu]-, (N$^n$Bu$_2$)$_2$-M-C$_5$H$_3$-1-Et-3-[(CH$_2$)$_2$—N$^t$Bu]-, (N$^i$Bu$_2$)$_2$-M-C$_5$H$_3$-1-Et-3-[(CH$_2$)$_2$—N$^t$Bu]-, (N$^s$Bu$_2$)$_2$-M-C$_5$H$_3$-1-Et-3-[(CH$_2$)$_2$—N$^t$Bu]-, (N$^t$Bu$_2$)$_2$-M-C$_5$H$_3$-1-Et-3-[(CH$_2$)$_2$—N$^t$Bu]-, (NH$_2$)(Cp)-M-C$_5$H$_3$-1-Et-3-[(CH$_2$)$_2$—N$^t$Bu]-, (NMe$_2$)(Cp)-M-C$_5$H$_3$-1-Et-3-[(CH$_2$)$_2$—N$^t$Bu]-, (NEt$_2$)(Cp)-M-C$_5$H$_3$-1-Et-3-[(CH$_2$)$_2$—N$^t$Bu]-, (N$^n$Pr$_2$)(Cp)-M-C$_5$H$_3$-1-Et-3-[(CH$_2$)$_2$—N$^t$Bu]-, (N$^i$Pr$_2$)(Cp)-M-C$_5$H$_3$-1-Et-3-[(CH$_2$)$_2$—N$^t$Bu]-, (N$^n$Bu$_2$)(Cp)-M-C$_5$H$_3$-1-Et-3-[(CH$_2$)$_2$—N$^t$Bu]-, (N$^i$Bu$_2$)(Cp)-M-C$_5$H$_3$-1-Et-3-[(CH$_2$)$_2$—N$^t$Bu]-, (N$^s$Bu$_2$)(Cp)-M-C$_5$H$_3$-1-Et-3-[(CH$_2$)$_2$—N$^t$Bu]-, (N$^t$Bu$_2$)(Cp)-M-C$_5$H$_3$-1-Et-3-[(CH$_2$)$_2$—N$^t$Bu]-, (OH)$_2$-M-C$_5$H$_3$-1-Et-3-[(CH$_2$)$_2$—N$^t$Bu]-, (OMe)$_2$-M-C$_5$H$_3$-1-Et-3-[(CH$_2$)$_2$—N$^t$Bu]-, (OEt)$_2$-M-C$_5$H$_3$-1-Et-3-[(CH$_2$)$_2$—N$^t$Bu]-, (O$^n$Pr)$_2$-M-C$_5$H$_3$-1-Et-3-[(CH$_2$)$_2$—N$^t$Bu]-, (O$^i$Pr)$_2$-M-C$_5$H$_3$-1-Et-3-[(CH$_2$)$_2$—N$^t$Bu]-, (O$^n$Bu)$_2$-M-C$_5$H$_3$-1-Et-3-[(CH$_2$)$_2$—N$^t$Bu]-, (O$^i$Bu$_2$-M-C$_5$H$_3$-1-Et-3-[(CH$_2$)$_2$—N$^t$Bu]-, (O$^t$Bu)$_2$-M-C$_5$H$_3$-1-Et-3-[(CH$_2$)$_2$—N$^t$Bu]-, (O$^s$Bu)$_2$-M-C$_5$H$_3$-1-Et-3-[(CH$_2$)$_2$—N$^t$Bu]-, (NH$_2$)$_2$-M-C$_5$H$_3$-1-$^i$Pr-2-[(CH$_2$)$_2$—N$^t$Bu]-, (NMe$_2$)$_2$-M-C$_5$H$_3$-1-$^i$Pr-2-[(CH$_2$)$_2$—N$^t$Bu]-, (NEt$_2$)$_2$-M-C$_5$H$_3$-1-$^i$Pr-2-[(CH$_2$)$_2$—N$^t$Bu]-, (N$^n$Pr$_2$)$_2$-M-C$_5$H$_3$-1-$^i$Pr-2-[(CH$_2$)$_2$—N$^t$Bu]-, (N$^i$Pr$_2$)$_2$-M-C$_5$H$_3$-1-$^i$Pr-2-[(CH$_2$)$_2$—N$^t$Bu]-, (N$^n$Bu$_2$)$_2$-M-C$_5$H$_3$-1-$^i$Pr-2-[(CH$_2$)$_2$—N$^t$Bu]-, (N$^i$Bu$_2$)$_2$-M-C$_5$H$_3$-1-$^i$Pr-2-[(CH$_2$)$_2$—N$^t$Bu]-, (N$^s$Bu$_2$)$_2$-M-C$_5$H$_3$-1-$^i$Pr-2-[(CH$_2$)$_2$—N$^t$Bu]-, (N$^t$Bu$_2$)$_2$-M-C$_5$H$_3$-1-$^i$Pr-2-[(CH$_2$)$_2$—N$^t$Bu]-, (NH$_2$)(Cp)-M-C$_5$H$_3$-1-$^i$Pr-2-[(CH$_2$)$_2$—N$^t$Bu]-, (NMe$_2$)(Cp)-M-C$_5$H$_3$-1-$^i$Pr-2-[(CH$_2$)$_2$—N$^t$Bu]-, (NEt$_2$)(Cp)-M-C$_5$H$_3$-1-$^i$Pr-2-[(CH$_2$)$_2$—N$^t$Bu]-, (N$^n$Pr$_2$)(Cp)-M-C$_5$H$_3$-1-$^i$Pr-2-[(CH$_2$)$_2$—N$^t$Bu]-, (N$^i$Pr$_2$)(Cp)-M-C$_5$H$_3$-1-$^i$Pr-2-[(CH$_2$)$_2$—N$^t$Bu]-, (N$^n$Bu$_2$)(Cp)-M-C$_5$H$_3$-1-$^i$Pr-2-[(CH$_2$)$_2$—N$^t$Bu]-, (N$^i$Bu$_2$)(Cp)-M-C$_5$H$_3$-1-$^i$Pr-2-[(CH$_2$)$_2$—N$^t$Bu]-, (N$^s$Bu$_2$)(Cp)-M-C$_5$H$_3$-1-$^i$Pr-2-[(CH$_2$)$_2$—N$^t$Bu]-, (N$^t$Bu$_2$)(Cp)-M-C$_5$H$_3$-1-$^i$Pr-2-[(CH$_2$)$_2$—N$^t$Bu]-, (OH)$_2$-M-C$_5$H$_3$-1-$^i$Pr-2-[(CH$_2$)$_2$—N$^t$Bu]-, (OMe)$_2$-M-C$_5$H$_3$-1-$^i$Pr-2-[(CH$_2$)$_2$—N$^t$Bu]-, (OEt)$_2$-M-C$_5$H$_3$-1-$^i$Pr-2-[(CH$_2$)$_2$—N$^t$Bu]-, (O$^n$Pr)$_2$-M-C$_5$H$_3$-1-$^i$Pr-2-[(CH$_2$)$_2$—N$^t$Bu]-, (O$^i$Pr)$_2$-M-C$_5$H$_3$-1-$^i$Pr-2-[(CH$_2$)$_2$—N$^t$Bu]-, (O$^n$Bu)$_2$-M-C$_5$H$_3$-1-$^i$Pr-2-[(CH$_2$)$_2$—N$^t$Bu]-, (O$^i$Bu$_2$-M-C$_5$H$_3$-1-$^i$Pr-2-[(CH$_2$)$_2$—N$^t$Bu]-, (O$^t$Bu)$_2$-M-C$_5$H$_3$-1-$^i$Pr-2-[(CH$_2$)$_2$—N$^t$Bu]-, (O$^s$Bu)$_2$-M-C$_5$H$_3$-1-$^i$Pr-2-[(CH$_2$)$_2$—N$^t$Bu]-, (NH$_2$)$_2$-M-C$_5$H$_3$-1-$^i$Pr-3-[(CH$_2$)$_2$—

N$^t$Bu]-, (NMe$_2$)$_2$-M-C$_5$H$_3$-1-$^i$Pr-3-[(CH$_2$)$_2$—N$^t$Bu]-, (NEt$_2$)$_2$-M-C$_5$H$_3$-1-$^i$Pr-3-[(CH$_2$)$_2$—N$^t$Bu]-, (N$^n$Pr$_2$)$_2$-M-C$_5$H$_3$-1-$^i$Pr-3-[(CH$_2$)$_2$—N$^t$Bu]-, (N$^i$Pr$_2$)$_2$-M-C$_5$H$_3$-1-$^i$Pr-3-[(CH$_2$)$_2$—N$^t$Bu]-, (N$^n$Bu$_2$)$_2$-M-C$_5$H$_3$-1-$^i$Pr-3-[(CH$_2$)$_2$—N$^t$Bu]-, (N$^i$Bu$_2$)$_2$-M-C$_5$H$_3$-1-$^i$Pr-3-[(CH$_2$)$_2$—N$^t$Bu]-, (N$^s$Bu$_2$)$_2$-M-C$_5$H$_3$-1-$^i$Pr-3-[(CH$_2$)$_2$—N$^t$Bu]-, (N$^t$Bu$_2$)$_2$-M-C$_5$H$_3$-1-$^i$Pr-3-[(CH$_2$)$_2$—N$^t$Bu]-, (NH$_2$)(Cp)-M-C$_5$H$_3$-1-$^i$Pr-3-[(CH$_2$)$_2$—N$^t$Bu]-, (NMe$_2$)(Cp)-M-C$_5$H$_3$-1-$^i$Pr-3-[(CH$_2$)$_2$—N$^t$Bu]-, (NEt$_2$)(Cp)-M-C$_5$H$_3$-1-$^i$Pr-3-[(CH$_2$)$_2$—N$^t$Bu]-, (N$^n$Pr$_2$)(Cp)-M-C$_5$H$_3$-1-$^i$Pr-3-[(CH$_2$)$_2$—N$^t$Bu]-, (N$^i$Pr$_2$)(Cp)-M-C$_5$H$_3$-1-$^i$Pr-3-[(CH$_2$)$_2$—N$^t$Bu]-, (N$^n$Bu$_2$)(Cp)-M-C$_5$H$_3$-1-$^i$Pr-3-[(CH$_2$)$_2$—N$^t$Bu]-, (N$^i$Bu$_2$)(Cp)-M-C$_5$H$_3$-1-$^i$Pr-3-[(CH$_2$)$_2$—N$^t$Bu]-, (N$^s$Bu$_2$)(Cp)-M-C$_5$H$_3$-1-$^i$Pr-3-[(CH$_2$)$_2$—N$^t$Bu]-, (N$^t$Bu$_2$)(Cp)-M-C$_5$H$_3$-1-$^i$Pr-3-[(CH$_2$)$_2$—N$^t$Bu]-, (OH)$_2$-M-C$_5$H$_3$-1-$^i$Pr-3-[(CH$_2$)$_2$—N$^t$Bu]-, (OMe)$_2$-M-C$_5$H$_3$-1-$^i$Pr-3-[(CH$_2$)$_2$—N$^t$Bu]-, (OEt)$_2$-M-C$_5$H$_3$-1-$^i$Pr-3-[(CH$_2$)$_2$—N$^t$Bu]-, (O$^n$Pr)$_2$-M-C$_5$H$_3$-1-$^i$Pr-3-[(CH$_2$)$_2$—N$^t$Bu]-, (O$^i$Pr)$_2$-M-C$_5$H$_3$-1-$^i$Pr-3-[(CH$_2$)$_2$—N$^t$Bu]-, (O$^n$Bu)$_2$-M-C$_5$H$_3$-1-$^i$Pr-3-[(CH$_2$)$_2$—N$^t$Bu]-, (O$^i$Bu$_2$-M-C$_5$H$_3$-1-$^i$Pr-3-[(CH$_2$)$_2$—N$^t$Bu]-, (O$^t$Bu)$_2$-M-C$_5$H$_3$-1-$^i$Pr-3-[(CH$_2$)$_2$—N$^t$Bu]-, (O$^s$Bu)$_2$-M-C$_5$H$_3$-1-$^i$Pr-3-[(CH$_2$)$_2$—N$^t$Bu]-, (NH$_2$)$_2$-M-C$_5$H$_3$-1-$^t$Bu-2-[(CH$_2$)$_2$—N$^t$Bu]-, (NMe$_2$)$_2$-M-C$_5$H$_3$-1-$^t$Bu-2-[(CH$_2$)$_2$—N$^t$Bu]-, (NEt$_2$)$_2$-M-C$_5$H$_3$-1-$^t$Bu-2-[(CH$_2$)$_2$—N$^t$Bu]-, (N$^n$Pr$_2$)$_2$-M-C$_5$H$_3$-1-$^t$Bu-2-[(CH$_2$)$_2$—N$^t$Bu]-, (N$^i$Pr$_2$)$_2$-M-C$_5$H$_3$-1-$^t$Bu-2-[(CH$_2$)$_2$—N$^t$Bu]-, (N$^n$Bu$_2$)$_2$-M-C$_5$H$_3$-1-$^t$Bu-2-[(CH$_2$)$_2$—N$^t$Bu]-, (N$^i$Bu$_2$)$_2$-M-C$_5$H$_3$-1-$^t$Bu-2-[(CH$_2$)$_2$—N$^t$Bu]-, (N$^s$Bu$_2$)$_2$-M-C$_5$H$_3$-1-$^t$Bu-2-[(CH$_2$)$_2$—N$^t$Bu]-, (N$^t$Bu$_2$)$_2$-M-C$_5$H$_3$-1-$^t$Bu-2-[(CH$_2$)$_2$—N$^t$Bu]-, (NH$_2$)(Cp)-M-C$_5$H$_3$-1-$^t$Bu-2-[(CH$_2$)$_2$—N$^t$Bu]-, (NMe$_2$)(Cp)-M-C$_5$H$_3$-1-$^t$Bu-2-[(CH$_2$)$_2$—N$^t$Bu]-, (NEt$_2$)(Cp)-M-C$_5$H$_3$-1-$^t$Bu-2-[(CH$_2$)$_2$—N$^t$Bu]-, (N$^n$Pr$_2$)(Cp)-M-C$_5$H$_3$-1-$^t$Bu-2-[(CH$_2$)$_2$—N$^t$Bu]-, (N$^i$Pr$_2$)(Cp)-M-C$_5$H$_3$-1-$^t$Bu-2-[(CH$_2$)$_2$—N$^t$Bu]-, (N$^n$Bu$_2$)(Cp)-M-C$_5$H$_3$-1-$^t$Bu-2-[(CH$_2$)$_2$—N$^t$Bu]-, (N$^i$Bu$_2$)(Cp)-M-C$_5$H$_3$-1-$^t$Bu-2-[(CH$_2$)$_2$—N$^t$Bu]-, (N$^s$Bu$_2$)(Cp)-M-C$_5$H$_3$-1-$^t$Bu-2-[(CH$_2$)$_2$—N$^t$Bu]-, (N$^t$Bu$_2$)(Cp)-M-C$_5$H$_3$-1-$^t$Bu-2-[(CH$_2$)$_2$—N$^t$Bu]-, (OH)$_2$-M-C$_5$H$_3$-1-$^t$Bu-2-[(CH$_2$)$_2$—N$^t$Bu]-, (OMe)$_2$-M-C$_5$H$_3$-1-$^t$Bu-2-[(CH$_2$)$_2$—N$^t$Bu]-, (OEt)$_2$-M-C$_5$H$_3$-1-$^t$Bu-2-[(CH$_2$)$_2$—N$^t$Bu]-, (O$^n$Pr)$_2$-M-C$_5$H$_3$-1-$^t$Bu-2-[(CH$_2$)$_2$—N$^t$Bu]-, (O$^i$Pr)$_2$-M-C$_5$H$_3$-1-$^t$Bu-2-[(CH$_2$)$_2$—N$^t$Bu]-, (O$^n$Bu)$_2$-M-C$_5$H$_3$-1-$^t$Bu-2-[(CH$_2$)$_2$—N$^t$Bu]-, (O$^i$Bu$_2$-M-C$_5$H$_3$-1-$^t$Bu-2-[(CH$_2$)$_2$—N$^t$Bu]-, (O$^t$Bu)$_2$-M-C$_5$H$_3$-1-$^t$Bu-2-[(CH$_2$)$_2$—N$^t$Bu]-, (O$^s$Bu)$_2$-M-C$_5$H$_3$-1-$^t$Bu-2-[(CH$_2$)$_2$—N$^t$Bu]-, (NH$_2$)$_2$-M-C$_5$H$_3$-1-$^t$Bu-3-[(CH$_2$)$_2$—N$^t$Bu]-, (NMe$_2$)$_2$-M-C$_5$H$_3$-1-$^t$Bu-3-[(CH$_2$)$_2$—N$^t$Bu]-, (NEt$_2$)$_2$-M-C$_5$H$_3$-1-$^t$Bu-3-[(CH$_2$)$_2$—N$^t$Bu]-, (N$^n$Pr$_2$)$_2$-M-C$_5$H$_3$-1-$^t$Bu-3-[(CH$_2$)$_2$—N$^t$Bu]-, (N$^i$Pr$_2$)$_2$-M-C$_5$H$_3$-1-$^t$Bu-3-[(CH$_2$)$_2$—N$^t$Bu]-, (N$^n$Bu$_2$)$_2$-M-C$_5$H$_3$-1-$^t$Bu-3-[(CH$_2$)$_2$—N$^t$Bu]-, (N$^i$Bu$_2$)$_2$-M-C$_5$H$_3$-1-$^t$Bu-3-[(CH$_2$)$_2$—N$^t$Bu]-, (N$^s$Bu$_2$)$_2$-M-C$_5$H$_3$-1-$^t$Bu-3-[(CH$_2$)$_2$—N$^t$Bu]-, (N$^t$Bu$_2$)$_2$-M-C$_5$H$_3$-1-$^t$Bu-3-[(CH$_2$)$_2$—N$^t$Bu]-, (NH$_2$)(Cp)-M-C$_5$H$_3$-1-$^t$Bu-3-[(CH$_2$)$_2$—N$^t$Bu]-, (NMe$_2$)(Cp)-M-C$_5$H$_3$-1-$^t$Bu-3-[(CH$_2$)$_2$—N$^t$Bu]-, (NEt$_2$)(Cp)-M-C$_5$H$_3$-1-$^t$Bu-3-[(CH$_2$)$_2$—N$^t$Bu]-, (N$^n$Pr$_2$)(Cp)-M-C$_5$H$_3$-1-$^t$Bu-3-[(CH$_2$)$_2$—N$^t$Bu]-, (N$^i$Pr$_2$)(Cp)-M-C$_5$H$_3$-1-$^t$Bu-3-[(CH$_2$)$_2$—N$^t$Bu]-, (N$^n$Bu$_2$)(Cp)-M-C$_5$H$_3$-1-$^t$Bu-3-[(CH$_2$)$_2$—N$^t$Bu]-, (N$^i$Bu$_2$)(Cp)-M-C$_5$H$_3$-1-$^t$Bu-3-[(CH$_2$)$_2$—N$^t$Bu]-, (N$^s$Bu$_2$)(Cp)-M-C$_5$H$_3$-1-$^t$Bu-3-[(CH$_2$)$_2$—N$^t$Bu]-, (N$^t$Bu$_2$)(Cp)-M-C$_5$H$_3$-1-$^t$Bu-3-[(CH$_2$)$_2$—N$^t$Bu]-, (OH)$_2$-M-C$_5$H$_3$-1-$^t$Bu-3-[(CH$_2$)$_2$—N$^t$Bu]-, (OMe)$_2$-M-C$_5$H$_3$-1-$^t$Bu-3-[(CH$_2$)$_2$—N$^t$Bu]-, (OEt)$_2$-M-C$_5$H$_3$-1-$^t$Bu-3-[(CH$_2$)$_2$—N$^t$Bu]-, (O$^n$Pr)$_2$-M-C$_5$H$_3$-1-$^t$Bu-3-[(CH$_2$)$_2$—N$^t$Bu]-, (O$^i$Pr)$_2$-M-C$_5$H$_3$-1-$^t$Bu-3-[(CH$_2$)$_2$—N$^t$Bu]-, (O$^n$Bu)$_2$-M-C$_5$H$_3$-1-$^t$Bu-3-[(CH$_2$)$_2$—N$^t$Bu]-, (O$^i$Bu$_2$-M-C$_5$H$_3$-1-$^t$Bu-3-[(CH$_2$)$_2$—N$^t$Bu]-, (O$^t$Bu)$_2$-M-C$_5$H$_3$-1-$^t$Bu-3-[(CH$_2$)$_2$—N$^t$Bu]-, (O$^s$Bu)$_2$-M-C$_5$H$_3$-1-$^t$Bu-3-[(CH$_2$)$_2$—N$^t$Bu]-, (NH$_2$)$_2$-M-C$_5$Me$_3$-1-Et-2-[(CH$_2$)$_2$—NH]—, (NMe$_2$)$_2$-M-C$_5$Me$_3$-1-Et-2-[(CH$_2$)$_2$—NH]—, (NEt$_2$)$_2$-M-C$_5$Me$_3$-1-Et-2-[(CH$_2$)$_2$—NH]—, (N$^n$Pr$_2$)$_2$-M-C$_5$Me$_3$-1-Et-2-[(CH$_2$)$_2$—NH]—, (N$^i$Pr$_2$)$_2$-M-C$_5$Me$_3$-1-Et-2-[(CH$_2$)$_2$—NH]—, (N$^n$Bu$_2$)$_2$-M-C$_5$Me$_3$-1-Et-2-[(CH$_2$)$_2$—NH]—, (N$^i$Bu$_2$)$_2$-M-C$_5$Me$_3$-1-Et-2-[(CH$_2$)$_2$—NH]—, (N$^s$Bu$_2$)$_2$-M-C$_5$Me$_3$-1-Et-2-[(CH$_2$)$_2$—NH]—, (N$^t$Bu$_2$)$_2$-M-C$_5$Me$_3$-1-Et-2-[(CH$_2$)$_2$—NH]—, (NH$_2$)(Cp)-M-C$_5$Me$_3$-1-Et-2-[(CH$_2$)$_2$—NH]—, (NMe$_2$)(Cp)-M-C$_5$Me$_3$-1-Et-2-[(CH$_2$)$_2$—NH]—, (NEt$_2$)(Cp)-M-C$_5$Me$_3$-1-Et-2-[(CH$_2$)$_2$—NH]—, (N$^n$Pr$_2$)(Cp)-M-C$_5$Me$_3$-1-Et-2-[(CH$_2$)$_2$—NH]—, (N$^i$Pr$_2$)(Cp)-M-C$_5$Me$_3$-1-Et-2-[(CH$_2$)$_2$—NH]—, (N$^n$Bu$_2$)(Cp)-M-C$_5$Me$_3$-1-Et-2-[(CH$_2$)$_2$—NH]—, (N$^i$Bu$_2$)(Cp)-M-C$_5$Me$_3$-1-Et-2-[(CH$_2$)$_2$—NH]—, (N$^s$Bu$_2$)(Cp)-M-C$_5$Me$_3$-1-Et-2-[(CH$_2$)$_2$—NH]—, (N$^t$Bu$_2$)(Cp)-M-C$_5$Me$_3$-1-Et-2-[(CH$_2$)$_2$—NH]—, (OH)$_2$-M-C$_5$Me$_3$-1-Et-2-[(CH$_2$)$_2$—NH]—, (OMe)$_2$-M-C$_5$Me$_3$-1-Et-2-[(CH$_2$)$_2$—NH]—, (OEt)$_2$-M-C$_5$Me$_3$-1-Et-2-[(CH$_2$)$_2$—NH]—, (O$^n$Pr)$_2$-M-C$_5$Me$_3$-1-Et-2-[(CH$_2$)$_2$—NH]—, (O$^i$Pr)$_2$-M-C$_5$Me$_3$-1-Et-2-[(CH$_2$)$_2$—NH]—, (O$^n$Bu)$_2$-M-C$_5$Me$_3$-1-Et-2-[(CH$_2$)$_2$—NH]—, (O$^i$Bu$_2$-M-C$_5$Me$_3$-1-Et-2-[(CH$_2$)$_2$—NH]—, (O$^t$Bu)$_2$-M-C$_5$Me$_3$-1-Et-2-[(CH$_2$)$_2$—NH]—, (O$^s$Bu)$_2$-M-C$_5$Me$_3$-1-Et-2-[(CH$_2$)$_2$—NH]—, (NH$_2$)$_2$-M-C$_5$Me$_3$-1-Et-3-[(CH$_2$)$_2$—NH]—, (NMe$_2$)$_2$-M-C$_5$Me$_3$-1-Et-3-[(CH$_2$)$_2$—NH]—, (NEt$_2$)$_2$-M-C$_5$Me$_3$-1-Et-3-[(CH$_2$)$_2$—NH]—, (N$^n$Pr$_2$)$_2$-M-C$_5$Me$_3$-1-Et-3-[(CH$_2$)$_2$—NH]—, (N$^i$Pr$_2$)$_2$-M-C$_5$Me$_3$-1-Et-3-[(CH$_2$)$_2$—NH]—, (N$^n$Bu$_2$)$_2$-M-C$_5$Me$_3$-1-Et-3-[(CH$_2$)$_2$—NH]—, (N$^i$Bu$_2$)$_2$-M-C$_5$Me$_3$-1-Et-3-[(CH$_2$)$_2$—NH]—, (N$^s$Bu$_2$)$_2$-M-C$_5$Me$_3$-1-Et-3-[(CH$_2$)$_2$—NH]—, (N$^t$Bu$_2$)$_2$-M-C$_5$Me$_3$-1-Et-3-[(CH$_2$)$_2$—NH]—, (NH$_2$)(Cp)-M-C$_5$Me$_3$-1-Et-3-[(CH$_2$)$_2$—NH]—, (NMe$_2$)(Cp)-M-C$_5$Me$_3$-1-Et-3-[(CH$_2$)$_2$—NH]—, (NEt$_2$)(Cp)-M-C$_5$Me$_3$-1-Et-3-[(CH$_2$)$_2$—NH]—, (N$^n$Pr$_2$)(Cp)-M-C$_5$Me$_3$-1-Et-3-[(CH$_2$)$_2$—NH]—, (N$^i$Pr$_2$)(Cp)-M-C$_5$Me$_3$-1-Et-3-[(CH$_2$)$_2$—NH]—, (N$^n$Bu$_2$)(Cp)-M-C$_5$Me$_3$-1-Et-3-[(CH$_2$)$_2$—NH]—, (N$^i$Bu$_2$)(Cp)-M-C$_5$Me$_3$-1-Et-3-[(CH$_2$)$_2$—NH]—, (N$^s$Bu$_2$)(Cp)-M-C$_5$Me$_3$-1-Et-3-[(CH$_2$)$_2$—NH]—, (N$^t$Bu$_2$)(Cp)-M-C$_5$Me$_3$-1-Et-3-[(CH$_2$)$_2$—NH]—, (OH)$_2$-M-C$_5$Me$_3$-1-Et-3-[(CH$_2$)$_2$—NH]—, (OMe)$_2$-M-C$_5$Me$_3$-1-Et-3-[(CH$_2$)$_2$—NH]—, (OEt)$_2$-M-C$_5$Me$_3$-1-Et-3-[(CH$_2$)$_2$—NH]—, (O$^n$Pr)$_2$-M-C$_5$Me$_3$-1-Et-3-[(CH$_2$)$_2$—NH]—, (O$^i$Pr)$_2$-M-C$_5$Me$_3$-1-Et-3-[(CH$_2$)$_2$—NH]—, (O$^n$Bu)$_2$-M-C$_5$Me$_3$-1-Et-3-[(CH$_2$)$_2$—NH]—, (O$^i$Bu$_2$-M-C$_5$Me$_3$-1-Et-3-[(CH$_2$)$_2$—NH]—, (O$^t$Bu)$_2$-M-C$_5$Me$_3$-1-Et-3-[(CH$_2$)$_2$—NH]—, (O$^s$Bu)$_2$-M-C$_5$Me$_3$-1-Et-3-[(CH$_2$)$_2$—NH]—, (NH$_2$)$_2$-M-C$_5$Me$_3$-1-$^i$Pr-2-[(CH$_2$)$_2$—NH]—, (NMe$_2$)$_2$-M-C$_5$Me$_3$-1-$^i$Pr-2-[(CH$_2$)$_2$—NH]—, (NEt$_2$)$_2$-M-C$_5$Me$_3$-1-$^i$Pr-2-[(CH$_2$)$_2$—NH]—, (N$^n$Pr$_2$)$_2$-M-C$_5$Me$_3$-1-$^i$Pr-2-[(CH$_2$)$_2$—NH]—, (N$^i$Pr$_2$)$_2$-M-C$_5$Me$_3$-1-$^i$Pr-2-[(CH$_2$)$_2$—NH]—, (N$^n$Bu$_2$)$_2$-M-C$_5$Me$_3$-1-$^i$Pr-2-[(CH$_2$)$_2$—NH]—, (N$^i$Bu$_2$)$_2$-M-C$_5$Me$_3$-1-$^i$Pr-2-[(CH$_2$)$_2$—NH]—, (N$^s$Bu$_2$)$_2$-M-C$_5$Me$_3$-1-$^i$Pr-2-[(CH$_2$)$_2$—NH]—, (N$^t$Bu$_2$)$_2$-M-C$_5$Me$_3$-1-$^i$Pr-2-[(CH$_2$)$_2$—NH]—, (NH$_2$)(Cp)-M-C$_5$Me$_3$-1-$^i$Pr-2-[(CH$_2$)$_2$—NH]—, (NMe$_2$)(Cp)-M-C$_5$Me$_3$-1-$^i$Pr-2-[(CH$_2$)$_2$—NH]—, (NEt$_2$)(Cp)-M-C$_5$Me$_3$-1-$^i$Pr-2-[(CH$_2$)$_2$—NH]—, (N$^n$Pr$_2$)(Cp)-M-C$_5$Me$_3$-1-$^i$Pr-2-[(CH$_2$)$_2$—NH]—, (N$^i$Pr$_2$)(Cp)-M-C$_5$Me$_3$-1-$^i$Pr-2-[(CH$_2$)$_2$—NH]—, (N$^n$Bu$_2$)(Cp)-M-C$_5$Me$_3$-1-$^i$Pr-2-[(CH$_2$)$_2$—NH]—, (N$^i$Bu$_2$)(Cp)-M-C$_5$Me$_3$-1-$^i$Pr-2-[(CH$_2$)$_2$—NH]—, (N$^s$Bu$_2$)(Cp)-M-C$_5$Me$_3$-1-$^i$Pr-2-[(CH$_2$)$_2$—NH]—, (N$^t$Bu$_2$)(Cp)-M-C$_5$Me$_3$-1-$^i$Pr-2-[(CH$_2$)$_2$—NH]—, (OH)$_2$-M-C$_5$Me$_3$-1-$^i$Pr-2-[(CH$_2$)$_2$—NH]—, (OMe)$_2$-M-C$_5$Me$_3$-1-$^i$Pr-2-[(CH$_2$)$_2$—NH]—, (OEt)$_2$-M-C$_5$Me$_3$-1-$^i$Pr-2-[(CH$_2$)$_2$—NH]—, (O$^n$Pr)$_2$-M-C$_5$Me$_3$-1-$^i$Pr-2-[(CH$_2$)$_2$—NH]—, (O$^i$Pr)$_2$-M-C$_5$Me$_3$-1-$^i$Pr-2-[(CH$_2$)$_2$—NH]—, (O$^n$Bu)$_2$-M-C$_5$Me$_3$-1-$^i$Pr-2-[(CH$_2$)$_2$—NH]—, (O$^i$Bu$_2$-M-C$_5$Me$_3$-1-$^i$Pr-2-[(CH$_2$)$_2$—NH]—, (O$^t$Bu)$_2$-M-C$_5$Me$_3$-1-$^i$Pr-2-[(CH$_2$)$_2$—NH]—, (O$^s$Bu)$_2$-M-C$_5$Me$_3$-1-$^i$Pr-2-[(CH$_2$)$_2$—NH]—, (NH$_2$)$_2$-M-C$_5$Me$_3$-1-$^i$Pr-

3-[(CH$_2$)$_2$—NH]—, (NMe$_2$)$_2$-M-C$_5$Me$_3$-1-$^i$Pr-3-[(CH$_2$)$_2$—NH]—, (NEt$_2$)$_2$-M-C$_5$Me$_3$-1-$^i$Pr-3-[(CH$_2$)$_2$—NH]—, (N$^n$Pr$_2$)$_2$-M-C$_5$Me$_3$-1-$^i$Pr-3-[(CH$_2$)$_2$—NH]—, (N$^i$Pr$_2$)$_2$-M-C$_5$Me$_3$-1-$^i$Pr-3-[(CH$_2$)$_2$—NH]—, (N$^n$Bu$_2$)$_2$-M-C$_5$Me$_3$-1-$^i$Pr-3-[(CH$_2$)$_2$—NH]—, (N$^i$Bu$_2$)$_2$-M-C$_5$Me$_3$-1-$^i$Pr-3-[(CH$_2$)$_2$—NH]—, (N$^s$Bu$_2$)$_2$-M-C$_5$Me$_3$-1-$^i$Pr-3-[(CH$_2$)$_2$—NH]—, (N$^t$Bu$_2$)$_2$-M-C$_5$Me$_3$-1-$^i$Pr-3-[(CH$_2$)$_2$—NH]—, (NH$_2$)(Cp)-M-C$_5$Me$_3$-1-$^i$Pr-3-[(CH$_2$)$_2$—NH]—, (NMe$_2$)(Cp)-M-C$_5$Me$_3$-1-$^i$Pr-3-[(CH$_2$)$_2$—NH]—, (NEt$_2$)(Cp)-M-C$_5$Me$_3$-1-$^i$Pr-3-[(CH$_2$)$_2$—NH]—, (N$^n$Pr$_2$)(Cp)-M-C$_5$Me$_3$-1-$^i$Pr-3-[(CH$_2$)$_2$—NH]—, (N$^i$Pr$_2$)(Cp)-M-C$_5$Me$_3$-1-$^i$Pr-3-[(CH$_2$)$_2$—NH]—, (N$^n$Bu$_2$)(Cp)-M-C$_5$Me$_3$-1-$^i$Pr-3-[(CH$_2$)$_2$—NH]—, (N$^i$Bu$_2$)(Cp)-M-C$_5$Me$_3$-1-$^i$Pr-3-[(CH$_2$)$_2$—NH]—, (N$^s$Bu$_2$)(Cp)-M-C$_5$Me$_3$-1-$^i$Pr-3-[(CH$_2$)$_2$—NH]—, (N$^t$Bu$_2$)(Cp)-M-C$_5$Me$_3$-1-$^i$Pr-3-[(CH$_2$)$_2$—NH]—, (OH)$_2$-M-C$_5$Me$_3$-1-$^i$Pr-3-[(CH$_2$)$_2$—NH]—, (OMe)$_2$-M-C$_5$Me$_3$-1-$^i$Pr-3-[(CH$_2$)$_2$—NH]—, (OEt)$_2$-M-C$_5$Me$_3$-1-$^i$Pr-3-[(CH$_2$)$_2$—NH]—, (O$^n$Pr)$_2$-M-C$_5$Me$_3$-1-$^i$Pr-3-[(CH$_2$)$_2$—NH]—, (O$^i$Pr)$_2$-M-C$_5$Me$_3$-1-$^i$Pr-3-[(CH$_2$)$_2$—NH]—, (O$^n$Bu)$_2$-M-C$_5$Me$_3$-1-$^i$Pr-3-[(CH$_2$)$_2$—NH]—, (O$^i$Bu$_2$-M-C$_5$Me$_3$-1-$^i$Pr-3-[(CH$_2$)$_2$—NH]—, (O$^t$Bu)$_2$-M-C$_5$Me$_3$-1-$^i$Pr-3-[(CH$_2$)$_2$—NH]—, (O$^s$Bu)$_2$-M-C$_5$Me$_3$-1-$^i$Pr-3-[(CH$_2$)$_2$—NH]—, (NH$_2$)$_2$-M-C$_5$Me$_3$-1-$^t$Bu-2-[(CH$_2$)$_2$—NH]—, (NMe$_2$)$_2$-M-C$_5$Me$_3$-1-$^t$Bu-2-[(CH$_2$)$_2$—NH]—, (NEt$_2$)$_2$-M-C$_5$Me$_3$-1-$^t$Bu-2-[(CH$_2$)$_2$—NH]—, (N$^n$Pr$_2$)$_2$-M-C$_5$Me$_3$-1-$^t$Bu-2-[(CH$_2$)$_2$—NH]—, (N$^i$Pr$_2$)$_2$-M-C$_5$Me$_3$-1-$^t$Bu-2-[(CH$_2$)$_2$—NH]—, (N$^n$Bu$_2$)$_2$-M-C$_5$Me$_3$-1-$^t$Bu-2-[(CH$_2$)$_2$—NH]—, (N$^i$Bu$_2$)$_2$-M-C$_5$Me$_3$-1-$^t$Bu-2-[(CH$_2$)$_2$—NH]—, (N$^s$Bu$_2$)$_2$-M-C$_5$Me$_3$-1-$^t$Bu-2-[(CH$_2$)$_2$—NH]—, (N$^t$Bu$_2$)$_2$-M-C$_5$Me$_3$-1-$^t$Bu-2-[(CH$_2$)$_2$—NH]—, (NH$_2$)(Cp)-M-C$_5$Me$_3$-1-$^t$Bu-2-[(CH$_2$)$_2$—NH]—, (NMe$_2$)(Cp)-M-C$_5$Me$_3$-1-$^t$Bu-2-[(CH$_2$)$_2$—NH]—, (NEt$_2$)(Cp)-M-C$_5$Me$_3$-1-$^t$Bu-2-[(CH$_2$)$_2$—NH]—, (N$^n$Pr$_2$)(Cp)-M-C$_5$Me$_3$-1-$^t$Bu-2-[(CH$_2$)$_2$—NH]—, (N$^i$Pr$_2$)(Cp)-M-C$_5$Me$_3$-1-$^t$Bu-2-[(CH$_2$)$_2$—NH]—, (N$^n$Bu$_2$)(Cp)-M-C$_5$Me$_3$-1-$^t$Bu-2-[(CH$_2$)$_2$—NH]—, (N$^i$Bu$_2$)(Cp)-M-C$_5$Me$_3$-1-$^t$Bu-2-[(CH$_2$)$_2$—NH]—, (N$^s$Bu$_2$)(Cp)-M-C$_5$Me$_3$-1-$^t$Bu-2-[(CH$_2$)$_2$—NH]—, (N$^t$Bu$_2$)(Cp)-M-C$_5$Me$_3$-1-$^t$Bu-2-[(CH$_2$)$_2$—NH]—, (OH)$_2$-M-C$_5$Me$_3$-1-$^t$Bu-2-[(CH$_2$)$_2$—NH]—, (OMe)$_2$-M-C$_5$Me$_3$-1-$^t$Bu-2-[(CH$_2$)$_2$—NH]—, (OEt)$_2$-M-C$_5$Me$_3$-1-$^t$Bu-2-[(CH$_2$)$_2$—NH]—, (O$^n$Pr)$_2$-M-C$_5$Me$_3$-1-$^t$Bu-2-[(CH$_2$)$_2$—NH]—, (O$^i$Pr)$_2$-M-C$_5$Me$_3$-1-$^t$Bu-2-[(CH$_2$)$_2$—NH]—, (O$^n$Bu)$_2$-M-C$_5$Me$_3$-1-$^t$Bu-2-[(CH$_2$)$_2$—NH]—, (O$^i$Bu$_2$-M-C$_5$Me$_3$-1-$^t$Bu-2-[(CH$_2$)$_2$—NH]—, (O$^t$Bu)$_2$-M-C$_5$Me$_3$-1-$^t$Bu-2-[(CH$_2$)$_2$—NH]—, (O$^s$Bu)$_2$-M-C$_5$Me$_3$-1-$^t$Bu-2-[(CH$_2$)$_2$—NH]—, (NH$_2$)$_2$-M-C$_5$Me$_3$-1-$^t$Bu-3-[(CH$_2$)$_2$—NH]—, (NMe$_2$)$_2$-M-C$_5$Me$_3$-1-$^t$Bu-3-[(CH$_2$)$_2$—NH]—, (NEt$_2$)$_2$-M-C$_5$Me$_3$-1-$^t$Bu-3-[(CH$_2$)$_2$—NH]—, (N$^n$Pr$_2$)$_2$-M-C$_5$Me$_3$-1-$^t$Bu-3-[(CH$_2$)$_2$—NH]—, (N$^i$Pr$_2$)$_2$-M-C$_5$Me$_3$-1-$^t$Bu-3-[(CH$_2$)$_2$—NH]—, (N$^n$Bu$_2$)$_2$-M-C$_5$Me$_3$-1-$^t$Bu-3-[(CH$_2$)$_2$—NH]—, (N$^i$Bu$_2$)$_2$-M-C$_5$Me$_3$-1-$^t$Bu-3-[(CH$_2$)$_2$—NH]—, (N$^s$Bu$_2$)$_2$-M-C$_5$Me$_3$-1-$^t$Bu-3-[(CH$_2$)$_2$—NH]—, (N$^t$Bu$_2$)$_2$-M-C$_5$Me$_3$-1-$^t$Bu-3-[(CH$_2$)$_2$—NH]—, (NH$_2$)(Cp)-M-C$_5$Me$_3$-1-$^t$Bu-3-[(CH$_2$)$_2$—NH]—, (NMe$_2$)(Cp)-M-C$_5$Me$_3$-1-$^t$Bu-3-[(CH$_2$)$_2$—NH]—, (NEt$_2$)(Cp)-M-C$_5$Me$_3$-1-$^t$Bu-3-[(CH$_2$)$_2$—NH]—, (N$^n$Pr$_2$)(Cp)-M-C$_5$Me$_3$-1-$^t$Bu-3-[(CH$_2$)$_2$—NH]—, (N$^i$Pr$_2$)(Cp)-M-C$_5$Me$_3$-1-$^t$Bu-3-[(CH$_2$)$_2$—NH]—, (N$^n$Bu$_2$)(Cp)-M-C$_5$Me$_3$-1-$^t$Bu-3-[(CH$_2$)$_2$—NH]—, (N$^i$Bu$_2$)(Cp)-M-C$_5$Me$_3$-1-$^t$Bu-3-[(CH$_2$)$_2$—NH]—, (N$^s$Bu$_2$)(Cp)-M-C$_5$Me$_3$-1-$^t$Bu-3-[(CH$_2$)$_2$—NH]—, (N$^t$Bu$_2$)(Cp)-M-C$_5$Me$_3$-1-$^t$Bu-3-[(CH$_2$)$_2$—NH]—, (OH)$_2$-M-C$_5$Me$_3$-1-$^t$Bu-3-[(CH$_2$)$_2$—NH]—, (OMe)$_2$-M-C$_5$Me$_3$-1-$^t$Bu-3-[(CH$_2$)$_2$—NH]—, (OEt)$_2$-M-C$_5$Me$_3$-1-$^t$Bu-3-[(CH$_2$)$_2$—NH]—, (O$^n$Pr)$^2$-M-C$_5$Me$_3$-1-$^t$Bu-3-[(CH$_2$)$_2$—NH]—, (O$^i$Pr)$_2$-M-C$_5$Me$_3$-1-$^t$Bu-3-[(CH$_2$)$_2$—NH]—, (O$^n$Bu)$_2$-M-C$_5$Me$_3$-1-$^t$Bu-3-[(CH$_2$)$_2$—NH]—, (O$^i$Bu$_2$-M-C$_5$Me$_3$-1-$^t$Bu-3-[(CH$_2$)$_2$—NH]—, (O$^t$Bu)$_2$-M-C$_5$Me$_3$-1-$^t$Bu-3-[(CH$_2$)$_2$—NH]—, (O$^s$Bu)$_2$-M-C$_5$Me$_3$-1-$^t$Bu-3-[(CH$_2$)$_2$—NH]—, (NH$_2$)$_2$-M-C$_5$Me$_3$-1-Et-2-[(CH$_2$)$_2$—NMe]-, (NMe$_2$)$_2$-M-C$_5$Me$_3$-1-Et-2-[(CH$_2$)$_2$—NMe]-, (NEt$_2$)$_2$-M-C$_5$Me$_3$-1-Et-2-[(CH$_2$)$_2$—NMe]-, (N$^n$Pr$_2$)$_2$-M-C$_5$Me$_3$-1-Et-2-[(CH$_2$)$_2$—NMe]-, (N$^i$Pr$_2$)$_2$-M-C$_5$Me$_3$-1-Et-2-[(CH$_2$)$_2$—NMe]-, (N$^n$Bu$_2$)$_2$-M-C$_5$Me$_3$-1-Et-2-[(CH$_2$)$_2$—NMe]-, (N$^i$Bu$_2$)$_2$-M-C$_5$Me$_3$-1-Et-2-[(CH$_2$)$_2$—NMe]-, (N$^s$Bu$_2$)$_2$-M-C$_5$Me$_3$-1-Et-2-[(CH$_2$)$_2$—NMe]-, (N$^t$Bu$_2$)$_2$-M-C$_5$Me$_3$-1-Et-2-[(CH$_2$)$_2$—NMe]-, (NH$_2$)(Cp)-M-C$_5$Me$_3$-1-Et-2-[(CH$_2$)$_2$—NMe]-, (NMe$_2$)(Cp)-M-C$_5$Me$_3$-1-Et-2-[(CH$_2$)$_2$—NMe]-, (NEt$_2$)(Cp)-M-C$_5$Me$_3$-1-Et-2-[(CH$_2$)$_2$—NMe]-, (N$^n$Pr$_2$)(Cp)-M-C$_5$Me$_3$-1-Et-2-[(CH$_2$)$_2$—NMe]-, (N$^i$Pr$_2$)(Cp)-M-C$_5$Me$_3$-1-Et-2-[(CH$_2$)$_2$—NMe]-, (N$^n$Bu$_2$)(Cp)-M-C$_5$Me$_3$-1-Et-2-[(CH$_2$)$_2$—NMe]-, (N$^i$Bu$_2$)(Cp)-M-C$_5$Me$_3$-1-Et-2-[(CH$_2$)$_2$—NMe]-, (N$^s$Bu$_2$)(Cp)-M-C$_5$Me$_3$-1-Et-2-[(CH$_2$)$_2$—NMe]-, (N$^t$Bu$_2$)(Cp)-M-C$_5$Me$_3$-1-Et-2-[(CH$_2$)$_2$—NMe]-, (OH)$_2$-M-C$_5$Me$_3$-1-Et-2-[(CH$_2$)$_2$—NMe]-, (OMe)$_2$-M-C$_5$Me$_3$-1-Et-2-[(CH$_2$)$_2$—NMe]-, (OEt)$_2$-M-C$_5$Me$_3$-1-Et-2-[(CH$_2$)$_2$—NMe]-, (O$^n$Pr)$_2$-M-C$_5$Me$_3$-1-Et-2-[(CH$_2$)$_2$—NMe]-, (O$^i$Pr)$_2$-M-C$_5$Me$_3$-1-Et-2-[(CH$_2$)$_2$—NMe]-, (O$^n$Bu)$_2$-M-C$_5$Me$_3$-1-Et-2-[(CH$_2$)$_2$—NMe]-, (O$^i$Bu$_2$-M-C$_5$Me$_3$-1-Et-2-[(CH$_2$)$_2$—NMe]-, (O$^t$Bu)$_2$-M-C$_5$Me$_3$-1-Et-2-[(CH$_2$)$_2$—NMe]-, (O$^s$Bu)$_2$-M-C$_5$Me$_3$-1-Et-2-[(CH$_2$)$_2$—NMe]-, (NH$_2$)$_2$-M-C$_5$Me$_3$-1-Et-3-[(CH$_2$)$_2$—NMe]-, (NMe$_2$)$_2$-M-C$_5$Me$_3$-1-Et-3-[(CH$_2$)$_2$—NMe]-, (NEt$_2$)$_2$-M-C$_5$Me$_3$-1-Et-3-[(CH$_2$)$_2$—NMe]-, (N$^n$Pr$_2$)$_2$-M-C$_5$Me$_3$-1-Et-3-[(CH$_2$)$_2$—NMe]-, (N$^i$Pr$_2$)$_2$-M-C$_5$Me$_3$-1-Et-3-[(CH$_2$)$_2$—NMe]-, (N$^n$Bu$_2$)$_2$-M-C$_5$Me$_3$-1-Et-3-[(CH$_2$)$_2$—NMe]-, (N$^i$Bu$_2$)$_2$-M-C$_5$Me$_3$-1-Et-3-[(CH$_2$)$_2$—NMe]-, (N$^s$Bu$_2$)$_2$-M-C$_5$Me$_3$-1-Et-3-[(CH$_2$)$_2$—NMe]-, (N$^t$Bu$_2$)$_2$-M-C$_5$Me$_3$-1-Et-3-[(CH$_2$)$_2$—NMe]-, (NH$_2$)(Cp)-M-C$_5$Me$_3$-1-Et-3-[(CH$_2$)$_2$—NMe]-, (NMe$_2$)(Cp)-M-C$_5$Me$_3$-1-Et-3-[(CH$_2$)$_2$—NMe]-, (NEt$_2$)(Cp)-M-C$_5$Me$_3$-1-Et-3-[(CH$_2$)$_2$—NMe]-, (N$^n$Pr$_2$)(Cp)-M-C$_5$Me$_3$-1-Et-3-[(CH$_2$)$_2$—NMe]-, (N$^i$Pr$_2$)(Cp)-M-C$_5$Me$_3$-1-Et-3-[(CH$_2$)$_2$—NMe]-, (N$^n$Bu$_2$)(Cp)-M-C$_5$Me$_3$-1-Et-3-[(CH$_2$)$_2$—NMe]-, (N$^i$Bu$_2$)(Cp)-M-C$_5$Me$_3$-1-Et-3-[(CH$_2$)$_2$—NMe]-, (N$^s$Bu$_2$)(Cp)-M-C$_5$Me$_3$-1-Et-3-[(CH$_2$)$_2$—NMe]-, (N$^t$Bu$_2$)(Cp)-M-C$_5$Me$_3$-1-Et-3-[(CH$_2$)$_2$—NMe]-, (OH)$_2$-M-C$_5$Me$_3$-1-Et-3-[(CH$_2$)$_2$—NMe]-, (OMe)$_2$-M-C$_5$Me$_3$-1-Et-3-[(CH$_2$)$_2$—NMe]-, (OEt)$_2$-M-C$_5$Me$_3$-1-Et-3-[(CH$_2$)$_2$—NMe]-, (O$^n$Pr)$_2$-M-C$_5$Me$_3$-1-Et-3-[(CH$_2$)$_2$—NMe]-, (O$^i$Pr)$_2$-M-C$_5$Me$_3$-1-Et-3-[(CH$_2$)$_2$—NMe]-, (O$^n$Bu)$_2$-M-C$_5$Me$_3$-1-Et-3-[(CH$_2$)$_2$—NMe]-, (O$^i$Bu$_2$-M-C$_5$Me$_3$-1-Et-3-[(CH$_2$)$_2$—NMe]-, (O$^t$Bu)$_2$-M-C$_5$Me$_3$-1-Et-3-[(CH$_2$)$_2$—NMe]-, (O$^s$Bu)$_2$-M-C$_5$Me$_3$-1-Et-3-[(CH$_2$)$_2$—NMe]-, (NH$_2$)$_2$-M-C$_5$Me$_3$-1-$^i$Pr-2-[(CH$_2$)$_2$—NMe]-, (NMe$_2$)$_2$-M-C$_5$Me$_3$-1-$^i$Pr-2-[(CH$_2$)$_2$—NMe]-, (NEt$_2$)$_2$-M-C$_5$Me$_3$-1-$^i$Pr-2-[(CH$_2$)$_2$—NMe]-, (N$^n$Pr$_2$)$_2$-M-C$_5$Me$_3$-1-$^i$Pr-2-[(CH$_2$)$_2$—NMe]-, (N$^i$Pr$_2$)$_2$-M-C$_5$Me$_3$-1-$^i$Pr-2-[(CH$_2$)$_2$—NMe]-, (N$^n$Bu$_2$)$_2$-M-C$_5$Me$_3$-1-$^i$Pr-2-[(CH$_2$)$_2$—NMe]-, (N$^i$Bu$_2$)$_2$-M-C$_5$Me$_3$-1-$^i$Pr-2-[(CH$_2$)$_2$—NMe]-, (N$^s$Bu$_2$)$_2$-M-C$_5$Me$_3$-1-$^i$Pr-2-[(CH$_2$)$_2$—NMe]-, (N$^t$Bu$_2$)$_2$-M-C$_5$Me$_3$-1-$^i$Pr-2-[(CH$_2$)$_2$—NMe]-, (NH$_2$)(Cp)-M-C$_5$Me$_3$-1-$^i$Pr-2-[(CH$_2$)$_2$—NMe]-, (NMe$_2$)(Cp)-M-C$_5$Me$_3$-1-$^i$Pr-2-[(CH$_2$)$_2$—NMe]-, (NEt$_2$)(Cp)-M-C$_5$Me$_3$-1-$^i$Pr-2-[(CH$_2$)$_2$—NMe]-, (N$^n$Pr$_2$)(Cp)-M-C$_5$Me$_3$-1-$^i$Pr-2-[(CH$_2$)$_2$—NMe]-, (N$^i$Pr$_2$)(Cp)-M-C$_5$Me$_3$-1-$^i$Pr-2-[(CH$_2$)$_2$—NMe]-, (N$^n$Bu$_2$)(Cp)-M-C$_5$Me$_3$-1-$^i$Pr-2-[(CH$_2$)$_2$—NMe]-, (N$^i$Bu$_2$)(Cp)-M-C$_5$Me$_3$-1-$^i$Pr-2-[(CH$_2$)$_2$—NMe]-, (N$^s$Bu$_2$)(Cp)-M-C$_5$Me$_3$-1-$^i$Pr-2-[(CH$_2$)$_2$—NMe]-, (N$^t$Bu$_2$)(Cp)-M-C$_5$Me$_3$-1-$^i$Pr-2-[(CH$_2$)$_2$—NMe]-, (OH)$_2$-M-C$_5$Me$_3$-1-$^i$Pr-2-[(CH$_2$)$_2$—NMe]-, (OMe)$_2$-M-C$_5$Me$_3$-1-$^i$Pr-2-[(CH$_2$)$_2$—NMe]-, (OEt)$_2$-M-C$_5$Me$_3$-1-$^i$Pr-2-[(CH$_2$)$_2$—NMe]-, (O$^n$Pr)$_2$-M-C$_5$Me$_3$-1-$^i$Pr-2-[(CH$_2$)$_2$—NMe]-, (O$^i$Pr)$_2$-M-C$_5$Me$_3$-1-$^i$Pr-2-[(CH$_2$)$_2$—NMe]-, (O$^n$Bu)$_2$-M-C$_5$Me$_3$-1-$^i$Pr-2-[(CH$_2$)$_2$—

NMe]-, (O$^i$Bu$_2$-M-C$_5$Me$_3$-1-$^i$Pr-2-[(CH$_2$)$_2$—NMe]-, (O$^t$Bu)$_2$-M-C$_5$Me$_3$-1-$^i$Pr-2-[(CH$_2$)$_2$—NMe]-, (O$^s$Bu)$_2$-M-C$_5$Me$_3$-1-$^i$Pr-2-[(CH$_2$)$_2$—NMe]-, (NH$_2$)$_2$-M-C$_5$Me$_3$-1-$^i$Pr-3-[(CH$_2$)$_2$—NMe]-, (NMe$_2$)$_2$-M-C$_5$Me$_3$-1-$^i$Pr-3-[(CH$_2$)$_2$—NMe]-, (NEt$_2$)$_2$-M-C$_5$Me$_3$-1-$^i$Pr-3-[(CH$_2$)$_2$—NMe]-, (N$^n$Pr$_2$)$_2$-M-C$_5$Me$_3$-1-$^i$Pr-3-[(CH$_2$)$_2$—NMe]-, (N$^i$Pr$_2$)$_2$-M-C$_5$Me$_3$-1-$^i$Pr-3-[(CH$_2$)$_2$—NMe]-, (N$^n$Bu$_2$)$_2$-M-C$_5$Me$_3$-1-$^i$Pr-3-[(CH$_2$)$_2$—NMe]-, (N$^i$Bu$_2$)$_2$-M-C$_5$Me$_3$-1-$^i$Pr-3-[(CH$_2$)$_2$—NMe]-, (N$^s$Bu$_2$)$_2$-M-C$_5$Me$_3$-1-$^i$Pr-3-[(CH$_2$)$_2$—NMe]-, (N$^t$Bu$_2$)$_2$-M-C$_5$Me$_3$-1-$^i$Pr-3-[(CH$_2$)$_2$—NMe]-, (NH$_2$)(Cp)-M-C$_5$Me$_3$-1-$^i$Pr-3-[(CH$_2$)$_2$—NMe]-, (NMe$_2$)(Cp)-M-C$_5$Me$_3$-1-$^i$Pr-3-[(CH$_2$)$_2$—NMe]-, (NEt$_2$)(Cp)-M-C$_5$Me$_3$-1-$^i$Pr-3-[(CH$_2$)$_2$—NMe]-, (N$^n$Pr$_2$)(Cp)-M-C$_5$Me$_3$-1-$^i$Pr-3-[(CH$_2$)$_2$—NMe]-, (N$^i$Pr$_2$)(Cp)-M-C$_5$Me$_3$-1-$^i$Pr-3-[(CH$_2$)$_2$—NMe]-, (N$^n$Bu$_2$)(Cp)-M-C$_5$Me$_3$-1-$^i$Pr-3-[(CH$_2$)$_2$—NMe]-, (N$^i$Bu$_2$)(Cp)-M-C$_5$Me$_3$-1-$^i$Pr-3-[(CH$_2$)$_2$—NMe]-, (N$^s$Bu$_2$)(Cp)-M-C$_5$Me$_3$-1-$^i$Pr-3-[(CH$_2$)$_2$—NMe]-, (N$^t$Bu$_2$)(Cp)-M-C$_5$Me$_3$-1-$^i$Pr-3-[(CH$_2$)$_2$—NMe]-, (OH)$_2$-M-C$_5$Me$_3$-1-$^i$Pr-3-[(CH$_2$)$_2$—NMe]-, (OMe)$_2$-M-C$_5$Me$_3$-1-$^i$Pr-3-[(CH$_2$)$_2$—NMe]-, (OEt)$_2$-M-C$_5$Me$_3$-1-$^i$Pr-3-[(CH$_2$)$_2$—NMe]-, (O$^n$Pr)$_2$-M-C$_5$Me$_3$-1-$^i$Pr-3-[(CH$_2$)$_2$—NMe]-, (O$^i$Pr)$_2$-M-C$_5$Me$_3$-1-$^i$Pr-3-[(CH$_2$)$_2$—NMe]-, (O$^n$Bu)$_2$-M-C$_5$Me$_3$-1-$^i$Pr-3-[(CH$_2$)$_2$—NMe]-, (O$^i$Bu$_2$-M-C$_5$Me$_3$-1-$^i$Pr-3-[(CH$_2$)$_2$—NMe]-, (O$^t$Bu)$_2$-M-C$_5$Me$_3$-1-$^i$Pr-3-[(CH$_2$)$_2$—NMe]-, (O$^s$Bu)$_2$-M-C$_5$Me$_3$-1-$^i$Pr-3-[(CH$_2$)$_2$—NMe]-, (NH$_2$)$_2$-M-C$_5$Me$_3$-1-$^t$Bu-2-[(CH$_2$)$_2$—NMe]-, (NMe$_2$)$_2$-M-C$_5$Me$_3$-1-$^t$Bu-2-[(CH$_2$)$_2$—NMe]-, (NEt$_2$)$_2$-M-C$_5$Me$_3$-1-$^t$Bu-2-[(CH$_2$)$_2$—NMe]-, (N$^n$Pr$_2$)$_2$-M-C$_5$Me$_3$-1-$^t$Bu-2-[(CH$_2$)$_2$—NMe]-, (N$^i$Pr$_2$)$_2$-M-C$_5$Me$_3$-1-$^t$Bu-2-[(CH$_2$)$_2$—NMe]-, (N$^n$Bu$_2$)$_2$-M-C$_5$Me$_3$-1-$^t$Bu-2-[(CH$_2$)$_2$—NMe]-, (N$^i$Bu$_2$)$_2$-M-C$_5$Me$_3$-1-$^t$Bu-2-[(CH$_2$)$_2$—NMe]-, (N$^s$Bu$_2$)$_2$-M-C$_5$Me$_3$-1-$^t$Bu-2-[(CH$_2$)$_2$—NMe]-, (N$^t$Bu$_2$)$_2$-M-C$_5$Me$_3$-1-$^t$Bu-2-[(CH$_2$)$_2$—NMe]-, (NH$_2$)(Cp)-M-C$_5$Me$_3$-1-$^t$Bu-2-[(CH$_2$)$_2$—NMe]-, (NMe$_2$)(Cp)-M-C$_5$Me$_3$-1-$^t$Bu-2-[(CH$_2$)$_2$—NMe]-, (NEt$_2$)(Cp)-M-C$_5$Me$_3$-1-$^t$Bu-2-[(CH$_2$)$_2$—NMe]-, (N$^n$Pr$_2$)(Cp)-M-C$_5$Me$_3$-1-$^t$Bu-2-[(CH$_2$)$_2$—NMe]-, (N$^i$Pr$_2$)(Cp)-M-C$_5$Me$_3$-1-$^t$Bu-2-[(CH$_2$)$_2$—NMe]-, (N$^n$Bu$_2$)(Cp)-M-C$_5$Me$_3$-1-$^t$Bu-2-[(CH$_2$)$_2$—NMe]-, (N$^i$Bu$_2$)(Cp)-M-C$_5$Me$_3$-1-$^t$Bu-2-[(CH$_2$)$_2$—NMe]-, (N$^s$Bu$_2$)(Cp)-M-C$_5$Me$_3$-1-$^t$Bu-2-[(CH$_2$)$_2$—NMe]-, (N$^t$Bu$_2$)(Cp)-M-C$_5$Me$_3$-1-$^t$Bu-2-[(CH$_2$)$_2$—NMe]-, (OH)$_2$-M-C$_5$Me$_3$-1-$^t$Bu-2-[(CH$_2$)$_2$—NMe]-, (OMe)$_2$-M-C$_5$Me$_3$-1-$^t$Bu-2-[(CH$_2$)$_2$—NMe]-, (OEt)$_2$-M-C$_5$Me$_3$-1-$^t$Bu-2-[(CH$_2$)$_2$—NMe]-, (O$^n$Pr)$_2$-M-C$_5$Me$_3$-1-$^t$Bu-2-[(CH$_2$)$_2$—NMe]-, (O$^i$Pr)$_2$-M-C$_5$Me$_3$-1-$^t$Bu-2-[(CH$_2$)$_2$—NMe]-, (O$^n$Bu)$_2$-M-C$_5$Me$_3$-1-$^t$Bu-2-[(CH$_2$)$_2$—NMe]-, (O$^i$Bu$_2$-M-C$_5$Me$_3$-1-$^t$Bu-2-[(CH$_2$)$_2$—NMe]-, (O$^t$Bu)$_2$-M-C$_5$Me$_3$-1-$^t$Bu-2-[(CH$_2$)$_2$—NMe]-, (O$^s$Bu)$_2$-M-C$_5$Me$_3$-1-$^t$Bu-2-[(CH$_2$)$_2$—NMe]-, (NH$_2$)$_2$-M-C$_5$Me$_3$-1-$^t$Bu-3-[(CH$_2$)$_2$—NMe]-, (NMe$_2$)$_2$-M-C$_5$Me$_3$-1-$^t$Bu-3-[(CH$_2$)$_2$—NMe]-, (NEt$_2$)$_2$-M-C$_5$Me$_3$-1-$^t$Bu-3-[(CH$_2$)$_2$—NMe]-, (N$^n$Pr$_2$)$_2$-M-C$_5$Me$_3$-1-$^t$Bu-3-[(CH$_2$)$_2$—NMe]-, (N$^i$Pr$_2$)$_2$-M-C$_5$Me$_3$-1-$^t$Bu-3-[(CH$_2$)$_2$—NMe]-, (N$^n$Bu$_2$)$_2$-M-C$_5$Me$_3$-1-$^t$Bu-3-[(CH$_2$)$_2$—NMe]-, (N$^i$Bu$_2$)$_2$-M-C$_5$Me$_3$-1-$^t$Bu-3-[(CH$_2$)$_2$—NMe]-, (N$^s$Bu$_2$)$_2$-M-C$_5$Me$_3$-1-$^t$Bu-3-[(CH$_2$)$_2$—NMe]-, (N$^t$Bu$_2$)$_2$-M-C$_5$Me$_3$-1-$^t$Bu-3-[(CH$_2$)$_2$—NMe]-, (NH$_2$)(Cp)-M-C$_5$Me$_3$-1-$^t$Bu-3-[(CH$_2$)$_2$—NMe]-, (NMe$_2$)(Cp)-M-C$_5$Me$_3$-1-$^t$Bu-3-[(CH$_2$)$_2$—NMe]-, (NEt$_2$)(Cp)-M-C$_5$Me$_3$-1-$^t$Bu-3-[(CH$_2$)$_2$—NMe]-, (N$^n$Pr$_2$)(Cp)-M-C$_5$Me$_3$-1-$^t$Bu-3-[(CH$_2$)$_2$—NMe]-, (N$^i$Pr$_2$)(Cp)-M-C$_5$Me$_3$-1-$^t$Bu-3-[(CH$_2$)$_2$—NMe]-, (N$^n$Bu$_2$)(Cp)-M-C$_5$Me$_3$-1-$^t$Bu-3-[(CH$_2$)$_2$—NMe]-, (N$^i$Bu$_2$)(Cp)-M-C$_5$Me$_3$-1-$^t$Bu-3-[(CH$_2$)$_2$—NMe]-, (N$^s$Bu$_2$)(Cp)-M-C$_5$Me$_3$-1-$^t$Bu-3-[(CH$_2$)$_2$—NMe]-, (N$^t$Bu$_2$)(Cp)-M-C$_5$Me$_3$-1-$^t$Bu-3-[(CH$_2$)$_2$—NMe]-, (OH)$_2$-M-C$_5$Me$_3$-1-$^t$Bu-3-[(CH$_2$)$_2$—NMe]-, (OMe)$_2$-M-C$_5$Me$_3$-1-$^t$Bu-3-[(CH$_2$)$_2$—NMe]-, (OEt)$_2$-M-C$_5$Me$_3$-1-$^t$Bu-3-[(CH$_2$)$_2$—NMe]-, (O$^n$Pr)$_2$-M-C$_5$Me$_3$-1-$^t$Bu-3-[(CH$_2$)$_2$—NMe]-, (O$^i$Pr)$_2$-M-C$_5$Me$_3$-1-$^t$Bu-3-[(CH$_2$)$_2$—NMe]-, (O$^n$Bu)$_2$-M-C$_5$Me$_3$-1-$^t$Bu-3-[(CH$_2$)$_2$—NMe]-, (O$^i$Bu$_2$-M-C$_5$Me$_3$-1-$^t$Bu-3-[(CH$_2$)$_2$—NMe]-, (O$^t$Bu)$_2$-M-C$_5$Me$_3$-1-$^t$Bu-3-[(CH$_2$)$_2$—NMe]-, (O$^s$Bu)$_2$-M-C$_5$Me$_3$-1-$^t$Bu-3-[(CH$_2$)$_2$—NMe]-, (NH$_2$)$_2$-M-C$_5$Me$_3$-1-Et-2-[(CH$_2$)$_2$—NEt]-, (NMe$_2$)$_2$-M-C$_5$Me$_3$-1-Et-2-[(CH$_2$)$_2$—NEt]-, (NEt$_2$)$_2$-M-C$_5$Me$_3$-1-Et-2-[(CH$_2$)$_2$—NEt]-, (N$^n$Pr$_2$)$_2$-M-C$_5$Me$_3$-1-Et-2-[(CH$_2$)$_2$—NEt]-, (N$^i$Pr$_2$)$_2$-M-C$_5$Me$_3$-1-Et-2-[(CH$_2$)$_2$—NEt]-, (N$^n$Bu$_2$)$_2$-M-C$_5$Me$_3$-1-Et-2-[(CH$_2$)$_2$—NEt]-, (N$^i$Bu$_2$)$_2$-M-C$_5$Me$_3$-1-Et-2-[(CH$_2$)$_2$—NEt]-, (N$^s$Bu$_2$)$_2$-M-C$_5$Me$_3$-1-Et-2-[(CH$_2$)$_2$—NEt]-, (N$^t$Bu$_2$)$_2$-M-C$_5$Me$_3$-1-Et-2-[(CH$_2$)$_2$—NEt]-, (NH$_2$)(Cp)-M-C$_5$Me$_3$-1-Et-2-[(CH$_2$)$_2$—NEt]-, (NMe$_2$)(Cp)-M-C$_5$Me$_3$-1-Et-2-[(CH$_2$)$_2$—NEt]-, (NEt$_2$)(Cp)-M-C$_5$Me$_3$-1-Et-2-[(CH$_2$)$_2$—NEt]-, (N$^n$Pr$_2$)(Cp)-M-C$_5$Me$_3$-1-Et-2-[(CH$_2$)$_2$—NEt]-, (N$^i$Pr$_2$)(Cp)-M-C$_5$Me$_3$-1-Et-2-[(CH$_2$)$_2$—NEt]-, (N$^n$Bu$_2$)(Cp)-M-C$_5$Me$_3$-1-Et-2-[(CH$_2$)$_2$—NEt]-, (N$^i$Bu$_2$)(Cp)-M-C$_5$Me$_3$-1-Et-2-[(CH$_2$)$_2$—NEt]-, (N$^s$Bu$_2$)(Cp)-M-C$_5$Me$_3$-1-Et-2-[(CH$_2$)$_2$—NEt]-, (N$^t$Bu$_2$)(Cp)-M-C$_5$Me$_3$-1-Et-2-[(CH$_2$)$_2$—NEt]-, (OH)$_2$-M-C$_5$Me$_3$-1-Et-2-[(CH$_2$)$_2$—NEt]-, (OMe)$_2$-M-C$_5$Me$_3$-1-Et-2-[(CH$_2$)$_2$—NEt]-, (OEt)$_2$-M-C$_5$Me$_3$-1-Et-2-[(CH$_2$)$_2$—NEt]-, (O$^n$Pr)$_2$-M-C$_5$Me$_3$-1-Et-2-[(CH$_2$)$_2$—NEt]-, (O$^i$Pr)$_2$-M-C$_5$Me$_3$-1-Et-2-[(CH$_2$)$_2$—NEt]-, (O$^n$Bu)$_2$-M-C$_5$Me$_3$-1-Et-2-[(CH$_2$)$_2$—NEt]-, (O$^i$Bu$_2$-M-C$_5$Me$_3$-1-Et-2-[(CH$_2$)$_2$—NEt]-, (O$^t$Bu)$_2$-M-C$_5$Me$_3$-1-Et-2-[(CH$_2$)$_2$—NEt]-, (O$^s$Bu)$_2$-M-C$_5$Me$_3$-1-Et-2-[(CH$_2$)$_2$—NEt]-, (NH$_2$)$_2$-M-C$_5$Me$_3$-1-Et-3-[(CH$_2$)$_2$—NEt]-, (NMe$_2$)$_2$-M-C$_5$Me$_3$-1-Et-3-[(CH$_2$)$_2$—NEt]-, (NEt$_2$)$_2$-M-C$_5$Me$_3$-1-Et-3-[(CH$_2$)$_2$—NEt]-, (N$^n$Pr$_2$)$_2$-M-C$_5$Me$_3$-1-Et-3-[(CH$_2$)$_2$—NEt]-, (N$^i$Pr$_2$)$_2$-M-C$_5$Me$_3$-1-Et-3-[(CH$_2$)$_2$—NEt]-, (N$^n$Bu$_2$)$_2$-M-C$_5$Me$_3$-1-Et-3-[(CH$_2$)$_2$—NEt]-, (N$^i$Bu$_2$)$_2$-M-C$_5$Me$_3$-1-Et-3-[(CH$_2$)$_2$—NEt]-, (N$^s$Bu$_2$)$_2$-M-C$_5$Me$_3$-1-Et-3-[(CH$_2$)$_2$—NEt]-, (N$^t$Bu$_2$)$_2$-M-C$_5$Me$_3$-1-Et-3-[(CH$_2$)$_2$—NEt]-, (NH$_2$)(Cp)-M-C$_5$Me$_3$-1-Et-3-[(CH$_2$)$_2$—NEt]-, (NMe$_2$)(Cp)-M-C$_5$Me$_3$-1-Et-3-[(CH$_2$)$_2$—NEt]-, (NEt$_2$)(Cp)-M-C$_5$Me$_3$-1-Et-3-[(CH$_2$)$_2$—NEt]-, (N$^n$Pr$_2$)(Cp)-M-C$_5$Me$_3$-1-Et-3-[(CH$_2$)$_2$—NEt]-, (N$^i$Pr$_2$)(Cp)-M-C$_5$Me$_3$-1-Et-3-[(CH$_2$)$_2$—NEt]-, (N$^n$Bu$_2$)(Cp)-M-C$_5$Me$_3$-1-Et-3-[(CH$_2$)$_2$—NEt]-, (N$^i$Bu$_2$)(Cp)-M-C$_5$Me$_3$-1-Et-3-[(CH$_2$)$_2$—NEt]-, (N$^s$Bu$_2$)(Cp)-M-C$_5$Me$_3$-1-Et-3-[(CH$_2$)$_2$—NEt]-, (N$^t$Bu$_2$)(Cp)-M-C$_5$Me$_3$-1-Et-3-[(CH$_2$)$_2$—NEt]-, (OH)$_2$-M-C$_5$Me$_3$-1-Et-3-[(CH$_2$)$_2$—NEt]-, (OMe)$_2$-M-C$_5$Me$_3$-1-Et-3-[(CH$_2$)$_2$—NEt]-, (OEt)$_2$-M-C$_5$Me$_3$-1-Et-3-[(CH$_2$)$_2$—NEt]-, (O$^n$Pr)$_2$-M-C$_5$Me$_3$-1-Et-3-[(CH$_2$)$_2$—NEt]-, (O$^i$Pr)$_2$-M-C$_5$Me$_3$-1-Et-3-[(CH$_2$)$_2$—NEt]-, (O$^n$Bu)$_2$-M-C$_5$Me$_3$-1-Et-3-[(CH$_2$)$_2$—NEt]-, (O$^i$Bu$_2$-M-C$_5$Me$_3$-1-Et-3-[(CH$_2$)$_2$—NEt]-, (O$^t$Bu)$_2$-M-C$_5$Me$_3$-1-Et-3-[(CH$_2$)$_2$—NEt]-, (O$^s$Bu)$_2$-M-C$_5$Me$_3$-1-Et-3-[(CH$_2$)$_2$—NEt]-, (NH$_2$)$_2$-M-C$_5$Me$_3$-1-$^i$Pr-2-[(CH$_2$)$_2$—NEt]-, (NMe$_2$)$_2$-M-C$_5$Me$_3$-1-$^i$Pr-2-[(CH$_2$)$_2$—NEt]-, (NEt$_2$)$_2$-M-C$_5$Me$_3$-1-$^i$Pr-2-[(CH$_2$)$_2$—NEt]-, (N$^n$Pr$_2$)$_2$-M-C$_5$Me$_3$-1-$^i$Pr-2-[(CH$_2$)$_2$—NEt]-, (N$^i$Pr$_2$)$_2$-M-C$_5$Me$_3$-1-$^i$Pr-2-[(CH$_2$)$_2$—NEt]-, (N$^n$Bu$_2$)$_2$-M-C$_5$Me$_3$-1-$^i$Pr-2-[(CH$_2$)$_2$—NEt]-, (N$^i$Bu$_2$)$_2$-M-C$_5$Me$_3$-1-$^i$Pr-2-[(CH$_2$)$_2$—NEt]-, (N$^s$Bu$_2$)$_2$-M-C$_5$Me$_3$-1-$^i$Pr-2-[(CH$_2$)$_2$—NEt]-, (N$^t$Bu$_2$)$_2$-M-C$_5$Me$_3$-1-$^i$Pr-2-[(CH$_2$)$_2$—NEt]-, (NH$_2$)(Cp)-M-C$_5$Me$_3$-1-$^i$Pr-2-[(CH$_2$)$_2$—NEt]-, (NMe$_2$)(Cp)-M-C$_5$Me$_3$-1-$^i$Pr-2-[(CH$_2$)$_2$—NEt]-, (NEt$_2$)(Cp)-M-C$_5$Me$_3$-1-$^i$Pr-2-[(CH$_2$)$_2$—NEt]-, (N$^n$Pr$_2$)(Cp)-M-C$_5$Me$_3$-1-$^i$Pr-2-[(CH$_2$)$_2$—NEt]-, (N$^i$Pr$_2$)(Cp)-M-C$_5$Me$_3$-1-$^i$Pr-2-[(CH$_2$)$_2$—NEt]-, (N$^n$Bu$_2$)(Cp)-M-C$_5$Me$_3$-1-$^i$Pr-2-[(CH$_2$)$_2$—NEt]-, (N$^i$Bu$_2$)(Cp)-M-C$_5$Me$_3$-1-$^i$Pr-2-[(CH$_2$)$_2$—NEt]-, (N$^s$Bu$_2$)(Cp)-M-C$_5$Me$_3$-1-$^i$Pr-2-[(CH$_2$)$_2$—NEt]-, (N$^t$Bu$_2$)(Cp)-M-C$_5$Me$_3$-1-$^i$Pr-2-[(CH$_2$)$_2$—NEt]-, (OH)$_2$-M-C$_5$Me$_3$-1-$^i$Pr-2-[(CH$_2$)$_2$—NEt]-, (OMe)$_2$-M-C$_5$Me$_3$-1-$^i$Pr-2-[(CH$_2$)$_2$—NEt]-, (OEt)$_2$-M-C$_5$Me$_3$-1-$^i$Pr-2-[(CH$_2$)$_2$—NEt]-, (O$^n$Pr)$_2$-M-C$_5$Me$_3$-1-$^i$Pr-2-[(CH$_2$)$_2$—NEt]-, (O$^i$Pr)$_2$-M-C$_5$Me$_3$-

1-$^i$Pr-2-[$(CH_2)_2$—NEt]-, (O$^n$Bu)$_2$-M-$C_5Me_3$-1-$^i$Pr-2-[$(CH_2)_2$—NEt]-, (O$^i$Bu$_2$-M-$C_5Me_3$-1-$^i$Pr-2-[$(CH_2)_2$—NEt]-, (O$^t$Bu)$_2$-M-$C_5Me_3$-1-$^i$Pr-2-[$(CH_2)_2$—NEt]-, (O$^s$Bu)$_2$-M-$C_5Me_3$-1-$^i$Pr-2-[$(CH_2)_2$—NEt]-, $(NH_2)_2$-M-$C_5Me_3$-1-$^i$Pr-3-[$(CH_2)_2$—NEt]-, $(NMe_2)_2$-M-$C_5Me_3$-1-$^i$Pr-3-[$(CH_2)_2$—NEt]-, $(NEt_2)_2$-M-$C_5Me_3$-1-$^i$Pr-3-[$(CH_2)_2$—NEt]-, (N$^n$Pr$_2$)$_2$-M-$C_5Me_3$-1-$^i$Pr-3-[$(CH_2)_2$—NEt]-, (N$^i$Pr$_2$)$_2$-M-$C_5Me_3$-1-$^i$Pr-3-[$(CH_2)_2$—NEt]-, (N$^n$Bu$_2$)$_2$-M-$C_5Me_3$-1-$^i$Pr-3-[$(CH_2)_2$—NEt]-, (N$^i$Bu$_2$)$_2$-M-$C_5Me_3$-1-$^i$Pr-3-[$(CH_2)_2$—NEt]-, (N$^s$Bu$_2$)$_2$-M-$C_5Me_3$-1-$^i$Pr-3-[$(CH_2)_2$—NEt]-, (N$^t$Bu$_2$)$_2$-M-$C_5Me_3$-1-$^i$Pr-3-[$(CH_2)_2$—NEt]-, $(NH_2)$(Cp)-M-$C_5Me_3$-1-$^i$Pr-3-[$(CH_2)_2$—NEt]-, $(NMe_2)$(Cp)-M-$C_5Me_3$-1-$^i$Pr-3-[$(CH_2)_2$—NEt]-, $(NEt_2)$(Cp)-M-$C_5Me_3$-1-$^i$Pr-3-[$(CH_2)_2$—NEt]-, (N$^n$Pr$_2$)(Cp)-M-$C_5Me_3$-1-$^i$Pr-3-[$(CH_2)_2$—NEt]-, (N$^i$Pr$_2$)(Cp)-M-$C_5Me_3$-1-$^i$Pr-3-[$(CH_2)_2$—NEt]-, (N$^n$Bu$_2$)(Cp)-M-$C_5Me_3$-1-$^i$Pr-3-[$(CH_2)_2$—NEt]-, (N$^i$Bu$_2$)(Cp)-M-$C_5Me_3$-1-$^i$Pr-3-[$(CH_2)_2$—NEt]-, (N$^s$Bu$_2$)(Cp)-M-$C_5Me_3$-1-$^i$Pr-3-[$(CH_2)_2$—NEt]-, (N$^t$Bu$_2$)(Cp)-M-$C_5Me_3$-1-$^i$Pr-3-[$(CH_2)_2$—NEt]-, $(OH)_2$-M-$C_5Me_3$-1-$^i$Pr-3-[$(CH_2)_2$—NEt]-, $(OMe)_2$-M-$C_5Me_3$-1-$^i$Pr-3-[$(CH_2)_2$—NEt]-, $(OEt)_2$-M-$C_5Me_3$-1-$^i$Pr-3-[$(CH_2)_2$—NEt]-, (O$^n$Pr)$_2$-M-$C_5Me_3$-1-$^i$Pr-3-[$(CH_2)_2$—NEt]-, (O$^i$Pr)$_2$-M-$C_5Me_3$-1-$^i$Pr-3-[$(CH_2)_2$—NEt]-, (O$^n$Bu)$_2$-M-$C_5Me_3$-1-$^i$Pr-3-[$(CH_2)_2$—NEt]-, (O$^i$Bu$_2$-M-$C_5Me_3$-1-$^i$Pr-3-[$(CH_2)_2$—NEt]-, (O$^t$Bu)$_2$-M-$C_5Me_3$-1-$^i$Pr-3-[$(CH_2)_2$—NEt]-, (O$^s$Bu)$_2$-M-$C_5Me_3$-1-$^i$Pr-3-[$(CH_2)_2$—NEt]-, $(NH_2)_2$-M-$C_5Me_3$-1-$^t$Bu-2-[$(CH_2)_2$—NEt]-, $(NMe_2)_2$-M-$C_5Me_3$-1-$^t$Bu-2-[$(CH_2)_2$—NEt]-, $(NEt_2)_2$-M-$C_5Me_3$-1-$^t$Bu-2-[$(CH_2)_2$—NEt]-, (N$^n$Pr$_2$)$_2$-M-$C_5Me_3$-1-$^t$Bu-2-[$(CH_2)_2$—NEt]-, (N$^i$Pr$_2$)$_2$-M-$C_5Me_3$-1-$^t$Bu-2-[$(CH_2)_2$—NEt]-, (N$^n$Bu$_2$)$_2$-M-$C_5Me_3$-1-$^t$Bu-2-[$(CH_2)_2$—NEt]-, (N$^i$Bu$_2$)$_2$-M-$C_5Me_3$-1-$^t$Bu-2-[$(CH_2)_2$—NEt]-, (N$^s$Bu$_2$)$_2$-M-$C_5Me_3$-1-$^t$Bu-2-[$(CH_2)_2$—NEt]-, (N$^t$Bu$_2$)$_2$-M-$C_5Me_3$-1-$^t$Bu-2-[$(CH_2)_2$—NEt]-, $(NH_2)$(Cp)-M-$C_5Me_3$-1-$^t$Bu-2-[$(CH_2)_2$—NEt]-, $(NMe_2)$(Cp)-M-$C_5Me_3$-1-$^t$Bu-2-[$(CH_2)_2$—NEt]-, $(NEt_2)$(Cp)-M-$C_5Me_3$-1-$^t$Bu-2-[$(CH_2)_2$—NEt]-, (N$^n$Pr$_2$)(Cp)-M-$C_5Me_3$-1-$^t$Bu-2-[$(CH_2)_2$—NEt]-, (N$^i$Pr$_2$)(Cp)-M-$C_5Me_3$-1-$^t$Bu-2-[$(CH_2)_2$—NEt]-, (N$^n$Bu$_2$)(Cp)-M-$C_5Me_3$-1-$^t$Bu-2-[$(CH_2)_2$—NEt]-, (N$^i$Bu$_2$)(Cp)-M-$C_5Me_3$-1-$^t$Bu-2-[$(CH_2)_2$—NEt]-, (N$^s$Bu$_2$)(Cp)-M-$C_5Me_3$-1-$^t$Bu-2-[$(CH_2)_2$—NEt]-, (N$^t$Bu$_2$)(Cp)-M-$C_5Me_3$-1-$^t$Bu-2-[$(CH_2)_2$—NEt]-, $(OH)_2$-M-$C_5Me_3$-1-$^t$Bu-2-[$(CH_2)_2$—NEt]-, $(OMe)_2$-M-$C_5Me_3$-1-$^t$Bu-2-[$(CH_2)_2$—NEt]-, $(OEt)_2$-M-$C_5Me_3$-1-$^t$Bu-2-[$(CH_2)_2$—NEt]-, (O$^n$Pr)$_2$-M-$C_5Me_3$-1-$^t$Bu-2-[$(CH_2)_2$—NEt]-, (O$^i$Pr)$_2$-M-$C_5Me_3$-1-$^t$Bu-2-[$(CH_2)_2$—NEt]-, (O$^n$Bu)$_2$-M-$C_5Me_3$-1-$^t$Bu-2-[$(CH_2)_2$—NEt]-, (O$^i$Bu$_2$-M-$C_5Me_3$-1-$^t$Bu-2-[$(CH_2)_2$—NEt]-, (O$^t$Bu)$_2$-M-$C_5Me_3$-1-$^t$Bu-2-[$(CH_2)_2$—NEt]-, (O$^s$Bu)$_2$-M-$C_5Me_3$-1-$^t$Bu-2-[$(CH_2)_2$—NEt]-, $(NH_2)_2$-M-$C_5Me_3$-1-$^t$Bu-3-[$(CH_2)_2$—NEt]-, $(NMe_2)_2$-M-$C_5Me_3$-1-$^t$Bu-3-[$(CH_2)_2$—NEt]-, $(NEt_2)_2$-M-$C_5Me_3$-1-$^t$Bu-3-[$(CH_2)_2$—NEt]-, (N$^n$Pr$_2$)$_2$-M-$C_5Me_3$-1-$^t$Bu-3-[$(CH_2)_2$—NEt]-, (N$^i$Pr$_2$)$_2$-M-$C_5Me_3$-1-$^t$Bu-3-[$(CH_2)_2$—NEt]-, (N$^n$Bu$_2$)$_2$-M-$C_5Me_3$-1-$^t$Bu-3-[$(CH_2)_2$—NEt]-, (N$^i$Bu$_2$)$_2$-M-$C_5Me_3$-1-$^t$Bu-3-[$(CH_2)_2$—NEt]-, (N$^s$Bu$_2$)$_2$-M-$C_5Me_3$-1-$^t$Bu-3-[$(CH_2)_2$—NEt]-, (N$^t$Bu$_2$)$_2$-M-$C_5Me_3$-1-$^t$Bu-3-[$(CH_2)_2$—NEt]-, $(NH_2)_2$-M-$C_5Me_3$-1-Et-2-[$(CH_2)_2$—N$^i$Pr]—, $(NMe_2)_2$-M-$C_5Me_3$-1-Et-2-[$(CH_2)_2$—N$^i$Pr]—, $(NEt_2)_2$-M-$C_5Me_3$-1-Et-2-[$(CH_2)_2$—N$^i$Pr]—, (N$^n$Pr$_2$)$_2$-M-$C_5Me_3$-1-Et-2-[$(CH_2)_2$—N$^i$Pr]—, (N$^i$Pr$_2$)$_2$-M-$C_5Me_3$-1-Et-2-[$(CH_2)_2$—N$^i$Pr]—, (N$^n$Bu$_2$)$_2$-M-$C_5Me_3$-1-Et-2-[$(CH_2)_2$—N$^i$Pr]—, (N$^i$Bu$_2$)$_2$-M-$C_5Me_3$-1-Et-2-[$(CH_2)_2$—N$^i$Pr]—, (N$^s$Bu$_2$)$_2$-M-$C_5Me_3$-1-Et-2-[$(CH_2)_2$—N$^i$Pr]—, (N$^t$Bu$_2$)$_2$-M-$C_5Me_3$-1-Et-2-[$(CH_2)_2$—N$^i$Pr]—, $(NH_2)$(Cp)-M-$C_5Me_3$-1-Et-2-[$(CH_2)_2$—N$^i$Pr]—, $(NMe_2)$(Cp)-M-$C_5Me_3$-1-Et-2-[$(CH_2)_2$—N$^i$Pr]—, $(NEt_2)$(Cp)-M-$C_5Me_3$-1-Et-2-[$(CH_2)_2$—N$^i$Pr]—, (N$^n$Pr$_2$)(Cp)-M-$C_5Me_3$-1-Et-2-[$(CH_2)_2$—N$^i$Pr]—, (N$^i$Pr$_2$)(Cp)-M-$C_5Me_3$-1-Et-2-[$(CH_2)_2$—N$^i$Pr]—, (N$^n$Bu$_2$)(Cp)-M-$C_5Me_3$-1-Et-2-[$(CH_2)_2$—N$^i$Pr]—, (N$^i$Bu$_2$)(Cp)-M-$C_5Me_3$-1-Et-2-[$(CH_2)_2$—N$^i$Pr]—, (N$^s$Bu$_2$)(Cp)-M-$C_5Me_3$-1-Et-2-[$(CH_2)_2$—N$^i$Pr]—, (N$^t$Bu$_2$)(Cp)-M-$C_5Me_3$-1-Et-2-[$(CH_2)_2$—N$^i$Pr]—, $(OH)_2$-M-$C_5Me_3$-1-Et-2-[$(CH_2)_2$—N$^i$Pr]—, $(OMe)_2$-M-$C_5Me_3$-1-Et-2-[$(CH_2)_2$—N$^i$Pr]—, $(OEt)_2$-M-$C_5Me_3$-1-Et-2-[$(CH_2)_2$—N$^i$Pr]—, (O$^n$Pr)$_2$-M-$C_5Me_3$-1-Et-2-[$(CH_2)_2$—N$^i$Pr]—, (O$^i$Pr)$_2$-M-$C_5Me_3$-1-Et-2-[$(CH_2)_2$—N$^i$Pr]—, (O$^n$Bu)$_2$-M-$C_5Me_3$-1-Et-2-[$(CH_2)_2$—N$^i$Pr]—, (O$^i$Bu$_2$-M-$C_5Me_3$-1-Et-2-[$(CH_2)_2$—N$^i$Pr]—, (O$^t$Bu)$_2$-M-$C_5Me_3$-1-Et-2-[$(CH_2)_2$—N$^i$Pr]—, (O$^s$Bu)$_2$-M-$C_5Me_3$-1-Et-2-[$(CH_2)_2$—N$^i$Pr]—, $(NH_2)_2$-M-$C_5Me_3$-1-Et-3-[$(CH_2)_2$—N$^i$Pr]—, $(NMe_2)_2$-M-$C_5Me_3$-1-Et-3-[$(CH_2)_2$—N$^i$Pr]—, $(NEt_2)_2$-M-$C_5Me_3$-1-Et-3-[$(CH_2)_2$—N$^i$Pr]—, (N$^n$Pr$_2$)$_2$-M-$C_5Me_3$-1-Et-3-[$(CH_2)_2$—N$^i$Pr]—, (N$^i$Pr$_2$)$_2$-M-$C_5Me_3$-1-Et-3-[$(CH_2)_2$—N$^i$Pr]—, (N$^n$Bu$_2$)$_2$-M-$C_5Me_3$-1-Et-3-[$(CH_2)_2$—N$^i$Pr]—, (N$^i$Bu$_2$)$_2$-M-$C_5Me_3$-1-Et-3-[$(CH_2)_2$—N$^i$Pr]—, (N$^s$Bu$_2$)$_2$-M-$C_5Me_3$-1-Et-3-[$(CH_2)_2$—N$^i$Pr]—, (N$^t$Bu$_2$)$_2$-M-$C_5Me_3$-1-Et-3-[$(CH_2)_2$—N$^i$Pr]—, $(NH_2)$(Cp)-M-$C_5Me_3$-1-Et-3-[$(CH_2)_2$—N$^i$Pr]—, $(NMe_2)$(Cp)-M-$C_5Me_3$-1-Et-3-[$(CH_2)_2$—N$^i$Pr]—, $(NEt_2)$(Cp)-M-$C_5Me_3$-1-Et-3-[$(CH_2)_2$—N$^i$Pr]—, (N$^n$Pr$_2$)(Cp)-M-$C_5Me_3$-1-Et-3-[$(CH_2)_2$—N$^i$Pr]—, (N$^i$Pr$_2$)(Cp)-M-$C_5Me_3$-1-Et-3-[$(CH_2)_2$—N$^i$Pr]—, (N$^n$Bu$_2$)(Cp)-M-$C_5Me_3$-1-Et-3-[$(CH_2)_2$—N$^i$Pr]—, (N$^i$Bu$_2$)(Cp)-M-$C_5Me_3$-1-Et-3-[$(CH_2)_2$—N$^i$Pr]—, (N$^s$Bu$_2$)(Cp)-M-$C_5Me_3$-1-Et-3-[$(CH_2)_2$—N$^i$Pr]—, (N$^t$Bu$_2$)(Cp)-M-$C_5Me_3$-1-Et-3-[$(CH_2)_2$—N$^i$Pr]—, $(OH)_2$-M-$C_5Me_3$-1-Et-3-[$(CH_2)_2$—N$^i$Pr]—, $(OMe)_2$-M-$C_5Me_3$-1-Et-3-[$(CH_2)_2$—N$^i$Pr]—, $(OEt)_2$-M-$C_5Me_3$-1-Et-3-[$(CH_2)_2$—N$^i$Pr]—, (O$^n$Pr)$_2$-M-$C_5Me_3$-1-Et-3-[$(CH_2)_2$—N$^i$Pr]—, (O$^i$Pr)$_2$-M-$C_5Me_3$-1-Et-3-[$(CH_2)_2$—N$^i$Pr]—, (O$^n$Bu)$_2$-M-$C_5Me_3$-1-Et-3-[$(CH_2)_2$—N$^i$Pr]—, (O$^i$Bu$_2$-M-$C_5Me_3$-1-Et-3-[$(CH_2)_2$—N$^i$Pr]—, (O$^t$Bu)$_2$-M-$C_5Me_3$-1-Et-3-[$(CH_2)_2)_2$—N$^i$Pr]—, (O$^s$Bu)$_2$-M-$C_5Me_3$-1-Et-3-[$(CH_2)_2$—N$^i$Pr]—, $(NH_2)_2$-M-$C_5Me_3$-1-$^i$Pr-2-[$(CH_2)_2$—N$^i$Pr]—, $(NMe_2)_2$-M-$C_5Me_3$-1-$^i$Pr-2-[$(CH_2)_2$—N$^i$Pr]—, $(NEt_2)_2$-M-$C_5Me_3$-1-$^i$Pr-2-[$(CH_2)_2$—N$^i$Pr]—, (N$^n$Pr$_2$)$_2$-M-$C_5Me_3$-1-$^i$Pr-2-[$(CH_2)_2$—N$^i$Pr]—, (N$^i$Pr$_2$)$_2$-M-$C_5Me_3$-1-$^i$Pr-2-[$(CH_2)_2$—N$^i$Pr]—, (N$^n$Bu$_2$)$_2$-M-$C_5Me_3$-1-$^i$Pr-2-[$(CH_2)_2$—N$^i$Pr]—, (N$^i$Bu$_2$)$_2$-M-$C_5Me_3$-1-$^i$Pr-2-[$(CH_2)_2$—N$^i$Pr]—, (N$^s$Bu$_2$)$_2$-M-$C_5Me_3$-1-$^i$Pr-2-[$(CH_2)_2$—N$^i$Pr]—, (N$^t$Bu$_2$)$_2$-M-$C_5Me_3$-1-$^i$Pr-2-[$(CH_2)_2$—N$^i$Pr]—, $(NH_2)$(Cp)-M-$C_5Me_3$-1-$^i$Pr-2-[$(CH_2)_2$—N$^i$Pr]—, $(NMe_2)$(Cp)-M-$C_5Me_3$-1-$^i$Pr-2-[$(CH_2)_2$—N$^i$Pr]—, $(NEt_2)$(Cp)-M-$C_5Me_3$-1-$^i$Pr-2-[$(CH_2)_2$—N$^i$Pr]—, (N$^n$Pr$_2$)(Cp)-M-$C_5Me_3$-1-$^i$Pr-2-[$(CH_2)_2$—N$^i$Pr]—, (N$^i$Pr$_2$)(Cp)-M-$C_5Me_3$-1-$^i$Pr-2-[$(CH_2)_2$—N$^i$Pr]—, (N$^n$Bu$_2$)(Cp)-M-$C_5Me_3$-1-$^i$Pr-2-[$(CH_2)_2$—N$^i$Pr]—, (N$^i$Bu$_2$)(Cp)-M-$C_5Me_3$-1-$^i$Pr-2-[$(CH_2)_2$—N$^i$Pr]—, (N$^s$Bu$_2$)(Cp)-M-$C_5Me_3$-1-$^i$Pr-2-[$(CH_2)_2$—N$^i$Pr]—, (N$^t$Bu$_2$)(Cp)-M-$C_5Me_3$-1-$^i$Pr-2-[$(CH_2)_2$—N$^i$Pr]—, $(OH)_2$-M-$C_5Me_3$-1-$^i$Pr-2-[$(CH_2)_2$—N$^i$Pr]—, $(OMe)_2$-M-$C_5Me_3$-1-$^i$Pr-2-[$(CH_2)_2$—N$^i$Pr]—, $(OEt)_2$-M-$C_5Me_3$-1-$^i$Pr-2-[$(CH_2)_2$—N$^i$Pr]—, (O$^n$Pr)$_2$-M-$C_5Me_3$-1-$^i$Pr-2-[$(CH_2)_2$—N$^i$Pr]—, (O$^i$Pr)$_2$-M-$C_5Me_3$-1-$^i$Pr-2-[$(CH_2)_2$—N$^i$Pr]—, (O$^n$Bu)$_2$-M-$C_5Me_3$-1-$^i$Pr-2-[$(CH_2)_2$—N$^i$Pr]—, (O$^i$Bu$_2$-M-$C_5Me_3$-1-$^i$Pr-2-[$(CH_2)_2$—N$^i$Pr]—, (O$^t$Bu)$_2$-M-$C_5Me_3$-1-$^i$Pr-2-[$(CH_2)_2$—N$^i$Pr]—, (O$^s$Bu)$_2$-M-$C_5Me_3$-1-$^i$Pr-2-[$(CH_2)_2$—N$^i$Pr]—, $(NH_2)_2$-M-$C_5Me_3$-1-$^i$Pr-3-[$(CH_2)_2$—N$^i$Pr]—, $(NMe_2)_2$-M-$C_5Me_3$-1-$^i$Pr-3-[$(CH_2)_2$—N$^i$Pr]—, $(NEt_2)_2$-M-$C_5Me_3$-1-$^i$Pr-3-[$(CH_2)_2$—N$^i$Pr]—, (N$^n$Pr$_2$)$_2$-M-$C_5Me_3$-1-$^i$Pr-3-[$(CH_2)_2$—N$^i$Pr]—, (N$^i$Pr$_2$)$_2$-M-$C_5Me_3$-1-$^i$Pr-3-[$(CH_2)_2$—N$^i$Pr]—, (N$^n$Bu$_2$)$_2$-M-$C_5Me_3$-1-$^i$Pr-3-[$(CH_2)_2$—N$^i$Pr]—, (N$^i$Bu$_2$)$_2$-M-$C_5Me_3$-1-$^i$Pr-3-[$(CH_2)_2$—N$^i$Pr]—, (N$^s$Bu$_2$)$_2$-M-$C_5Me_3$-1-$^i$Pr-3-[$(CH_2)_2$—N$^i$Pr]—, (N$^t$Bu$_2$)$_2$-M-$C_5Me_3$-1-$^i$Pr-3-[$(CH_2)_2$—N$^i$Pr]—, $(NH_2)$(Cp)-M-$C_5Me_3$-1-$^i$Pr-3-[$(CH_2)_2$—N$^i$Pr]—, $(NMe_2)$(Cp)-M-$C_5Me_3$-1-$^i$Pr-3-[$(CH_2)_2$—N$^i$Pr]—, $(NEt_2)$ (Cp)-M-$C_5Me_3$-1-$^i$Pr-3-[$(CH_2)_2$—N$^i$Pr]—, (N$^n$Pr$_2$)(Cp)-M-$C_5Me_3$-1-$^i$Pr-3-[$(CH_2)_2$—N$^i$Pr]—, (N$^i$Pr$_2$)(Cp)-M-$C_5Me_3$-1-$^i$Pr-3-[$(CH_2)_2$—N$^i$Pr]—, (N$^n$Bu$_2$)(Cp)-M-$C_5Me_3$-1-$^i$Pr-3-[$(CH_2)_2$—N$^i$Pr]—, (N$^i$Bu$_2$)(Cp)-M-$C_5Me_3$-1-$^i$Pr-3-[$(CH_2)_2$—N$^i$Pr]—, (N$^s$Bu$_2$)(Cp)-M-$C_5Me_3$-1-$^i$Pr-3-[$(CH_2)_2$—N$^i$Pr]—, (N$^t$Bu$_2$)(Cp)-M-$C_5Me_3$-1-$^i$Pr-3-[$(CH_2)_2$—N$^i$Pr]—, (OH)$_2$-M-$C_5Me_3$-1-$^i$Pr-3-[$(CH_2)_2$—N$^i$Pr]—, (OMe)$_2$-M-$C_5Me_3$-1-$^i$Pr-3-[$(CH_2)_2$—N$^i$Pr]—, (OEt)$_2$-M-$C_5Me_3$-1-$^i$Pr-3-[$(CH_2)_2$—N$^i$Pr]—, (O$^n$Pr)$_2$-M-$C_5Me_3$-1-$^i$Pr-3-[$(CH_2)_2$—N$^i$Pr]—, (O$^i$Pr)$_2$-M-$C_5Me_3$-1-$^i$Pr-3-[$(CH_2)_2$—N$^i$Pr]—, (O$^n$Bu)$_2$-M-$C_5Me_3$-1-$^i$Pr-3-[$(CH_2)_2$—N$^i$Pr]—, (O$^i$Bu$_2$-M-$C_5Me_3$-1-$^i$Pr-3-[$(CH_2)_2$—N$^i$Pr]—, (O$^t$Bu)$_2$-M-$C_5Me_3$-1-$^i$Pr-3-[$(CH_2)_2$—N$^i$Pr]—, (O$^s$Bu)$_2$-M-$C_5Me_3$-1-$^i$Pr-3-[$(CH_2)_2$—N$^i$Pr]—, (NH$_2$)$_2$-M-$C_5Me_3$-1-$^t$Bu-2-[$(CH_2)_2$—N$^i$Pr]—, (NMe$_2$)$_2$-M-$C_5Me_3$-1-$^t$Bu-2-[$(CH_2)_2$—N$^i$Pr]—, (NEt$_2$)$_2$-M-$C_5Me_3$-1-$^t$Bu-2-[$(CH_2)_2$—N$^i$Pr]—, (N$^n$Pr$_2$)$_2$-M-$C_5Me_3$-1-$^t$Bu-2-[$(CH_2)_2$—N$^i$Pr]—, (N$^i$Pr$_2$)$_2$-M-$C_5Me_3$-1-$^t$Bu-2-[$(CH_2)_2$—N$^i$Pr]—, (N$^n$Bu$_2$)$_2$-M-$C_5Me_3$-1-$^t$Bu-2-[$(CH_2)_2$—N$^i$Pr]—, (N$^i$Bu$_2$)$_2$-M-$C_5Me_3$-1-$^t$Bu-2-[$(CH_2)_2$—N$^i$Pr]—, (N$^s$Bu$_2$)$_2$-M-$C_5Me_3$-1-$^t$Bu-2-[$(CH_2)_2$—N$^i$Pr]—, (N$^t$Bu$_2$)$_2$-M-$C_5Me_3$-1-$^t$Bu-2-[$(CH_2)_2$—N$^i$Pr]—, (NH$_2$)(Cp)-M-$C_5Me_3$-1-$^t$Bu-2-[$(CH_2)_2$—N$^i$Pr]—, (NMe$_2$)(Cp)-M-$C_5Me_3$-1-$^t$Bu-2-[$(CH_2)_2$—N$^i$Pr]—, (NEt$_2$)(Cp)-M-$C_5Me_3$-1-$^t$Bu-2-[$(CH_2)_2$—N$^i$Pr]—, (N$^n$Pr$_2$)(Cp)-M-$C_5Me_3$-1-$^t$Bu-2-[$(CH_2)_2$—N$^i$Pr]—, (N$^i$Pr$_2$)(Cp)-M-$C_5Me_3$-1-$^t$Bu-2-[$(CH_2)_2$—N$^i$Pr]—, (N$^n$Bu$_2$)(Cp)-M-$C_5Me_3$-1-$^t$Bu-2-[$(CH_2)_2$—N$^i$Pr]—, (N$^i$Bu$_2$)(Cp)-M-$C_5Me_3$-1-$^t$Bu-2-[$(CH_2)_2$—N$^i$Pr]—, (N$^s$Bu$_2$)(Cp)-M-$C_5Me_3$-1-$^t$Bu-2-[$(CH_2)_2$—N$^i$Pr]—, (N$^t$Bu$_2$)(Cp)-M-$C_5Me_3$-1-$^t$Bu-2-[$(CH_2)_2$—N$^i$Pr]—, (OH)$_2$-M-$C_5Me_3$-1-$^t$Bu-2-[$(CH_2)_2$—N$^i$Pr]—, (OMe)$_2$-M-$C_5Me_3$-1-$^t$Bu-2-[$(CH_2)_2$—N$^i$Pr]—, (OEt)$_2$-M-$C_5Me_3$-1-$^t$Bu-2-[$(CH_2)_2$—N$^i$Pr]—, (O$^n$Pr)$_2$-M-$C_5Me_3$-1-$^t$Bu-2-[$(CH_2)_2$—N$^i$Pr]—, (O$^i$Pr)$_2$-M-$C_5Me_3$-1-$^t$Bu-2-[$(CH_2)_2$—N$^i$Pr]—, (O$^n$Bu)$_2$-M-$C_5Me_3$-1-$^t$Bu-2-[$(CH_2)_2$—N$^i$Pr]—, (O$^i$Bu$_2$-M-$C_5Me_3$-1-$^t$Bu-2-[$(CH_2)_2$—N$^i$Pr]—, (O$^t$Bu)$_2$-M-$C_5Me_3$-1-$^t$Bu-2-[$(CH_2)_2$—N$^i$Pr]—, (O$^s$Bu)$_2$-M-$C_5Me_3$-1-$^t$Bu-2-[$(CH_2)_2$—N$^i$Pr]—, (NH$_2$)$_2$-M-$C_5Me_3$-1-$^t$Bu-3-[$(CH_2)_2$—N$^i$Pr]—, (NMe$_2$)$_2$-M-$C_5Me_3$-1-$^t$Bu-3-[$(CH_2)_2$—N$^i$Pr]—, (NEt$_2$)$_2$-M-$C_5Me_3$-1-$^t$Bu-3-[$(CH_2)_2$—N$^i$Pr]—, (N$^n$Pr$_2$)$_2$-M-$C_5Me_3$-1-$^t$Bu-3-[$(CH_2)_2$—N$^i$Pr]—, (N$^i$Pr$_2$)$_2$-M-$C_5Me_3$-1-$^t$Bu-3-[$(CH_2)_2$—N$^i$Pr]—, (N$^n$Bu$_2$)$_2$-M-$C_5Me_3$-1-$^t$Bu-3-[$(CH_2)_2$—N$^i$Pr]—, (N$^i$Bu$_2$)$_2$-M-$C_5Me_3$-1-$^t$Bu-3-[$(CH_2)_2$—N$^i$Pr]—, (N$^s$Bu$_2$)$_2$-M-$C_5Me_3$-1-$^t$Bu-3-[$(CH_2)_2$—N$^i$Pr]—, (N$^t$Bu$_2$)$_2$-M-$C_5Me_3$-1-$^t$Bu-3-[$(CH_2)_2$—N$^i$Pr]—, (NH$_2$)(Cp)-M-$C_5Me_3$-1-$^t$Bu-3-[$(CH_2)_2$—N$^i$Pr]—, (NMe$_2$)(Cp)-M-$C_5Me_3$-1-$^t$Bu-3-[$(CH_2)_2$—N$^i$Pr]—, (NEt$_2$)(Cp)-M-$C_5Me_3$-1-$^t$Bu-3-[$(CH_2)_2$—N$^i$Pr]—, (N$^n$Pr$_2$)(Cp)-M-$C_5Me_3$-1-$^t$Bu-3-[$(CH_2)_2$—N$^i$Pr]—, (N$^i$Pr$_2$)(Cp)-M-$C_5Me_3$-1-$^t$Bu-3-[$(CH_2)_2$—N$^i$Pr]—, (N$^n$Bu$_2$)(Cp)-M-$C_5Me_3$-1-$^t$Bu-3-[$(CH_2)_2$—N$^i$Pr]—, (N$^i$Bu$_2$)(Cp)-M-$C_5Me_3$-1-$^t$Bu-3-[$(CH_2)_2$—N$^i$Pr]—, (N$^s$Bu$_2$)(Cp)-M-$C_5Me_3$-1-$^t$Bu-3-[$(CH_2)_2$—N$^i$Pr]—, (N$^t$Bu$_2$)(Cp)-M-$C_5Me_3$-1-$^t$Bu-3-[$(CH_2)_2$—N$^i$Pr]—, (OH)$_2$-M-$C_5Me_3$-1-$^t$Bu-3-[$(CH_2)_2$—N$^i$Pr]—, (OMe)$_2$-M-$C_5Me_3$-1-$^t$Bu-3-[$(CH_2)_2$—N$^i$Pr]—, (OEt)$_2$-M-$C_5Me_3$-1-$^t$Bu-3-[$(CH_2)_2$—N$^i$Pr]—, (O$^n$Pr)$_2$-M-$C_5Me_3$-1-$^t$Bu-3-[$(CH_2)_2$—N$^i$Pr]—, (O$^i$Pr)$_2$-M-$C_5Me_3$-1-$^t$Bu-3-[$(CH_2)_2$—N$^i$Pr]—, (O$^n$Bu)$_2$-M-$C_5Me_3$-1-$^t$Bu-3-[$(CH_2)_2$—N$^i$Pr]—, (O$^i$Bu$_2$-M-$C_5Me_3$-1-$^t$Bu-3-[$(CH_2)_2$—N$^i$Pr]—, (O$^t$Bu)$_2$-M-$C_5Me_3$-1-$^t$Bu-3-[$(CH_2)_2$—N$^i$Pr]—, (O$^s$Bu)$_2$-M-$C_5Me_3$-1-$^t$Bu-3-[$(CH_2)_2$—N$^i$Pr]—, (NH$_2$)$_2$-M-$C_5Me_3$-1-Me-2-[$(CH_2)_2$—N$^n$Pr]—, (O$^s$Bu)$_2$-M-$C_5Me_3$-1-Me-3-[$(CH_2)_2$—N$^n$Pr]—, (NH$_2$)$_2$-M-$C_5Me_3$-1-Et-2-[$(CH_2)_2$—N$^n$Pr]—, (NMe$_2$)$_2$-M-$C_5Me_3$-1-Et-2-[$(CH_2)_2$—N$^n$Pr]—, (NEt$_2$)$_2$-M-$C_5Me_3$-1-Et-2-[$(CH_2)_2$—N$^n$Pr]—, (N$^n$Pr$_2$)$_2$-M-$C_5Me_3$-1-Et-2-[$(CH_2)_2$—N$^n$Pr]—, (N$^i$Pr$_2$)$_2$-M-$C_5Me_3$-1-Et-2-[$(CH_2)_2$—N$^n$Pr]—, (N$^n$Bu$_2$)$_2$-M-$C_5Me_3$-1-Et-2-[$(CH_2)_2$—N$^n$Pr]—, (N$^i$Bu$_2$)$_2$-M-$C_5Me_3$-1-Et-2-[$(CH_2)_2$—N$^n$Pr]—, (N$^s$Bu$_2$)$_2$-M-$C_5Me_3$-1-Et-2-[$(CH_2)_2$—N$^n$Pr]—, (N$^t$Bu$_2$)$_2$-M-$C_5Me_3$-1-Et-2-[$(CH_2)_2$—N$^n$Pr]—, (NH$_2$)(Cp)-M-$C_5Me_3$-1-Et-2-[$(CH_2)_2$—N$^n$Pr]—, (NMe$_2$)(Cp)-M-$C_5Me_3$-1-Et-2-[$(CH_2)_2$—N$^n$Pr]—, (NEt$_2$)(Cp)-M-$C_5Me_3$-1-Et-2-[$(CH_2)_2$—N$^n$Pr]—, (N$^n$Pr$_2$)(Cp)-M-$C_5Me_3$-1-Et-2-[$(CH_2)_2$—N$^n$Pr]—, (N$^i$Pr$_2$)(Cp)-M-$C_5Me_3$-1-Et-2-[$(CH_2)_2$—N$^n$Pr]—, (N$^n$Bu$_2$)(Cp)-M-$C_5Me_3$-1-Et-2-[$(CH_2)_2$—N$^n$Pr]—, (N$^i$Bu$_2$)(Cp)-M-$C_5Me_3$-1-Et-2-[$(CH_2)_2$—N$^n$Pr]—, (N$^s$Bu$_2$)(Cp)-M-$C_5Me_3$-1-Et-2-[$(CH_2)_2$—N$^n$Pr]—, (N$^t$Bu$_2$)(Cp)-M-$C_5Me_3$-1-Et-2-[$(CH_2)_2$—N$^n$Pr]—, (OH)$_2$-M-$C_5Me_3$-1-Et-2-[$(CH_2)_2$—N$^n$Pr]—, (OMe)$_2$-M-$C_5Me_3$-1-Et-2-[$(CH_2)_2$—N$^n$Pr]—, (OEt)$_2$-M-$C_5Me_3$-1-Et-2-[$(CH_2)_2$—N$^n$Pr]—, (O$^n$Pr)$_2$-M-$C_5Me_3$-1-Et-2-[$(CH_2)_2$—N$^n$Pr]—, (O$^i$Pr)$_2$-M-$C_5Me_3$-1-Et-2-[$(CH_2)_2$—N$^n$Pr]—, (O$^n$Bu)$_2$-M-$C_5Me_3$-1-Et-2-[$(CH_2)_2$—N$^n$Pr]—, (O$^i$Bu$_2$-M-$C_5Me_3$-1-Et-2-[$(CH_2)_2$—N$^n$Pr]—, (O$^t$Bu)$_2$-M-$C_5Me_3$-1-Et-2-[$(CH_2)_2$—N$^n$Pr]—, (O$^s$Bu)$_2$-M-$C_5Me_3$-1-Et-2-[$(CH_2)_2$—N$^n$Pr]—, (NH$_2$)$_2$-M-$C_5Me_3$-1-Et-3-[$(CH_2)_2$—N$^n$Pr]—, (NMe$_2$)$_2$-M-$C_5Me_3$-1-Et-3-[$(CH_2)_2$—N$^n$Pr]—, (NEt$_2$)$_2$-M-$C_5Me_3$-1-Et-3-[$(CH_2)_2$—N$^n$Pr]—, (N$^n$Pr$_2$)$_2$-M-$C_5Me_3$-1-Et-3-[$(CH_2)_2$—N$^n$Pr]—, (N$^i$Pr$_2$)$_2$-M-$C_5Me_3$-1-Et-3-[$(CH_2)_2$—N$^n$Pr]—, (N$^n$Bu$_2$)$_2$-M-$C_5Me_3$-1-Et-3-[$(CH_2)_2$—N$^n$Pr]—, (N$^i$Bu$_2$)$_2$-M-$C_5Me_3$-1-Et-3-[$(CH_2)_2$—N$^n$Pr]—, (N$^s$Bu$_2$)$_2$-M-$C_5Me_3$-1-Et-3-[$(CH_2)_2$—N$^n$Pr]—, (N$^t$Bu$_2$)$_2$-M-$C_5Me_3$-1-Et-3-[$(CH_2)_2$—N$^n$Pr]—, (NH$_2$)(Cp)-M-$C_5Me_3$-1-Et-3-[$(CH_2)_2$—N$^n$Pr]—, (NMe$_2$)(Cp)-M-$C_5Me_3$-1-Et-3-[$(CH_2)_2$—N$^n$Pr]—, (NEt$_2$)(Cp)-M-$C_5Me_3$-1-Et-3-[$(CH_2)_2$—N$^n$Pr]—, (N$^n$Pr$_2$)(Cp)-M-$C_5Me_3$-1-Et-3-[$(CH_2)_2$—N$^n$Pr]—, (N$^i$Pr$_2$)(Cp)-M-$C_5Me_3$-1-Et-3-[$(CH_2)_2$—N$^n$Pr]—, (N$^n$Bu$_2$)(Cp)-M-$C_5Me_3$-1-Et-3-[$(CH_2)_2$—N$^n$Pr]—, (N$^i$Bu$_2$)(Cp)-M-$C_5Me_3$-1-Et-3-[$(CH_2)_2$—N$^n$Pr]—, (N$^s$Bu$_2$)(Cp)-M-$C_5Me_3$-1-Et-3-[$(CH_2)_2$—N$^n$Pr]—, (N$^t$Bu$_2$)(Cp)-M-$C_5Me_3$-1-Et-3-[$(CH_2)_2$—N$^n$Pr]—, (OH)$_2$-M-$C_5Me_3$-1-Et-3-[$(CH_2)_2$—N$^n$Pr]—, (OMe)$_2$-M-$C_5Me_3$-1-Et-3-[$(CH_2)_2$—N$^n$Pr]—, (OEt)$_2$-M-$C_5Me_3$-1-Et-3-[$(CH_2)_2$—N$^n$Pr]—, (O$^n$Pr)$_2$-M-$C_5Me_3$-1-Et-3-[$(CH_2)_2$—N$^n$Pr]—, (O$^i$Pr)$_2$-M-$C_5Me_3$-1-Et-3-[$(CH_2)_2$—N$^n$Pr]—, (O$^n$Bu)$_2$-M-$C_5Me_3$-1-Et-3-[$(CH_2)_2$—N$^n$Pr]—, (O$^i$Bu$_2$-M-$C_5Me_3$-1-Et-3-[$(CH_2)_2$—N$^n$Pr]—, (O$^t$Bu)$_2$-M-$C_5Me_3$-1-Et-3-[$(CH_2)_2$—N$^n$Pr]—, (O$^s$Bu)$_2$-M-$C_5Me_3$-1-Et-3-[$(CH_2)_2$—N$^n$Pr]—, (NH$_2$)$_2$-M-$C_5Me_3$-1-$^i$Pr-2-[$(CH_2)_2$—N$^n$Pr]—, (NMe$_2$)$_2$-M-$C_5Me_3$-1-$^i$Pr-2-[$(CH_2)_2$—N$^n$Pr]—, (NEt$_2$)$_2$-M-$C_5Me_3$-1-$^i$Pr-2-[$(CH_2)_2$—N$^n$Pr]—, (N$^n$Pr$_2$)$_2$-M-$C_5Me_3$-1-$^i$Pr-2-[$(CH_2)_2$—N$^n$Pr]—, (N$^i$Pr$_2$)$_2$-M-$C_5Me_3$-1-$^i$Pr-2-[$(CH_2)_2$—N$^n$Pr]—, (N$^n$Bu$_2$)$_2$-M-$C_5Me_3$-1-$^i$Pr-2-[$(CH_2)_2$—N$^n$Pr]—, (N$^i$Bu$_2$)$_2$-M-$C_5Me_3$-1-$^i$Pr-2-[$(CH_2)_2$—N$^n$Pr]—, (N$^s$Bu$_2$)$_2$-M-$C_5Me_3$-1-$^i$Pr-2-[$(CH_2)_2$—N$^n$Pr]—, (N$^t$Bu$_2$)$_2$-M-$C_5Me_3$-1-$^i$Pr-2-[$(CH_2)_2$—N$^n$Pr]—, (NH$_2$)(Cp)-M-$C_5Me_3$-1-$^i$Pr-2-[$(CH_2)_2$—N$^n$Pr]—, (NMe$_2$)(Cp)-M-$C_5Me_3$-1-$^i$Pr-2-[$(CH_2)_2$—N$^n$Pr]—, (NEt$_2$)(Cp)-M-$C_5Me_3$-1-$^i$Pr-2-[$(CH_2)_2$—N$^n$Pr]—, (N$^n$Pr$_2$)(Cp)-M-$C_5Me_3$-1-$^i$Pr-2-[$(CH_2)_2$—N$^n$Pr]—, (N$^i$Pr$_2$)(Cp)-M-$C_5Me_3$-1-$^i$Pr-2-[$(CH_2)_2$—N$^n$Pr]—, (N$^n$Bu$_2$)(Cp)-M-$C_5Me_3$-1-$^i$Pr-2-[$(CH_2)_2$—N$^n$Pr]—, (N$^i$Bu$_2$)(Cp)-M-$C_5Me_3$-1-$^i$Pr-2-[$(CH_2)_2$—N$^n$Pr]—, (N$^s$Bu$_2$)(Cp)-M-$C_5Me_3$-1-$^i$Pr-2-[$(CH_2)_2$—N$^n$Pr]—, (N$^t$Bu$_2$)(Cp)-M-$C_5Me_3$-1-$^i$Pr-2-[$(CH_2)_2$—N$^n$Pr]—, (OH)$_2$-M-$C_5Me_3$-1-$^i$Pr-2-[$(CH_2)_2$—N$^n$Pr]—, (OMe)$_2$-M-$C_5Me_3$-1-$^i$Pr-2-[$(CH_2)_2$—N$^n$Pr]—, (OEt)$_2$-M-$C_5Me_3$-1-$^i$Pr-2-[$(CH_2)_2$—N$^n$Pr]—, (O$^n$Pr)$_2$-M-$C_5Me_3$-1-$^i$Pr-2-[$(CH_2)_2$—N$^n$Pr]—, (O$^i$Pr)$_2$-M-$C_5Me_3$-1-$^i$Pr-2-[$(CH_2)_2$—N$^n$Pr]—, (O$^n$Bu)$_2$-M-$C_5Me_3$-1-$^i$Pr-2-[$(CH_2)_2$—N$^n$Pr]—, (O$^i$Bu$_2$-M-$C_5Me_3$-1-$^i$Pr-2-[$(CH_2)_2$—N$^n$Pr]—, (O$^t$Bu)$_2$-M-$C_5Me_3$-1-$^i$Pr-2-[$(CH_2)_2$—N$^n$Pr]—, (O$^s$Bu)$_2$-M-$C_5Me_3$-1-$^i$Pr-2-[$(CH_2)_2$—N$^n$Pr]—, (NH$_2$)$_2$-M-$C_5Me_3$-1-$^i$Pr-3-[$(CH_2)_2$—N$^n$Pr]—, (NMe$_2$)$_2$-M-$C_5Me_3$-1-$^i$Pr-3-[$(CH_2)_2$—N$^n$Pr]—, (NEt$_2$)$_2$-M-$C_5Me_3$-1-$^i$Pr-3-

[(CH$_2$)$_2$—N$^n$Pr]—, (N$^n$Pr$_2$)$_2$-M-C$_5$Me$_3$-1-$^i$Pr-3-[(CH$_2$)$_2$—N$^n$Pr]—, (N$^i$Pr$_2$)$_2$-M-C$_5$Me$_3$-1-$^i$Pr-3-[(CH$_2$)$_2$—N$^n$Pr]—, (N$^n$Bu$_2$)$_2$-M-C$_5$Me$_3$-1-$^i$Pr-3-[(CH$_2$)$_2$—N$^n$Pr]—, (N$^i$Bu$_2$)$_2$-M-C$_5$Me$_3$-1-$^i$Pr-3-[(CH$_2$)$_2$—N$^n$Pr]—, (N$^s$Bu$_2$)$_2$-M-C$_5$Me$_3$-1-$^i$Pr-3-[(CH$_2$)$_2$—N$^n$Pr]—, (N$^t$Bu$_2$)$_2$-M-C$_5$Me$_3$-1-$^i$Pr-3-[(CH$_2$)$_2$—N$^n$Pr]—, (NH$_2$)(Cp)-M-C$_5$Me$_3$-1-$^i$Pr-3-[(CH$_2$)$_2$—N$^n$Pr]—, (NMe$_2$)(Cp)-M-C$_5$Me$_3$-1-$^i$Pr-3-[(CH$_2$)$_2$—N$^n$Pr]—, (NEt$_2$)(Cp)-M-C$_5$Me$_3$-1-$^i$Pr-3-[(CH$_2$)$_2$—N$^n$Pr]—, (N$^n$Pr$_2$)(Cp)-M-C$_5$Me$_3$-1-$^i$Pr-3-[(CH$_2$)$_2$—N$^n$Pr]—, (N$^i$Pr$_2$)(Cp)-M-C$_5$Me$_3$-1-$^i$Pr-3-[(CH$_2$)$_2$—N$^n$Pr]—, (N$^n$Bu$_2$)(Cp)-M-C$_5$Me$_3$-1-$^i$Pr-3-[(CH$_2$)$_2$—N$^n$Pr]—, (N$^i$Bu$_2$)(Cp)-M-C$_5$Me$_3$-1-$^i$Pr-3-[(CH$_2$)$_2$—N$^n$Pr]—, (N$^s$Bu$_2$)(Cp)-M-C$_5$Me$_3$-1-$^i$Pr-3-[(CH$_2$)$_2$—N$^n$Pr]—, (N$^t$Bu$_2$)(Cp)-M-C$_5$Me$_3$-1-$^i$Pr-3-[(CH$_2$)$_2$—N$^n$Pr]—, (OH)$_2$-M-C$_5$Me$_3$-1-$^i$Pr-3-[(CH$_2$)$_2$—N$^n$Pr]—, (OMe)$_2$-M-C$_5$Me$_3$-1-$^i$Pr-3-[(CH$_2$)$_2$—N$^n$Pr]—, (OEt)$_2$-M-C$_5$Me$_3$-1-$^i$Pr-3-[(CH$_2$)$_2$—N$^n$Pr]—, (O$^n$Pr)$_2$-M-C$_5$Me$_3$-1-$^i$Pr-3-[(CH$_2$)$_2$—N$^n$Pr]—, (O$^i$Pr)$_2$-M-C$_5$Me$_3$-1-$^i$Pr-3-[(CH$_2$)$_2$—N$^n$Pr]—, (O$^n$Bu)$_2$-M-C$_5$Me$_3$-1-$^i$Pr-3-[(CH$_2$)$_2$—N$^n$Pr]—, (O$^i$Bu$_2$-M-C$_5$Me$_3$-1-$^i$Pr-3-[(CH$_2$)$_2$—N$^n$Pr]—, (O$^t$Bu)$_2$-M-C$_5$Me$_3$-1-$^i$Pr-3-[(CH$_2$)$_2$—N$^n$Pr]—, (O$^s$Bu)$_2$-M-C$_5$Me$_3$-1-$^i$Pr-3-[(CH$_2$)$_2$—N$^n$Pr]—, (NH$_2$)$_2$-M-C$_5$Me$_3$-1-$^t$Bu-2-[(CH$_2$)$_2$—N$^n$Pr]—, (NMe$_2$)$_2$-M-C$_5$Me$_3$-1-$^t$Bu-2-[(CH$_2$)$_2$—N$^n$Pr]—, (NEt$_2$)$_2$-M-C$_5$Me$_3$-1-$^t$Bu-2-[(CH$_2$)$_2$—N$^n$Pr]—, (N$^n$Pr$_2$)$_2$-M-C$_5$Me$_3$-1-$^t$Bu-2-[(CH$_2$)$_2$—N$^n$Pr]—, (N$^i$Pr$_2$)$_2$-M-C$_5$Me$_3$-1-$^t$Bu-2-[(CH$_2$)$_2$—N$^n$Pr]—, (N$^n$Bu$_2$)$_2$-M-C$_5$Me$_3$-1-$^t$Bu-2-[(CH$_2$)$_2$—N$^n$Pr]—, (N$^i$Bu$_2$)$_2$-M-C$_5$Me$_3$-1-$^t$Bu-2-[(CH$_2$)$_2$—N$^n$Pr]—, (N$^s$Bu$_2$)$_2$-M-C$_5$Me$_3$-1-$^t$Bu-2-[(CH$_2$)$_2$—N$^n$Pr]—, (N$^t$Bu$_2$)$_2$-M-C$_5$Me$_3$-1-$^t$Bu-2-[(CH$_2$)$_2$—N$^n$Pr]—, (NH$_2$)(Cp)-M-C$_5$Me$_3$-1-$^t$Bu-2-[(CH$_2$)$_2$—N$^n$Pr]—, (NMe$_2$)(Cp)-M-C$_5$Me$_3$-1-$^t$Bu-2-[(CH$_2$)$_2$—N$^n$Pr]—, (NEt$_2$)(Cp)-M-C$_5$Me$_3$-1-$^t$Bu-2-[(CH$_2$)$_2$—N$^n$Pr]—, (N$^n$Pr$_2$)(Cp)-M-C$_5$Me$_3$-1-$^t$Bu-2-[(CH$_2$)$_2$—N$^n$Pr]—, (N$^i$Pr$_2$)(Cp)-M-C$_5$Me$_3$-1-$^t$Bu-2-[(CH$_2$)$_2$—N$^n$Pr]—, (N$^n$Bu$_2$)(Cp)-M-C$_5$Me$_3$-1-$^t$Bu-2-[(CH$_2$)$_2$—N$^n$Pr]—, (N$^i$Bu$_2$)(Cp)-M-C$_5$Me$_3$-1-$^t$Bu-2-[(CH$_2$)$_2$—N$^n$Pr]—, (N$^s$Bu$_2$)(Cp)-M-C$_5$Me$_3$-1-$^t$Bu-2-[(CH$_2$)$_2$—N$^n$Pr]—, (N$^t$Bu$_2$)(Cp)-M-C$_5$Me$_3$-1-$^t$Bu-2-[(CH$_2$)$_2$—N$^n$Pr]—, (OH)$_2$-M-C$_5$Me$_3$-1-$^t$Bu-2-[(CH$_2$)$_2$—N$^n$Pr]—, (OMe)$_2$-M-C$_5$Me$_3$-1-$^t$Bu-2-[(CH$_2$)$_2$—N$^n$Pr]—, (OEt)$_2$-M-C$_5$Me$_3$-1-$^t$Bu-2-[(CH$_2$)$_2$—N$^n$Pr]—, (O$^n$Pr)$_2$-M-C$_5$Me$_3$-1-$^t$Bu-2-[(CH$_2$)$_2$—N$^n$Pr]—, (O$^i$Pr)$_2$-M-C$_5$Me$_3$-1-$^t$Bu-2-[(CH$_2$)$_2$—N$^n$Pr]—, (O$^n$Bu)$_2$-M-C$_5$Me$_3$-1-$^t$Bu-2-[(CH$_2$)$_2$—N$^n$Pr]—, (O$^i$Bu$_2$-M-C$_5$Me$_3$-1-$^t$Bu-2-[(CH$_2$)$_2$—N$^n$Pr]—, (O$^t$Bu)$_2$-M-C$_5$Me$_3$-1-$^t$Bu-2-[(CH$_2$)$_2$—N$^n$Pr]—, (O$^s$Bu)$_2$-M-C$_5$Me$_3$-1-$^t$Bu-2-[(CH$_2$)$_2$—N$^n$Pr]—, (NH$_2$)$_2$-M-C$_5$Me$_3$-1-$^t$Bu-3-[(CH$_2$)$_2$—N$^n$Pr]—, (NMe$_2$)$_2$-M-C$_5$Me$_3$-1-$^t$Bu-3-[(CH$_2$)$_2$—N$^n$Pr]—, (NEt$_2$)$_2$-M-C$_5$Me$_3$-1-$^t$Bu-3-[(CH$_2$)$_2$—N$^n$Pr]—, (N$^n$Pr$_2$)$_2$-M-C$_5$Me$_3$-1-$^t$Bu-3-[(CH$_2$)$_2$—N$^n$Pr]—, (N$^i$Pr$_2$)$_2$-M-C$_5$Me$_3$-1-$^t$Bu-3-[(CH$_2$)$_2$—N$^n$Pr]—, (N$^n$Bu$_2$)$_2$-M-C$_5$Me$_3$-1-$^t$Bu-3-[(CH$_2$)$_2$—N$^n$Pr]—, (N$^i$Bu$_2$)$_2$-M-C$_5$Me$_3$-1-$^t$Bu-3-[(CH$_2$)$_2$—N$^n$Pr]—, (N$^s$Bu$_2$)$_2$-M-C$_5$Me$_3$-1-$^t$Bu-3-[(CH$_2$)$_2$—N$^n$Pr]—, (N$^t$Bu$_2$)$_2$-M-C$_5$Me$_3$-1-$^t$Bu-3-[(CH$_2$)$_2$—N$^n$Pr]—, (NH$_2$)(Cp)-M-C$_5$Me$_3$-1-$^t$Bu-3-[(CH$_2$)$_2$—N$^n$Pr]—, (NMe$_2$)(Cp)-M-C$_5$Me$_3$-1-$^t$Bu-3-[(CH$_2$)$_2$—N$^n$Pr]—, (NEt$_2$)(Cp)-M-C$_5$Me$_3$-1-$^t$Bu-3-[(CH$_2$)$_2$—N$^n$Pr]—, (N$^n$Pr$_2$)(Cp)-M-C$_5$Me$_3$-1-$^t$Bu-3-[(CH$_2$)$_2$—N$^n$Pr]—, (N$^i$Pr$_2$)(Cp)-M-C$_5$Me$_3$-1-$^t$Bu-3-[(CH$_2$)$_2$—N$^n$Pr]—, (N$^n$Bu$_2$)(Cp)-M-C$_5$Me$_3$-1-$^t$Bu-3-[(CH$_2$)$_2$—N$^n$Pr]—, (N$^i$Bu$_2$)(Cp)-M-C$_5$Me$_3$-1-$^t$Bu-3-[(CH$_2$)$_2$—N$^n$Pr]—, (N$^s$Bu$_2$)(Cp)-M-C$_5$Me$_3$-1-$^t$Bu-3-[(CH$_2$)$_2$—N$^n$Pr]—, (N$^t$Bu$_2$)(Cp)-M-C$_5$Me$_3$-1-$^t$Bu-3-[(CH$_2$)$_2$—N$^n$Pr]—, (OH)$_2$-M-C$_5$Me$_3$-1-$^t$Bu-3-[(CH$_2$)$_2$—N$^n$Pr]—, (OMe)$_2$-M-C$_5$Me$_3$-1-$^t$Bu-3-[(CH$_2$)$_2$—N$^n$Pr]—, (OEt)$_2$-M-C$_5$Me$_3$-1-$^t$Bu-3-[(CH$_2$)$_2$—N$^n$Pr]—, (O$^n$Pr)$_2$-M-C$_5$Me$_3$-1-$^t$Bu-3-[(CH$_2$)$_2$—N$^n$Pr]—, (O$^i$Pr)$_2$-M-C$_5$Me$_3$-1-$^t$Bu-3-[(CH$_2$)$_2$—N$^n$Pr]—, (O$^n$Bu)$_2$-M-C$_5$Me$_3$-1-$^t$Bu-3-[(CH$_2$)$_2$—N$^n$Pr]—, (O$^i$Bu$_2$-M-C$_5$Me$_3$-1-$^t$Bu-3-[(CH$_2$)$_2$—N$^n$Pr]—, (O$^t$Bu)$_2$-M-C$_5$Me$_3$-1-$^t$Bu-3-[(CH$_2$)$_2$—N$^n$Pr]—, (O$^s$Bu)$_2$-M-C$_5$Me$_3$-1-$^t$Bu-3-[(CH$_2$)$_2$—N$^n$Pr]—, (NH$_2$)$_2$-M-C$_5$Me$_3$-1-Et-2-[(CH$_2$)$_2$—N$^n$Bu]-, (NMe$_2$)$_2$-M-C$_5$Me$_3$-1-Et-2-[(CH$_2$)$_2$—N$^n$Bu]-, (NEt$_2$)$_2$-M-C$_5$Me$_3$-1-Et-2-[(CH$_2$)$_2$—N$^n$Bu]-, (N$^n$Pr$_2$)$_2$-M-C$_5$Me$_3$-1-Et-2-[(CH$_2$)$_2$—N$^n$Bu]-, (N$^i$Pr$_2$)$_2$-M-C$_5$Me$_3$-1-Et-2-[(CH$_2$)$_2$—N$^n$Bu]-, (N$^n$Bu$_2$)$_2$-M-C$_5$Me$_3$-1-Et-2-[(CH$_2$)$_2$—N$^n$Bu]-, (N$^i$Bu$_2$)$_2$-M-C$_5$Me$_3$-1-Et-2-[(CH$_2$)$_2$—N$^n$Bu]-, (N$^s$Bu$_2$)$_2$-M-C$_5$Me$_3$-1-Et-2-[(CH$_2$)$_2$—N$^n$Bu]-, (N$^t$Bu$_2$)$_2$-M-C$_5$Me$_3$-1-Et-2-[(CH$_2$)$_2$—N$^n$Bu]-, (NH$_2$)(Cp)-M-C$_5$Me$_3$-1-Et-2-[(CH$_2$)$_2$—N$^n$Bu]-, (NMe$_2$)(Cp)-M-C$_5$Me$_3$-1-Et-2-[(CH$_2$)$_2$—N$^n$Bu]-, (NEt$_2$)(Cp)-M-C$_5$Me$_3$-1-Et-2-[(CH$_2$)$_2$—N$^n$Bu]-, (N$^n$Pr$_2$)(Cp)-M-C$_5$Me$_3$-1-Et-2-[(CH$_2$)$_2$—N$^n$Bu]-, (N$^i$Pr$_2$)(Cp)-M-C$_5$Me$_3$-1-Et-2-[(CH$_2$)$_2$—N$^n$Bu]-, (N$^n$Bu$_2$)(Cp)-M-C$_5$Me$_3$-1-Et-2-[(CH$_2$)$_2$—N$^n$Bu]-, (N$^i$Bu$_2$)(Cp)-M-C$_5$Me$_3$-1-Et-2-[(CH$_2$)$_2$—N$^n$Bu]-, (N$^s$Bu$_2$)(Cp)-M-C$_5$Me$_3$-1-Et-2-[(CH$_2$)$_2$—N$^n$Bu]-, (N$^t$Bu$_2$)(Cp)-M-C$_5$Me$_3$-1-Et-2-[(CH$_2$)$_2$—N$^n$Bu]-, (OH)$_2$-M-C$_5$Me$_3$-1-Et-2-[(CH$_2$)$_2$—N$^n$Bu]-, (OMe)$_2$-M-C$_5$Me$_3$-1-Et-2-[(CH$_2$)$_2$—N$^n$Bu]-, (OEt)$_2$-M-C$_5$Me$_3$-1-Et-2-[(CH$_2$)$_2$—N$^n$Bu]-, (O$^n$Pr)$_2$-M-C$_5$Me$_3$-1-Et-2-[(CH$_2$)$_2$—N$^n$Bu]-, (O$^i$Pr)$_2$-M-C$_5$Me$_3$-1-Et-2-[(CH$_2$)$_2$—N$^n$Bu]-, (O$^n$Bu)$_2$-M-C$_5$Me$_3$-1-Et-2-[(CH$_2$)$_2$—N$^n$Bu]-, (O$^i$Bu$_2$-M-C$_5$Me$_3$-1-Et-2-[(CH$_2$)$_2$—N$^n$Bu]-, (O$^t$Bu)$_2$-M-C$_5$Me$_3$-1-Et-2-[(CH$_2$)$_2$—N$^n$Bu]-, (O$^s$Bu)$_2$-M-C$_5$Me$_3$-1-Et-2-[(CH$_2$)$_2$—N$^n$Bu]-, (NH$_2$)$_2$-M-C$_5$Me$_3$-1-Et-3-[(CH$_2$)$_2$—N$^n$Bu]-, (NMe$_2$)$_2$-M-C$_5$Me$_3$-1-Et-3-[(CH$_2$)$_2$—N$^n$Bu]-, (NEt$_2$)$_2$-M-C$_5$Me$_3$-1-Et-3-[(CH$_2$)$_2$—N$^n$Bu]-, (N$^n$Pr$_2$)$_2$-M-C$_5$Me$_3$-1-Et-3-[(CH$_2$)$_2$—N$^n$Bu]-, (N$^i$Pr$_2$)$_2$-M-C$_5$Me$_3$-1-Et-3-[(CH$_2$)$_2$—N$^n$Bu]-, (N$^n$Bu$_2$)$_2$-M-C$_5$Me$_3$-1-Et-3-[(CH$_2$)$_2$—N$^n$Bu]-, (N$^i$Bu$_2$)$_2$-M-C$_5$Me$_3$-1-Et-3-[(CH$_2$)$_2$—N$^n$Bu]-, (N$^s$Bu$_2$)$_2$-M-C$_5$Me$_3$-1-Et-3-[(CH$_2$)$_2$—N$^n$Bu]-, (N$^t$Bu$_2$)$_2$-M-C$_5$Me$_3$-1-Et-3-[(CH$_2$)$_2$—N$^n$Bu]-, (NH$_2$)(Cp)-M-C$_5$Me$_3$-1-Et-3-[(CH$_2$)$_2$—N$^n$Bu]-, (NMe$_2$)(Cp)-M-C$_5$Me$_3$-1-Et-3-[(CH$_2$)$_2$—N$^n$Bu]-, (NEt$_2$)(Cp)-M-C$_5$Me$_3$-1-Et-3-[(CH$_2$)$_2$—N$^n$Bu]-, (N$^n$Pr$_2$)(Cp)-M-C$_5$Me$_3$-1-Et-3-[(CH$_2$)$_2$—N$^n$Bu]-, (N$^i$Pr$_2$)(Cp)-M-C$_5$Me$_3$-1-Et-3-[(CH$_2$)$_2$—N$^n$Bu]-, (N$^n$Bu$_2$)(Cp)-M-C$_5$Me$_3$-1-Et-3-[(CH$_2$)$_2$—N$^n$Bu]-, (N$^i$Bu$_2$)(Cp)-M-C$_5$Me$_3$-1-Et-3-[(CH$_2$)$_2$—N$^n$Bu]-, (N$^s$Bu$_2$)(Cp)-M-C$_5$Me$_3$-1-Et-3-[(CH$_2$)$_2$—N$^n$Bu]-, (N$^t$Bu$_2$)(Cp)-M-C$_5$Me$_3$-1-Et-3-[(CH$_2$)$_2$—N$^n$Bu]-, (OH)$_2$-M-C$_5$Me$_3$-1-Et-3-[(CH$_2$)$_2$—N$^n$Bu]-, (OMe)$_2$-M-C$_5$Me$_3$-1-Et-3-[(CH$_2$)$_2$—N$^n$Bu]-, (OEt)$_2$-M-C$_5$Me$_3$-1-Et-3-[(CH$_2$)$_2$—N$^n$Bu]-, (O$^n$Pr)$_2$-M-C$_5$Me$_3$-1-Et-3-[(CH$_2$)$_2$—N$^n$Bu]-, (O$^i$Pr)$_2$-M-C$_5$Me$_3$-1-Et-3-[(CH$_2$)$_2$—N$^n$Bu]-, (O$^n$Bu)$_2$-M-C$_5$Me$_3$-1-Et-3-[(CH$_2$)$_2$—N$^n$Bu]-, (O$^i$Bu$_2$-M-C$_5$Me$_3$-1-Et-3-[(CH$_2$)$_2$—N$^n$Bu]-, (O$^t$Bu)$_2$-M-C$_5$Me$_3$-1-Et-3-[(CH$_2$)$_2$—N$^n$Bu]-, (O$^s$Bu)$_2$-M-C$_5$Me$_3$-1-Et-3-[(CH$_2$)$_2$—N$^n$Bu]-, (NH$_2$)$_2$-M-C$_5$Me$_3$-1-$^i$Pr-2-[(CH$_2$)$_2$—N$^n$Bu]-, (NMe$_2$)$_2$-M-C$_5$Me$_3$-1-$^i$Pr-2-[(CH$_2$)$_2$—N$^n$Bu]-, (NEt$_2$)$_2$-M-C$_5$Me$_3$-1-$^i$Pr-2-[(CH$_2$)$_2$—N$^n$Bu]-, (N$^n$Pr$_2$)$_2$-M-C$_5$Me$_3$-1-$^i$Pr-2-[(CH$_2$)$_2$—N$^n$Bu]-, (N$^i$Pr$_2$)$_2$-M-C$_5$Me$_3$-1-$^i$Pr-2-[(CH$_2$)$_2$—N$^n$Bu]-, (N$^n$Bu$_2$)$_2$-M-C$_5$Me$_3$-1-$^i$Pr-2-[(CH$_2$)$_2$—N$^n$Bu]-, (N$^i$Bu$_2$)$_2$-M-C$_5$Me$_3$-1-$^i$Pr-2-[(CH$_2$)$_2$—N$^n$Bu]-, (N$^s$Bu$_2$)$_2$-M-C$_5$Me$_3$-1-$^i$Pr-2-[(CH$_2$)$_2$—N$^n$Bu]-, (N$^t$Bu$_2$)$_2$-M-C$_5$Me$_3$-1-$^i$Pr-2-[(CH$_2$)$_2$—N$^n$Bu]-, (NH$_2$)(Cp)-M-C$_5$Me$_3$-1-$^i$Pr-2-[(CH$_2$)$_2$—N$^n$Bu]-, (NMe$_2$)(Cp)-M-C$_5$Me$_3$-1-$^i$Pr-2-[(CH$_2$)$_2$—N$^n$Bu]-, (NEt$_2$)(Cp)-M-C$_5$Me$_3$-1-$^i$Pr-2-[(CH$_2$)$_2$—N$^n$Bu]-, (N$^n$Pr$_2$)(Cp)-M-C$_5$Me$_3$-1-$^i$Pr-2-[(CH$_2$)$_2$—N$^n$Bu]-, (N$^i$Pr$_2$)(Cp)-M-C$_5$Me$_3$-1-$^i$Pr-2-[(CH$_2$)$_2$—N$^n$Bu]-, (N$^n$Bu$_2$)(Cp)-M-C$_5$Me$_3$-1-$^i$Pr-2-[(CH$_2$)$_2$—N$^n$Bu]-, (N$^i$Bu$_2$)(Cp)-M-C$_5$Me$_3$-1-$^i$Pr-2-[(CH$_2$)$_2$—N$^n$Bu]-, (N$^s$Bu$_2$)(Cp)-M-C$_5$Me$_3$-1-$^i$Pr-2-[(CH$_2$)$_2$—N$^n$Bu]-, (N$^t$Bu$_2$)(Cp)-M-C$_5$Me$_3$-1-$^i$Pr-2-[(CH$_2$)$_2$—N$^n$Bu]-, (OH)$_2$-M-C$_5$Me$_3$-1-$^i$Pr-2-[(CH$_2$)$_2$—N$^n$Bu]-, (OMe)$_2$-M-C$_5$Me$_3$-1-$^i$Pr-2-[(CH$_2$)$_2$—N$^n$Bu]-, (OEt)$_2$-M-C$_5$Me$_3$-1-$^i$Pr-2-[(CH$_2$)$_2$—N$^n$Bu]-, (O$^n$Pr)$_2$-M-C$_5$Me$_3$-1-$^i$Pr-2-[(CH$_2$)$_2$—N$^n$Bu]-, (O$^i$Pr)$_2$-M-C$_5$Me$_3$-1-$^i$Pr-2-[(CH$_2$)$_2$—N$^n$Bu]-, (O$^n$Bu)$_2$-M-C$_5$Me$_3$-1-$^i$Pr-2-[(CH$_2$)$_2$—

$N^nBu]$-, $(O^iBu_2$-M-$C_5Me_3$-1-$^i$Pr-2-$[(CH_2)_2$—$N^nBu]$-, $(O^tBu)_2$-M-$C_5Me_3$-1-$^i$Pr-2-$[(CH_2)_2$—$N^nBu]$-, $(O^sBu)_2$-M-$C_5Me_3$-1-$^i$Pr-2-$[(CH_2)_2$—$N^nBu]$-, $(NH_2)_2$-M-$C_5Me_3$-1-$^i$Pr-3-$[(CH_2)_2$—$N^nBu]$-, $(NMe_2)_2$-M-$C_5Me_3$-1-$^i$Pr-3-$[(CH_2)_2$—$N^nBu]$-, $(NEt_2)_2$-M-$C_5Me_3$-1-$^i$Pr-3-$[(CH_2)_2$—$N^nBu]$-, $(N^nPr_2)_2$-M-$C_5Me_3$-1-$^i$Pr-3-$[(CH_2)_2$—$N^nBu]$-, $(N^iPr_2)_2$-M-$C_5Me_3$-1-$^i$Pr-3-$[(CH_2)_2$—$N^nBu]$-, $(N^nBu_2)_2$-M-$C_5Me_3$-1-$^i$Pr-3-$[(CH_2)_2$—$N^nBu]$-, $(N^iBu_2)_2$-M-$C_5Me_3$-1-$^i$Pr-3-$[(CH_2)_2$—$N^nBu]$-, $(N^sBu_2)_2$-M-$C_5Me_3$-1-$^i$Pr-3-$[(CH_2)_2$—$N^nBu]$-, $(N^tBu_2)_2$-M-$C_5Me_3$-1-$^i$Pr-3-$[(CH_2)_2$—$N^nBu]$-, $(NH_2)(Cp)$-M-$C_5Me_3$-1-$^i$Pr-3-$[(CH_2)_2$—$N^nBu]$-, $(NMe_2)(Cp)$-M-$C_5Me_3$-1-$^i$Pr-3-$[(CH_2)_2$—$N^nBu]$-, $(NEt_2)(Cp)$-M-$C_5Me_3$-1-$^i$Pr-3-$[(CH_2)_2$—$N^nBu]$-, $(N^nPr_2)(Cp)$-M-$C_5Me_3$-1-$^i$Pr-3-$[(CH_2)_2$—$N^nBu]$-, $(N^iPr_2)(Cp)$-M-$C_5Me_3$-1-$^i$Pr-3-$[(CH_2)_2$—$N^nBu]$-, $(N^nBu_2)(Cp)$-M-$C_5Me_3$-1-$^i$Pr-3-$[(CH_2)_2$—$N^nBu]$-, $(N^iBu_2)(Cp)$-M-$C_5Me_3$-1-$^i$Pr-3-$[(CH_2)_2$—$N^nBu]$-, $(N^sBu_2)(Cp)$-M-$C_5Me_3$-1-$^i$Pr-3-$[(CH_2)_2$—$N^nBu]$-, $(N^tBu_2)(Cp)$-M-$C_5Me_3$-1-$^i$Pr-3-$[(CH_2)_2$—$N^nBu]$-, $(OH)_2$-M-$C_5Me_3$-1-$^i$Pr-3-$[(CH_2)_2$—$N^nBu]$-, $(OMe)_2$-M-$C_5Me_3$-1-$^i$Pr-3-$[(CH_2)_2$—$N^nBu]$-, $(OEt)_2$-M-$C_5Me_3$-1-$^i$Pr-3-$[(CH_2)_2$—$N^nBu]$-, $(O^nPr)_2$-M-$C_5Me_3$-1-$^i$Pr-3-$[(CH_2)_2$—$N^nBu]$-, $(O^iPr)_2$-M-$C_5Me_3$-1-$^i$Pr-3-$[(CH_2)_2$—$N^nBu]$-, $(O^nBu)_2$-M-$C_5Me_3$-1-$^i$Pr-3-$[(CH_2)_2$—$N^nBu]$-, $(O^iBu_2$-M-$C_5Me_3$-1-$^i$Pr-3-$[(CH_2)_2$—$N^nBu]$-, $(O^tBu)_2$-M-$C_5Me_3$-1-$^i$Pr-3-$[(CH_2)_2$—$N^nBu]$-, $(O^sBu)_2$-M-$C_5Me_3$-1-$^i$Pr-3-$[(CH_2)_2$—$N^nBu]$-, $(NH_2)_2$-M-$C_5Me_3$-1-$^t$Bu-2-$[(CH_2)_2$—$N^nBu]$-, $(NMe_2)_2$-M-$C_5Me_3$-1-$^t$Bu-2-$[(CH_2)_2$—$N^nBu]$-, $(NEt_2)_2$-M-$C_5Me_3$-1-$^t$Bu-2-$[(CH_2)_2$—$N^nBu]$-, $(N^nPr_2)_2$-M-$C_5Me_3$-1-$^t$Bu-2-$[(CH_2)_2$—$N^nBu]$-, $(N^iPr_2)_2$-M-$C_5Me_3$-1-$^t$Bu-2-$[(CH_2)_2$—$N^nBu]$-, $(N^nBu_2)_2$-M-$C_5Me_3$-1-$^t$Bu-2-$[(CH_2)_2$—$N^nBu]$-, $(N^iBu_2)_2$-M-$C_5Me_3$-1-$^t$Bu-2-$[(CH_2)_2$—$N^nBu]$-, $(N^sBu_2)_2$-M-$C_5Me_3$-1-$^t$Bu-2-$[(CH_2)_2$—$N^nBu]$-, $(N^tBu_2)_2$-M-$C_5Me_3$-1-$^t$Bu-2-$[(CH_2)_2$—$N^nBu]$-, $(NH_2)(Cp)$-M-$C_5Me_3$-1-$^t$Bu-2-$[(CH_2)_2$—$N^nBu]$-, $(NMe_2)(Cp)$-M-$C_5Me_3$-1-$^t$Bu-2-$[(CH_2)_2$—$N^nBu]$-, $(NEt_2)(Cp)$-M-$C_5Me_3$-1-$^t$Bu-2-$[(CH_2)_2$—$N^nBu]$-, $(N^nPr_2)(Cp)$-M-$C_5Me_3$-1-$^t$Bu-2-$[(CH_2)_2$—$N^nBu]$-, $(N^iPr_2)(Cp)$-M-$C_5Me_3$-1-$^t$Bu-2-$[(CH_2)_2$—$N^nBu]$-, $(N^nBu_2)(Cp)$-M-$C_5Me_3$-1-$^t$Bu-2-$[(CH_2)_2$—$N^nBu]$-, $(N^iBu_2)(Cp)$-M-$C_5Me_3$-1-$^t$Bu-2-$[(CH_2)_2$—$N^nBu]$-, $(N^sBu_2)(Cp)$-M-$C_5Me_3$-1-$^t$Bu-2-$[(CH_2)_2$—$N^nBu]$-, $(N^tBu_2)(Cp)$-M-$C_5Me_3$-1-$^t$Bu-2-$[(CH_2)_2$—$N^nBu]$-, $(OH)_2$-M-$C_5Me_3$-1-$^t$Bu-2-$[(CH_2)_2$—$N^nBu]$-, $(OMe)_2$-M-$C_5Me_3$-1-$^t$Bu-2-$[(CH_2)_2$—$N^nBu]$-, $(OEt)_2$-M-$C_5Me_3$-1-$^t$Bu-2-$[(CH_2)_2$—$N^nBu]$-, $(O^nPr)_2$-M-$C_5Me_3$-1-$^t$Bu-2-$[(CH_2)_2$—$N^nBu]$-, $(O^iPr)_2$-M-$C_5Me_3$-1-$^t$Bu-2-$[(CH_2)_2$—$N^nBu]$-, $(O^nBu)_2$-M-$C_5Me_3$-1-$^t$Bu-2-$[(CH_2)_2$—$N^nBu]$-, $(O^iBu_2$-M-$C_5Me_3$-1-$^t$Bu-2-$[(CH_2)_2$—$N^nBu]$-, $(O^tBu)_2$-M-$C_5Me_3$-1-$^t$Bu-2-$[(CH_2)_2$—$N^nBu]$-, $(O^sBu)_2$-M-$C_5Me_3$-1-$^t$Bu-2-$[(CH_2)_2$—$N^nBu]$-, $(NH_2)_2$-M-$C_5Me_3$-1-$^t$Bu-3-$[(CH_2)_2$—$N^nBu]$-, $(NMe_2)_2$-M-$C_5Me_3$-1-$^t$Bu-3-$[(CH_2)_2$—$N^nBu]$-, $(NEt_2)_2$-M-$C_5Me_3$-1-$^t$Bu-3-$[(CH_2)_2$—$N^nBu]$-, $(N^nPr_2)_2$-M-$C_5Me_3$-1-$^t$Bu-3-$[(CH_2)_2$—$N^nBu]$-, $(N^iPr_2)_2$-M-$C_5Me_3$-1-$^t$Bu-3-$[(CH_2)_2$—$N^nBu]$-, $(N^nBu_2)_2$-M-$C_5Me_3$-1-$^t$Bu-3-$[(CH_2)_2$—$N^nBu]$-, $(N^iBu_2)_2$-M-$C_5Me_3$-1-$^t$Bu-3-$[(CH_2)_2$—$N^nBu]$-, $(N^sBu_2)_2$-M-$C_5Me_3$-1-$^t$Bu-3-$[(CH_2)_2$—$N^nBu]$-, $(N^tBu_2)_2$-M-$C_5Me_3$-1-$^t$Bu-3-$[(CH_2)_2$—$N^nBu]$-, $(NH_2)(Cp)$-M-$C_5Me_3$-1-$^t$Bu-3-$[(CH_2)_2$—$N^nBu]$-, $(NMe_2)(Cp)$-M-$C_5Me_3$-1-$^t$Bu-3-$[(CH_2)_2$—$N^nBu]$-, $(NEt_2)(Cp)$-M-$C_5Me_3$-1-$^t$Bu-3-$[(CH_2)_2$—$N^nBu]$-, $(N^nPr_2)(Cp)$-M-$C_5Me_3$-1-$^t$Bu-3-$[(CH_2)_2$—$N^nBu]$-, $(N^iPr_2)(Cp)$-M-$C_5Me_3$-1-$^t$Bu-3-$[(CH_2)_2$—$N^nBu]$-, $(N^nBu_2)(Cp)$-M-$C_5Me_3$-1-$^t$Bu-3-$[(CH_2)_2$—$N^nBu]$-, $(N^iBu_2)(Cp)$-M-$C_5Me_3$-1-$^t$Bu-3-$[(CH_2)_2$—$N^nBu]$-, $(N^sBu_2)(Cp)$-M-$C_5Me_3$-1-$^t$Bu-3-$[(CH_2)_2$—$N^nBu]$-, $(N^tBu_2)(Cp)$-M-$C_5Me_3$-1-$^t$Bu-3-$[(CH_2)_2$—$N^nBu]$-, $(OH)_2$-M-$C_5Me_3$-1-$^t$Bu-3-$[(CH_2)_2$—$N^nBu]$-, $(OMe)_2$-M-$C_5Me_3$-1-$^t$Bu-3-$[(CH_2)_2$—$N^nBu]$-, $(OEt)_2$-M-$C_5Me_3$-1-$^t$Bu-3-$[(CH_2)_2$—$N^nBu]$-, $(O^nPr)_2$-M-$C_5Me_3$-1-$^t$Bu-3-$[(CH_2)_2$—$N^nBu]$-, $(O^iPr)_2$-M-$C_5Me_3$-1-$^t$Bu-3-$[(CH_2)_2$—$N^nBu]$-, $(O^nBu)_2$-M-$C_5Me_3$-1-$^t$Bu-3-$[(CH_2)_2$—$N^nBu]$-, $(O^iBu_2$-M-$C_5Me_3$-1-$^t$Bu-3-$[(CH_2)_2$—$N^nBu]$-, $(O^tBu)_2$-M-$C_5Me_3$-1-$^t$Bu-3-$[(CH_2)_2$—$N^nBu]$-, $(O^sBu)_2$-M-$C_5Me_3$-1-$^t$Bu-3-$[(CH_2)_2$—$N^nBu]$-, $(NH_2)_2$-M-$C_5Me_3$-1-Et-2-$[(CH_2)_2$—$N^iBu]$-, $(NMe_2)_2$-M-$C_5Me_3$-1-Et-2-$[(CH_2)_2$—$N^iBu]$-, $(NEt_2)_2$-M-$C_5Me_3$-1-Et-2-$[(CH_2)_2$—$N^iBu]$-, $(N^nPr_2)_2$-M-$C_5Me_3$-1-Et-2-$[(CH_2)_2$—$N^iBu]$-, $(N^iPr_2)_2$-M-$C_5Me_3$-1-Et-2-$[(CH_2)_2$—$N^iBu]$-, $(N^nBu_2)_2$-M-$C_5Me_3$-1-Et-2-$[(CH_2)_2$—$N^iBu]$-, $(N^iBu_2)_2$-M-$C_5Me_3$-1-Et-2-$[(CH_2)_2$—$N^iBu]$-, $(N^sBu_2)_2$-M-$C_5Me_3$-1-Et-2-$[(CH_2)_2$—$N^iBu]$-, $(N^tBu_2)_2$-M-$C_5Me_3$-1-Et-2-$[(CH_2)_2$—$N^iBu]$-, $(NH_2)(Cp)$-M-$C_5Me_3$-1-Et-2-$[(CH_2)_2$—$N^iBu]$-, $(NMe_2)(Cp)$-M-$C_5Me_3$-1-Et-2-$[(CH_2)_2$—$N^iBu]$-, $(NEt_2)(Cp)$-M-$C_5Me_3$-1-Et-2-$[(CH_2)_2$—$N^iBu]$-, $(N^nPr_2)(Cp)$-M-$C_5Me_3$-1-Et-2-$[(CH_2)_2$—$N^iBu]$-, $(N^iPr_2)(Cp)$-M-$C_5Me_3$-1-Et-2-$[(CH_2)_2$—$N^iBu]$-, $(N^nBu_2)(Cp)$-M-$C_5Me_3$-1-Et-2-$[(CH_2)_2$—$N^iBu]$-, $(N^iBu_2)(Cp)$-M-$C_5Me_3$-1-Et-2-$[(CH_2)_2$—$N^iBu]$-, $(N^sBu_2)(Cp)$-M-$C_5Me_3$-1-Et-2-$[(CH_2)_2$—$N^iBu]$-, $(N^tBu_2)(Cp)$-M-$C_5Me_3$-1-Et-2-$[(CH_2)_2$—$N^iBu]$-, $(OH)_2$-M-$C_5Me_3$-1-Et-2-$[(CH_2)_2$—$N^iBu]$-, $(OMe)_2$-M-$C_5Me_3$-1-Et-2-$[(CH_2)_2$—$N^iBu]$-, $(OEt)_2$-M-$C_5Me_3$-1-Et-2-$[(CH_2)_2$—$N^iBu]$-, $(O^nPr)_2$-M-$C_5Me_3$-1-Et-2-$[(CH_2)_2$—$N^iBu]$-, $(O^iPr)_2$-M-$C_5Me_3$-1-Et-2-$[(CH_2)_2$—$N^iBu]$-, $(O^nBu)_2$-M-$C_5Me_3$-1-Et-2-$[(CH_2)_2$—$N^iBu]$-, $(O^iBu_2$-M-$C_5Me_3$-1-Et-2-$[(CH_2)_2$—$N^iBu]$-, $(O^tBu)_2$-M-$C_5Me_3$-1-Et-2-$[(CH_2)_2$—$N^iBu]$-, $(O^sBu)_2$-M-$C_5Me_3$-1-Et-2-$[(CH_2)_2$—$N^iBu]$-, $(NH_2)_2$-M-$C_5Me_3$-1-Et-3-$[(CH_2)_2$—$N^iBu]$-, $(NMe_2)_2$-M-$C_5Me_3$-1-Et-3-$[(CH_2)_2$—$N^iBu]$-, $(NEt_2)_2$-M-$C_5Me_3$-1-Et-3-$[(CH_2)_2$—$N^iBu]$-, $(N^nPr_2)_2$-M-$C_5Me_3$-1-Et-3-$[(CH_2)_2$—$N^iBu]$-, $(N^iPr_2)_2$-M-$C_5Me_3$-1-Et-3-$[(CH_2)_2$—$N^iBu]$-, $(N^nBu_2)_2$-M-$C_5Me_3$-1-Et-3-$[(CH_2)_2$—$N^iBu]$-, $(N^iBu_2)_2$-M-$C_5Me_3$-1-Et-3-$[(CH_2)_2$—$N^iBu]$-, $(N^sBu_2)_2$-M-$C_5Me_3$-1-Et-3-$[(CH_2)_2$—$N^iBu]$-, $(N^tBu_2)_2$-M-$C_5Me_3$-1-Et-3-$[(CH_2)_2$—$N^iBu]$-, $(NH_2)(Cp)$-M-$C_5Me_3$-1-Et-3-$[(CH_2)_2$—$N^iBu]$-, $(NMe_2)(Cp)$-M-$C_5Me_3$-1-Et-3-$[(CH_2)_2$—$N^iBu]$-, $(NEt_2)(Cp)$-M-$C_5Me_3$-1-Et-3-$[(CH_2)_2$—$N^iBu]$-, $(N^nPr_2)(Cp)$-M-$C_5Me_3$-1-Et-3-$[(CH_2)_2$—$N^iBu]$-, $(N^iPr_2)(Cp)$-M-$C_5Me_3$-1-Et-3-$[(CH_2)_2$—$N^iBu]$-, $(N^nBu_2)(Cp)$-M-$C_5Me_3$-1-Et-3-$[(CH_2)_2$—$N^iBu]$-, $(N^iBu_2)(Cp)$-M-$C_5Me_3$-1-Et-3-$[(CH_2)_2$—$N^iBu]$-, $(N^sBu_2)(Cp)$-M-$C_5Me_3$-1-Et-3-$[(CH_2)_2$—$N^iBu]$-, $(N^tBu_2)(Cp)$-M-$C_5Me_3$-1-Et-3-$[(CH_2)_2$—$N^iBu]$-, $(OH)_2$-M-$C_5Me_3$-1-Et-3-$[(CH_2)_2$—$N^iBu]$-, $(OMe)_2$-M-$C_5Me_3$-1-Et-3-$[(CH_2)_2$—$N^iBu]$-, $(OEt)_2$-M-$C_5Me_3$-1-Et-3-$[(CH_2)_2$—$N^iBu]$-, $(O^nPr)_2$-M-$C_5Me_3$-1-Et-3-$[(CH_2)_2$—$N^iBu]$-, $(O^iPr)_2$-M-$C_5Me_3$-1-Et-3-$[(CH_2)_2$—$N^iBu]$-, $(O^nBu)_2$-M-$C_5Me_3$-1-Et-3-$[(CH_2)_2$—$N^iBu]$-, $(O^iBu_2$-M-$C_5Me_3$-1-Et-3-$[(CH_2)_2$—$N^iBu]$-, $(O^tBu)_2$-M-$C_5Me_3$-1-Et-3-$[(CH_2)_2$—$N^iBu]$-, $(O^sBu)_2$-M-$C_5Me_3$-1-Et-3-$[(CH_2)_2$—$N^iBu]$-, $(NH_2)_2$-M-$C_5Me_3$-1-$^i$Pr-2-$[(CH_2)_2$—$N^iBu]$-, $(NMe_2)_2$-M-$C_5Me_3$-1-$^i$Pr-2-$[(CH_2)_2$—$N^iBu]$-, $(NEt_2)_2$-M-$C_5Me_3$-1-$^i$Pr-2-$[(CH_2)_2$—$N^iBu]$-, $(N^nPr_2)_2$-M-$C_5Me_3$-1-$^i$Pr-2-$[(CH_2)_2$—$N^iBu]$-, $(N^iPr_2)_2$-M-$C_5Me_3$-1-$^i$Pr-2-$[(CH_2)_2$—$N^iBu]$-, $(N^nBu_2)_2$-M-$C_5Me_3$-1-$^i$Pr-2-$[(CH_2)_2$—$N^iBu]$-, $(N^iBu_2)_2$-M-$C_5Me_3$-1-$^i$Pr-2-$[(CH_2)_2$—$N^iBu]$-, $(N^sBu_2)_2$-M-$C_5Me_3$-1-$^i$Pr-2-$[(CH_2)_2$—$N^iBu]$-, $(N^tBu_2)_2$-M-$C_5Me_3$-1-$^i$Pr-2-$[(CH_2)_2$—$N^iBu]$-, $(NH_2)(Cp)$-M-$C_5Me_3$-1-$^i$Pr-2-$[(CH_2)_2$—$N^iBu]$-, $(NMe_2)(Cp)$-M-$C_5Me_3$-1-$^i$Pr-2-$[(CH_2)_2$—$N^iBu]$-, $(NEt_2)(Cp)$-M-$C_5Me_3$-1-$^i$Pr-2-$[(CH_2)_2$—$N^iBu]$-, $(N^nPr_2)(Cp)$-M-$C_5Me_3$-1-$^i$Pr-2-$[(CH_2)_2$—$N^iBu]$-, $(N^iPr_2)(Cp)$-M-$C_5Me_3$-1-$^i$Pr-2-$[(CH_2)_2$—$N^iBu]$-, $(N^nBu_2)(Cp)$-M-$C_5Me_3$-1-$^i$Pr-2-$[(CH_2)_2$—$N^iBu]$-, $(N^iBu_2)(Cp)$-M-$C_5Me_3$-1-$^i$Pr-2-$[(CH_2)_2$—$N^iBu]$-, $(N^sBu_2)(Cp)$-M-$C_5Me_3$-1-$^i$Pr-2-$[(CH_2)_2$—$N^iBu]$-, $(N^tBu_2)(Cp)$-M-$C_5Me_3$-1-$^i$Pr-2-$[(CH_2)_2$—$N^iBu]$-, $(OH)_2$-M-$C_5Me_3$-1-$^i$Pr-2-$[(CH_2)_2$—$N^iBu]$-, $(OMe)_2$-M-$C_5Me_3$-1-$^i$Pr-2-$[(CH_2)_2$—$N^iBu]$-, $(OEt)_2$-M-

C$_5$Me$_3$-1-$^i$Pr-2-[(CH$_2$)$_2$—N$^t$Bu]-, (O$^n$Pr)$_2$-M-C$_5$Me$_3$-1-$^i$Pr-2-[(CH$_2$)$_2$—N$^t$Bu]-, (O$^i$Pr)$_2$-M-C$_5$Me$_3$-1-$^i$Pr-2-[(CH$_2$)$_2$—N$^t$Bu]-, (O$^n$Bu)$_2$-M-C$_5$Me$_3$-1-$^i$Pr-2-[(CH$_2$)$_2$—N$^t$Bu]-, (O$^i$Bu$_2$-M-C$_5$Me$_3$-1-$^i$Pr-2-[(CH$_2$)$_2$—N$^t$Bu]-, (O$^t$Bu)$_2$-M-C$_5$Me$_3$-1-$^i$Pr-2-[(CH$_2$)$_2$—N$^t$Bu]-, (O$^s$Bu)$_2$-M-C$_5$Me$_3$-1-$^i$Pr-2-[(CH$_2$)$_2$—N$^t$Bu]-, (NH$_2$)$_2$-M-C$_5$Me$_3$-1-$^i$Pr-3-[(CH$_2$)$_2$—N$^t$Bu]-, (NMe$_2$)$_2$-M-C$_5$Me$_3$-1-$^i$Pr-3-[(CH$_2$)$_2$—N$^t$Bu]-, (NEt$_2$)$_2$-M-C$_5$Me$_3$-1-$^i$Pr-3-[(CH$_2$)$_2$—N$^t$Bu]-, (N$^n$Pr$_2$)$_2$-M-C$_5$Me$_3$-1-$^i$Pr-3-[(CH$_2$)$_2$—N$^t$Bu]-, (N$^i$Pr$_2$)$_2$-M-C$_5$Me$_3$-1-$^i$Pr-3-[(CH$_2$)$_2$—N$^t$Bu]-, (N$^n$Bu$_2$)$_2$-M-C$_5$Me$_3$-1-$^i$Pr-3-[(CH$_2$)$_2$—N$^t$Bu]-, (N$^i$Bu$_2$)$_2$-M-C$_5$Me$_3$-1-$^i$Pr-3-[(CH$_2$)$_2$—N$^t$Bu]-, (N$^s$Bu$_2$)$_2$-M-C$_5$Me$_3$-1-$^i$Pr-3-[(CH$_2$)$_2$—N$^t$Bu]-, (N$^t$Bu$_2$)$_2$-M-C$_5$Me$_3$-1-$^i$Pr-3-[(CH$_2$)$_2$—N$^t$Bu]-, (NH$_2$)(Cp)-M-C$_5$Me$_3$-1-$^i$Pr-3-[(CH$_2$)$_2$—N$^t$Bu]-, (NMe$_2$)(Cp)-M-C$_5$Me$_3$-1-$^i$Pr-3-[(CH$_2$)$_2$—N$^t$Bu]-, (NEt$_2$)(Cp)-M-C$_5$Me$_3$-1-$^i$Pr-3-[(CH$_2$)$_2$—N$^t$Bu]-, (N$^n$Pr$_2$)(Cp)-M-C$_5$Me$_3$-1-$^i$Pr-3-[(CH$_2$)$_2$—N$^t$Bu]-, (N$^i$Pr$_2$)(Cp)-M-C$_5$Me$_3$-1-$^i$Pr-3-[(CH$_2$)$_2$—N$^t$Bu]-, (N$^n$Bu$_2$)(Cp)-M-C$_5$Me$_3$-1-$^i$Pr-3-[(CH$_2$)$_2$—N$^t$Bu]-, (N$^i$Bu$_2$)(Cp)-M-C$_5$Me$_3$-1-$^i$Pr-3-[(CH$_2$)$_2$—N$^t$Bu]-, (N$^s$Bu$_2$)(Cp)-M-C$_5$Me$_3$-1-$^i$Pr-3-[(CH$_2$)$_2$—N$^t$Bu]-, (N$^t$Bu$_2$)(Cp)-M-C$_5$Me$_3$-1-$^i$Pr-3-[(CH$_2$)$_2$—N$^t$Bu]-, (OH)$_2$-M-C$_5$Me$_3$-1-$^i$Pr-3-[(CH$_2$)$_2$—N$^t$Bu]-, (OMe)$_2$-M-C$_5$Me$_3$-1-$^i$Pr-3-[(CH$_2$)$_2$—N$^t$Bu]-, (OEt)$_2$-M-C$_5$Me$_3$-1-$^i$Pr-3-[(CH$_2$)$_2$—N$^t$Bu]-, (O$^n$Pr)$_2$-M-C$_5$Me$_3$-1-$^i$Pr-3-[(CH$_2$)$_2$—N$^t$Bu]-, (O$^i$Pr)$_2$-M-C$_5$Me$_3$-1-$^i$Pr-3-[(CH$_2$)$_2$—N$^t$Bu]-, (O$^n$Bu)$_2$-M-C$_5$Me$_3$-1-$^i$Pr-3-[(CH$_2$)$_2$—N$^t$Bu]-, (O$^i$Bu$_2$-M-C$_5$Me$_3$-1-$^i$Pr-3-[(CH$_2$)$_2$—N$^t$Bu]-, (O$^t$Bu)$_2$-M-C$_5$Me$_3$-1-$^i$Pr-3-[(CH$_2$)$_2$—N$^t$Bu]-, (O$^s$Bu)$_2$-M-C$_5$Me$_3$-1-$^i$Pr-3-[(CH$_2$)$_2$—N$^t$Bu]-, (NH$_2$)$_2$-M-C$_5$Me$_3$-1-$^t$Bu-2-[(CH$_2$)$_2$—N$^t$Bu]-, (NMe$_2$)$_2$-M-C$_5$Me$_3$-1-$^t$Bu-2-[(CH$_2$)$_2$—N$^t$Bu]-, (NEt$_2$)$_2$-M-C$_5$Me$_3$-1-$^t$Bu-2-[(CH$_2$)$_2$—N$^t$Bu]-, (N$^n$Pr$_2$)$_2$-M-C$_5$Me$_3$-1-$^t$Bu-2-[(CH$_2$)$_2$—N$^t$Bu]-, (N$^i$Pr$_2$)$_2$-M-C$_5$Me$_3$-1-$^t$Bu-2-[(CH$_2$)$_2$—N$^t$Bu]-, (N$^n$Bu$_2$)$_2$-M-C$_5$Me$_3$-1-$^t$Bu-2-[(CH$_2$)$_2$—N$^t$Bu]-, (N$^i$Bu$_2$)$_2$-M-C$_5$Me$_3$-1-$^t$Bu-2-[(CH$_2$)$_2$—N$^t$Bu]-, (N$^s$Bu$_2$)$_2$-M-C$_5$Me$_3$-1-$^t$Bu-2-[(CH$_2$)$_2$—N$^t$Bu]-, (N$^t$Bu$_2$)$_2$-M-C$_5$Me$_3$-1-$^t$Bu-2-[(CH$_2$)$_2$—N$^t$Bu]-, (NH$_2$)(Cp)-M-C$_5$Me$_3$-1-$^t$Bu-2-[(CH$_2$)$_2$—N$^t$Bu]-, (NMe$_2$)(Cp)-M-C$_5$Me$_3$-1-$^t$Bu-2-[(CH$_2$)$_2$—N$^t$Bu]-, (NEt$_2$)(Cp)-M-C$_5$Me$_3$-1-$^t$Bu-2-[(CH$_2$)$_2$—N$^t$Bu]-, (N$^n$Pr$_2$)(Cp)-M-C$_5$Me$_3$-1-$^t$Bu-2-[(CH$_2$)$_2$—N$^t$Bu]-, (N$^i$Pr$_2$)(Cp)-M-C$_5$Me$_3$-1-$^t$Bu-2-[(CH$_2$)$_2$—N$^t$Bu]-, (N$^n$Bu$_2$)(Cp)-M-C$_5$Me$_3$-1-$^t$Bu-2-[(CH$_2$)$_2$—N$^t$Bu]-, (N$^i$Bu$_2$)(Cp)-M-C$_5$Me$_3$-1-$^t$Bu-2-[(CH$_2$)$_2$—N$^t$Bu]-, (N$^s$Bu$_2$)(Cp)-M-C$_5$Me$_3$-1-$^t$Bu-2-[(CH$_2$)$_2$—N$^t$Bu]-, (N$^t$Bu$_2$)(Cp)-M-C$_5$Me$_3$-1-$^t$Bu-2-[(CH$_2$)$_2$—N$^t$Bu]-, (OH)$_2$-M-C$_5$Me$_3$-1-$^t$Bu-2-[(CH$_2$)$_2$—N$^t$Bu]-, (OMe)$_2$-M-C$_5$Me$_3$-1-$^t$Bu-2-[(CH$_2$)$_2$—N$^t$Bu]-, (OEt)$_2$-M-C$_5$Me$_3$-1-$^t$Bu-2-[(CH$_2$)$_2$—N$^t$Bu]-, (O$^n$Pr)$_2$-M-C$_5$Me$_3$-1-$^t$Bu-2-[(CH$_2$)$_2$—N$^t$Bu]-, (O$^i$Pr)$_2$-M-C$_5$Me$_3$-1-$^t$Bu-2-[(CH$_2$)$_2$—N$^t$Bu]-, (O$^n$Bu)$_2$-M-C$_5$Me$_3$-1-$^t$Bu-2-[(CH$_2$)$_2$—N$^t$Bu]-, (O$^i$Bu$_2$-M-C$_5$Me$_3$-1-$^t$Bu-2-[(CH$_2$)$_2$—N$^t$Bu]-, (O$^t$Bu)$_2$-M-C$_5$Me$_3$-1-$^t$Bu-2-[(CH$_2$)$_2$—N$^t$Bu]-, (O$^s$Bu)$_2$-M-C$_5$Me$_3$-1-$^t$Bu-2-[(CH$_2$)$_2$—N$^t$Bu]-, (NH$_2$)$_2$-M-C$_5$Me$_3$-1-$^t$Bu-3-[(CH$_2$)$_2$—N$^t$Bu]-, (NMe$_2$)$_2$-M-C$_5$Me$_3$-1-$^t$Bu-3-[(CH$_2$)$_2$—N$^t$Bu]-, (NEt$_2$)$_2$-M-C$_5$Me$_3$-1-$^t$Bu-3-[(CH$_2$)$_2$—N$^t$Bu]-, (N$^n$Pr$_2$)$_2$-M-C$_5$Me$_3$-1-$^t$Bu-3-[(CH$_2$)$_2$—N$^t$Bu]-, (N$^i$Pr$_2$)$_2$-M-C$_5$Me$_3$-1-$^t$Bu-3-[(CH$_2$)$_2$—N$^t$Bu]-, (N$^n$Bu$_2$)$_2$-M-C$_5$Me$_3$-1-$^t$Bu-3-[(CH$_2$)$_2$—N$^t$Bu]-, (N$^i$Bu$_2$)$_2$-M-C$_5$Me$_3$-1-$^t$Bu-3-[(CH$_2$)$_2$—N$^t$Bu]-, (N$^s$Bu$_2$)$_2$-M-C$_5$Me$_3$-1-$^t$Bu-3-[(CH$_2$)$_2$—N$^t$Bu]-, (N$^t$Bu$_2$)$_2$-M-C$_5$Me$_3$-1-$^t$Bu-3-[(CH$_2$)$_2$—N$^t$Bu]-, (NH$_2$)(Cp)-M-C$_5$Me$_3$-1-$^t$Bu-3-[(CH$_2$)$_2$—N$^t$Bu]-, (NMe$_2$)(Cp)-M-C$_5$Me$_3$-1-$^t$Bu-3-[(CH$_2$)$_2$—N$^t$Bu]-, (NEt$_2$)(Cp)-M-C$_5$Me$_3$-1-$^t$Bu-3-[(CH$_2$)$_2$—N$^t$Bu]-, (N$^n$Pr$_2$)(Cp)-M-C$_5$Me$_3$-1-$^t$Bu-3-[(CH$_2$)$_2$—N$^t$Bu]-, (N$^i$Pr$_2$)(Cp)-M-C$_5$Me$_3$-1-$^t$Bu-3-[(CH$_2$)$_2$—N$^t$Bu]-, (N$^n$Bu$_2$)(Cp)-M-C$_5$Me$_3$-1-$^t$Bu-3-[(CH$_2$)$_2$—N$^t$Bu]-, (N$^i$Bu$_2$)(Cp)-M-C$_5$Me$_3$-1-$^t$Bu-3-[(CH$_2$)$_2$—N$^t$Bu]-, (N$^s$Bu$_2$)(Cp)-M-C$_5$Me$_3$-1-$^t$Bu-3-[(CH$_2$)$_2$—N$^t$Bu]-, (N$^t$Bu$_2$)(Cp)-M-C$_5$Me$_3$-1-$^t$Bu-3-[(CH$_2$)$_2$—N$^t$Bu]-, (OH)$_2$-M-C$_5$Me$_3$-1-$^t$Bu-3-[(CH$_2$)$_2$—N$^t$Bu]-, (OMe)$_2$-M-C$_5$Me$_3$-1-$^t$Bu-3-[(CH$_2$)$_2$—N$^t$Bu]-, (OEt)$_2$-M-C$_5$Me$_3$-1-$^t$Bu-3-[(CH$_2$)$_2$—N$^t$Bu]-, (O$^n$Pr)$_2$-M-C$_5$Me$_3$-1-$^t$Bu-3-[(CH$_2$)$_2$—N$^t$Bu]-, (O$^i$Pr)$_2$-M-C$_5$Me$_3$-1-$^t$Bu-3-[(CH$_2$)$_2$—N$^t$Bu]-, (O$^n$Bu)$_2$-M-C$_5$Me$_3$-1-$^t$Bu-3-[(CH$_2$)$_2$—N$^t$Bu]-, (O$^i$Bu$_2$-M-C$_5$Me$_3$-1-$^t$Bu-3-[(CH$_2$)$_2$—N$^t$Bu]-, (O$^t$Bu)$_2$-M-C$_5$Me$_3$-1-$^t$Bu-3-[(CH$_2$)$_2$—N$^t$Bu]-, (O$^s$Bu)$_2$-M-C$_5$Me$_3$-1-$^t$Bu-3-[(CH$_2$)$_2$—N$^t$Bu]-, (NH$_2$)$_2$-M-C$_5$Me$_3$-1-Et-2-[(CH$_2$)$_2$—N$^s$Bu]-, (NMe$_2$)$_2$-M-C$_5$Me$_3$-1-Et-2-[(CH$_2$)$_2$—N$^s$Bu]-, (NEt$_2$)$_2$-M-C$_5$Me$_3$-1-Et-2-[(CH$_2$)$_2$—N$^s$Bu]-, (N$^n$Pr$_2$)$_2$-M-C$_5$Me$_3$-1-Et-2-[(CH$_2$)$_2$—N$^s$Bu]-, (N$^i$Pr$_2$)$_2$-M-C$_5$Me$_3$-1-Et-2-[(CH$_2$)$_2$—N$^s$Bu]-, (N$^n$Bu$_2$)$_2$-M-C$_5$Me$_3$-1-Et-2-[(CH$_2$)$_2$—N$^s$Bu]-, (N$^i$Bu$_2$)$_2$-M-C$_5$Me$_3$-1-Et-2-[(CH$_2$)$_2$—N$^s$Bu]-, (N$^s$Bu$_2$)$_2$-M-C$_5$Me$_3$-1-Et-2-[(CH$_2$)$_2$—N$^s$Bu]-, (N$^t$Bu$_2$)$_2$-M-C$_5$Me$_3$-1-Et-2-[(CH$_2$)$_2$—N$^s$Bu]-, (NH$_2$)(Cp)-M-C$_5$Me$_3$-1-Et-2-[(CH$_2$)$_2$—N$^s$Bu]-, (NMe$_2$)(Cp)-M-C$_5$Me$_3$-1-Et-2-[(CH$_2$)$_2$—N$^s$Bu]-, (NEt$_2$)(Cp)-M-C$_5$Me$_3$-1-Et-2-[(CH$_2$)$_2$—N$^s$Bu]-, (N$^n$Pr$_2$)(Cp)-M-C$_5$Me$_3$-1-Et-2-[(CH$_2$)$_2$—N$^s$Bu]-, (N$^i$Pr$_2$)(Cp)-M-C$_5$Me$_3$-1-Et-2-[(CH$_2$)$_2$—N$^s$Bu]-, (N$^n$Bu$_2$)(Cp)-M-C$_5$Me$_3$-1-Et-2-[(CH$_2$)$_2$—N$^s$Bu]-, (N$^i$Bu$_2$)(Cp)-M-C$_5$Me$_3$-1-Et-2-[(CH$_2$)$_2$—N$^s$Bu]-, (N$^s$Bu$_2$)(Cp)-M-C$_5$Me$_3$-1-Et-2-[(CH$_2$)$_2$—N$^s$Bu]-, (N$^t$Bu$_2$)(Cp)-M-C$_5$Me$_3$-1-Et-2-[(CH$_2$)$_2$—N$^s$Bu]-, (OH)$_2$-M-C$_5$Me$_3$-1-Et-2-[(CH$_2$)$_2$—N$^s$Bu]-, (OMe)$_2$-M-C$_5$Me$_3$-1-Et-2-[(CH$_2$)$_2$—N$^s$Bu]-, (OEt)$_2$-M-C$_5$Me$_3$-1-Et-2-[(CH$_2$)$_2$—N$^s$Bu]-, (O$^n$Pr)$_2$-M-C$_5$Me$_3$-1-Et-2-[(CH$_2$)$_2$—N$^s$Bu]-, (O$^i$Pr)$_2$-M-C$_5$Me$_3$-1-Et-2-[(CH$_2$)$_2$—N$^s$Bu]-, (O$^n$Bu)$_2$-M-C$_5$Me$_3$-1-Et-2-[(CH$_2$)$_2$—N$^s$Bu]-, (O$^i$Bu$_2$-M-C$_5$Me$_3$-1-Et-2-[(CH$_2$)$_2$—N$^s$Bu]-, (O$^t$Bu)$_2$-M-C$_5$Me$_3$-1-Et-2-[(CH$_2$)$_2$—N$^s$Bu]-, (O$^s$Bu)$_2$-M-C$_5$Me$_3$-1-Et-2-[(CH$_2$)$_2$—N$^s$Bu]-, (NH$_2$)$_2$-M-C$_5$Me$_3$-1-Et-3-[(CH$_2$)$_2$—N$^s$Bu]-, (NMe$_2$)$_2$-M-C$_5$Me$_3$-1-Et-3-[(CH$_2$)$_2$—N$^s$Bu]-, (NEt$_2$)$_2$-M-C$_5$Me$_3$-1-Et-3-[(CH$_2$)$_2$—N$^s$Bu]-, (N$^n$Pr$_2$)$_2$-M-C$_5$Me$_3$-1-Et-3-[(CH$_2$)$_2$—N$^s$Bu]-, (N$^i$Pr$_2$)$_2$-M-C$_5$Me$_3$-1-Et-3-[(CH$_2$)$_2$—N$^s$Bu]-, (N$^n$Bu$_2$)$_2$-M-C$_5$Me$_3$-1-Et-3-[(CH$_2$)$_2$—N$^s$Bu]-, (N$^i$Bu$_2$)$_2$-M-C$_5$Me$_3$-1-Et-3-[(CH$_2$)$_2$—N$^s$Bu]-, (N$^s$Bu$_2$)$_2$-M-C$_5$Me$_3$-1-Et-3-[(CH$_2$)$_2$—N$^s$Bu]-, (N$^t$Bu$_2$)$_2$-M-C$_5$Me$_3$-1-Et-3-[(CH$_2$)$_2$—N$^s$Bu]-, (NH$_2$)(Cp)-M-C$_5$Me$_3$-1-Et-3-[(CH$_2$)$_2$—N$^s$Bu]-, (NMe$_2$)(Cp)-M-C$_5$Me$_3$-1-Et-3-[(CH$_2$)$_2$—N$^s$Bu]-, (NEt$_2$)(Cp)-M-C$_5$Me$_3$-1-Et-3-[(CH$_2$)$_2$—N$^s$Bu]-, (N$^n$Pr$_2$)(Cp)-M-C$_5$Me$_3$-1-Et-3-[(CH$_2$)$_2$—N$^s$Bu]-, (N$^i$Pr$_2$)(Cp)-M-C$_5$Me$_3$-1-Et-3-[(CH$_2$)$_2$—N$^s$Bu]-, (N$^n$Bu$_2$)(Cp)-M-C$_5$Me$_3$-1-Et-3-[(CH$_2$)$_2$—N$^s$Bu]-, (N$^i$Bu$_2$)(Cp)-M-C$_5$Me$_3$-1-Et-3-[(CH$_2$)$_2$—N$^s$Bu]-, (N$^s$Bu$_2$)(Cp)-M-C$_5$Me$_3$-1-Et-3-[(CH$_2$)$_2$—N$^s$Bu]-, (N$^t$Bu$_2$)(Cp)-M-C$_5$Me$_3$-1-Et-3-[(CH$_2$)$_2$—N$^s$Bu]-, (OH)$_2$-M-C$_5$Me$_3$-1-Et-3-[(CH$_2$)$_2$—N$^s$Bu]-, (OMe)$_2$-M-C$_5$Me$_3$-1-Et-3-[(CH$_2$)$_2$—N$^s$Bu]-, (OEt)$_2$-M-C$_5$Me$_3$-1-Et-3-[(CH$_2$)$_2$—N$^s$Bu]-, (O$^n$Pr)$_2$-M-C$_5$Me$_3$-1-Et-3-[(CH$_2$)$_2$—N$^s$Bu]-, (O$^i$Pr)$_2$-M-C$_5$Me$_3$-1-Et-3-[(CH$_2$)$_2$—N$^s$Bu]-, (O$^n$Bu)$_2$-M-C$_5$Me$_3$-1-Et-3-[(CH$_2$)$_2$—N$^s$Bu]-, (O$^i$Bu$_2$-M-C$_5$Me$_3$-1-Et-3-[(CH$_2$)$_2$—N$^s$Bu]-, (O$^t$Bu)$_2$-M-C$_5$Me$_3$-1-Et-3-[(CH$_2$)$_2$—N$^s$Bu]-, (O$^s$Bu)$_2$-M-C$_5$Me$_3$-1-Et-3-[(CH$_2$)$_2$—N$^s$Bu]-, (NH$_2$)$_2$-M-C$_5$Me$_3$-1-$^i$Pr-2-[(CH$_2$)$_2$—N$^s$Bu]-, (NMe$_2$)$_2$-M-C$_5$Me$_3$-1-$^i$Pr-2-[(CH$_2$)$_2$—N$^s$Bu]-, (NEt$_2$)$_2$-M-C$_5$Me$_3$-1-$^i$Pr-2-[(CH$_2$)$_2$—N$^s$Bu]-, (N$^n$Pr$_2$)$_2$-M-C$_5$Me$_3$-1-$^i$Pr-2-[(CH$_2$)$_2$—N$^s$Bu]-, (N$^i$Pr$_2$)$_2$-M-C$_5$Me$_3$-1-$^i$Pr-2-[(CH$_2$)$_2$—N$^s$Bu]-, (N$^n$Bu$_2$)$_2$-M-C$_5$Me$_3$-1-$^i$Pr-2-[(CH$_2$)$_2$—N$^s$Bu]-, (N$^i$Bu$_2$)$_2$-M-C$_5$Me$_3$-1-$^i$Pr-2-[(CH$_2$)$_2$—N$^s$Bu]-, (N$^s$Bu$_2$)$_2$-M-C$_5$Me$_3$-1-$^i$Pr-2-[(CH$_2$)$_2$—N$^s$Bu]-, (N$^t$Bu$_2$)$_2$-M-C$_5$Me$_3$-1-$^i$Pr-2-[(CH$_2$)$_2$—N$^s$Bu]-, (NH$_2$)(Cp)-M-C$_5$Me$_3$-1-$^i$Pr-2-[(CH$_2$)$_2$—N$^s$Bu]-, (NMe$_2$)(Cp)-M-C$_5$Me$_3$-1-$^i$Pr-2-[(CH$_2$)$_2$—N$^s$Bu]-, (NEt$_2$)(Cp)-M-C$_5$Me$_3$-1-$^i$Pr-2-[(CH$_2$)$_2$—N$^s$Bu]-, (N$^n$Pr$_2$)(Cp)-M-C$_5$Me$_3$-1-$^i$Pr-2-[(CH$_2$)$_2$—N$^s$Bu]-, (N$^i$Pr$_2$)(Cp)-M-C$_5$Me$_3$-1-$^i$Pr-2-[(CH$_2$)$_2$—N$^s$Bu]-, (N$^n$Bu$_2$)(Cp)-M-C$_5$Me$_3$-1-$^i$Pr-2-[(CH$_2$)$_2$—N$^s$Bu]-, (N$^i$Bu$_2$)(Cp)-M-C$_5$Me$_3$-1-$^i$Pr-2-[(CH$_2$)$_2$—N$^s$Bu]-, (N$^s$Bu$_2$)(Cp)-M-C$_5$Me$_3$-1-$^i$Pr-2-[(CH$_2$)$_2$—N$^s$Bu]-, (N$^t$Bu$_2$)(Cp)-M-C$_5$Me$_3$-1-$^i$Pr-2-[(CH$_2$)$_2$—

N$^s$Bu]-, (OH)$_2$-M-C$_5$Me$_3$-1-$^i$Pr-2-[(CH$_2$)$_2$—N$^s$Bu]-, (OMe)$_2$-M-C$_5$Me$_3$-1-$^i$Pr-2-[(CH$_2$)$_2$—N$^s$Bu]-, (OEt)$_2$-M-C$_5$Me$_3$-1-$^i$Pr-2-[(CH$_2$)$_2$—N$^s$Bu]-, (O$^n$Pr)$_2$-M-C$_5$Me$_3$-1-$^i$Pr-2-[(CH$_2$)$_2$—N$^s$Bu]-, (O$^i$Pr)$_2$-M-C$_5$Me$_3$-1-$^i$Pr-2-[(CH$_2$)$_2$—N$^s$Bu]-, (O$^n$Bu)$_2$-M-C$_5$Me$_3$-1-$^i$Pr-2-[(CH$_2$)$_2$—N$^s$Bu]-, (O$^i$Bu$_2$-M-C$_5$Me$_3$-1-$^i$Pr-2-[(CH$_2$)$_2$—N$^s$Bu]-, (O$^t$Bu)$_2$-M-C$_5$Me$_3$-1-$^i$Pr-2-[(CH$_2$)$_2$—N$^s$Bu]-, (O$^s$Bu)$_2$-M-C$_5$Me$_3$-1-$^i$Pr-2-[(CH$_2$)$_2$—N$^s$Bu]-, (NH$_2$)$_2$-M-C$_5$Me$_3$-1-$^i$Pr-3-[(CH$_2$)$_2$—N$^s$Bu]-, (NMe$_2$)$_2$-M-C$_5$Me$_3$-1-$^i$Pr-3-[(CH$_2$)$_2$—N$^s$Bu]-, (NEt$_2$)$_2$-M-C$_5$Me$_3$-1-$^i$Pr-3-[(CH$_2$)$_2$—N$^s$Bu]-, (N$^n$Pr$_2$)$_2$-M-C$_5$Me$_3$-1-$^i$Pr-3-[(CH$_2$)$_2$—N$^s$Bu]-, (N$^i$Pr$_2$)$_2$-M-C$_5$Me$_3$-1-$^i$Pr-3-[(CH$_2$)$_2$—N$^s$Bu]-, (N$^n$Bu$_2$)$_2$-M-C$_5$Me$_3$-1-$^i$Pr-3-[(CH$_2$)$_2$—N$^s$Bu]-, (N$^i$Bu$_2$)$_2$-M-C$_5$Me$_3$-1-$^i$Pr-3-[(CH$_2$)$_2$—N$^s$Bu]-, (N$^s$Bu$_2$)$_2$-M-C$_5$Me$_3$-1-$^i$Pr-3-[(CH$_2$)$_2$—N$^s$Bu]-, (N$^t$Bu$_2$)$_2$-M-C$_5$Me$_3$-1-$^i$Pr-3-[(CH$_2$)$_2$—N$^s$Bu]-, (NH$_2$)(Cp)-M-C$_5$Me$_3$-1-$^i$Pr-3-[(CH$_2$)$_2$—N$^s$Bu]-, (NMe$_2$)(Cp)-M-C$_5$Me$_3$-1-$^i$Pr-3-[(CH$_2$)$_2$—N$^s$Bu]-, (NEt$_2$)(Cp)-M-C$_5$Me$_3$-1-$^i$Pr-3-[(CH$_2$)$_2$—N$^s$Bu]-, (N$^n$Pr$_2$)(Cp)-M-C$_5$Me$_3$-1-$^i$Pr-3-[(CH$_2$)$_2$—N$^s$Bu]-, (N$^i$Pr$_2$)(Cp)-M-C$_5$Me$_3$-1-$^i$Pr-3-[(CH$_2$)$_2$—N$^s$Bu]-, (N$^n$Bu$_2$)(Cp)-M-C$_5$Me$_3$-1-$^i$Pr-3-[(CH$_2$)$_2$—N$^s$Bu]-, (N$^i$Bu$_2$)(Cp)-M-C$_5$Me$_3$-1-$^i$Pr-3-[(CH$_2$)$_2$—N$^s$Bu]-, (N$^s$Bu$_2$)(Cp)-M-C$_5$Me$_3$-1-$^i$Pr-3-[(CH$_2$)$_2$—N$^s$Bu]-, (N$^t$Bu$_2$)(Cp)-M-C$_5$Me$_3$-1-$^i$Pr-3-[(CH$_2$)$_2$—N$^s$Bu]-, (OH)$_2$-M-C$_5$Me$_3$-1-$^i$Pr-3-[(CH$_2$)$_2$—N$^s$Bu]-, (OMe)$_2$-M-C$_5$Me$_3$-1-$^i$Pr-3-[(CH$_2$)$_2$—N$^s$Bu]-, (OEt)$_2$-M-C$_5$Me$_3$-1-$^i$Pr-3-[(CH$_2$)$_2$—N$^s$Bu]-, (O$^n$Pr)$_2$-M-C$_5$Me$_3$-1-$^i$Pr-3-[(CH$_2$)$_2$—N$^s$Bu]-, (O$^i$Pr)$_2$-M-C$_5$Me$_3$-1-$^i$Pr-3-[(CH$_2$)$_2$—N$^s$Bu]-, (O$^n$Bu)$_2$-M-C$_5$Me$_3$-1-$^i$Pr-3-[(CH$_2$)$_2$—N$^s$Bu]-, (O$^i$Bu$_2$-M-C$_5$Me$_3$-1-$^i$Pr-3-[(CH$_2$)$_2$—N$^s$Bu]-, (O$^t$Bu)$_2$-M-C$_5$Me$_3$-1-$^i$Pr-3-[(CH$_2$)$_2$—N$^s$Bu]-, (O$^s$Bu)$_2$-M-C$_5$Me$_3$-1-$^i$Pr-3-[(CH$_2$)$_2$—N$^s$Bu]-, (NH$_2$)$_2$-M-C$_5$Me$_3$-1-$^t$Bu-2-[(CH$_2$)$_2$—N$^s$Bu]-, (NMe$_2$)$_2$-M-C$_5$Me$_3$-1-$^t$Bu-2-[(CH$_2$)$_2$—N$^s$Bu]-, (NEt$_2$)$_2$-M-C$_5$Me$_3$-1-$^t$Bu-2-[(CH$_2$)$_2$—N$^s$Bu]-, (N$^n$Pr$_2$)$_2$-M-C$_5$Me$_3$-1-$^t$Bu-2-[(CH$_2$)$_2$—N$^s$Bu]-, (N$^i$Pr$_2$)$_2$-M-C$_5$Me$_3$-1-$^t$Bu-2-[(CH$_2$)$_2$—N$^s$Bu]-, (N$^n$Bu$_2$)$_2$-M-C$_5$Me$_3$-1-$^t$Bu-2-[(CH$_2$)$_2$—N$^s$Bu]-, (N$^i$Bu$_2$)$_2$-M-C$_5$Me$_3$-1-$^t$Bu-2-[(CH$_2$)$_2$—N$^s$Bu]-, (N$^s$Bu$_2$)$_2$-M-C$_5$Me$_3$-1-$^t$Bu-2-[(CH$_2$)$_2$—N$^s$Bu]-, (N$^t$Bu$_2$)$_2$-M-C$_5$Me$_3$-1-$^t$Bu-2-[(CH$_2$)$_2$—N$^s$Bu]-, (NH$_2$)(Cp)-M-C$_5$Me$_3$-1-$^t$Bu-2-[(CH$_2$)$_2$—N$^s$Bu]-, (NMe$_2$)(Cp)-M-C$_5$Me$_3$-1-$^t$Bu-2-[(CH$_2$)$_2$—N$^s$Bu]-, (NEt$_2$)(Cp)-M-C$_5$Me$_3$-1-$^t$Bu-2-[(CH$_2$)$_2$—N$^s$Bu]-, (N$^n$Pr$_2$)(Cp)-M-C$_5$Me$_3$-1-$^t$Bu-2-[(CH$_2$)$_2$—N$^s$Bu]-, (N$^i$Pr$_2$)(Cp)-M-C$_5$Me$_3$-1-$^t$Bu-2-[(CH$_2$)$_2$—N$^s$Bu]-, (N$^n$Bu$_2$)(Cp)-M-C$_5$Me$_3$-1-$^t$Bu-2-[(CH$_2$)$_2$—N$^s$Bu]-, (N$^i$Bu$_2$)(Cp)-M-C$_5$Me$_3$-1-$^t$Bu-2-[(CH$_2$)$_2$—N$^s$Bu]-, (N$^s$Bu$_2$)(Cp)-M-C$_5$Me$_3$-1-$^t$Bu-2-[(CH$_2$)$_2$—N$^s$Bu]-, (N$^t$Bu$_2$)(Cp)-M-C$_5$Me$_3$-1-$^t$Bu-2-[(CH$_2$)$_2$—N$^s$Bu]-, (OH)$_2$-M-C$_5$Me$_3$-1-$^t$Bu-2-[(CH$_2$)$_2$—N$^s$Bu]-, (OMe)$_2$-M-C$_5$Me$_3$-1-$^t$Bu-2-[(CH$_2$)$_2$—N$^s$Bu]-, (OEt)$_2$-M-C$_5$Me$_3$-1-$^t$Bu-2-[(CH$_2$)$_2$—N$^s$Bu]-, (O$^n$Pr)$_2$-M-C$_5$Me$_3$-1-$^t$Bu-2-[(CH$_2$)$_2$—N$^s$Bu]-, (O$^i$Pr)$_2$-M-C$_5$Me$_3$-1-$^t$Bu-2-[(CH$_2$)$_2$—N$^s$Bu]-, (O$^n$Bu)$_2$-M-C$_5$Me$_3$-1-$^t$Bu-2-[(CH$_2$)$_2$—N$^s$Bu]-, (O$^i$Bu$_2$-M-C$_5$Me$_3$-1-$^t$Bu-2-[(CH$_2$)$_2$—N$^s$Bu]-, (O$^t$Bu)$_2$-M-C$_5$Me$_3$-1-$^t$Bu-2-[(CH$_2$)$_2$—N$^s$Bu]-, (O$^s$Bu)$_2$-M-C$_5$Me$_3$-1-$^t$Bu-2-[(CH$_2$)$_2$—N$^s$Bu]-, (NH$_2$)$_2$-M-C$_5$Me$_3$-1-$^t$Bu-3-[(CH$_2$)$_2$—N$^s$Bu]-, (NMe$_2$)$_2$-M-C$_5$Me$_3$-1-$^t$Bu-3-[(CH$_2$)$_2$—N$^s$Bu]-, (NEt$_2$)$_2$-M-C$_5$Me$_3$-1-$^t$Bu-3-[(CH$_2$)$_2$—N$^s$Bu]-, (N$^n$Pr$_2$)$_2$-M-C$_5$Me$_3$-1-$^t$Bu-3-[(CH$_2$)$_2$—N$^s$Bu]-, (N$^i$Pr$_2$)$_2$-M-C$_5$Me$_3$-1-$^t$Bu-3-[(CH$_2$)$_2$—N$^s$Bu]-, (N$^n$Bu$_2$)$_2$-M-C$_5$Me$_3$-1-$^t$Bu-3-[(CH$_2$)$_2$—N$^s$Bu]-, (N$^i$Bu$_2$)$_2$-M-C$_5$Me$_3$-1-$^t$Bu-3-[(CH$_2$)$_2$—N$^s$Bu]-, (N$^s$Bu$_2$)$_2$-M-C$_5$Me$_3$-1-$^t$Bu-3-[(CH$_2$)$_2$—N$^s$Bu]-, (N$^t$Bu$_2$)$_2$-M-C$_5$Me$_3$-1-$^t$Bu-3-[(CH$_2$)$_2$—N$^s$Bu]-, (NH$_2$)(Cp)-M-C$_5$Me$_3$-1-$^t$Bu-3-[(CH$_2$)$_2$—N$^s$Bu]-, (NMe$_2$)(Cp)-M-C$_5$Me$_3$-1-$^t$Bu-3-[(CH$_2$)$_2$—N$^s$Bu]-, (NEt$_2$)(Cp)-M-C$_5$Me$_3$-1-$^t$Bu-3-[(CH$_2$)$_2$—N$^s$Bu]-, (N$^n$Pr$_2$)(Cp)-M-C$_5$Me$_3$-1-$^t$Bu-3-[(CH$_2$)$_2$—N$^s$Bu]-, (N$^i$Pr$_2$)(Cp)-M-C$_5$Me$_3$-1-$^t$Bu-3-[(CH$_2$)$_2$—N$^s$Bu]-, (N$^n$Bu$_2$)(Cp)-M-C$_5$Me$_3$-1-$^t$Bu-3-[(CH$_2$)$_2$—N$^s$Bu]-, (N$^i$Bu$_2$)(Cp)-M-C$_5$Me$_3$-1-$^t$Bu-3-[(CH$_2$)$_2$—N$^s$Bu]-, (N$^s$Bu$_2$)(Cp)-M-C$_5$Me$_3$-1-$^t$Bu-3-[(CH$_2$)$_2$—N$^s$Bu]-, (N$^t$Bu$_2$)(Cp)-M-C$_5$Me$_3$-1-$^t$Bu-3-[(CH$_2$)$_2$—N$^s$Bu]-, (OH)$_2$-M-C$_5$Me$_3$-1-$^t$Bu-3-[(CH$_2$)$_2$—N$^s$Bu]-, (OMe)$_2$-M-C$_5$Me$_3$-1-$^t$Bu-3-[(CH$_2$)$_2$—N$^s$Bu]-, (OEt)$_2$-M-C$_5$Me$_3$-1-$^t$Bu-3-[(CH$_2$)$_2$—N$^s$Bu]-, (O$^n$Pr)$_2$-M-C$_5$Me$_3$-1-$^t$Bu-3-[(CH$_2$)$_2$—N$^s$Bu]-, (O$^i$Pr)$_2$-M-C$_5$Me$_3$-1-$^t$Bu-3-[(CH$_2$)$_2$—N$^s$Bu]-, (O$^n$Bu)$_2$-M-C$_5$Me$_3$-1-$^t$Bu-3-[(CH$_2$)$_2$—N$^s$Bu]-, (O$^i$Bu$_2$-M-C$_5$Me$_3$-1-$^t$Bu-3-[(CH$_2$)$_2$—N$^s$Bu]-, (O$^t$Bu)$_2$-M-C$_5$Me$_3$-1-$^t$Bu-3-[(CH$_2$)$_2$—N$^s$Bu]-, (O$^s$Bu)$_2$-M-C$_5$Me$_3$-1-$^t$Bu-3-[(CH$_2$)$_2$—N$^s$Bu]-, (NH$_2$)$_2$-M-C$_5$Me$_3$-1-Et-2-[(CH$_2$)$_2$—N$^t$Bu]-, (NMe$_2$)$_2$-M-C$_5$Me$_3$-1-Et-2-[(CH$_2$)$_2$—N$^t$Bu]-, (NEt$_2$)$_2$-M-C$_5$Me$_3$-1-Et-2-[(CH$_2$)$_2$—N$^t$Bu]-, (N$^n$Pr$_2$)$_2$-M-C$_5$Me$_3$-1-Et-2-[(CH$_2$)$_2$—N$^t$Bu]-, (N$^i$Pr$_2$)$_2$-M-C$_5$Me$_3$-1-Et-2-[(CH$_2$)$_2$—N$^t$Bu]-, (N$^n$Bu$_2$)$_2$-M-C$_5$Me$_3$-1-Et-2-[(CH$_2$)$_2$—N$^t$Bu]-, (N$^i$Bu$_2$)$_2$-M-C$_5$Me$_3$-1-Et-2-[(CH$_2$)$_2$—N$^t$Bu]-, (N$^s$Bu$_2$)$_2$-M-C$_5$Me$_3$-1-Et-2-[(CH$_2$)$_2$—N$^t$Bu]-, (N$^t$Bu$_2$)$_2$-M-C$_5$Me$_3$-1-Et-2-[(CH$_2$)$_2$—N$^t$Bu]-, (NH$_2$)(Cp)-M-C$_5$Me$_3$-1-Et-2-[(CH$_2$)$_2$—N$^t$Bu]-, (NMe$_2$)(Cp)-M-C$_5$Me$_3$-1-Et-2-[(CH$_2$)$_2$—N$^t$Bu]-, (NEt$_2$)(Cp)-M-C$_5$Me$_3$-1-Et-2-[(CH$_2$)$_2$—N$^t$Bu]-, (N$^n$Pr$_2$)(Cp)-M-C$_5$Me$_3$-1-Et-2-[(CH$_2$)$_2$—N$^t$Bu]-, (N$^i$Pr$_2$)(Cp)-M-C$_5$Me$_3$-1-Et-2-[(CH$_2$)$_2$—N$^t$Bu]-, (N$^n$Bu$_2$)(Cp)-M-C$_5$Me$_3$-1-Et-2-[(CH$_2$)$_2$—N$^t$Bu]-, (N$^i$Bu$_2$)(Cp)-M-C$_5$Me$_3$-1-Et-2-[(CH$_2$)$_2$—N$^t$Bu]-, (N$^s$Bu$_2$)(Cp)-M-C$_5$Me$_3$-1-Et-2-[(CH$_2$)$_2$—N$^t$Bu]-, (N$^t$Bu$_2$)(Cp)-M-C$_5$Me$_3$-1-Et-2-[(CH$_2$)$_2$—N$^t$Bu]-, (OH)$_2$-M-C$_5$Me$_3$-1-Et-2-[(CH$_2$)$_2$—N$^t$Bu]-, (OMe)$_2$-M-C$_5$Me$_3$-1-Et-2-[(CH$_2$)$_2$—N$^t$Bu]-, (OEt)$_2$-M-C$_5$Me$_3$-1-Et-2-[(CH$_2$)$_2$—N$^t$Bu]-, (O$^n$Pr)$_2$-M-C$_5$Me$_3$-1-Et-2-[(CH$_2$)$_2$—N$^t$Bu]-, (O$^i$Pr)$_2$-M-C$_5$Me$_3$-1-Et-2-[(CH$_2$)$_2$—N$^t$Bu]-, (O$^n$Bu)$_2$-M-C$_5$Me$_3$-1-Et-2-[(CH$_2$)$_2$—N$^t$Bu]-, (O$^i$Bu$_2$-M-C$_5$Me$_3$-1-Et-2-[(CH$_2$)$_2$—N$^t$Bu]-, (O$^t$Bu)$_2$-M-C$_5$Me$_3$-1-Et-2-[(CH$_2$)$_2$—N$^t$Bu]-, (O$^s$Bu)$_2$-M-C$_5$Me$_3$-1-Et-2-[(CH$_2$)$_2$—N$^t$Bu]-, (NH$_2$)$_2$-M-C$_5$Me$_3$-1-Et-3-[(CH$_2$)$_2$—N$^t$Bu]-, (NMe$_2$)$_2$-M-C$_5$Me$_3$-1-Et-3-[(CH$_2$)$_2$—N$^t$Bu]-, (NEt$_2$)$_2$-M-C$_5$Me$_3$-1-Et-3-[(CH$_2$)$_2$—N$^t$Bu]-, (N$^n$Pr$_2$)$_2$-M-C$_5$Me$_3$-1-Et-3-[(CH$_2$)$_2$—N$^t$Bu]-, (N$^i$Pr$_2$)$_2$-M-C$_5$Me$_3$-1-Et-3-[(CH$_2$)$_2$—N$^t$Bu]-, (N$^n$Bu$_2$)$_2$-M-C$_5$Me$_3$-1-Et-3-[(CH$_2$)$_2$—N$^t$Bu]-, (N$^i$Bu$_2$)$_2$-M-C$_5$Me$_3$-1-Et-3-[(CH$_2$)$_2$—N$^t$Bu]-, (N$^s$Bu$_2$)$_2$-M-C$_5$Me$_3$-1-Et-3-[(CH$_2$)$_2$—N$^t$Bu]-, (N$^t$Bu$_2$)$_2$-M-C$_5$Me$_3$-1-Et-3-[(CH$_2$)$_2$—N$^t$Bu]-, (NH$_2$)(Cp)-M-C$_5$Me$_3$-1-Et-3-[(CH$_2$)$_2$—N$^t$Bu]-, (NMe$_2$)(Cp)-M-C$_5$Me$_3$-1-Et-3-[(CH$_2$)$_2$—N$^t$Bu]-, (NEt$_2$)(Cp)-M-C$_5$Me$_3$-1-Et-3-[(CH$_2$)$_2$—N$^t$Bu]-, (N$^n$Pr$_2$)(Cp)-M-C$_5$Me$_3$-1-Et-3-[(CH$_2$)$_2$—N$^t$Bu]-, (N$^i$Pr$_2$)(Cp)-M-C$_5$Me$_3$-1-Et-3-[(CH$_2$)$_2$—N$^t$Bu]-, (N$^n$Bu$_2$)(Cp)-M-C$_5$Me$_3$-1-Et-3-[(CH$_2$)$_2$—N$^t$Bu]-, (N$^i$Bu$_2$)(Cp)-M-C$_5$Me$_3$-1-Et-3-[(CH$_2$)$_2$—N$^t$Bu]-, (N$^s$Bu$_2$)(Cp)-M-C$_5$Me$_3$-1-Et-3-[(CH$_2$)$_2$—N$^t$Bu]-, (N$^t$Bu$_2$)(Cp)-M-C$_5$Me$_3$-1-Et-3-[(CH$_2$)$_2$—N$^t$Bu]-, (OH)$_2$-M-C$_5$Me$_3$-1-Et-3-[(CH$_2$)$_2$—N$^t$Bu]-, (OMe)$_2$-M-C$_5$Me$_3$-1-Et-3-[(CH$_2$)$_2$—N$^t$Bu]-, (OEt)$_2$-M-C$_5$Me$_3$-1-Et-3-[(CH$_2$)$_2$—N$^t$Bu]-, (O$^n$Pr)$_2$-M-C$_5$Me$_3$-1-Et-3-[(CH$_2$)$_2$—N$^t$Bu]-, (O$^i$Pr)$_2$-M-C$_5$Me$_3$-1-Et-3-[(CH$_2$)$_2$—N$^t$Bu]-, (O$^n$Bu)$_2$-M-C$_5$Me$_3$-1-Et-3-[(CH$_2$)$_2$—N$^t$Bu]-, (O$^i$Bu$_2$-M-C$_5$Me$_3$-1-Et-3-[(CH$_2$)$_2$—N$^t$Bu]-, (O$^t$Bu)$_2$-M-C$_5$Me$_3$-1-Et-3-[(CH$_2$)$_2$—N$^t$Bu]-, (O$^s$Bu)$_2$-M-C$_5$Me$_3$-1-Et-3-[(CH$_2$)$_2$—N$^t$Bu]-, (NH$_2$)$_2$-M-C$_5$Me$_3$-1-$^i$Pr-2-[(CH$_2$)$_2$—N$^t$Bu]-, (NMe$_2$)$_2$-M-C$_5$Me$_3$-1-$^i$Pr-2-[(CH$_2$)$_2$—N$^t$Bu]-, (NEt$_2$)$_2$-M-C$_5$Me$_3$-1-$^i$Pr-2-[(CH$_2$)$_2$—N$^t$Bu]-, (N$^n$Pr$_2$)$_2$-M-C$_5$Me$_3$-1-$^i$Pr-2-[(CH$_2$)$_2$—N$^t$Bu]-, (N$^i$Pr$_2$)$_2$-M-C$_5$Me$_3$-1-$^i$Pr-2-[(CH$_2$)$_2$—N$^t$Bu]-, (N$^n$Bu$_2$)$_2$-M-C$_5$Me$_3$-1-$^i$Pr-2-[(CH$_2$)$_2$—N$^t$Bu]-, (N$^i$Bu$_2$)$_2$-M-C$_5$Me$_3$-1-$^i$Pr-2-[(CH$_2$)$_2$—N$^t$Bu]-, (N$^s$Bu$_2$)$_2$-M-C$_5$Me$_3$-1-$^i$Pr-2-[(CH$_2$)$_2$—N$^t$Bu]-, (N$^t$Bu$_2$)$_2$-M-C$_5$Me$_3$-1-$^i$Pr-2-[(CH$_2$)$_2$—N$^t$Bu]-, (NH$_2$)(Cp)-M-C$_5$Me$_3$-1-$^i$Pr-2-[(CH$_2$)$_2$—N$^t$Bu]-, (NMe$_2$)(Cp)-M-C$_5$Me$_3$-1-$^i$Pr-2-[(CH$_2$)$_2$—N$^t$Bu]-, (NEt$_2$)(Cp)-M-C$_5$Me$_3$-1-$^i$Pr-2-[(CH$_2$)$_2$—N$^t$Bu]-, (N$^n$Pr$_2$)(Cp)-M-C$_5$Me$_3$-1-$^i$Pr-2-[(CH$_2$)$_2$—N$^t$Bu]-, (N$^i$Pr$_2$)(Cp)-M-C$_5$Me$_3$-1-$^i$Pr-2-[(CH$_2$)$_2$—N$^t$Bu]-, (N$^n$Bu$_2$)(Cp)-M-C$_5$Me$_3$-1-$^i$Pr-2-

[(CH$_2$)$_2$—N$^t$Bu]-, (N$^i$Bu$_2$)(Cp)-M-C$_5$Me$_3$-1-$^i$Pr-2-[(CH$_2$)$_2$—N$^t$Bu]-, (N$^s$Bu$_2$)(Cp)-M-C$_5$Me$_3$-1-$^i$Pr-2-[(CH$_2$)$_2$—N$^t$Bu]-, (N$^t$Bu$_2$)(Cp)-M-C$_5$Me$_3$-1-$^i$Pr-2-[(CH$_2$)$_2$—N$^t$Bu]-, (OH)$_2$-M-C$_5$Me$_3$-1-$^i$Pr-2-[(CH$_2$)$_2$—N$^t$Bu]-, (OMe)$_2$-M-C$_5$Me$_3$-1-$^i$Pr-2-[(CH$_2$)$_2$—N$^t$Bu]-, (OEt)$_2$-M-C$_5$Me$_3$-1-$^i$Pr-2-[(CH$_2$)$_2$—N$^t$Bu]-, (O$^n$Pr)$_2$-M-C$_5$Me$_3$-1-$^i$Pr-2-[(CH$_2$)$_2$—N$^t$Bu]-, (O$^i$Pr)$_2$-M-C$_5$Me$_3$-1-$^i$Pr-2-[(CH$_2$)$_2$—N$^t$Bu]-, (O$^n$Bu)$_2$-M-C$_5$Me$_3$-1-$^i$Pr-2-[(CH$_2$)$_2$—N$^t$Bu]-, (O$^i$Bu$_2$-M-C$_5$Me$_3$-1-$^i$Pr-2-[(CH$_2$)$_2$—N$^t$Bu]-, (O$^t$Bu)$_2$-M-C$_5$Me$_3$-1-$^i$Pr-2-[(CH$_2$)$_2$—N$^t$Bu]-, (O$^s$Bu)$_2$-M-C$_5$Me$_3$-1-$^i$Pr-2-[(CH$_2$)$_2$—N$^t$Bu]-, (NH$_2$)$_2$-M-C$_5$Me$_3$-1-$^i$Pr-3-[(CH$_2$)$_2$—N$^t$Bu]-, (NMe$_2$)$_2$-M-C$_5$Me$_3$-1-$^i$Pr-3-[(CH$_2$)$_2$—N$^t$Bu]-, (NEt$_2$)$_2$-M-C$_5$Me$_3$-1-$^i$Pr-3-[(CH$_2$)$_2$—N$^t$Bu]-, (N$^n$Pr$_2$)$_2$-M-C$_5$Me$_3$-1-$^i$Pr-3-[(CH$_2$)$_2$—N$^t$Bu]-, (N$^i$Pr$_2$)$_2$-M-C$_5$Me$_3$-1-$^i$Pr-3-[(CH$_2$)$_2$—N$^t$Bu]-, (N$^n$Bu$_2$)$_2$-M-C$_5$Me$_3$-1-$^i$Pr-3-[(CH$_2$)$_2$—N$^t$Bu]-, (N$^i$Bu$_2$)$_2$-M-C$_5$Me$_3$-1-$^i$Pr-3-[(CH$_2$)$_2$—N$^t$Bu]-, (N$^s$Bu$_2$)$_2$-M-C$_5$Me$_3$-1-$^i$Pr-3-[(CH$_2$)$_2$—N$^t$Bu]-, (N$^t$Bu$_2$)$_2$-M-C$_5$Me$_3$-1-$^i$Pr-3-[(CH$_2$)$_2$—N$^t$Bu]-, (NH$_2$)(Cp)-M-C$_5$Me$_3$-1-$^i$Pr-3-[(CH$_2$)$_2$—N$^t$Bu]-, (NMe$_2$)(Cp)-M-C$_5$Me$_3$-1-$^i$Pr-3-[(CH$_2$)$_2$—N$^t$Bu]-, (NEt$_2$)(Cp)-M-C$_5$Me$_3$-1-$^i$Pr-3-[(CH$_2$)$_2$—N$^t$Bu]-, (N$^n$Pr$_2$)(Cp)-M-C$_5$Me$_3$-1-$^i$Pr-3-[(CH$_2$)$_2$—N$^t$Bu]-, (N$^i$Pr$_2$)(Cp)-M-C$_5$Me$_3$-1-$^i$Pr-3-[(CH$_2$)$_2$—N$^t$Bu]-, (N$^n$Bu$_2$)(Cp)-M-C$_5$Me$_3$-1-$^i$Pr-3-[(CH$_2$)$_2$—N$^t$Bu]-, (N$^i$Bu$_2$)(Cp)-M-C$_5$Me$_3$-1-$^i$Pr-3-[(CH$_2$)$_2$—N$^t$Bu]-, (N$^s$Bu$_2$)(Cp)-M-C$_5$Me$_3$-1-$^i$Pr-3-[(CH$_2$)$_2$—N$^t$Bu]-, (N$^t$Bu$_2$)(Cp)-M-C$_5$Me$_3$-1-$^i$Pr-3-[(CH$_2$)$_2$—N$^t$Bu]-, (OH)$_2$-M-C$_5$Me$_3$-1-$^i$Pr-3-[(CH$_2$)$_2$—N$^t$Bu]-, (OMe)$_2$-M-C$_5$Me$_3$-1-$^i$Pr-3-[(CH$_2$)$_2$—N$^t$Bu]-, (OEt)$_2$-M-C$_5$Me$_3$-1-$^i$Pr-3-[(CH$_2$)$_2$—N$^t$Bu]-, (O$^n$Pr)$_2$-M-C$_5$Me$_3$-1-$^i$Pr-3-[(CH$_2$)$_2$—N$^t$Bu]-, (O$^i$Pr)$_2$-M-C$_5$Me$_3$-1-$^i$Pr-3-[(CH$_2$)$_2$—N$^t$Bu]-, (O$^n$Bu)$_2$-M-C$_5$Me$_3$-1-$^i$Pr-3-[(CH$_2$)$_2$—N$^t$Bu]-, (O$^i$Bu$_2$-M-C$_5$Me$_3$-1-$^i$Pr-3-[(CH$_2$)$_2$—N$^t$Bu]-, (O$^t$Bu)$_2$-M-C$_5$Me$_3$-1-$^i$Pr-3-[(CH$_2$)$_2$—N$^t$Bu]-, (O$^s$Bu)$_2$-M-C$_5$Me$_3$-1-$^i$Pr-3-[(CH$_2$)$_2$—N$^t$Bu]-, (NH$_2$)$_2$-M-C$_5$Me$_3$-1-$^t$Bu-2-[(CH$_2$)$_2$—N$^t$Bu]-, (NMe$_2$)$_2$-M-C$_5$Me$_3$-1-$^t$Bu-2-[(CH$_2$)$_2$—N$^t$Bu]-, (NEt$_2$)$_2$-M-C$_5$Me$_3$-1-$^t$Bu-2-[(CH$_2$)$_2$—N$^t$Bu]-, (N$^n$Pr$_2$)$_2$-M-C$_5$Me$_3$-1-$^t$Bu-2-[(CH$_2$)$_2$—N$^t$Bu]-, (N$^i$Pr$_2$)$_2$-M-C$_5$Me$_3$-1-$^t$Bu-2-[(CH$_2$)$_2$—N$^t$Bu]-, (N$^n$Bu$_2$)$_2$-M-C$_5$Me$_3$-1-$^t$Bu-2-[(CH$_2$)$_2$—N$^t$Bu]-, (N$^i$Bu$_2$)$_2$-M-C$_5$Me$_3$-1-$^t$Bu-2-[(CH$_2$)$_2$—N$^t$Bu]-, (N$^s$Bu$_2$)$_2$-M-C$_5$Me$_3$-1-$^t$Bu-2-[(CH$_2$)$_2$—N$^t$Bu]-, (N$^t$Bu$_2$)$_2$-M-C$_5$Me$_3$-1-$^t$Bu-2-[(CH$_2$)$_2$—N$^t$Bu]-, (NH$_2$)(Cp)-M-C$_5$Me$_3$-1-$^t$Bu-2-[(CH$_2$)$_2$—N$^t$Bu]-, (NMe$_2$)(Cp)-M-C$_5$Me$_3$-1-$^t$Bu-2-[(CH$_2$)$_2$—N$^t$Bu]-, (NEt$_2$)(Cp)-M-C$_5$Me$_3$-1-$^t$Bu-2-[(CH$_2$)$_2$—N$^t$Bu]-, (N$^n$Pr$_2$)(Cp)-M-C$_5$Me$_3$-1-$^t$Bu-2-[(CH$_2$)$_2$—N$^t$Bu]-, (N$^i$Pr$_2$)(Cp)-M-C$_5$Me$_3$-1-$^t$Bu-2-[(CH$_2$)$_2$—N$^t$Bu]-, (N$^n$Bu$_2$)(Cp)-M-C$_5$Me$_3$-1-$^t$Bu-2-[(CH$_2$)$_2$—N$^t$Bu]-, (N$^i$Bu$_2$)(Cp)-M-C$_5$Me$_3$-1-$^t$Bu-2-[(CH$_2$)$_2$—N$^t$Bu]-, (N$^s$Bu$_2$)(Cp)-M-C$_5$Me$_3$-1-$^t$Bu-2-[(CH$_2$)$_2$—N$^t$Bu]-, (N$^t$Bu$_2$)(Cp)-M-C$_5$Me$_3$-1-$^t$Bu-2-[(CH$_2$)$_2$—N$^t$Bu]-, (OH)$_2$-M-C$_5$Me$_3$-1-$^t$Bu-2-[(CH$_2$)$_2$—N$^t$Bu]-, (OMe)$_2$-M-C$_5$Me$_3$-1-$^t$Bu-2-[(CH$_2$)$_2$—N$^t$Bu]-, (OEt)$_2$-M-C$_5$Me$_3$-1-$^t$Bu-2-[(CH$_2$)$_2$—N$^t$Bu]-, (O$^n$Pr)$_2$-M-C$_5$Me$_3$-1-$^t$Bu-2-[(CH$_2$)$_2$—N$^t$Bu]-, (O$^i$Pr)$_2$-M-C$_5$Me$_3$-1-$^t$Bu-2-[(CH$_2$)$_2$—N$^t$Bu]-, (O$^n$Bu)$_2$-M-C$_5$Me$_3$-1-$^t$Bu-2-[(CH$_2$)$_2$—N$^t$Bu]-, (O$^i$Bu$_2$-M-C$_5$Me$_3$-1-$^t$Bu-2-[(CH$_2$)$_2$—N$^t$Bu]-, (O$^t$Bu)$_2$-M-C$_5$Me$_3$-1-$^t$Bu-2-[(CH$_2$)$_2$—N$^t$Bu]-, (O$^s$Bu)$_2$-M-C$_5$Me$_3$-1-$^t$Bu-2-[(CH$_2$)$_2$—N$^t$Bu]-, (NH$_2$)$_2$-M-C$_5$Me$_3$-1-$^t$Bu-3-[(CH$_2$)$_2$—N$^t$Bu]-, (NMe$_2$)$_2$-M-C$_5$Me$_3$-1-$^t$Bu-3-[(CH$_2$)$_2$—N$^t$Bu]-, (NEt$_2$)$_2$-M-C$_5$Me$_3$-1-$^t$Bu-3-[(CH$_2$)$_2$—N$^t$Bu]-, (N$^n$Pr$_2$)$_2$-M-C$_5$Me$_3$-1-$^t$Bu-3-[(CH$_2$)$_2$—N$^t$Bu]-, (N$^i$Pr$_2$)$_2$-M-C$_5$Me$_3$-1-$^t$Bu-3-[(CH$_2$)$_2$—N$^t$Bu]-, (N$^n$Bu$_2$)$_2$-M-C$_5$Me$_3$-1-$^t$Bu-3-[(CH$_2$)$_2$—N$^t$Bu]-, (N$^i$Bu$_2$)$_2$-M-C$_5$Me$_3$-1-$^t$Bu-3-[(CH$_2$)$_2$—N$^t$Bu]-, (N$^s$Bu$_2$)$_2$-M-C$_5$Me$_3$-1-$^t$Bu-3-[(CH$_2$)$_2$—N$^t$Bu]-, (N$^t$Bu$_2$)$_2$-M-C$_5$Me$_3$-1-$^t$Bu-3-[(CH$_2$)$_2$—N$^t$Bu]-, (NH$_2$)(Cp)-M-C$_5$Me$_3$-1-$^t$Bu-3-[(CH$_2$)$_2$—N$^t$Bu]-, (NMe$_2$)(Cp)-M-C$_5$Me$_3$-1-$^t$Bu-3-[(CH$_2$)$_2$—N$^t$Bu]-, (NEt$_2$)(Cp)-M-C$_5$Me$_3$-1-$^t$Bu-3-[(CH$_2$)$_2$—N$^t$Bu]-, (N$^n$Pr$_2$)(Cp)-M-C$_5$Me$_3$-1-$^t$Bu-3-[(CH$_2$)$_2$—N$^t$Bu]-, (N$^i$Pr$_2$)(Cp)-M-C$_5$Me$_3$-1-$^t$Bu-3-

[(CH$_2$)$_2$—N$^t$Bu]-, (N$^n$Bu$_2$)(Cp)-M-C$_5$Me$_3$-1-$^t$Bu-3-[(CH$_2$)$_2$—N$^t$Bu]-, (N$^i$Bu$_2$)(Cp)-M-C$_5$Me$_3$-1-$^t$Bu-3-[(CH$_2$)$_2$—N$^t$Bu]-, (N$^s$Bu$_2$)(Cp)-M-C$_5$Me$_3$-1-$^t$Bu-3-[(CH$_2$)$_2$—N$^t$Bu]-, (N$^t$Bu$_2$)(Cp)-M-C$_5$Me$_3$-1-$^t$Bu-3-[(CH$_2$)$_2$—N$^t$Bu]-, (OH)$_2$-M-C$_5$Me$_3$-1-$^t$Bu-3-[(CH$_2$)$_2$—N$^t$Bu]-, (OMe)$_2$-M-C$_5$Me$_3$-1-$^t$Bu-3-[(CH$_2$)$_2$—N$^t$Bu]-, (OEt)$_2$-M-C$_5$Me$_3$-1-$^t$Bu-3-[(CH$_2$)$_2$—N$^t$Bu]-, (O$^n$Pr)$_2$-M-C$_5$Me$_3$-1-$^t$Bu-3-[(CH$_2$)$_2$—N$^t$Bu]-, (O$^i$Pr)$_2$-M-C$_5$Me$_3$-1-$^t$Bu-3-[(CH$_2$)$_2$—N$^t$Bu]-, (O$^n$Bu)$_2$-M-C$_5$Me$_3$-1-$^t$Bu-3-[(CH$_2$)$_2$—N$^t$Bu]-, (O$^i$Bu$_2$-M-C$_5$Me$_3$-1-$^t$Bu-3-[(CH$_2$)$_2$—N$^t$Bu]-, (O$^t$Bu)$_2$-M-C$_5$Me$_3$-1-$^t$Bu-3-[(CH$_2$)$_2$—N$^t$Bu]-, (O$^s$Bu)$_2$-M-C$_5$Me$_3$-1-$^t$Bu-3-[(CH$_2$)$_2$—N$^t$Bu]-, (NH$_2$)$_2$-M-C$_5$Me$_4$-[(CH$_2$)$_2$—NH]—, (NMe$_2$)$_2$-M-C$_5$Me$_4$-[(CH$_2$)$_2$—NH]—, (NEt$_2$)$_2$-M-C$_5$Me$_4$-[(CH$_2$)$_2$—NH]—, (N$^n$Pr$_2$)$_2$-M-C$_5$Me$_4$-[(CH$_2$)$_2$—NH]—, (N$^i$Pr$_2$)$_2$-M-C$_5$Me$_4$-[(CH$_2$)$_2$—NH]—, (N$^n$Bu$_2$)$_2$-M-C$_5$Me$_4$-[(CH$_2$)$_2$—NH]—, (N$^i$Bu$_2$)$_2$-M-C$_5$Me$_4$-[(CH$_2$)$_2$—NH]—, (N$^s$Bu$_2$)$_2$-M-C$_5$Me$_4$-[(CH$_2$)$_2$—NH]—, (N$^t$Bu$_2$)$_2$-M-C$_5$Me$_4$-[(CH$_2$)$_2$—NH]—, (NH$_2$)(Cp)-M-C$_5$Me$_4$-[(CH$_2$)$_2$—NH]—, (NMe$_2$)(Cp)-M-C$_5$Me$_4$-[(CH$_2$)$_2$—NH]—, (NEt$_2$)(Cp)-M-C$_5$Me$_4$-[(CH$_2$)$_2$—NH]—, (N$^n$Pr$_2$)(Cp)-M-C$_5$Me$_4$-[(CH$_2$)$_2$—NH]—, (N$^i$Pr$_2$)(Cp)-M-C$_5$Me$_4$-[(CH$_2$)$_2$—NH]—, (N$^i$Bu$_2$)(Cp)-M-C$_5$Me$_4$-[(CH$_2$)$_2$—NH]—, (N$^i$Bu$_2$)(Cp)-M-C$_5$Me$_4$-[(CH$_2$)$_2$—NH]—, (N$^s$Bu$_2$)(Cp)-M-C$_5$Me$_4$-[(CH$_2$)$_2$—NH]—, (N$^t$Bu$_2$)(Cp)-M-C$_5$Me$_4$-[(CH$_2$)$_2$—NH]—, (OH)$_2$-M-C$_5$Me$_4$-[(CH$_2$)$_2$—NH]—, (OMe)$_2$-M-C$_5$Me$_4$-[(CH$_2$)$_2$—NH]—, (OEt)$_2$-M-C$_5$Me$_4$-[(CH$_2$)$_2$—NH]—, (O$^n$Pr)$_2$-M-C$_5$Me$_4$-[(CH$_2$)$_2$—NH]—, (O$^i$Pr)$_2$-M-C$_5$Me$_4$-[(CH$_2$)$_2$—NH]—, (O$^n$Bu)$_2$-M-C$_5$Me$_4$-[(CH$_2$)$_2$—NH]—, (O$^i$Bu$_2$-M-C$_5$Me$_4$-[(CH$_2$)$_2$—NH]—, (O$^t$Bu)$_2$-M-C$_5$Me$_4$-[(CH$_2$)$_2$—NH]—, (O$^s$Bu)$_2$-M-C$_5$Me$_4$-[(CH$_2$)$_2$—NH]—, (NH$_2$)$_2$-M-C$_5$Me$_4$-[(CH$_2$)$_2$—NH]—, (NMe$_2$)$_2$-M-C$_5$Me$_4$-[(CH$_2$)$_2$—NH]—, (NEt$_2$)$_2$-M-C$_5$Me$_4$-[(CH$_2$)$_2$—NH]—, (N$^n$Pr$_2$)$_2$-M-C$_5$Me$_4$-[(CH$_2$)$_2$—NH]—, (N$^i$Pr$_2$)$_2$-M-C$_5$Me$_4$-[(CH$_2$)$_2$—NH]—, (N$^n$Bu$_2$)$_2$-M-C$_5$Me$_4$-[(CH$_2$)$_2$—NH]—, (N$^i$Bu$_2$)$_2$-M-C$_5$Me$_4$-[(CH$_2$)$_2$—NH]—, (N$^s$Bu$_2$)$_2$-M-C$_5$Me$_4$-[(CH$_2$)$_2$—NH]—, (N$^t$Bu$_2$)$_2$-M-C$_5$Me$_4$-[(CH$_2$)$_2$—NH]—, (NH$_2$)(Cp)-M-C$_5$Me$_4$-[(CH$_2$)$_2$—NH]—, (NMe$_2$)(Cp)-M-C$_5$Me$_4$-[(CH$_2$)$_2$—NH]—, (NEt$_2$)(Cp)-M-C$_5$Me$_4$-[(CH$_2$)$_2$—NH]—, (N$^n$Pr$_2$)(Cp)-M-C$_5$Me$_4$-[(CH$_2$)$_2$—NH]—, (N$^i$Pr$_2$)(Cp)-M-C$_5$Me$_4$-[(CH$_2$)$_2$—NH]—, (N$^n$Bu$_2$)(Cp)-M-C$_5$Me$_4$-[(CH$_2$)$_2$—NH]—, (N$^i$Bu$_2$)(Cp)-M-C$_5$Me$_4$-[(CH$_2$)$_2$—NH]—, (N$^s$Bu$_2$)(Cp)-M-C$_5$Me$_4$-[(CH$_2$)$_2$—NH]—, (N$^t$Bu$_2$)(Cp)-M-C$_5$Me$_4$-[(CH$_2$)$_2$—NH]—, (OH)$_2$-M-C$_5$Me$_4$-[(CH$_2$)$_2$—NH]—, (OMe)$_2$-M-C$_5$Me$_4$-[(CH$_2$)$_2$—NH]—, (OEt)$_2$-M-C$_5$Me$_4$-[(CH$_2$)$_2$—NH]—, (O$^n$Pr)$_2$-M-C$_5$Me$_4$-[(CH$_2$)$_2$—NH]—, (O$^i$Pr)$_2$-M-C$_5$Me$_4$-[(CH$_2$)$_2$—NH]—, (O$^n$Bu)$_2$-M-C$_5$Me$_4$-[(CH$_2$)$_2$—NH]—, (O$^i$Bu$_2$-M-C$_5$Me$_4$-[(CH$_2$)$_2$—NH]—, (O$^t$Bu)$_2$-M-C$_5$Me$_4$-[(CH$_2$)$_2$—NH]—, (O$^s$Bu)$_2$-M-C$_5$Me$_4$-[(CH$_2$)$_2$—NH]—, (NH$_2$)$_2$-M-C$_5$Me$_4$-[(CH$_2$)$_2$—NMe]-, (NMe$_2$)$_2$-M-C$_5$Me$_4$-[(CH$_2$)$_2$—NMe]-, (NEt$_2$)$_2$-M-C$_5$Me$_4$-[(CH$_2$)$_2$—NMe]-, (N$^n$Pr$_2$)$_2$-M-C$_5$Me$_4$-[(CH$_2$)$_2$—NMe]-, (N$^i$Pr$_2$)$_2$-M-C$_5$Me$_4$-[(CH$_2$)$_2$—NMe]-, (N$^n$Bu$_2$)$_2$-M-C$_5$Me$_4$-[(CH$_2$)$_2$—NMe]-, (N$^i$Bu$_2$)$_2$-M-C$_5$Me$_4$-[(CH$_2$)$_2$—NMe]-, (N$^s$Bu$_2$)$_2$-M-C$_5$Me$_4$-[(CH$_2$)$_2$—NMe]-, (N$^t$Bu$_2$)$_2$-M-C$_5$Me$_4$-[(CH$_2$)$_2$—NMe]-, (NH$_2$)(Cp)-M-C$_5$Me$_4$-[(CH$_2$)$_2$—NMe]-, (NMe$_2$)(Cp)-M-C$_5$Me$_4$-[(CH$_2$)$_2$—NMe]-, (NEt$_2$)(Cp)-M-C$_5$Me$_4$-[(CH$_2$)$_2$—NMe]-, (N$^n$Pr$_2$)(Cp)-M-C$_5$Me$_4$-[(CH$_2$)$_2$—NMe]-, (N$^i$Pr$_2$)(Cp)-M-C$_5$Me$_4$-[(CH$_2$)$_2$—NMe]-, (N$^n$Bu$_2$)(Cp)-M-C$_5$Me$_4$-[(CH$_2$)$_2$—NMe]-, (N$^i$Bu$_2$)(Cp)-M-C$_5$Me$_4$-[(CH$_2$)$_2$—NMe]-, (N$^s$Bu$_2$)(Cp)-M-C$_5$Me$_4$-[(CH$_2$)$_2$—NMe]-, (N$^t$Bu$_2$)(Cp)-M-C$_5$Me$_4$-[(CH$_2$)$_2$—NMe]-, (OH)$_2$-M-C$_5$Me$_4$-[(CH$_2$)$_2$—NMe]-, (OMe)$_2$-M-C$_5$Me$_4$-[(CH$_2$)$_2$—NMe]-, (OEt)$_2$-M-C$_5$Me$_4$-[(CH$_2$)$_2$—NMe]-, (O$^n$Pr)$_2$-M-C$_5$Me$_4$-[(CH$_2$)$_2$—NMe]-, (O$^i$Pr)$_2$-M-C$_5$Me$_4$-[(CH$_2$)$_2$—NMe]-, (O$^n$Bu)$_2$-M-C$_5$Me$_4$-[(CH$_2$)$_2$—NMe]-, (O$^i$Bu$_2$-M-C$_5$Me$_4$-[(CH$_2$)$_2$—NMe]-, (O$^t$Bu)$_2$-M-C$_5$Me$_4$-[(CH$_2$)$_2$—NMe]-, (O$^s$Bu)$_2$-M-C$_5$Me$_4$-[(CH$_2$)$_2$—NMe]-, (NH$_2$)$_2$-M-

C$_5$Me$_4$-[(CH$_2$)$_2$—NMe]-, (NMe$_2$)$_2$-M-C$_5$Me$_4$-[(CH$_2$)$_2$—NMe]-, (NEt$_2$)$_2$-M-C$_5$Me$_4$-[(CH$_2$)$_2$—NMe]-, (N$^n$Pr$_2$)$_2$-M-C$_5$Me$_4$-[(CH$_2$)$_2$—NMe]-, (N$^i$Pr$_2$)$_2$-M-C$_5$Me$_4$-[(CH$_2$)$_2$—NMe]-, (N$^n$Bu$_2$)$_2$-M-C$_5$Me$_4$-[(CH$_2$)$_2$—NMe]-, (N$^i$Bu$_2$)$_2$-M-C$_5$Me$_4$-[(CH$_2$)$_2$—NMe]-, (N$^s$Bu$_2$)$_2$-M-C$_5$Me$_4$-[(CH$_2$)$_2$—NMe]-, (N$^t$Bu$_2$)$_2$-M-C$_5$Me$_4$-[(CH$_2$)$_2$—NMe]-, (NH$_2$)(Cp)-M-C$_5$Me$_4$-[(CH$_2$)$_2$—NMe]-, (NMe$_2$)(Cp)-M-C$_5$Me$_4$-[(CH$_2$)$_2$—NMe]-, (NEt$_2$)(Cp)-M-C$_5$Me$_4$-[(CH$_2$)$_2$—NMe]-, (N$^n$Pr$_2$)(Cp)-M-C$_5$Me$_4$-[(CH$_2$)$_2$—NMe]-, (N$^i$Pr$_2$)(Cp)-M-C$_5$Me$_4$-[(CH$_2$)$_2$—NMe]-, (N$^n$Bu$_2$)(Cp)-M-C$_5$Me$_4$-[(CH$_2$)$_2$—NMe]-, (N$^i$Bu$_2$)(Cp)-M-C$_5$Me$_4$-[(CH$_2$)$_2$—NMe]-, (N$^s$Bu$_2$)(Cp)-M-C$_5$Me$_4$-[(CH$_2$)$_2$—NMe]-, (N$^t$Bu$_2$)(Cp)-M-C$_5$Me$_4$-[(CH$_2$)$_2$—NMe]-, (OH)$_2$-M-C$_5$Me$_4$-[(CH$_2$)$_2$ —NMe]-, (OMe)$_2$-M-C$_5$Me$_4$-[(CH$_2$)$_2$—NMe]-, (OEt)$_2$-M-C$_5$Me$_4$-[(CH$_2$)$_2$—NMe]-, (O$^n$Pr)$_2$-M-C$_5$Me$_4$-[(CH$_2$)$_2$—NMe]-, (O$^i$Pr)$_2$-M-C$_5$Me$_4$-[(CH$_2$)$_2$—NMe]-, (O$^n$Bu)$_2$-M-C$_5$Me$_4$-[(CH$_2$)$_2$—NMe]-, (O$^i$Bu$_2$-M-C$_5$Me$_4$-[(CH$_2$)$_2$—NMe]-, (O$^t$Bu)$_2$-M-C$_5$Me$_4$-[(CH$_2$)$_2$—NMe]-, (O$^s$Bu)$_2$-M-C$_5$Me$_4$-[(CH$_2$)$_2$—NMe]-, (NH$_2$)$_2$-M-C$_5$Me$_4$-[(CH$_2$)$_2$—NEt]-, (NMe$_2$)$_2$-M-C$_5$Me$_4$-[(CH$_2$)$_2$—NEt]-, (NEt$_2$)$_2$-M-C$_5$Me$_4$-[(CH$_2$)$_2$—NEt]-, (N$^n$Pr$_2$)$_2$-M-C$_5$Me$_4$-[(CH$_2$)$_2$—NEt]-, (N$^i$Pr$_2$)$_2$-M-C$_5$Me$_4$-[(CH$_2$)$_2$—NEt]-, (N$^n$Bu$_2$)$_2$-M-C$_5$Me$_4$-[(CH$_2$)$_2$—NEt]-, (N$^i$Bu$_2$)$_2$-M-C$_5$Me$_4$-[(CH$_2$)$_2$—NEt]-, (N$^s$Bu$_2$)$_2$-M-C$_5$Me$_4$-[(CH$_2$)$_2$—NEt]-, (N$^t$Bu$_2$)$_2$-M-C$_5$Me$_4$-[(CH$_2$)$_2$—NEt]-, (NH$_2$)(Cp)-M-C$_5$Me$_4$-[(CH$_2$)$_2$—NEt]-, (NMe$_2$)(Cp)-M-C$_5$Me$_4$-[(CH$_2$)$_2$—NEt]-, (NEt$_2$)(Cp)-M-C$_5$Me$_4$-[(CH$_2$)$_2$—NEt]-, (N$^n$Pr$_2$)(Cp)-M-C$_5$Me$_4$-[(CH$_2$)$_2$—NEt]-, (N$^i$Pr$_2$)(Cp)-M-C$_5$Me$_4$-[(CH$_2$)$_2$—NEt]-, (N$^n$Bu$_2$)(Cp)-M-C$_5$Me$_4$-[(CH$_2$)$_2$—NEt]-, (N$^i$Bu$_2$)(Cp)-M-C$_5$Me$_4$-[(CH$_2$)$_2$—NEt]-, (N$^s$Bu$_2$)(Cp)-M-C$_5$Me$_4$-[(CH$_2$)$_2$—NEt]-, (N$^t$Bu$_2$)(Cp)-M-C$_5$Me$_4$-[(CH$_2$)$_2$—NEt]-, (OH)$_2$-M-C$_5$Me$_4$-[(CH$_2$)$_2$—NEt]-, (OMe)$_2$-M-C$_5$Me$_4$-[(CH$_2$)$_2$—NEt]-, (OEt)$_2$-M-C$_5$Me$_4$-[(CH$_2$)$_2$—NEt]-, (O$^n$Pr)$_2$-M-C$_5$Me$_4$-[(CH$_2$)$_2$—NEt]-, (O$^i$Pr)$_2$-M-C$_5$Me$_4$-[(CH$_2$)$_2$—NEt]-, (O$^n$Bu)$_2$-M-C$_5$Me$_4$-[(CH$_2$)$_2$—NEt]-, (O$^i$Bu$_2$-M-C$_5$Me$_4$-[(CH$_2$)$_2$—NEt]-, (O$^t$Bu)$_2$-M-C$_5$Me$_4$-[(CH$_2$)$_2$—NEt]-, (O$^s$Bu)$_2$-M-C$_5$Me$_4$-[(CH$_2$)$_2$—NEt]-, (NH$_2$)$_2$-M-C$_5$Me$_4$-[(CH$_2$)$_2$—NEt]-, (NMe$_2$)$_2$-M-C$_5$Me$_4$-[(CH$_2$)$_2$—NEt]-, (NEt$_2$)$_2$-M-C$_5$Me$_4$-[(CH$_2$)$_2$—NEt]-, (N$^n$Pr$_2$)$_2$-M-C$_5$Me$_4$-[(CH$_2$)$_2$—NEt]-, (N$^i$Pr$_2$)$_2$-M-C$_5$Me$_4$-[(CH$_2$)$_2$—NEt]-, (N$^n$Bu$_2$)$_2$-M-C$_5$Me$_4$-[(CH$_2$)$_2$—NEt]-, (N$^i$Bu$_2$)$_2$-M-C$_5$Me$_4$-[(CH$_2$)$_2$—NEt]-, (N$^s$Bu$_2$)$_2$-M-C$_5$Me$_4$-[(CH$_2$)$_2$—NEt]-, (N$^t$Bu$_2$)$_2$-M-C$_5$Me$_4$-[(CH$_2$)$_2$—NEt]-, (NH$_2$)(Cp)-M-C$_5$Me$_4$-[(CH$_2$)$_2$—NEt]-, (NMe$_2$)(Cp)-M-C$_5$Me$_4$-[(CH$_2$)$_2$—NEt]-, (NEt$_2$)(Cp)-M-C$_5$Me$_4$-[(CH$_2$)$_2$—NEt]-, (N$^n$Pr$_2$)(Cp)-M-C$_5$Me$_4$-[(CH$_2$)$_2$—NEt]-, (N$^i$Pr$_2$)(Cp)-M-C$_5$Me$_4$-[(CH$_2$)$_2$—NEt]-, (N$^n$Bu$_2$)(Cp)-M-C$_5$Me$_4$-[(CH$_2$)$_2$—NEt]-, (N$^i$Bu$_2$)(Cp)-M-C$_5$Me$_4$-[(CH$_2$)$_2$—NEt]-, (N$^s$Bu$_2$)(Cp)-M-C$_5$Me$_4$-[(CH$_2$)$_2$—NEt]-, (N$^t$Bu$_2$)(Cp)-M-C$_5$Me$_4$-[(CH$_2$)$_2$—NEt]-, (OH)$_2$-M-C$_5$Me$_4$-[(CH$_2$)$_2$—NEt]-, (OMe)$_2$-M-C$_5$Me$_4$-[(CH$_2$)$_2$—NEt]-, (OEt)$_2$-M-C$_5$Me$_4$-[(CH$_2$)$_2$—NEt]-, (O$^n$Pr)$_2$-M-C$_5$Me$_4$-[(CH$_2$)$_2$—NEt]-, (O$^i$Pr)$_2$-M-C$_5$Me$_4$-[(CH$_2$)$_2$—NEt]-, (O$^n$Bu)$_2$-M-C$_5$Me$_4$-[(CH$_2$)$_2$—NEt]-, (O$^i$Bu$_2$-M-C$_5$Me$_4$-[(CH$_2$)$_2$—NEt]-, (O$^t$Bu)$_2$-M-C$_5$Me$_4$-[(CH$_2$)$_2$—NEt]-, (O$^s$Bu)$_2$-M-C$_5$Me$_4$-[(CH$_2$)$_2$—NEt]-, (NH$_2$)$_2$-M-C$_5$Me$_4$-[(CH$_2$)$_2$—NiPr]—, (NMe$_2$)$_2$-M-C$_5$Me$_4$-[(CH$_2$)$_2$—NiPr]—, (NEt$_2$)$_2$-M-C$_5$Me$_4$-[(CH$_2$)$_2$—NiPr]—, (N$^n$Pr$_2$)$_2$-M-C$_5$Me$_4$-[(CH$_2$)$_2$—NiPr]—, (N$^i$Pr$_2$)$_2$-M-C$_5$Me$_4$-[(CH$_2$)$_2$—NiPr]—, (N$^n$Bu$_2$)$_2$-M-C$_5$Me$_4$-[(CH$_2$)$_2$—NiPr]—, (N$^i$Bu$_2$)$_2$-M-C$_5$Me$_4$-[(CH$_2$)$_2$—NiPr]—, (N$^s$Bu$_2$)$_2$-M-C$_5$Me$_4$-[(CH$_2$)$_2$—NiPr]—, (N$^t$Bu$_2$)$_2$-M-C$_5$Me$_4$-[(CH$_2$)$_2$—NiPr]—, (NH$_2$)(Cp)-M-C$_5$Me$_4$-[(CH$_2$)$_2$—NiPr]—, (NMe$_2$)(Cp)-M-C$_5$Me$_4$-[(CH$_2$)$_2$—NiPr]—, (NEt$_2$)(Cp)-M-C$_5$Me$_4$-[(CH$_2$)$_2$—NiPr]—, (N$^n$Pr$_2$)(Cp)-M-C$_5$Me$_4$-[(CH$_2$)$_2$—NiPr]—, (N$^i$Pr$_2$)(Cp)-M-C$_5$Me$_4$-[(CH$_2$)$_2$—NiPr]—, (N$^n$Bu$_2$)(Cp)-M-C$_5$Me$_4$-[(CH$_2$)$_2$—NiPr]—, (N$^i$Bu$_2$)(Cp)-M-C$_5$Me$_4$-[(CH$_2$)$_2$—NiPr]—, (N$^s$Bu$_2$)(Cp)-M-C$_5$Me$_4$-[(CH$_2$)$_2$—NiPr]—, (N$^t$Bu$_2$)(Cp)-M-C$_5$Me$_4$-[(CH$_2$)$_2$—NiPr]—, (OH)$_2$-M-C$_5$Me$_4$-[(CH$_2$)$_2$—NiPr]—, (OMe)$_2$-M-C$_5$Me$_4$-[(CH$_2$)$_2$—NiPr]—, (OEt)$_2$-M-C$_5$Me$_4$-[(CH$_2$)$_2$—NiPr]—, (O$^n$Pr)$_2$-M-C$_5$Me$_4$-[(CH$_2$)$_2$—NiPr]—, (O$^i$Pr)$_2$-M-C$_5$Me$_4$-[(CH$_2$)$_2$—NiPr]—, (O$^n$Bu)$_2$-M-C$_5$Me$_4$-[(CH$_2$)$_2$—NiPr]—, (O$^i$Bu$_2$-M-C$_5$Me$_4$-[(CH$_2$)$_2$—NiPr]—, (O$^t$Bu)$_2$-M-C$_5$Me$_4$-[(CH$_2$)$_2$—NiPr]—, (O$^s$Bu)$_2$-M-C$_5$Me$_4$-[(CH$_2$)$_2$—NiPr]—, (NH$_2$)$_2$-M-C$_5$Me$_4$-[(CH$_2$)$_2$—NiPr]—, (NMe$_2$)$_2$-M-C$_5$Me$_4$-[(CH$_2$)$_2$—NiPr]—, (NEt$_2$)$_2$-M-C$_5$Me$_4$-[(CH$_2$)$_2$—NiPr]—, (N$^n$Pr$_2$)$_2$-M-C$_5$Me$_4$-[(CH$_2$)$_2$—NiPr]—, (N$^i$Pr$_2$)$_2$-M-C$_5$Me$_4$-[(CH$_2$)$_2$—NiPr]—, (N$^n$Bu$_2$)$_2$-M-C$_5$Me$_4$-[(CH$_2$)$_2$—NiPr]—, (N$^i$Bu$_2$)$_2$-M-C$_5$Me$_4$-[(CH$_2$)$_2$—NiPr]—, (N$^s$Bu$_2$)$_2$-M-C$_5$Me$_4$-[(CH$_2$)$_2$—NiPr]—, (N$^t$Bu$_2$)$_2$-M-C$_5$Me$_4$-[(CH$_2$)$_2$—NiPr]—, (NH$_2$)(Cp)-M-C$_5$Me$_4$-[(CH$_2$)$_2$—NiPr]—, (NMe$_2$)(Cp)-M-C$_5$Me$_4$-[(CH$_2$)$_2$—NiPr]—, (NEt$_2$)(Cp)-M-C$_5$Me$_4$-[(CH$_2$)$_2$—NiPr]—, (N$^n$Pr$_2$)(Cp)-M-C$_5$Me$_4$-[(CH$_2$)$_2$—NiPr]—, (N$^i$Pr$_2$)(Cp)-M-C$_5$Me$_4$-[(CH$_2$)$_2$—NiPr]—, (N$^n$Bu$_2$)(Cp)-M-C$_5$Me$_4$-[(CH$_2$)$_2$—NiPr]—, (N$^i$Bu$_2$)(Cp)-M-C$_5$Me$_4$-[(CH$_2$)$_2$—NiPr]—, (N$^s$Bu$_2$)(Cp)-M-C$_5$Me$_4$-[(CH$_2$)$_2$—NiPr]—, (N$^t$Bu$_2$)(Cp)-M-C$_5$Me$_4$-[(CH$_2$)$_2$—NiPr]—, (OH)$_2$-M-C$_5$Me$_4$-[(CH$_2$)$_2$—NiPr]—, (OMe)$_2$-M-C$_5$Me$_4$-[(CH$_2$)$_2$—NiPr]—, (OEt)$_2$-M-C$_5$Me$_4$-[(CH$_2$)$_2$—NiPr]—, (O$^n$Pr)$_2$-M-C$_5$Me$_4$-[(CH$_2$)$_2$—NiPr]—, (O$^i$Pr)$_2$-M-C$_5$Me$_4$-[(CH$_2$)$_2$—NiPr]—, (O$^n$Bu)$_2$-M-C$_5$Me$_4$-[(CH$_2$)$_2$—NiPr]—, (O$^i$Bu$_2$-M-C$_5$Me$_4$-[(CH$_2$)$_2$—NiPr]—, (O$^t$Bu)$_2$-M-C$_5$Me$_4$-[(CH$_2$)$_2$—NiPr]—, (O$^s$Bu)$_2$-M-C$_5$Me$_4$-[(CH$_2$)$_2$—NiPr]—, (NH$_2$)$_2$-M-C$_5$Me$_4$-[(CH$_2$)$_2$—NnPr]—, (NMe$_2$)$_2$-M-C$_5$Me$_4$-[(CH$_2$)$_2$—NnPr]—, (NEt$_2$)$_2$-M-C$_5$Me$_4$-[(CH$_2$)$_2$—NnPr]—, (N$^n$Pr$_2$)$_2$-M-C$_5$Me$_4$-[(CH$_2$)$_2$—NnPr]—, (N$^i$Pr$_2$)$_2$-M-C$_5$Me$_4$-[(CH$_2$)$_2$—NnPr]—, (N$^n$Bu$_2$)$_2$-M-C$_5$Me$_4$-[(CH$_2$)$_2$—NnPr]—, (N$^i$Bu$_2$)$_2$-M-C$_5$Me$_4$-[(CH$_2$)$_2$—NnPr]—, (N$^s$Bu$_2$)$_2$-M-C$_5$Me$_4$-[(CH$_2$)$_2$—NnPr]—, (N$^t$Bu$_2$)$_2$-M-C$_5$Me$_4$-[(CH$_2$)$_2$—NnPr]—, (NH$_2$)(Cp)-M-C$_5$Me$_4$-[(CH$_2$)$_2$—NnPr]—, (NMe$_2$)(Cp)-M-C$_5$Me$_4$-[(CH$_2$)$_2$—NnPr]—, (NEt$_2$)(Cp)-M-C$_5$Me$_4$-[(CH$_2$)$_2$—NnPr]—, (N$^n$Pr$_2$)(Cp)-M-C$_5$Me$_4$-[(CH$_2$)$_2$—NnPr]—, (N$^i$Pr$_2$)(Cp)-M-C$_5$Me$_4$-[(CH$_2$)$_2$—NnPr]—, (N$^n$Bu$_2$)(Cp)-M-C$_5$Me$_4$-[(CH$_2$)$_2$—NnPr]—, (N$^i$Bu$_2$)(Cp)-M-C$_5$Me$_4$-[(CH$_2$)$_2$—NnPr]—, (N$^s$Bu$_2$)(Cp)-M-C$_5$Me$_4$-[(CH$_2$)$_2$—NnPr]—, (N$^t$Bu$_2$)(Cp)-M-C$_5$Me$_4$-[(CH$_2$)$_2$—NnPr]—, (OH)$_2$-M-C$_5$Me$_4$-[(CH$_2$)$_2$—NnPr]—, (OMe)$_2$-M-C$_5$Me$_4$-[(CH$_2$)$_2$—NnPr]—, (OEt)$_2$-M-C$_5$Me$_4$-[(CH$_2$)$_2$—NnPr]—, (O$^n$Pr)$_2$-M-C$_5$Me$_4$-[(CH$_2$)$_2$—NnPr]—, (O$^i$Pr)$_2$-M-C$_5$Me$_4$-[(CH$_2$)$_2$—NnPr]—, (O$^n$Bu)$_2$-M-C$_5$Me$_4$-[(CH$_2$)$_2$—NnPr]—, (O$^i$Bu$_2$-M-C$_5$Me$_4$-[(CH$_2$)$_2$—NnPr]—, (O$^t$Bu)$_2$-M-C$_5$Me$_4$-[(CH$_2$)$_2$ —NnPr]—, (O$^s$Bu)$_2$-M-C$_5$Me$_4$-[(CH$_2$)$_2$—NnPr]—, (NH$_2$)$_2$-M-C$_5$Me$_4$-[(CH$_2$)$_2$—NnPr]—, (NMe$_2$)$_2$-M-C$_5$Me$_4$-[(CH$_2$)$_2$—NnPr]—, (NEt$_2$)$_2$-M-C$_5$Me$_4$-[(CH$_2$)$_2$—NnPr]—, (N$^n$Pr$_2$)$_2$-M-C$_5$Me$_4$-[(CH$_2$)$_2$—NnPr]—, (N$^i$Pr$_2$)$_2$-M-C$_5$Me$_4$-[(CH$_2$)$_2$—NnPr]—, (N$^n$Bu$_2$)$_2$-M-C$_5$Me$_4$-[(CH$_2$)$_2$—NnPr]—, (N$^i$Bu$_2$)$_2$-M-C$_5$Me$_4$-[(CH$_2$)$_2$—NnPr]—, (N$^s$Bu$_2$)$_2$-M-C$_5$Me$_4$-[(CH$_2$)$_2$—NnPr]—, (N$^t$Bu$_2$)$_2$-M-C$_5$Me$_4$-[(CH$_2$)$_2$—NnPr]—, (NH$_2$)(Cp)-M-C$_5$Me$_4$-[(CH$_2$)$_2$ —NnPr]—, (NMe$_2$)(Cp)-M-C$_5$Me$_4$-[(CH$_2$)$_2$—NnPr]—, (NEt$_2$)(Cp)-M-C$_5$Me$_4$-[(CH$_2$)$_2$—NnPr]—, (N$^n$Pr$_2$)(Cp)-M-C$_5$Me$_4$-[(CH$_2$)$_2$—NnPr]—, (N$^i$Pr$_2$)(Cp)-M-C$_5$Me$_4$-[(CH$_2$)$_2$—NnPr]—, (N$^n$Bu$_2$)(Cp)-M-C$_5$Me$_4$-[(CH$_2$)$_2$—NnPr]—, (N$^i$Bu$_2$)(Cp)-M-C$_5$Me$_4$-[(CH$_2$)$_2$—NnPr]—, (N$^s$Bu$_2$)(Cp)-M-C$_5$Me$_4$-[(CH$_2$)$_2$—NnPr]—, (N$^t$Bu$_2$)(Cp)-M-C$_5$Me$_4$-[(CH$_2$)$_2$—NnPr]—, (OH)$_2$-M-C$_5$Me$_4$-[(CH$_2$)$_2$—NnPr]—, (OMe)$_2$-M-C$_5$Me$_4$-[(CH$_2$)$_2$—NnPr]—, (OEt)$_2$-M-C$_5$Me$_4$-[(CH$_2$)$_2$—NnPr]—, (O$^n$Pr)$_2$-M-C$_5$Me$_4$-[(CH$_2$)$_2$—NnPr]—, (O$^i$Pr)$_2$-M-C$_5$Me$_4$-[(CH$_2$)$_2$—NnPr]—, (O$^n$Bu)$_2$-M-C$_5$Me$_4$-[(CH$_2$)$_2$—NnPr]—, (O$^i$Bu$_2$-M-C$_5$Me$_4$-[(CH$_2$)$_2$—NnPr]—(O$^t$Bu)$_2$-M-C$_5$Me$_4$-[(CH$_2$)$_2$—NnPr]—, (O$^s$Bu)$_2$-M-C$_5$Me$_4$-[(CH$_2$)$_2$—NnPr]—, (NH$_2$)$_2$-M-C$_5$Me$_4$-

$[(CH_2)_2$—NnBu]-, $(NMe_2)_2$-M-$C_5Me_4$-$[(CH_2)_2$—NnBu]-, $(NEt_2)_2$-M-$C_5Me_4$-$[(CH_2)_2$—NnBu]-, $(N^nPr_2)_2$-M-$C_5Me_4$-$[(CH_2)_2$—NnBu]-, $(N^iPr_2)_2$-M-$C_5Me_4$-$[(CH_2)_2$—NnBu]-, $(N^nBu_2)_2$-M-$C_5Me_4$-$[(CH_2)_2$—NnBu]-, $(N^iBu_2)_2$-M-$C_5Me_4$-$[(CH_2)_2$—NnBu]-, $(N^sBu_2)_2$-M-$C_5Me_4$-$[(CH_2)_2$—NnBu]-, $(N^tBu_2)_2$-M-$C_5Me_4$-$[(CH_2)_2$—NnBu]-, $(NH_2)(Cp)$-M-$C_5Me_4$-$[(CH_2)_2$—NnBu]-, $(NMe_2)(Cp)$-M-$C_5Me_4$-$[(CH_2)_2$—NnBu]-, $(NEt_2)(Cp)$-M-$C_5Me_4$-$[(CH_2)_2$—NnBu]-, $(N^nPr_2)(Cp)$-M-$C_5Me_4$-$[(CH_2)_2$—NnBu]-, $(N^iPr_2)(Cp)$-M-$C_5Me_4$-$[(CH_2)_2$—NnBu]-, $(N^nBu_2)(Cp)$-M-$C_5Me_4$-$[(CH_2)_2$—NnBu]-, $(N^iBu_2)(Cp)$-M-$C_5Me_4$-$[(CH_2)_2$—NnBu]-, $(N^sBu_2)(Cp)$-M-$C_5Me_4$-$[(CH_2)_2$—NnBu]-, $(N^tBu_2)(Cp)$-M-$C_5Me_4$-$[(CH_2)_2$—NnBu]-, $(OH)_2$-M-$C_5Me_4$-$[(CH_2)_2$—NnBu]-, $(OMe)_2$-M-$C_5Me_4$-$[(CH_2)_2$—NnBu]-, $(OEt)_2$-M-$C_5Me_4$-$[(CH_2)_2$—NnBu]-, $(O^nPr)_2$-M-$C_5Me_4$-$[(CH_2)_2$—NnBu]-, $(O^iPr)_2$-M-$C_5Me_4$-$[(CH_2)_2$—NnBu]-, $(O^nBu)_2$-M-$C_5Me_4$-$[(CH_2)_2$—NnBu]-, $(O^iBu_2$-M-$C_5Me_4$-$[(CH_2)_2$—NnBu]-, $(O^tBu)_2$-M-$C_5Me_4$-$[(CH_2)_2$—NnBu]-, $(O^sBu)_2$-M-$C_5Me_4$-$[(CH_2)_2$—NnBu]-, $(NH_2)_2$-M-$C_5Me_4$-$[(CH_2)_2$—NnBu]-, $(NMe_2)_2$-M-$C_5Me_4$-$[(CH_2)_2$—NnBu]-, $(NEt_2)_2$-M-$C_5Me_4$-$[(CH_2)_2$—NnBu]-, $(N^nPr_2)_2$-M-$C_5Me_4$-$[(CH_2)_2$—NnBu]-, $(N^iPr_2)_2$-M-$C_5Me_4$-$[(CH_2)_2$—NnBu]-, $(N^nBu_2)_2$-M-$C_5Me_4$-$[(CH_2)_2$—NnBu]-, $(N^iBu_2)_2$-M-$C_5Me_4$-$[(CH_2)_2$—NnBu]-, $(N^sBu_2)_2$-M-$C_5Me_4$-$[(CH_2)_2$—NnBu]-, $(N^tBu_2)_2$-M-$C_5Me_4$-$[(CH_2)_2$—NnBu]-, $(NH_2)(Cp)$-M-$C_5Me_4$-$[(CH_2)_2$—NnBu]-, $(NMe_2)(Cp)$-M-$C_5Me_4$-$[(CH_2)_2$—NnBu]-, $(NEt_2)(Cp)$-M-$C_5Me_4$-$[(CH_2)_2$—NnBu]-, $(N^nPr_2)(Cp)$-M-$C_5Me_4$-$[(CH_2)_2$—NnBu]-, $(N^iPr_2)(Cp)$-M-$C_5Me_4$-$[(CH_2)_2$—NnBu]-, $(N^nBu_2)(Cp)$-M-$C_5Me_4$-$[(CH_2)_2$—NnBu]-, $(N^iBu_2)(Cp)$-M-$C_5Me_4$-$[(CH_2)_2$—NnBu]-, $(N^sBu_2)(Cp)$-M-$C_5Me_4$-$[(CH_2)_2$—NnBu]-, $(N^tBu_2)(Cp)$-M-$C_5Me_4$-$[(CH_2)_2$—NnBu]-, $(OH)_2$-M-$C_5Me_4$-$[(CH_2)_2$—NnBu]-, $(OMe)_2$-M-$C_5Me_4$-$[(CH_2)_2$—NnBu]-, $(OEt)_2$-M-$C_5Me_4$-$[(CH_2)_2$—NnBu]-, $(O^nPr)_2$-M-$C_5Me_4$-$[(CH_2)_2$—NnBu]-, $(O^iPr)_2$-M-$C_5Me_4$-$[(CH_2)_2$—NnBu]-, $(O^nBu)_2$-M-$C_5Me_4$-$[(CH_2)_2$—NnBu]-, $(O^iBu_2$-M-$C_5Me_4$-$[(CH_2)_2$—NnBu]-, $(O^tBu)_2$-M-$C_5Me_4$-$[(CH_2)_2$—NnBu]-, $(O^sBu)_2$-M-$C_5Me_4$-$[(CH_2)_2$—NnBu]-, $(NH_2)_2$-M-$C_5Me_4$-$[(CH_2)_2$—NiBu]-, $(NMe_2)_2$-M-$C_5Me_4$-$[(CH_2)_2$—NiBu]-, $(NEt_2)_2$-M-$C_5Me_4$-$[(CH_2)_2$—NiBu]-, $(N^nPr_2)_2$-M-$C_5Me_4$-$[(CH_2)_2$—NiBu]-, $(N^iPr_2)_2$-M-$C_5Me_4$-$[(CH_2)_2$—NiBu]-, $(N^nBu_2)_2$-M-$C_5Me_4$-$[(CH_2)_2$—NiBu]-, $(N^iBu_2)_2$-M-$C_5Me_4$-$[(CH_2)_2$—NiBu]-, $(N^sBu_2)_2$-M-$C_5Me_4$-$[(CH_2)_2$—NiBu]-, $(N^tBu_2)_2$-M-$C_5Me_4$-$[(CH_2)_2$—NiBu]-, $(NH_2)(Cp)$-M-$C_5Me_4$-$[(CH_2)_2$—NiBu]-, $(NMe_2)(Cp)$-M-$C_5Me_4$-$[(CH_2)_2$—NiBu]-, $(NEt_2)(Cp)$-M-$C_5Me_4$-$[(CH_2)_2$—NiBu]-, $(N^nPr_2)(Cp)$-M-$C_5Me_4$-$[(CH_2)_2$—NiBu]-, $(N^iPr_2)(Cp)$-M-$C_5Me_4$-$[(CH_2)_2$—NiBu]-, $(N^nBu_2)(Cp)$-M-$C_5Me_4$-$[(CH_2)_2$—NiBu]-, $(N^iBu_2)(Cp)$-M-$C_5Me_4$-$[(CH_2)_2$—NiBu]-, $(N^sBu_2)(Cp)$-M-$C_5Me_4$-$[(CH_2)_2$—NiBu]-, $(N^tBu_2)(Cp)$-M-$C_5Me_4$-$[(CH_2)_2$—NiBu]-, $(OH)_2$-M-$C_5Me_4$-$[(CH_2)_2$—NiBu]-, $(OMe)_2$-M-$C_5Me_4$-$[(CH_2)_2$—NiBu]-, $(OEt)_2$-M-$C_5Me_4$-$[(CH_2)_2$—NiBu]-, $(O^nPr)_2$-M-$C_5Me_4$-$[(CH_2)_2$—NiBu]-, $(O^iPr)_2$-M-$C_5Me_4$-$[(CH_2)_2$—NiBu]-, $(O^nBu)_2$-M-$C_5Me_4$-$[(CH_2)_2$—NiBu]-, $(O^iBu_2$-M-$C_5Me_4$-$[(CH_2)_2$—NiBu]-, $(O^tBu)_2$-M-$C_5Me_4$-$[(CH_2)_2$—NiBu]-, $(O^sBu)_2$-M-$C_5Me_4$-$[(CH_2)_2$—NiBu]-, $(NH_2)_2$-M-$C_5Me_4$-$[(CH_2)_2$—NiBu]-, $(NMe_2)_2$-M-$C_5Me_4$-$[(CH_2)_2$—NiBu]-, $(NEt_2)_2$-M-$C_5Me_4$-$[(CH_2)_2$—NiBu]-, $(N^nPr_2)_2$-M-$C_5Me_4$-$[(CH_2)_2$—NiBu]-, $(N^iPr_2)_2$-M-$C_5Me_4$-$[(CH_2)_2$—NiBu]-, $(N^nBu_2)_2$-M-$C_5Me_4$-$[(CH_2)_2$—NiBu]-, $(N^iBu_2)_2$-M-$C_5Me_4$-$[(CH_2)_2$—NiBu]-, $(N^sBu_2)_2$-M-$C_5Me_4$-$[(CH_2)_2$—NiBu]-, $(N^tBu_2)_2$-M-$C_5Me_4$-$[(CH_2)_2$—NiBu]-, $(NH_2)(Cp)$-M-$C_5Me_4$-$[(CH_2)_2$—NiBu]-, $(NMe_2)(Cp)$-M-$C_5Me_4$-$[(CH_2)_2$—NiBu]-, $(NEt_2)(Cp)$-M-$C_5Me_4$-$[(CH_2)_2$—NiBu]-, $(N^nPr_2)(Cp)$-M-$C_5Me_4$-$[(CH_2)_2$—NiBu]-, $(N^iPr_2)(Cp)$-M-$C_5Me_4$-$[(CH_2)_2$—NiBu]-, $(N^nBu_2)(Cp)$-M-$C_5Me_4$-$[(CH_2)_2$—NiBu]-, $(N^iBu_2)(Cp)$-M-$C_5Me_4$-$[(CH_2)_2$—NiBu]-, $(N^sBu_2)(Cp)$-M-$C_5Me_4$-$[(CH_2)_2$—NiBu]-, $(N^tBu_2)(Cp)$-M-$C_5Me_4$-$[(CH_2)_2$—NiBu]-, $(OH)_2$-M-$C_5Me_4$-$[(CH_2)_2$—NiBu]-, $(OMe)_2$-M-$C_5Me_4$-$[(CH_2)_2$—NiBu]-, $(OEt)_2$-M-$C_5Me_4$-$[(CH_2)_2$—NiBu]-, $(O^nPr)_2$-M-$C_5Me_4$-$[(CH_2)_2$—NiBu]-, $(O^iPr)_2$-M-$C_5Me_4$-$[(CH_2)_2$—NiBu]-, $(O^nBu)_2$-M-$C_5Me_4$-$[(CH_2)_2$—NiBu]-, $(O^iBu_2$-M-$C_5Me_4$-$[(CH_2)_2$—NiBu]-, $(O^tBu)_2$-M-$C_5Me_4$-$[(CH_2)_2$—NiBu]-, $(O^sBu)_2$-M-$C_5Me_4$-$[(CH_2)_2$—NiBu]-, $(NH_2)_2$-M-$C_5Me_4$-$[(CH_2)_2$—NsBu]-, $(NMe_2)_2$-M-$C_5Me_4$-$[(CH_2)_2$—NsBu]-, $(NEt_2)_2$-M-$C_5Me_4$-$[(CH_2)_2$—NsBu]-, $(N^nPr_2)_2$-M-$C_5Me_4$-$[(CH_2)_2$—NsBu]-, $(N^iPr_2)_2$-M-$C_5Me_4$-$[(CH_2)_2$—NsBu]-, $(N^nBu_2)_2$-M-$C_5Me_4$-$[(CH_2)_2$—NsBu]-, $(N^iBu_2)_2$-M-$C_5Me_4$-$[(CH_2)_2$—NsBu]-, $(N^sBu_2)_2$-M-$C_5Me_4$-$[(CH_2)_2$—NsBu]-, $(N^tBu_2)_2$-M-$C_5Me_4$-$[(CH_2)_2$—NsBu]-, $(NH_2)(Cp)$-M-$C_5Me_4$-$[(CH_2)_2$—NsBu]-, $(NMe_2)(Cp)$-M-$C_5Me_4$-$[(CH_2)_2$—NsBu]-, $(NEt_2)(Cp)$-M-$C_5Me_4$-$[(CH_2)_2$—NsBu]-, $(N^nPr_2)(Cp)$-M-$C_5Me_4$-$[(CH_2)_2$—NsBu]-, $(N^iPr_2)(Cp)$-M-$C_5Me_4$-$[(CH_2)_2$—NsBu]-, $(N^nBu_2)(Cp)$-M-$C_5Me_4$-$[(CH_2)_2$—NsBu]-, $(N^iBu_2)(Cp)$-M-$C_5Me_4$-$[(CH_2)_2$—NsBu]-, $(N^sBu_2)(Cp)$-M-$C_5Me_4$-$[(CH_2)_2$—NsBu]-, $(N^tBu_2)(Cp)$-M-$C_5Me_4$-$[(CH_2)_2$—NsBu]-, $(OH)_2$-M-$C_5Me_4$-$[(CH_2)_2$—NsBu]-, $(OMe)_2$-M-$C_5Me_4$-$[(CH_2)_2$—NsBu]-, $(OEt)_2$-M-$C_5Me_4$-$[(CH_2)_2$—NsBu]-, $(O^nPr)_2$-M-$C_5Me_4$-$[(CH_2)_2$—NsBu]$(O^iPr)_2$-M-$C_5Me_4$-$[(CH_2)_2$—NsBu]-, $(O^nBu)_2$-M-$C_5Me_4$-$[(CH_2)_2$—NsBu]-, $(O^iBu_2$-M-$C_5Me_4$-$[(CH_2)_2$—NsBu]-, $(O^tBu)_2$-M-$C_5Me_4$-$[(CH_2)_2$—NsBu]-, $(O^sBu)_2$-M-$C_5Me_4$-$[(CH_2)_2$—NsBu]-, $(NH_2)_2$-M-$C_5Me_4$-$[(CH_2)_2$—NsBu]-, $(NMe_2)_2$-M-$C_5Me_4$-$[(CH_2)_2$—NsBu]-, $(NEt_2)_2$-M-$C_5Me_4$-$[(CH_2)_2$—NsBu]-, $(N^nPr_2)_2$-M-$C_5Me_4$-$[(CH_2)_2$—NsBu]-, $(N^iPr_2)_2$-M-$C_5Me_4$-$[(CH_2)_2$—NsBu]-, $(N^nBu_2)_2$-M-$C_5Me_4$-$[(CH_2)_2$—NsBu]-, $(N^iBu_2)_2$-M-$C_5Me_4$-$[(CH_2)_2$—NsBu]-, $(N^sBu_2)_2$-M-$C_5Me_4$-$[(CH_2)_2$—NsBu]-, $(N^tBu_2)_2$-M-$C_5Me_4$-$[(CH_2)_2$—NsBu]-, $(NH_2)(Cp)$-M-$C_5Me_4$-$[(CH_2)_2$—NsBu]-, $(NMe_2)(Cp)$-M-$C_5Me_4$-$[(CH_2)_2$—NsBu]-, $(NEt_2)(Cp)$-M-$C_5Me_4$-$[(CH_2)_2$—NsBu]-, $(N^nPr_2)(Cp)$-M-$C_5Me_4$-$[(CH_2)_2$—NsBu]-, $(N^iPr_2)(Cp)$-M-$C_5Me_4$-$[(CH_2)_2$—NsBu]-, $(N^nBu_2)(Cp)$-M-$C_5Me_4$-$[(CH_2)_2$—NsBu]-, $(N^iBu_2)(Cp)$-M-$C_5Me_4$-$[(CH_2)_2$—NsBu]-, $(N^sBu_2)(Cp)$-M-$C_5Me_4$-$[(CH_2)_2$—NsBu]-, $(N^tBu_2)(Cp)$-M-$C_5Me_4$-$[(CH_2)_2$—NsBu]-, $(OH)_2$-M-$C_5Me_4$-$[(CH_2)_2$—NsBu]-, $(OMe)_2$-M-$C_5Me_4$-$[(CH_2)_2$—NsBu]-, $(OEt)_2$-M-$C_5Me_4$-$[(CH_2)_2$—NsBu]-, $(O^nPr)_2$-M-$C_5Me_4$-$[(CH_2)_2$—NsBu]-, $(O^iPr)_2$-M-$C_5Me_4$-$[(CH_2)_2$—NsBu]-, $(O^nBu)_2$-M-$C_5Me_4$-$[(CH_2)_2$—NsBu]-, $(O^iBu_2$-M-$C_5Me_4$-$[(CH_2)_2$—NsBu]-, $(O^tBu)_2$-M-$C_5Me_4$-$[(CH_2)_2$—NsBu]-, $(O^sBu)_2$-M-$C_5Ma_4$-$[(CH_2)_2$—NsBu]-, $(NH_2)_2$-M-$C_5Me_4$-$[(CH_2)_2$—NtBu]-, $(NMe_2)_2$-M-$C_5Me_4$-$[(CH_2)_2$—NtBu]-, $(NEt_2)_2$-M-$C_5Me_4$-$[(CH_2)_2$—NtBu]-, $(N^nPr_2)_2$-M-$C_5Me_4$-$[(CH_2)_2$—NtBu]-, $(N^iPr_2)_2$-M-$C_5Me_4$-$[(CH_2)_2$—NtBu]-, $(N^nBu_2)_2$-M-$C_5Me_4$-$[(CH_2)_2$—NtBu]-, $(N^iBu_2)_2$-M-$C_5Me_4$-$[(CH_2)_2$—NtBu]-, $(N^sBu_2)_2$-M-$C_5Me_4$-$[(CH_2)_2$—NtBu]-, $(N^tBu_2)_2$-M-$C_5Me_4$-$[(CH_2)_2$—NtBu]-, $(NH_2)(Cp)$-M-$C_5Me_4$-$[(CH_2)_2$—NtBu]-, $(NMe_2)(Cp)$-M-$C_5Me_4$-$[(CH_2)_2$—NtBu]-, $(NEt_2)(Cp)$-M-$C_5Me_4$-$[(CH_2)_2$—NtBu]-, $(N^nPr_2)(Cp)$-M-$C_5Me_4$-$[(CH_2)_2$—NtBu]-, $(N^iPr_2)(Cp)$-M-$C_5Me_4$-$[(CH_2)_2$—NtBu]-, $(N^nBu_2)(Cp)$-M-$C_5Me_4$-$[(CH_2)_2$—NtBu]-, $(N^iBu_2)(Cp)$-M-$C_5Me_4$-$[(CH_2)_2$—NtBu]-, $(N^sBu_2)(Cp)$-M-$C_5Me_4$-$[(CH_2)_2$—NtBu]-, $(N^tBu_2)(Cp)$-M-$C_5Me_4$-$[(CH_2)_2$—NtBu]-, $(OH)_2$-M-$C_5Me_4$-$[(CH_2)_2$ —NtBu]-, $(OMe)_2$-M-$C_5Me_4$-$[(CH_2)_2$—NtBu]-, $(OEt)_2$-M-$C_5Me_4$-$[(CH_2)_2$—NtBu]-, $(O^nPr)_2$-M-$C_5Me_4$-$[(CH_2)_2$—NtBu]-, $(O^iPr)_2$-M-$C_5Me_4$-$[(CH_2)_2$—NtBu]-, $(O^nBu)_2$-M-$C_5Me_4$-$[(CH_2)_2$—NtBu]-, $(O^iBu_2$-M-$C_5Me_4$-$[(CH_2)_2$—NtBu]-, $(O^tBu)_2$-M-$C_5Me_4$-$[(CH_2)_2$—NtBu]-, $(O^sBu)_2$-M-$C_5Me_4$-$[(CH_2)_2$—NtBu]-, $(NH_2)_2$-M-$C_5Me_4$-$[(CH_2)_2$—NtBu]-, $(NMe_2)_2$-M-$C_5Me_4$-$[(CH_2)_2$—NtBu]-, $(NEt_2)_2$-M-$C_5Me_4$-$[(CH_2)_2$—NtBu]-, $(N^nPr_2)_2$-M-$C_5Me_4$-

$[(CH_2)_2$—NtBu]-, $(N^iPr_2)_2$-M-$C_5Me_4$-$[(CH_2)_2$—NtBu]-, $(N^nBu_2)_2$-M-$C_5Me_4$-$[(CH_2)_2$—NtBu]-, $(N^iBu_2)_2$-M-$C_5Me_4$-$[(CH_2)_2$—NtBu]-, $(N^sBu_2)_2$-M-$C_5Me_4$-$[(CH_2)_2$—NtBu]-, $(N^tBu_2)_2$-M-$C_5Me_4$-$[(CH_2)_2$—NtBu]-, $(NH_2)$(Cp)-M-$C_5Me_4$-$[(CH_2)_2$—NtBu]-, $(NMe_2)$(Cp)-M-$C_5Me_4$-$[(CH_2)_2$—NtBu]-, $(NEt_2)$(Cp)-M-$C_5Me_4$-$[(CH_2)_2$—NtBu]-, $(N^nPr_2)$(Cp)-M-$C_5Me_4$-$[(CH_2)_2$—NtBu]-, $(N^iPr_2)$(Cp)-M-$C_5Me_4$-$[(CH_2)_2$—NtBu]-, $(N^nBu_2)$(Cp)-M-$C_5Me_4$-$[(CH_2)_2$—NtBu]-, $(N^iBu_2)$(Cp)-M-$C_5Me_4$-$[(CH_2)_2$—NtBu]-, $(N^sBu_2)$(Cp)-M-$C_5Me_4$-$[(CH_2)_2$—NtBu]-, $(N^tBu_2)$(Cp)-M-$C_5Me_4$-$[(CH_2)_2$—NtBu]-, $(OH)_2$-M-$C_5Me_4$-$[(CH_2)_2$ —NtBu]-, $(OMe)_2$-M-$C_5Me_4$-$[(CH_2)_2$—NtBu]-, $(OEt)_2$-M-$C_5Me_4$-$[(CH_2)_2$—NtBu]-, $(O^nPr)_2$-M-$C_5Me_4$-$[(CH_2)_2$—NtBu]-, $(O^iPr)_2$-M-$C_5Me_4$-$[(CH_2)_2$—NtBu]-, $(O^nBu)_2$-M-$C_5Me_4$-$[(CH_2)_2$—NtBu]-, $(O^iBu_2$-M-$C_5Me_4$-$[(CH_2)_2$—NtBu]-, $(O^tBu)_2$-M-$C_5Me_4$-$[(CH_2)_2$—NtBu]-, and $(O^sBu)_2$-M-$C_5Me_4$-$[(CH_2)_2$—NtBu]-, wherein M is Ti, Zr or Hf bonded in an $\eta^5$ bonding mode to the Cp group and carbons other than those in the Cp group may be replaced with Si, B or P.

Preferred Zr precursors include $(Me_2N)_2$—Zr—$C_5H_3$-1-Me-3-($CH_2$—$CH_2$—NMe)-, $(Me_2N)_2$—Zr—$C_5H_3$-1-Et-3-($CH_2$—$CH_2$—NMe)-, $(Me_2N)_2$—Zr—$C_5H_3$-1-$^i$Pr-3-($CH_2$—$CH_2$—NMe)-, $(Me_2N)$(Cp)-Zr—$C_5H_3$-1-Me-3-($CH_2$—$CH_2$—NMe)-, $(Me_2N)$(Cp)-Zr—$C_5H_3$-1-Et-3-($CH_2$—$CH_2$—NMe)-, $(Me_2N)$(Cp)-Zr—$C_5H_3$-1-$^i$Pr-3-($CH_2$—$CH_2$—NMe)-, $(Me_2N)_2$—Zr—$C_5Me_4$-($CH_2$—$CH_2$—NMe)-, $(Me_2N)_2$—Zr—$C_5Me_3$-1-Et-3-($CH_2$—$CH_2$—NMe)-, $(Me_2N)_2$—Zr—$C_5Me_3$-1-$^i$Pr-3-($CH_2$—$CH_2$—NMe)-, $(Me_2N)$(Cp)-Zr—$C_5Me_4$-($CH_2$—$CH_2$—NMe)-, $(Me_2N)$(Cp)-Zr—$C_5Me_3$-1-Et-3-($CH_2$—$CH_2$—NMe)-, $(Me_2N)$(Cp)-Zr—$C_5Me_3$-1-$^i$Pr-3-($CH_2$—$C_2$—$CH_2$—NMe)-, $(Me_2N)_2$—Hf—$C_5H_3$-1-Me-3-($CH_2$—$CH_2$—NMe)-, $(Me_2N)_2$—Hf—$C_5H_3$-1-Et-3-($CH_2$—$CH_2$—NMe)-, $(Me_2N)_2$—Hf—$C_5H_3$-1-$^i$Pr-3-($CH_2$—$CH_2$—NMe)-, $(Me_2N)$(Cp)-Hf—$C_5H_3$-1-Me-3-($CH_2$—$CH_2$—NMe)-, $(Me_2N)$(Cp)-Hf—$C_5H_3$-1-Et-3-($CH_2$—$CH_2$—NMe)-, $(Me_2N)$(Cp)-Hf—$C_5H_3$-1-$^i$Pr-3-($CH_2$—$CH_2$—NMe)-, $(Me_2N)_2$—Hf—$C_5Me_4$-($CH_2$—$CH_2$—NMe)-, $(Me_2N)_2$—Hf—$C_5Me_3$-1-Et-3-($CH_2$—$CH_2$—NMe)-, $(Me_2N)_2$—Hf—$C_5Me_3$-1-$^i$Pr-3-($CH_2$—$CH_2$—NMe)-, $(Me_2N)$(Cp)-Hf—$C_5Me_4$-($CH_2$—$CH_2$—NMe)-, $(Me_2N)$(Cp)-Hf—$C_5Me_3$-1-Et-3-($CH_2$—$CH_2$—NMe)-, and $(Me_2N)$(Cp)-Hf—$C_5Me_3$-1-$^i$Pr-3-($CH_2$—$CH_2$—NMe)-.

The inventors recognize that the Group 4 transition metal precursors having the above structures i.e., having bridge between the Cp group and the Group 4 transition metal, one nitrogen ligand in the bridge, may provide similar or better thermal stability than Cp-amino bridged precursors of U.S. Pat. No. 8,946,096, for example, having stable thermal stability and high vapor pressure. In addition, the liquid state of the disclosed Group 4 transition metal precursors may be used in direct liquid injection (DLI) where the precursor is fed in a liquid state and then vaporized before it is introduced into a reactor.

The Group 4 transition metal precursors may exhibit (i) sufficient volatility to provide a rapid and reproducible delivery into the reaction chamber from the vessel in which they are stored, (ii) high thermal stability to avoid decomposition during the storage in the canister and to enable self limiting growth in ALD mode at high temperature, typically >275° C., (iii) appropriate reactivity toward the substrate terminal functions and with the reacting gas to an easy conversion into the desired film, and (iv) high purity to obtain a film with low impurities.

While precursors are ideally liquids and vaporized in bubblers or direct liquid injection systems, the use of solid precursors for ALD and CVD precursor vaporization is also possible using sublimators such as ones disclosed in PCT Publication WO2009/087609 to Xu et al. Alternatively, solid precursors may be mixed or dissolved in a solvent to reach a usable melting point and viscosity for usage by Direct Liquid Injection systems.

Preferably, the R in the Group 4 transition metal-containing precursors is H or Me or $^i$Pr on the Cp group because of their excellent vaporization results in atmospheric thermogravimetric analysis, leaving a small amount of final residue.

The disclosed Group 4 transition metal-containing precursors may be synthesized by reacting at low temperature the corresponding halogenated Group 4 transition metal-containing R group compound (i.e., $RMX_3$, wherein R and M are defined above and X is Cl, Br, or I) with the corresponding alkanolamine and alkylamine in a suitable solvent, such as dichloromethane, THF or ether. The $RMX_3$, alkanolamine, and alkylamine are commercially available. After completion of the addition, the mixture warms to room temperature with stirring. The solvent is removed under vacuum. The residue is dissolved in a solvent, such as toluene. The resulting mixture is filtered. Removal of the solvent produces the crude Group 4 transition metal-containing precursor.

Alternatively, the disclosed Group 4 transition metal-containing precursors may be synthesized by reacting at low temperature the corresponding Group 4 transition metal-containing alkoxy and R group compound (i.e., $RM(OR'')_3$), wherein R and M are defined above and R'' is a $C_1$-$C_6$ alkyl group) with the corresponding alkanolamine in a suitable solvent, such as heptanes, dichloromethane, THF or ether. The $RM(OR'')_3$ and alkanolamine are commercially available. After completion of the addition, the mixture warms to room temperature with stirring. The solvent is removed under vacuum to produce the crude Group 4 transition metal-containing precursor.

In another alternative, the disclosed Group 4 transition metal-containing precursors may be synthesized by reacting at low temperature the corresponding Group 4 transition metal-containing amide and R group compound (i.e., $RM(NR'''_2)_3$), wherein R and M are defined above and R''' is a C1-C6 alkyl group) with the corresponding alkanolamine in a suitable solvent, such as heptanes, dichloromethane, THF or ether. The $RM(NR'''_2)_3$ and alkanolamine are commercially available. After completion of the addition, the mixture warms to room temperature with stirring. The solvent is removed under vacuum to produce the crude Group 4 transition metal-containing precursor.

In another alternative, the disclosed Group 4 transition metal-containing precursors may be synthesized by reacting at low temperature the corresponding Group 4 transition metal-containing amide (i.e., $M(NR'''_2)_4$), wherein M is defined above and R''' is a C1-C6 alkyl group) with the corresponding Cp-containing amine or Cp*-containing amine in a suitable solvent, such as toluene, heptanes, dichloromethane, THF or ether. The $M(NR'''_2)_4$ and Cp-containing amine or Cp*-containing amine are commercially available. After completion of the addition, the mixture warms to room temperature with stirring. The solvent is removed under vacuum to produce the crude Group 4 transition metal-containing precursor. Exemplary synthesis methods containing further details are provided in the Examples that follow.

To ensure process reliability, the Group 4 transition metal-containing film forming compositions may be purified by continuous or fractional batch distillation or sublimation prior to use to a purity ranging from approximately 93% w/w to approximately 100% w/w, preferably ranging from approximately 99% w/w to approximately 100% w/w. The Group 4 transition metal-containing film forming compositions may contain any of the following impurities: undesired congeneric species; solvents; chlorinated metal compounds; or other reaction products. In one alternative, the total quantity of these impurities is below 0.1% w/w.

The concentration of each of hexane, pentane, dimethyl ether, or anisole in the purified Group 4 transition metal-containing film forming compositions may range from approximately 0% w/w to approximately 5% w/w, preferably from approximately 0% w/w to approximately 0.1% w/w. Solvents may be used in the composition's synthesis. Separation of the solvents from the precursor may be difficult if both have similar boiling points. Cooling the mixture may produce solid precursor in liquid solvent, which may be separated by filtration. Vacuum distillation may also be used, provided the precursor product is not heated above approximately its decomposition point.

In one alternative, the disclosed Group 4 transition metal-containing film forming compositions contain less than 5% v/v, preferably less than 1% v/v, more preferably less than 0.1% v/v, and even more preferably less than 0.01% v/v of any of its undesired congeneric species, reactants, or other reaction products. This alternative may provide better process repeatability. This alternative may be produced by distillation of the Group 4 transition metal-containing precursors.

In another alternative, the disclosed Group 4 transition metal-containing film forming compositions may contain between 5% v/v and 50% v/v of one or more of cogeneric Group 4 transition metal-containing precursors, reactants, or other reaction products, particularly when the mixture provides improved process parameters or isolation of the target compound is too difficult or expensive. For example, a mixture of two Group 4 transition metal precursors may produce a stable, liquid mixture suitable for vapor deposition.

The concentration of trace metals and metalloids in the purified Group 4 transition metal-containing film forming compositions may each range from approximately 0 ppb to approximately 100 ppb, and more preferably from approximately 0 ppb to approximately 10 ppb. These metal impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), Vanadium (V) and Zinc (Zn).

Also disclosed are methods for forming Group 4 transition metal-containing layers on a substrate using a vapor deposition process. The method may be useful in the manufacture of semiconductor, photovoltaic, LCD-TFT, or flat panel type devices. The disclosed Group 4 transition metal-containing film forming compositions may be used to deposit thin Group 4 transition metal-containing films using any deposition methods known to those of skill in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, spatial ALD, or PE-ALD to provide suitable step coverage and film thickness control. Additionally, the disclosed Group 4 transition metal-containing film forming compositions are particularly suitable for ALD processes because their thermal stability enables perfect self-limited growth.

Applicants believe the N-M bond may stabilize the precursor making it thermally robust, which may help during conformal ALD deposition in high aspect ratio structures. When R is Cp (substituted or not), Applicants believe that the Cp may remain like an umbrella over the M atom on the surface and ensure perfect self ALD growth.

The disclosed Group 4 transition metal-containing film forming composition may be supplied either neat or may further comprise a suitable solvent, such as ethyl benzene, xylene, mesitylene, decane, and/or dodecane. The disclosed Group 4 transition metal precursors may be present in varying concentrations in the solvent.

The neat or blended Group 4 transition metal-containing film forming compositions are introduced into a reactor in vapor form by conventional means, such as tubing and/or flow meters. The vapor form may be produced by vaporizing the neat or blended composition through a conventional vaporization step such as direct vaporization, distillation, or by bubbling, or by using a sublimator such as the one disclosed in PCT Publication WO2009/087609 to Xu et al. The composition may be fed in a liquid state to a vaporizer (direct liquid injection or "DLI") where it is vaporized before it is introduced into the reactor. Alternatively, the composition may be vaporized by passing a carrier gas into a container containing the compound or by bubbling the carrier gas into the compound. The carrier gas may include, but is not limited to, Ar, He, $N_2$, and mixtures thereof. Bubbling with a carrier gas may also remove any dissolved oxygen present in the neat or blended compound solution. The carrier gas and vapor form of the composition are then introduced into the reactor as a vapor.

If necessary, the container may be heated to a temperature that permits the composition to be in its liquid phase and to have a sufficient vapor pressure. The container may be maintained at temperatures in the range of, for example, approximately 50° C. to approximately 180° C. Those skilled in the art recognize that the temperature of the container may be adjusted in a known manner to control the amount of composition vaporized.

Figure 2:
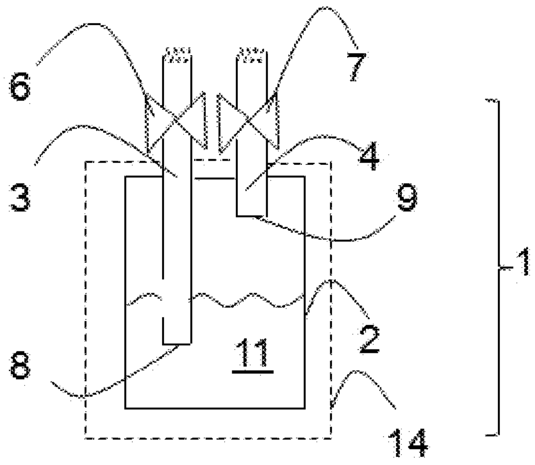
FIG. 2 is a side view of a second embodiment of the Group 4 transition metal-containing film forming composition delivery device 1.

The Group 4 transition metal-containing film forming compositions may be delivered to a semiconductor processing tool by the disclosed Group 4 transition metal-containing film forming composition delivery devices. FIGS. 1 and 2 show two embodiments of the disclosed delivery devices 1.

FIG. 1 is a side view of one embodiment of the Group 4 transition metal-containing film forming composition delivery device 1. In FIG. 1, the disclosed Group 4 transition metal-containing film forming composition 11 is contained within a container 2 having at least two conduits, an inlet conduit 3 and an outlet conduit 4. One of ordinary skill in the precursor art will recognize that the container 2, inlet conduit 3, and outlet conduit 4 are manufactured to prevent the escape of the gaseous form of the Group 4 transition metal-containing film forming composition 11, even at elevated temperature and pressure.

Suitable valves include spring-loaded or tied diaphragm valves. The valve may further comprise a restrictive flow orifice (RFO). The delivery device 1 should be connected to a gas manifold and in an enclosure. The gas manifold should permit the safe evacuation and purging of the piping that may be exposed to air when the delivery device 1 is replaced so that any residual amount of the material does not react.

The delivery device 1 must be leak tight and be equipped with valves that do not permit escape of even minute amounts of the material when closed. The delivery device 1 fluidly connects to other components of the semiconductor processing tool, such as the gas cabinet disclosed above, via valves 6 and 7. Preferably, the container 2, inlet conduit 3, valve 6, outlet conduit 4, and valve 7 are typically made of 316L EP stainless steel.

In FIG. 1, the end 8 of inlet conduit 3 is located above the surface of the Group 4 transition metal-containing film forming composition 11, whereas the end 9 of the outlet conduit 4 is located below the surface of the Group 4 transition metal-containing film forming composition 11. In this embodiment, the Group 4 transition metal-containing film forming composition 11 is preferably in liquid form. An inert gas, including but not limited to nitrogen, argon, helium, and mixtures thereof, may be introduced into the inlet conduit 3. The inert gas pressurizes the container 2 so that the liquid Group 4 transition metal-containing film forming composition 11 is forced through the outlet conduit 4 and to components in the semiconductor processing tool (not shown). The semiconductor processing tool may include a vaporizer which transforms the liquid Group 4 transition metal-containing film forming composition 11 into a vapor, with or without the use of a carrier gas such as helium, argon, nitrogen or mixtures thereof, in order to deliver the vapor to a chamber where a wafer to be repaired is located and treatment occurs in the vapor phase. Alternatively, the liquid Group 4 transition metal-containing film forming composition 11 may be delivered directly to the wafer surface as a jet or aerosol.

FIG. 2 is a side view of a second embodiment of the Group 4 transition metal-containing film forming composition delivery device 1. In FIG. 2, the end 8 of inlet conduit 3 is located below the surface of the Group 4 transition metal-containing film forming composition 11, whereas the end 9 of the outlet conduit 4 is located above the surface of the Group 4 transition metal-containing film forming composition 11. FIG. 2 also includes an optional heating element 14, which may increase the temperature of the Group 4 transition metal-containing film forming composition 11. The Group 4 transition metal-containing film forming composition 11 may be in solid or liquid form. An inert gas, including but not limited to nitrogen, argon, helium, and mixtures thereof, is introduced into the inlet conduit 3. The inert gas flows through the Group 4 transition metal-containing film forming composition 11 and carries a mixture of the inert gas and vaporized Group 4 transition metal-containing film forming composition 11 to the outlet conduit 4 and to the components in the semiconductor processing tool.

Both FIGS. 1 and 2 include valves 6 and 7. One of ordinary skill in the art will recognize that valves 6 and 7 may be placed in an open or closed position to allow flow through conduits 3 and 4, respectively. Either delivery device 1 in FIG. 1 or 2, or a simpler delivery device having a single conduit terminating above the surface of any solid or liquid present, may be used if the Group 4 transition metal-containing film forming composition 11 is in vapor form or if sufficient vapor pressure is present above the solid/liquid phase. In this case, the Group 4 transition metal-containing film forming composition 11 is delivered in vapor form through the conduit 3 or 4 simply by opening the valve 6 in FIG. 1 or 7 in FIG. 2, respectively. The delivery device 1 may be maintained at a suitable temperature to provide sufficient vapor pressure for the Group 4 transition metal-containing film forming composition 11 to be delivered in vapor form, for example by the use of an optional heating element 14.

While FIGS. 1 and 2 disclose two embodiments of the Group 4 transition metal-containing film forming composition delivery device 1, one of ordinary skill in the art will recognize that the inlet conduit 3 and outlet conduit 4 may both be located above the surface of the Group 4 transition metal-containing film forming composition 11 without departing from the disclosure herein. Furthermore, inlet conduit 3 may be a filling port.

Figure 3:
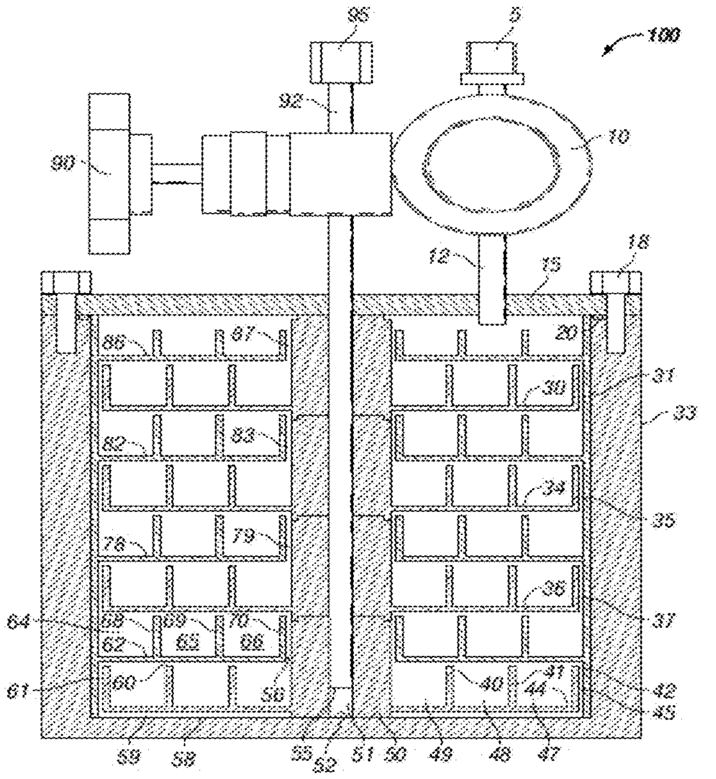
FIG. 3 is an exemplary embodiment of a solid precursor sublimator 100 for subliming solid Group 4 transition metal-containing film forming compositions.

When the Group 4 transition metal-containing film forming compositions are solids, their vapors may be delivered to the reactor using a sublimator. FIG. 3 shows one embodiment of a suitable sublimator 100. The sublimator 100 comprises a container 33. Container 33 may be a cylindrical container, or alternatively, may be any shape, without limitation. The container 33 is constructed of materials such as stainless steel, nickel and its alloys, quartz, glass, and other chemically compatible materials, without limitation. In certain instances, the container 33 is constructed of another metal or metal alloy, without limitation. In certain instances, the container 33 has an internal diameter from about 8 centimeters to about 55 centimeters and, alternatively, an internal diameter from about 8 centimeters to about 30 centimeters. As understood by one skilled in the art, alternate configurations may have different dimensions.

Container 33 comprises a sealable top 15, sealing member 18, and gasket 20. Sealable top 15 is configured to seal container 33 from the outer environment. Sealable top 15 is configured to allow access to the container 33. Additionally, sealable top 15 is configured for passage of conduits into container 33. Alternatively, sealable top 15 is configured to permit fluid flow into container 33. Sealable top 15 is configured to receive and pass through a conduit comprising a dip tube 92 to remain in fluid contact with container 33. Dip tube 92 having a control valve 90 and a fitting 95 is configured for flowing carrier gas into container 33. In certain instances, dip tube 92 extends down the center axis of container 33. Further, sealable top 15 is configured to receive and pass through a conduit comprising outlet tube 12. The carrier gas and vapor of the Group 4 transition metal-containing film forming composition is removed from container 33 through the outlet tube 12. Outlet tube 12 comprises a control valve 10 and fitting 5. In certain instances, outlet tube 12 is fluidly coupled to a gas delivery manifold, for conducting carrier gas from the sublimator 100 to a film deposition chamber.

Container 33 and sealable top 15 are sealed by at least two sealing members 18; alternatively, by at least about four sealing members. In certain instance, sealable top 15 is sealed to container 33 by at least about eight sealing members 18. As understood by one skilled in the art, sealing member 18 releasably couples sealable top 15 to container 33, and forms a gas resistant seal with gasket 20. Sealing member 18 may comprise any suitable means known to one skilled in the art for sealing container 33. In certain instances, sealing member 18 comprises a thumbscrew.

As illustrated in FIG. 3, container 33 further comprises at least one disk disposed therein. The disk comprises a shelf, or horizontal support, for solid material. In certain embodiments, an interior disk 30 is disposed annularly within the container 33, such that the disk 30 includes an outer diameter or circumference that is less than the inner diameter or circumference of the container 33, forming an opening 31. An exterior disk 86 is disposed circumferentially within the container 33, such that the disk 86 comprises an outer diameter or circumference that is the same, about the same, or generally coincides with the inner diameter of the container 33. Exterior disk 86 forms an opening 87 disposed at the center of the disk. A plurality of disks is disposed within container 33. The disks are stacked in an alternating fashion, wherein interior disks 30, 34, 36, 44 are vertically stacked within the container with alternating exterior disks 62, 78, 82, 86. In embodiments, interior disks 30, 34, 36, 44 extend annularly outward, and exterior disks 62, 78, 82, 86 extend annularly toward the center of container 33. As illustrated in the embodiment of FIG. 3, interior disks 30, 34, 36, 44 are not in physical contact with exterior disks 62, 78, 82, 86.

The assembled sublimator 100 comprises interior disks 30, 34, 36, 44 comprising aligned and coupled support legs 50, interior passage 51, concentric walls 40, 41, 42, and concentric slots 47, 48, 49. The interior disks 30, 34, 36, 44 are vertically stacked, and annularly oriented about the dip tube 92. Additionally, the sublimator comprises exterior disks 62, 78, 82, 86. As illustrated in FIG. 3, the exterior disks 62, 78, 82, 86 should be tightly fit into the container 33 for a good contact for conducting heat from the container 33 to the disks 62, 78, 82, 86. Preferably, the exterior disks 62, 78, 82, 86 are coupled to, or in physical contact with, the inner wall of the container 33.

As illustrated, exterior disks 62, 78, 82, 86 and interior disks 30, 34, 36, 44 are stacked inside the container 33. When assembled in container 33 to form sublimator 100, the interior disks 30, 34, 36, 44 form outer gas passages 31, 35, 37, 45 between the assembled exterior disks 62, 78, 82, 86. Further, exterior disks 62, 78, 82, 86 form inner gas passages 56, 79, 83, 87 with the support legs of the interior disks 30, 34, 36, 44. The walls 40, 41, 42 of interior disks 30, 34, 36, form the grooved slots for holding solid precursors. Exterior disks 62, 78, 82, 86 comprise walls 68, 69, 70 for holding solid precursors. During assembly, the solid precursors are loaded into the annular slots 47, 48, 49 of interior disks 30, 34, 36, 44 and annular slots 64, 65, 66 of exterior disks 62, 78, 82, 86.

While FIG. 3 discloses one embodiment of a sublimator capable of delivering the vapor of any solid Group 4 transition metal-containing film forming composition to the reactor, one of ordinary skill in the art will recognize that other sublimator designs may also be suitable, without departing from the teachings herein. Finally, one of ordinary skill in the art will recognize that the disclosed Group 4 transition metal-containing film forming composition 11 may be delivered to semiconductor processing tools using other delivery devices, such as the ampoules disclosed in WO 2006/059187 to Jurcik et al., without departing from the teachings herein.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr, preferably between about 0.1 Torr and about 5 Torr. In addition, the temperature within the reaction chamber may range from about 50° C. to about 600° C. One of ordinary skill in the art will recognize that the optimal deposition temperature range for each Group IV transition metal-containing precursors may be determined experimentally to achieve the desired result.

The reactor contains one or more substrates onto which the thin films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, SiGe, silica, glass, or Ge. Plastic substrates, such as poly(3,4-ethylenedioxythiophene)poly (styrenesulfonte) [PEDOT:PSS], may also be used. The substrate may also have one or more layers of differing materials already deposited upon it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper, cobalt, ruthenium, tungsten and/or other metal layers (e.g. platinum, palladium, nickel, ruthenium, or gold). The wafers may include barrier layers or electrodes, such as tantalum, tantalum nitride, etc. Plastic layers, such as poly(3,4-ethylenedioxythiophene)poly (styrenesulfonate) [PEDOT:PSS] may also be used. The layers may be planar or patterned. The substrate may be an organic patterned photoresist film. The substrate may include layers of oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN, TiN, NbN) that are used as electrodes. The disclosed processes may deposit the Group IV-containing layer directly on the wafer or directly on one or more than one (when patterned layers form the substrate) of the layers on top of the wafer. Furthermore, one of ordinary skill in the art will recognize that the terms “film” or “layer” used herein refer to a thickness of some material laid on or spread over a surface and that the surface may be a trench or a line. Throughout the specification and claims, the wafer and any associated layers thereon are referred to as substrates. The actual substrate utilized may also depend upon the specific precursor embodiment utilized. In many instances though, the preferred substrate utilized will be selected from TiN, NbN, Ru, Si, and SiGe type substrates, such as polysilicon or crystalline silicon substrates. For example, a Group 4 metal oxide film may be deposited onto a TiN substrate. In subsequent processing, a TiN layer may be deposited on the Group 4 metal oxide layer, forming a TiN/Group 4 metal oxide/TiN stack used as DRAM capacitor. The Metal Oxide layer itself may be made of a stack of several layers of various metal oxides, generally selected from Group 4 metal oxide, Group 5 metal oxide, $Al_2O_3$, $SiO_2$, and $MoO_2$.

The temperature and the pressure within the reactor are held at conditions suitable for vapor depositions. In other words, after introduction of the vaporized composition into the chamber, conditions within the chamber are such that at least part of the vaporized Group 4 transition metal-containing precursor is deposited onto the substrate to form a Group 4 transition metal-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 200° C. and about 450° C. One of ordinary skill in the art will recognize that “at least part of the vaporized Group 4 transition metal-containing precursor is deposited" means that some or all of the precursor reacts with or adheres to the substrate.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 50° C. to approximately 400° C. Alternatively, when a thermal process is performed, the deposition temperature may range from approximately 200° C. to approximately 450° C.

In addition to the disclosed Group 4 transition metal-containing film forming composition, a reactant may also be introduced into the reactor. The reactant may be an oxidizing gas such as one of $O_2$, $O_3$, $H_2O$, $H_2O_2$, NO, $N_2O$, $NO_2$, a diol (such as ethylene glycol or hydrated hexafluoroacetone), oxygen containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as O. or OH., and mixtures thereof.

Alternatively, the reactant may be $H_2$, $NH_3$, hydrazines (such as $N_2H_4$, $MeHNNH_2$, $Me_2NNH_2$, MeHNNHMe, phenyl hydrazine), organic amines (such as $NMeH_2$, $NEtH_2$, $NMe_2H$, $NEt_2H$, $NMe_3$, $NEt_3$, $(SiMe_3)_2NH$, cyclic amines like pyrrolidine or pyrimidine), diamines (such as ethylene diamine, dimethylethylene diamine, tetramethylethylene diamine), aminoalcohols (such as ethanolamine [HO—$CH_2$—$CH_2$—$NH_2$], bis ethanolamine [$HN(C_2H_5OH)_2$] or tris ethanolamine[$N(C_2H_5OH)_3$]), pyrazoline, pyridine, radicals thereof, or mixtures thereof. Preferably the reactant is $H_2$, $NH_3$, radicals thereof, or mixtures thereof.

In another alternative, the reactant may be $(SiH_3)_3N$, hydridosilanes (such as $SiH_4$, $Si_2H_6$, $Si_3H_8$, $Si_4H_{10}$, $Si_5H_{10}$, or $Si_6H_{12}$), chlorosilanes and chloropolysilanes (such as $SiHCl_3$, $SiH_2Cl_2$, $SiH_3Cl$, $Si_2Cl_6$, $Si_2HCl_5$, or $Si_3Cl_8$), alkylsilanes (such as $Me_2SiH_2$, $Et_2SiH_2$, $MeSiH_3$, $EtSiH_3$, or phenyl silane), and aminosilanes (such as tris-dimethylaminosilane, bis-diethylaminosilane, di-isopropylaminosilane or other mono, dis or tris aminosilanes), radicals thereof, or mixtures thereof. Preferably, the reactant is $(SiH_3)_3N$ or an aminosilane.

The reactant may be treated by a plasma, in order to decompose the reactant into its radical form. $N_2$ may also be utilized as a reducing gas when treated with plasma. For instance, the plasma may be generated with a power ranging from about 50 W to about 2500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Group 4 transition metal-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O. radicals. Preferably, the remote plasma may be generated with a power ranging from about 1 kW to about 10 kW, more preferably from about 2.5 kW to about 7.5 kW.

The vapor deposition conditions within the chamber allow the disclosed Group IV transition metal-containing film forming composition and the reactant to react and form a Group 4 transition metal-containing film on the substrate. In some embodiments, Applicants believe that plasma-treating the reactant may provide the reactant with the energy needed to react with the disclosed composition.

Depending on what type of film is desired to be deposited, an additional precursor compound may be introduced into the reactor. The precursor may be used to provide additional elements to the Group 4 transition metal-containing film. The additional elements may include lanthanides (e.g., Ytterbium, Erbium, Dysprosium, Gadolinium, Praseodymium, Cerium, Lanthanum, Yttrium), germanium, silicon, aluminum, boron, phosphorous, a Group 3 element (i.e., Sc, Y, La, or Ac), a different Group 4 element, or a Group 5 element (i.e., V, Nb, or Ta), or mixtures of these. When an additional precursor compound is utilized, the resultant film deposited on the substrate contains the Group 4 transition metal in combination with at least one additional element.

The Group 4 transition metal-containing film forming compositions and reactants may be introduced into the reactor either simultaneously (chemical vapor deposition), sequentially (atomic layer deposition) or different combinations thereof. The reactor may be purged with an inert gas between the introduction of the composition and the introduction of the reactant. Alternatively, the reactant and the composition may be mixed together to form a reactant/compound mixture, and then introduced to the reactor in mixture form. Another example is to introduce the reactant continuously and to introduce the Group 4 transition metal-containing film forming composition by pulse (pulsed chemical vapor deposition).

The vaporized composition and the reactant may be pulsed sequentially or simultaneously (e.g. pulsed CVD) into the reactor. Each pulse of composition may last for a time period ranging from about 0.01 seconds to about 100 seconds, alternatively from about 0.3 seconds to about 30 seconds, alternatively from about 0.5 seconds to about 10 seconds. The reactant may also be pulsed into the reactor. In such embodiments, the pulse of each gas may last from about 0.01 seconds to about 100 seconds, alternatively from about 0.3 seconds to about 30 seconds, alternatively from about 0.5 seconds to about 10 seconds. In another alternative, the vaporized composition and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed Group 4 transition metal-containing film forming composition and a reactant are simultaneously introduced into the reactor. The two react to form the resulting Group 4 transition metal-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed Group 4 transition metal-containing film forming composition is introduced into the reactor, where the Group 4 transition metal-containing precursor physi- or chemisorbs on the substrate. Excess composition may then be removed from the reactor by purging and/or evacuating the reactor. A desired gas (for example, $O_3$) is introduced into the reactor where it reacts with the physi- or chemisorped precursor in a self-limiting manner. Any excess reducing gas is removed from the reactor by purging and/or evacuating the reactor. If the desired film is a Group 4 transition metal film, this two-step process may provide the desired film thickness or may be repeated until a film having the necessary thickness has been obtained.

Alternatively, if the desired film contains Group 4 transition metal and a second element, the two-step process above may be followed by introduction of the vapor of an additional precursor compound into the reactor. The additional precursor compound will be selected based on the nature of the Group 4 transition metal film being deposited. After introduction into the reactor, the additional precursor compound is contacted with the substrate. Any excess precursor compound is removed from the reactor by purging and/or evacuating the reactor. Once again, a desired gas may be introduced into the reactor to react with the precursor compound. Excess gas is removed from the reactor by purging and/or evacuating the reactor. If a desired film thickness has been achieved, the process may be terminated. However, if a thicker film is desired, the entire four-step process may be repeated. By alternating the provision of the Group 4 transition metal-containing compound, additional precursor compound, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

In a second non-limiting exemplary ALD type process, the vapor phase of one of the disclosed Zr-containing precursors, for example $Me_5CpZr((—O—CH_2—CH_2—)_3N)$, is introduced into the reactor, where it is contacted with a TiN substrate. Excess Zr-containing precursor may then be removed from the reactor by purging and/or evacuating the reactor. A desired gas (for example, $O_3$) is introduced into the reactor where it reacts with the absorbed Zr-containing precursor in a self-limiting manner to form a $ZrO_2$ film. Any excess oxidizing gas is removed from the reactor by purging and/or evacuating the reactor. These two steps may be repeated until the $ZrO_2$ film obtains a desired thickness. The resulting $TiN/ZrO_2/TiN$ stack may be used in DRAM capacitors. The $ZrO_2$ metal oxide film may be included within a more complex stack containing a laminate of various metal oxides. Typically, $ZrO_2/Al_2O_3/ZrO_2$ stacks are used, but also $TiO_2/ZrO_2/Al_2O_3/ZrO_2$, $ZrO_2/Nb_2O_3/ZrO_2$, $ZrO_2/HfO_2/TiO_2/ZrO_2$, etc.

The Group 4 transition metal-containing films resulting from the processes discussed above may include a Group 4 transition metal oxide ($MM'_iO_x$, wherein i ranges from 0 to 1; x ranges from 1 to 6; and M' is selected from a Group 3 element, a different Group 4 element (i.e., M≠M), a Group 5 element, a lanthanide, Si, Al, B, P or Ge) or a Group 4 transition metal oxynitride ($MM'_iN_yO_x$, wherein i ranges from 0 to 1; x and y range from 1 to 6; and M' is selected from a Group 3 element, a different Group 4 element (i.e., M≠M'), a Group 5 element, a lanthanide, Si, Al, B, P or Ge). One of ordinary skill in the art will recognize that by judicial selection of the appropriate disclosed compound, optional precursor compounds, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Group 4 transition metal-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Group 4 transition metal-containing film. This in turn tends to improve the resistivity of the film.

EXAMPLES

The following examples illustrate experiments performed in conjunction with the disclosure herein. The examples are not intended to be all inclusive and are not intended to limit the scope of disclosure described herein.

Example 1: Synthesis of $(Me_2N)_2$—Zr—$C_5H_3$-1-Me-3-($CH_2$—$CH_2$—NMe)-

Figure 4:
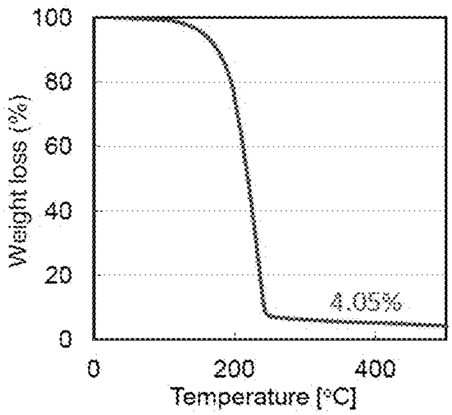
FIG. 4 is a Thermal Gravimetric Analysis (TGA) graph showing the percent residual mass versus temperature in open cup configuration for blends of $(Me_2N)_2$—Zr—$C_5H_3$-1-Me-3-($CH_2$—$CH_2$—NMe)- and $Zr(NMe_2)_4$.
Figure 5:
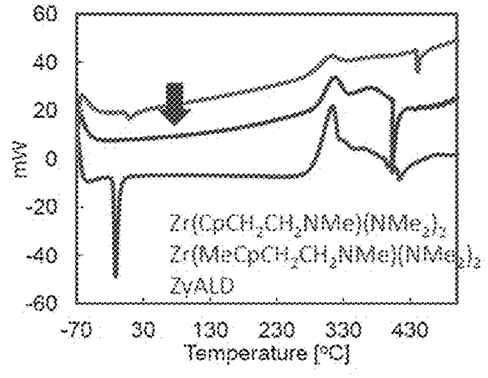
FIG. 5 is a Differential Scanning calorimetry (DSC) graph showing the phase transitions for blends of $(Me_2N)_2$—Zr—$C_5H_3$-1-Me-3-($CH_2$—$CH_2$—NMe)- and $Zr(NMe_2)_4$.
Figure 6:
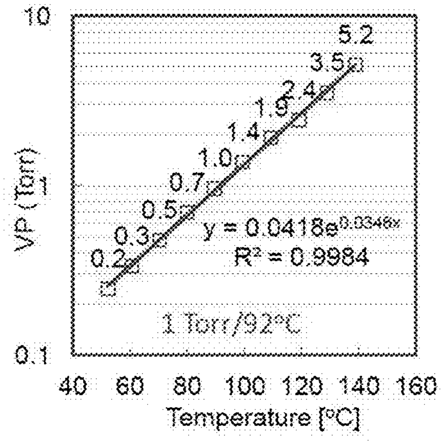
FIG. 6 is a pressure-temperature graph showing the vapor pressure for blends of $(Me_2N)_2$—Zr—$C_5H_3$-1-Me-3-($CH_2$—$CH_2$—NMe)- and $Zr(NMe_2)_4$.

$(Me_2N)_2$—Zr—$C_5H_3$-1-Me-3-($CH_2$—$CH_2$—NMe)- was synthesized by reacting $Zr(NMe_2)_4$ and $MeNHCH_2CH_2MeCp$ in toluene at around −78° C. and isolated as yellow liquid. Open cup vacuum thermal gravimetric analysis (TGA), differential scanning calorimetry (DSC) and vapor pressure of the mixtures were performed after the 24 hours of stirring. The results are shown in FIG. 4 (TGA), FIG. 5 (DSC) and FIG. 6. The solid left approximately 4% residual mass during open cup vacuum TGA measured at a temperature rising rate of 10° C./min. These results are shown in FIG. 4, which is a TGA graph illustrating the percentage of weight loss upon temperature increase for both atmospheric and vacuum open cup. FIG. 5 is the difference in the amount of heat required to increase the temperature of the mixture and reference (e.g., ZyALD) is measured as a function of temperature, showing an almost flat linear curve between −40° C. to 300° C. FIG. 6 is the vapor pressure curve of the mixture versus temperature, showing a linear increase of the vapor pressure over the temperature increase within 40° C. to 140° C. The low amount of residue demonstrated by the TGA results, the thermal stability demonstrated by the DSC and high vapor pressure are promising for vapor deposition applications.

Example 2: ALD Results of $(Me_2N)_2$—Zr—$C_5H_3$-1-Me-3-($CH_2$—$CH_2$—NMe)-

Figure 7:
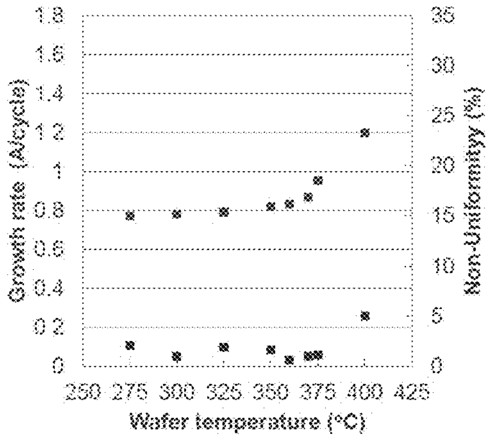
FIG. 7 is a graph of the ALD results of $(Me_2N)_2$—Zr—$C_5H_3$-1-Me-3-($CH_2$—$CH_2$—NMe)-.

FIG. 7 is the ALD results of $(Me_2N)_2$—Zr—$C_5H_3$-1-Me-3-($CH_2$—$CH_2$—NMe)-. The growth rate was 0.8 A per cycle and the ALD window was up to 360-370° C.

Comparative Example $Zr(CpCH_2CH_2NMe)(NMe_2)_2$ was synthesized and the DSC was shown in FIG. 5. As shown, the thermal stability of $Zr(CpCH_2CH_2NMe)(NMe_2)_2$ is less than that of $(Me_2N)_2$—Zr—$C_5H_3$-1-Me-3-($CH_2$—$CH_2$—NMe)-.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A Group 4 transition metal-containing film forming composition comprising a Group 4 transition metal precursor having the formula —$(R_2N)_2$-M-$C_5R_4$—[$C_2H_4$—NR]— referring to the following structure formula:

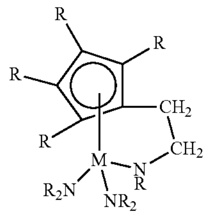

wherein M is Ti, Zr, or Hf bonded in an $\eta^5$ bonding mode to the Cp group and each R is independently a hydrogen or a $C_1$-$C_4$ hydrocarbon group; provided that at least one R on the Cp is $C_1$ to $C_4$.

2. The Group 4 transition metal-containing film forming composition of claim 1, wherein M is Zr.

3. The Group 4 transition metal-containing film forming composition of claim 2, wherein the Group 4 transitional metal precursor is selected from the group consisting of $(Me_2N)_2$—Zr—$C_5H_3$-1-Me-3-($CH_2$—$CH_2$—NMe)-, $(Me_2N)_2$—Zr—$C_5H_3$-1-Et-3-($CH_2$—$CH_2$—NMe)-, $(Me_2N)_2$—Zr—$C_5H_3$-1-$^i$Pr-3-($CH_2$—$CH_2$—NMe)-, $(Me_2N)$(Cp)-Zr—$C_5H_3$-1-Me-3-($CH_2$—$CH_2$—NMe)-, $(Me_2N)$(Cp)-Zr—$C_5H_3$-1-Et-3-($CH_2$—$CH_2$—NMe)-, $(Me_2N)$(Cp)-Zr—$C_5H_3$-1-$^i$Pr-3-($CH_2$—$CH_2$—NMe)-, $(Me_2N)_2$—Zr—$C_5Me_4$-($CH_2$—$CH_2$—NMe)-, $(Me_2N)_2$—Zr—$C_5Me_3$-1-Et-3-($CH_2$—$CH_2$—NMe)-, $(Me_2N)_2$—Zr—$C_5Me_3$-1-$^i$Pr-3-($CH_2$—$CH_2$—NMe)-, $(Me_2N)$(Cp)-Zr—$C_5Me_4$-($CH_2$—$CH_2$—NMe)-, $(Me_2N)$(Cp)-Zr—$C_5Me_3$-1-Et-3-($CH_2$—$CH_2$—NMe)-, and $Me_2N)$(Cp)-Zr—$C_5Me_3$-1-$^i$Pr-3-($CH_2$—$CH_2$—NMe)-.

4. The Group 4 transition metal-containing film forming composition of claim 3, wherein the Group 4 transitional metal precursor is $(Me_2N)_2$—Zr-$MeC_5H_3$-($CH_2$—$CH_2$—NMe)-.

5. The Group 4 transition metal-containing film forming composition of claim 1, wherein M is Hf.

6. The Group 4 transition metal-containing film forming composition of claim 5, wherein the Group 4 transitional metal precursor is selected from the group consisting of $(Me_2N)_2$—Hf—$C_5H_3$-1-Me-3-($CH_2$—$CH_2$—NMe)-, $(Me_2N)_2$—Hf—$C_5H_3$-1-Et-3-($CH_2$—$CH_2$—NMe)-, $(Me_2N)_2$—Hf—$C_5H_3$-1-$^i$Pr-3-($CH_2$—$CH_2$—NMe)-, $(Me_2N)$(Cp)-Hf—$C_5H_3$-1-Me-3-($CH_2$—$CH_2$—NMe)-, $(Me_2N)$(Cp)-Hf—$C_5H_3$-1-Et-3-($CH_2$—$CH_2$—NMe)-, $(Me_2N)$(Cp)-Hf—$C_5H_3$-1-$^i$Pr-3-($CH_2$—$CH_2$—NMe)-, $(Me_2N)_2$—Hf—$C_5Me_4$-($CH_2$—$CH_2$—NMe)-, $(Me_2N)_2$—Hf—$C_5Me_3$-1-Et-3-($CH_2$—$CH_2$—NMe)-, $(Me_2N)_2$—Hf—$C_5Me_3$-1-$^i$Pr-3-($CH_2$—$CH_2$—NMe)-, $(Me_2N)$(Cp)-Hf—$C_5Me_4$-($CH_2$—$CH_2$—NMe)-, $(Me_2N)$(Cp)-Hf—$C_5Me_3$-1-Et-3-($CH_2$—$CH_2$—NMe)-, and $(Me_2N)$(Cp)-Hf—$C_5Me_3$-1-$^i$Pr-3-($CH_2$—$CH_2$—NMe)-.

7. The Group 4 transition metal-containing film forming composition of claim 6, wherein the Group 4 transitional metal precursor is $(Me_2N)_2$—Hf-$MeC_5H_3$-($CH_2$—$CH_2$—NMe)-.

8. The Group 4 transition metal-containing film forming composition of claim 1, wherein M is Ti.

9. A method of depositing of a Group 4 transition metal-containing film on a substrate, comprising the steps of:

introducing a vapor of the Group 4 transition metal-containing film forming composition of claim 1 into a reactor having a substrate disposed therein and depositing at least part of the Group 4 transition metal-containing precursor onto the substrate.

10. The method of claim 9, further comprising introducing at least one reactant into the reactor.

11. The method of claim 10, wherein the reactant is a M'-containing precursor and the Group 4 transition metal-containing film is $MM'_iO_x$, wherein i ranges from 0 to 1; x ranges from 1 to 6; and M' is selected from a Group 3 element, a different Group 4 element, a Group 5 element, a lanthanide, Si, Al, B, P or Ge.

12. The method of claim 10, wherein the Group 4 transition metal-containing film forming composition and the reactant are introduced into the reactor simultaneously and the reactor is configured for chemical vapor deposition.

13. The method of claim 12, wherein the chemical vapor deposition is plasma enhanced.

14. The method of claim 10, wherein the Group 4 transition metal-containing film forming composition and the reactant are introduced into the chamber sequentially and the reactor is configured for atomic layer deposition.

15. The method of claim 14, wherein the atomic layer deposition is plasma enhanced.

16. The method of claim 10, wherein the precursor is used to form a DRAM capacitor.

17. The method of claim 10, wherein the reactant is selected from the group consisting of: $O_2$, $O_3$, $H_2O$, $H_2O_2$, NO, $N_2O$, $NO_2$, oxygen radicals thereof, and mixtures thereof.

18. The method of claim 9, wherein the Group 4 transitional metal precursor has the formula:

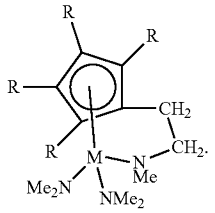

19. The method of claim 9, wherein the Group 4 transitional metal precursor is $(Me_2N)_2$—Zr-$MeC_5H_3$-($CH_2$—$CH_2$—NMe)-.

20. The method of claim 9, wherein the Group 4 transitional metal precursor is $(Me_2N)_2$—Hf-$MeC_5H_3$-($CH_2$—$CH_2$—NMe)-.

21. The Group 4 transition metal-containing film forming composition of claim 1, wherein the Group 4 transitional metal precursor has the formula:

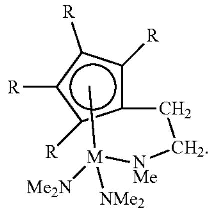

* * * * *